US011021537B2

(12) United States Patent
Chand et al.

(10) Patent No.: US 11,021,537 B2
(45) Date of Patent: Jun. 1, 2021

(54) ANTI-TIGIT ANTIBODIES AND METHODS OF USE THEREOF

(71) Applicant: Agenus Inc., Lexington, MA (US)

(72) Inventors: Dhan Sidhartha Chand, Woburn, MA (US); Nicholas Stuart Wilson, San Carlos, CA (US); Dennis John Underwood, Boston, MA (US); Benjamin Maxime Morin, Somerville, MA (US)

(73) Assignee: AGENUS INC., Lexington, MA (US)

( * ) Notice: Subject to any disclaimer, the term of this patent is extended or adjusted under 35 U.S.C. 154(b) by 363 days.

(21) Appl. No.: 15/968,094

(22) Filed: May 1, 2018

(65) Prior Publication Data

US 2018/0355040 A1    Dec. 13, 2018

Related U.S. Application Data

(60) Provisional application No. 62/500,345, filed on May 2, 2017, provisional application No. 62/492,829, filed on May 1, 2017.

(51) Int. Cl.
| | | |
|---|---|---|
| *A61K 39/395* | (2006.01) | |
| *C07K 16/28* | (2006.01) | |
| *A61P 35/04* | (2006.01) | |
| *C07K 16/30* | (2006.01) | |
| *G01N 33/50* | (2006.01) | |
| *A61K 39/00* | (2006.01) | |

(52) U.S. Cl.
CPC ........ *C07K 16/2818* (2013.01); *A61K 39/395* (2013.01); *A61P 35/04* (2018.01); *C07K 16/28* (2013.01); *C07K 16/2875* (2013.01); *C07K 16/2878* (2013.01); *C07K 16/30* (2013.01); *G01N 33/505* (2013.01); *A61K 2039/57* (2013.01); *C07K 2317/24* (2013.01); *C07K 2317/33* (2013.01); *C07K 2317/34* (2013.01); *C07K 2317/52* (2013.01); *C07K 2317/71* (2013.01); *C07K 2317/72* (2013.01); *C07K 2317/73* (2013.01); *C07K 2317/734* (2013.01); *C07K 2317/74* (2013.01); *C07K 2317/76* (2013.01); *C07K 2317/92* (2013.01); *C07K 2319/30* (2013.01)

(58) Field of Classification Search
None
See application file for complete search history.

(56) References Cited

U.S. PATENT DOCUMENTS

| | | |
|---|---|---|
| 9,499,596 B2 | 11/2016 | Clark et al. |
| 9,695,238 B2 | 7/2017 | Gao et al. |
| 9,713,641 B2 | 7/2017 | Hicklin et al. |
| RE46,534 E | 9/2017 | Baldwin et al. |
| 9,873,740 B2 | 1/2018 | Grogan et al. |
| 10,017,572 B2 | 7/2018 | Grogan et al. |
| 10,112,997 B2 | 10/2018 | Gurney et al. |
| 10,124,061 B2 | 11/2018 | White et al. |
| 10,144,778 B2 | 12/2018 | Eisenbach-Schwartz et al. |
| 10,189,902 B2 | 1/2019 | Maurer et al. |
| 10,329,349 B2 | 6/2019 | Cooper et al. |
| 10,537,633 B2 | 1/2020 | Tso et al. |
| 10,537,637 B2 | 1/2020 | Sheng et al. |
| 2009/0258013 A1 | 10/2009 | Clark et al. |
| 2013/0287797 A1 | 10/2013 | Heider et al. |
| 2016/0108123 A1 | 4/2016 | Freeman et al. |
| 2016/0152720 A1 | 6/2016 | Kim et al. |
| 2016/0193239 A1 | 7/2016 | Baylin et al. |
| 2016/0376371 A1 | 12/2016 | Ravetch et al. |
| 2017/0037127 A1 | 2/2017 | Grogan et al. |
| 2017/0107300 A1 | 4/2017 | Kuchroo et al. |
| 2017/0143825 A1 | 5/2017 | Grogan |
| 2017/0239338 A1 | 8/2017 | Szalay et al. |
| 2017/0260271 A1 | 9/2017 | Igawa et al. |
| 2017/0360932 A1 | 12/2017 | Parry |
| 2018/0066055 A1 | 3/2018 | Williams et al. |
| 2018/0078625 A1 | 3/2018 | Moon et al. |
| 2018/0155422 A1 | 6/2018 | Bhatt et al. |
| 2018/0169239 A1 | 6/2018 | Grogan |
| 2018/0185480 A1 | 7/2018 | Mandelboim et al. |
| 2018/0251548 A1 | 9/2018 | Sabzevari et al. |
| 2018/0371083 A1 | 12/2018 | Williams et al. |
| 2019/0077869 A1 | 3/2019 | Fiedler et al. |

(Continued)

FOREIGN PATENT DOCUMENTS

| | | |
|---|---|---|
| WO | WO 2011109789 A2 | 9/2011 |
| WO | WO 2013184912 A2 | 12/2013 |
| WO | WO 2016004875 A1 | 1/2016 |

(Continued)

OTHER PUBLICATIONS

White et al. (2001, Ann. Rev. Med., 2001, 52:125-145) (Year: 2001).*
Meibohm (Pharmacokinetics and Pharmacodynamics of Biotech Drugs, Wiley-VHC, 2006, chapter 3, p. 45-91) (Year: 2006).*
Agenus, "Corporate Presentation", Cantor Fitzgerald Global Healthcare Conference, Sep. 2017, 30 pages.
Agenus, Integrated Immunotherapy: Enabling Best-in-Class I-O Combinations, Non-Confidential Overview, Nov. 2017, 33 pages.

(Continued)

*Primary Examiner* — Meera Natarajan
(74) *Attorney, Agent, or Firm* — Dechert LLP; Andrew T. Wilkins; Robin L. Brese

(57) ABSTRACT

The instant disclosure provides antibodies that specifically bind to T-cell immunoreceptor with Ig and ITIM domains (TIGIT) (e.g., human TIGIT) and antagonize TIGIT function. Also provided are pharmaceutical compositions comprising these antibodies, nucleic acids encoding these antibodies, expression vectors and host cells for making these antibodies, and methods of treating a subject using these antibodies.

70 Claims, 40 Drawing Sheets

Specification includes a Sequence Listing.

(56) References Cited

U.S. PATENT DOCUMENTS

2020/0040082 A1 2/2020 Piasecki et al.

FOREIGN PATENT DOCUMENTS

| | | |
|---|---|---|
| WO | WO 2016011264 A1 | 1/2016 |
| WO | WO 2016180781 A1 | 11/2016 |
| WO | WO 2016191643 A2 | 12/2016 |
| WO | WO 2017023749 A1 | 2/2017 |
| WO | WO 2017030823 A2 | 2/2017 |
| WO | WO 2017040790 A1 | 3/2017 |
| WO | WO 2017048824 A1 | 3/2017 |
| WO | WO 2017059095 A1 | 4/2017 |
| WO | WO 2017062619 A2 | 4/2017 |
| WO | WO 2017062620 A1 | 4/2017 |
| WO | WO 2017123981 A1 | 7/2017 |
| WO | WO 2017223085 A2 | 12/2017 |
| WO | WO 2018053242 A1 | 3/2018 |
| WO | WO 2018102536 A1 | 6/2018 |
| WO | WO 2018183889 A1 | 10/2018 |
| WO | WO 2018204405 A1 | 11/2018 |
| WO | WO 2018229163 A1 | 12/2018 |
| WO | WO 2018234793 A2 | 12/2018 |
| WO | WO 2019062832 A1 | 4/2019 |
| WO | WO 2019129221 A1 | 7/2019 |
| WO | WO 2019129261 A1 | 7/2019 |
| WO | WO 2019137548 A1 | 7/2019 |
| WO | WO 2019152574 A1 | 8/2019 |
| WO | WO 2019154415 A1 | 8/2019 |
| WO | WO 2019165434 A1 | 8/2019 |
| WO | WO 2019168382 A1 | 9/2019 |

OTHER PUBLICATIONS

Agenus; Stein MD, Ph.D., Robert; "Next Generation Immunomodulatory Antibodies: Optimizing Therapeutic Impact", 2017, 16 pages.

Blake et al., "Molecular Pathways: Targeting CD96 and TIGIT for Cancer Immunotherapy", Clin. Cancer Res., 2016, vol. 22, No. 21, pp. 1-6.

Cattaruzza et al., "Pharmacodynamic biomarkers for anti-TIGIT treatment and prevalence of TIGIT expression in multiple solid tumor types", Oncomed Pharmaceuticals, 2017.

Chauvin et al., "TIGIT and PD-1 impair tumor antigen-specific CD8+ T cells in melanoma patients" J. Clin. Invest., 2015, 13 pages.

Chew et al., "TIGIT Marks Exhausted T Cells, Correlates with Disease Progression, and Serves as a Target for Immune Restoration in HIV and SIV Infection", PLOS Pathogens, 2016, vol. 12, No. 1, 28 pages.

Dougall et al., "TIGIT and CD96: new checkpoint receptor targets for cancer immunotherapy", Immunological Reviews, 2017, vol. 276, pp. 112-120.

Gur et al., "Binding of the Fap2 Protein of Fusobacterium nucleatum to Human Inhibitory Receptor TIGIT Protects Tumors from Immune Cell Attack", Immunity, 2015, vol. 42, pp. 344-355.

He et al., "CD155T/TIGIT Signaling Regulates CD8b T-cell Metabolism and Promotes Tumor Progression in Human Gastric Cancer", Cancer Research, vol. 77, No. 22, pp. 6375-6388.

Hung et al, "TIGIT and PD-1 dual checkpoint blockade enhances antitumor immunity and survival in GBM", Oncoimmunology, 2018, vol. 7, No. 8, 13 pages.

International Search Report and Written Opinion for PCT International Patent Application No. PCT/US2018/030453, dated Sep. 21, 2018, 18 pages.

Johnston et al., "The Immunoreceptor TIGIT Regulates Antitumor and Antiviral CD8+ T Cell Effector Function", Cancer Cell, 2014, vol. 26, pp. 923-937.

Joller et al., "Treg Cells Expressing the Coinhibitory Molecule TIGIT Selectively Inhibit Proinflammatory Th1 and Th17 Cell Responses", Immunity, 2014, vol. 40, pp. 569-581.

Kurtulus et al., "TIGIT predominantly regulates the immune response via regulatory T cells", J Clin Invest., 2015, vol. 125, No. 11, pp. 4053-4062.

Lozano et al., "The TIGIT/CD226 Axis Regulates Human T Cell Function", J. Immunol., 2012, vol. 188, pp. 3869-3875.

Manieri et al., "TIGIT: A Key Inhibitor of the Cancer Immunity Cycle", Trends in Immunology, 2016, vol. 38, No. 1, pp. 20-28.

Pauken et al., "TIGIT and CD226: Tipping the Balance between Costimulatory and Coinhibitory Molecules to Augment the Cancer Immunotherapy Toolkit", Cancer Cell, 2014, vol. 26, pp. 785-787.

Samanta et al., "Structural, mutational and biophysical studies reveal a canonical mode of molecular recognition between immune receptor TIGIT andnectin-2", Molecular Immunology, 2017, vol. 81, pp. 151-159.

Stanietsky et al., "The interaction of TIGIT with PVR and PVRL2 inhibits human NK cell cytotoxicity", PNAS, 2009, vol. 106, No. 42, pp. 17858-17863.

Stengel et al., "Structure of TIGIT immunoreceptor bound to poliovirus receptor reveals a cell—cell adhesion and signaling mechanism that requires cis-trans receptor clustering", PNAS, 2012, vol. 109, No. 14, pp. 5399-5404.

Yu et al., "The surface protein TIGIT suppresses T cell activation by promoting the generation of mature immunoregulatory dendritic cells", Nature Immunology, 2009, vol. 10, No. 1, pp. 48-57.

Zhou et al., "Intrinsic Expression of Immune Checkpoint Molecule Tigit Could Help Tumor Growth in vivo by Suppressing the Function of NK and CD8+ T Cells", Frontiers in Immunology, 2018, vol. 9, Article 2821, pp. 1-11.

* cited by examiner

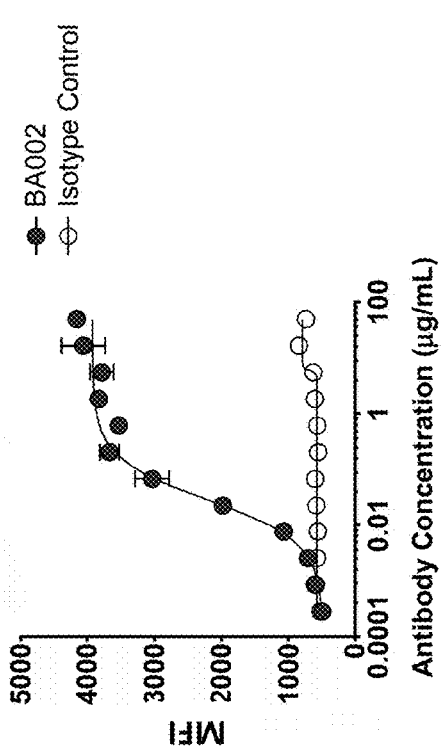
FIG. 2A
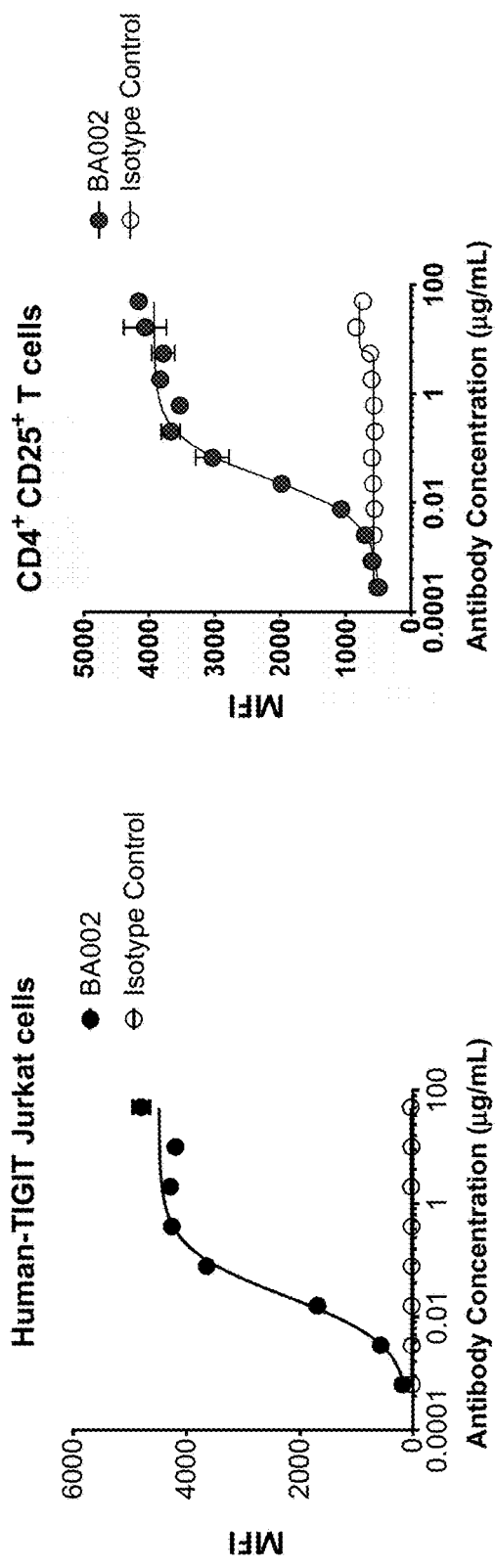
FIG. 2B
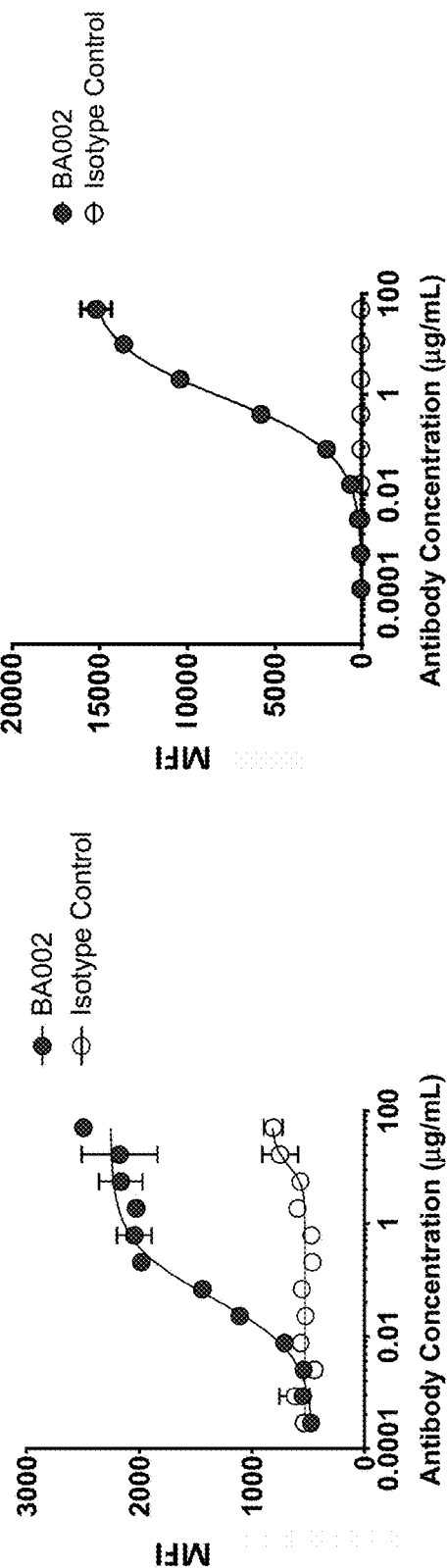
FIG. 2C
FIG. 2D

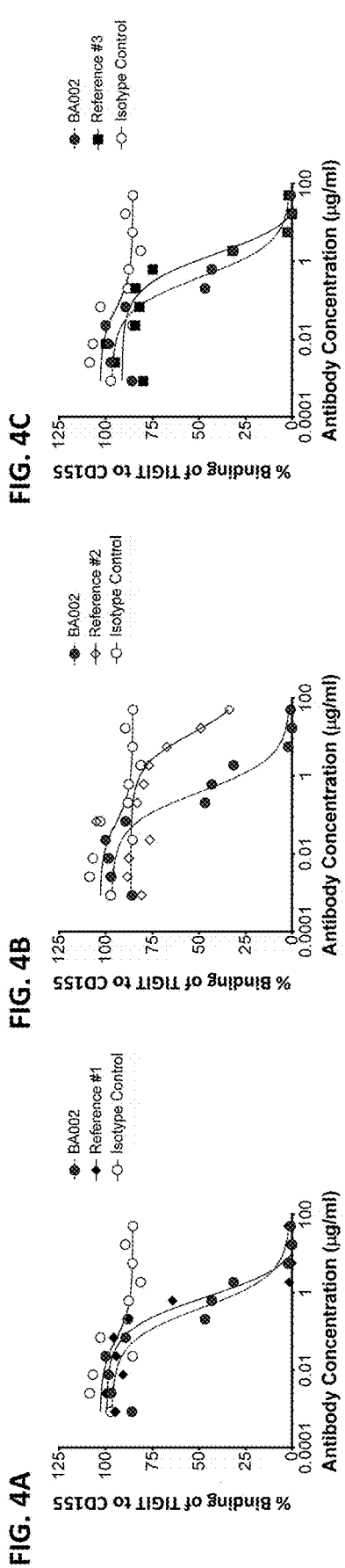
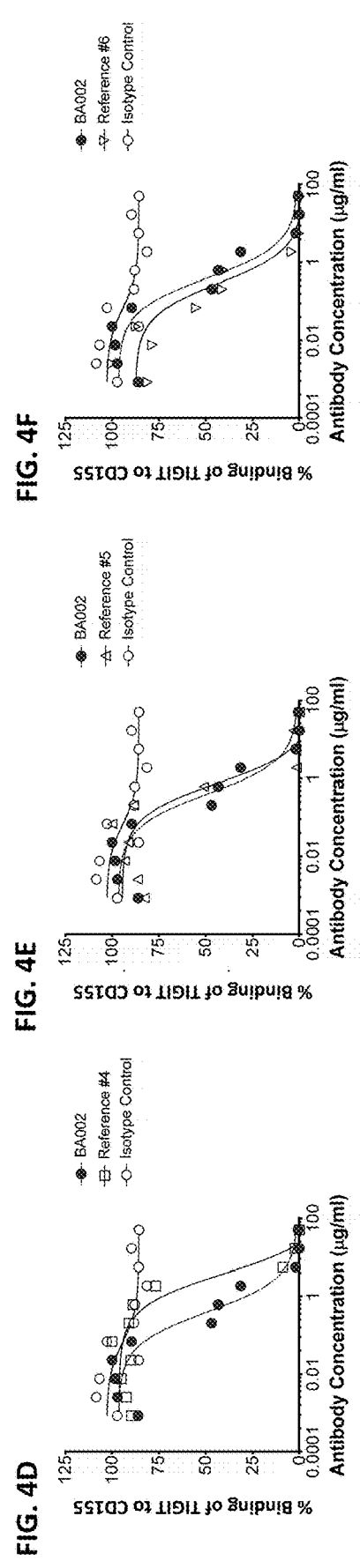

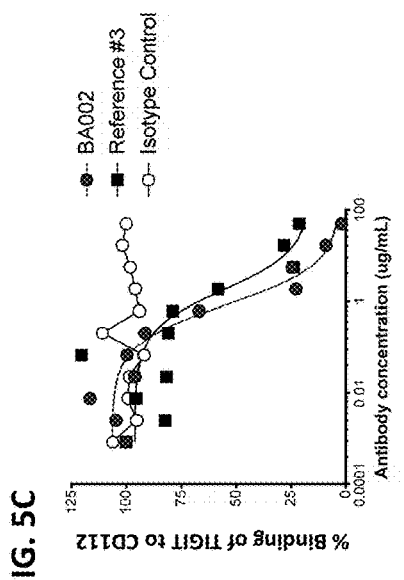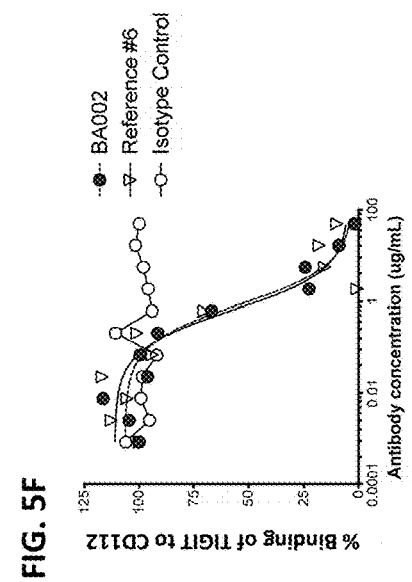
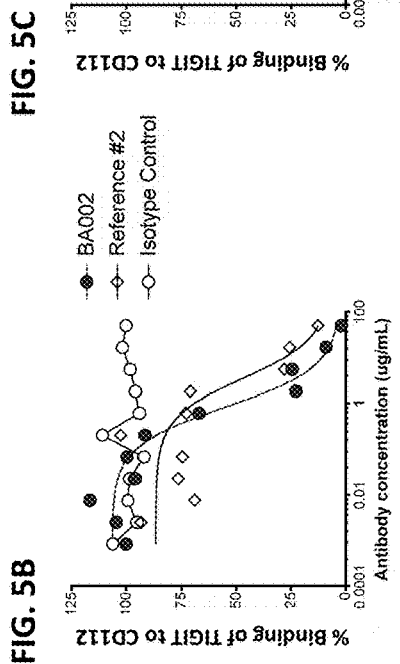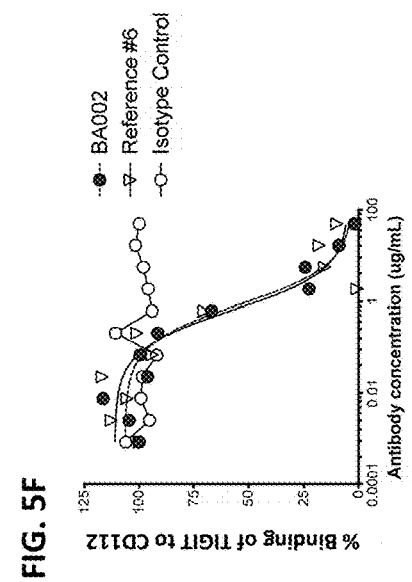
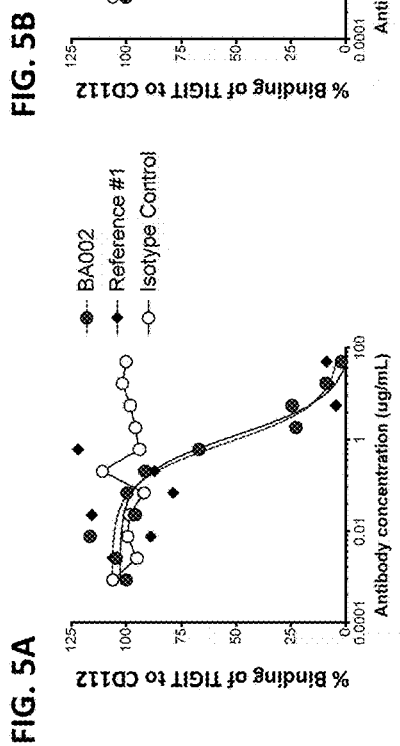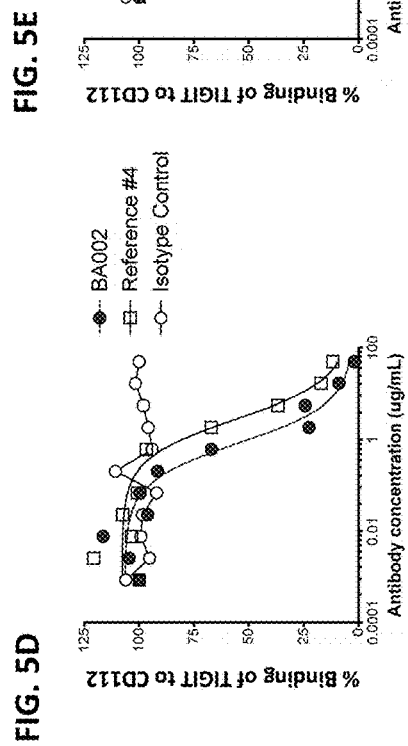
FIG. 5A  FIG. 5B  FIG. 5C
FIG. 5D  FIG. 5E  FIG. 5F

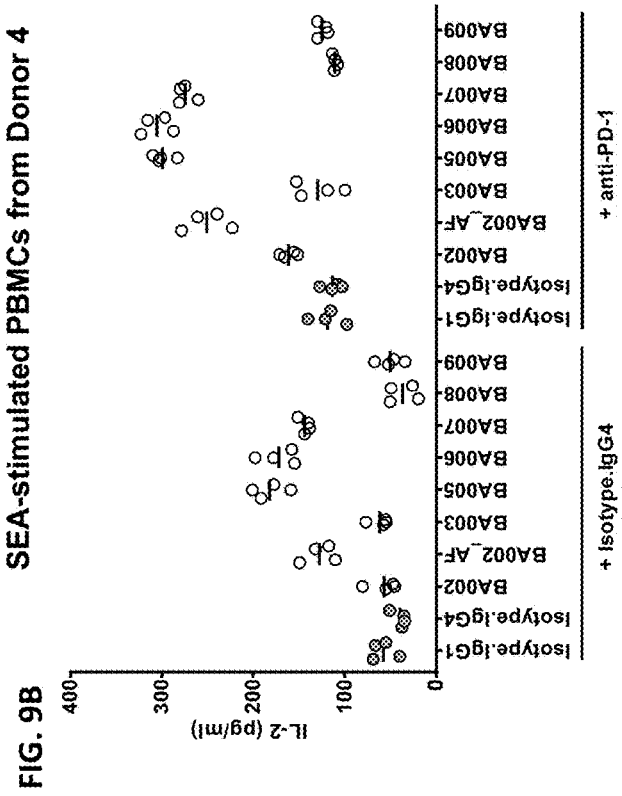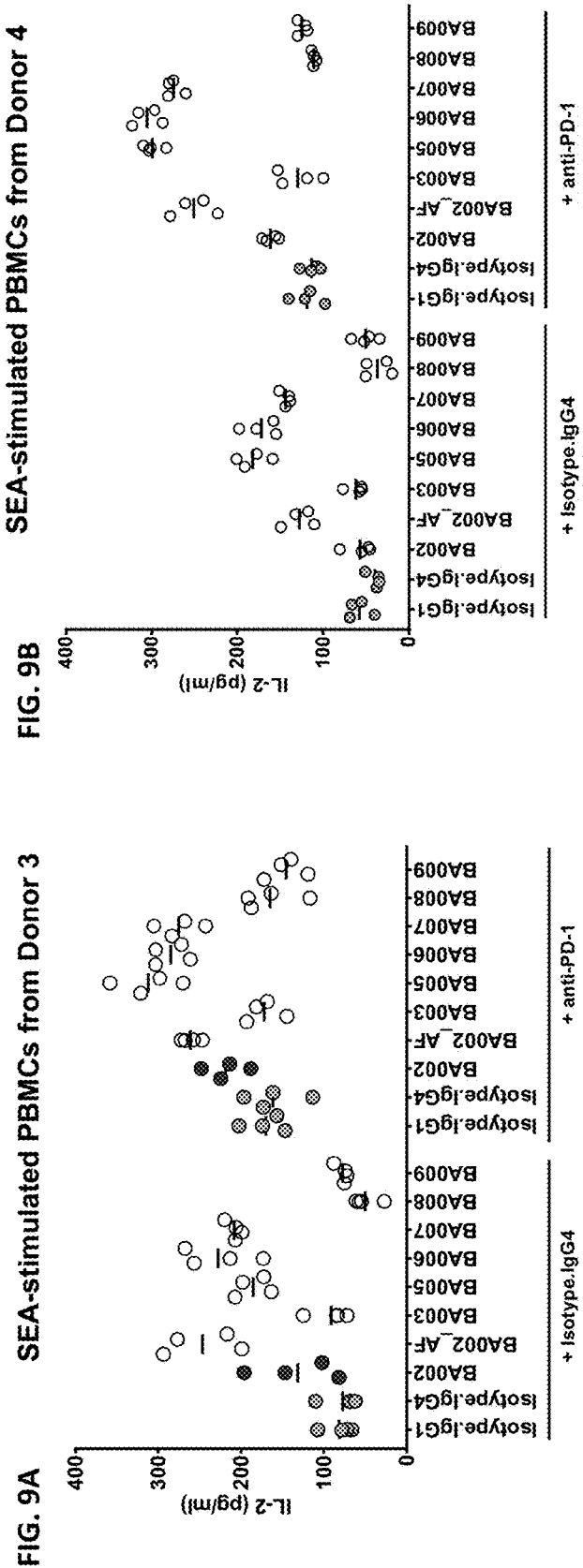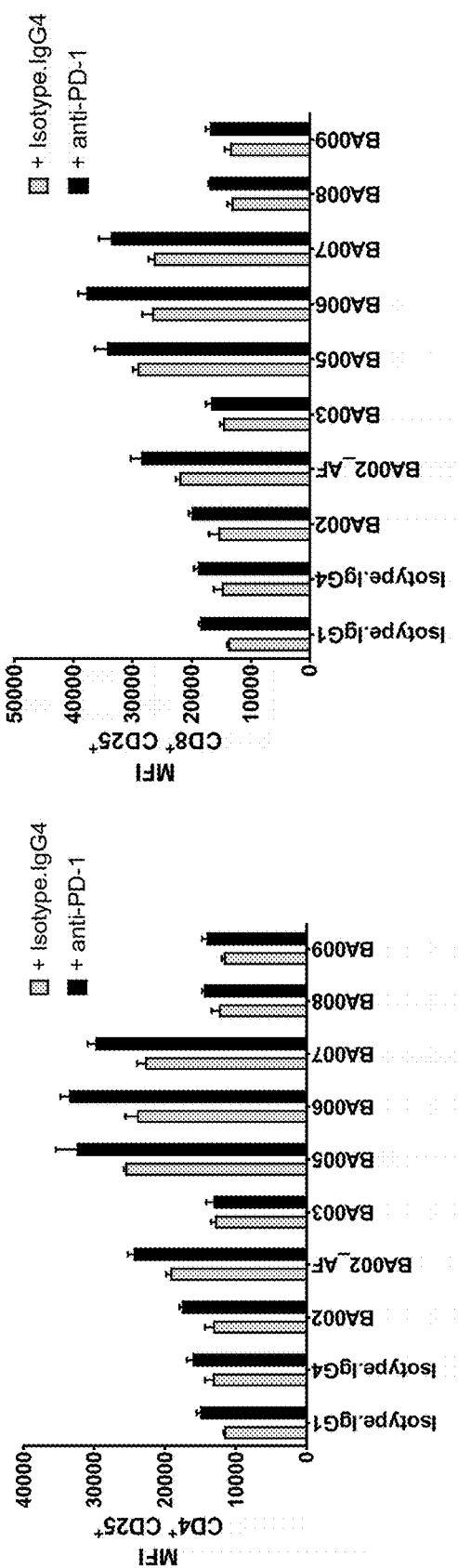

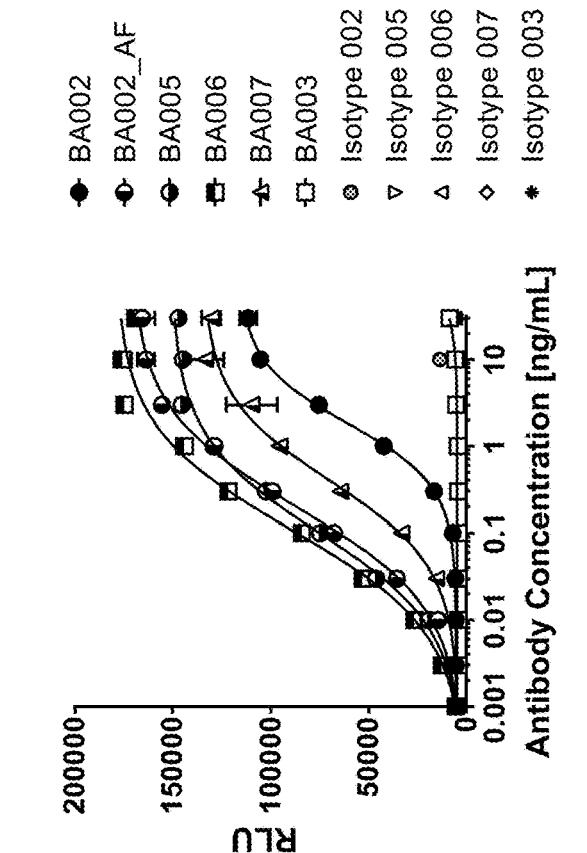
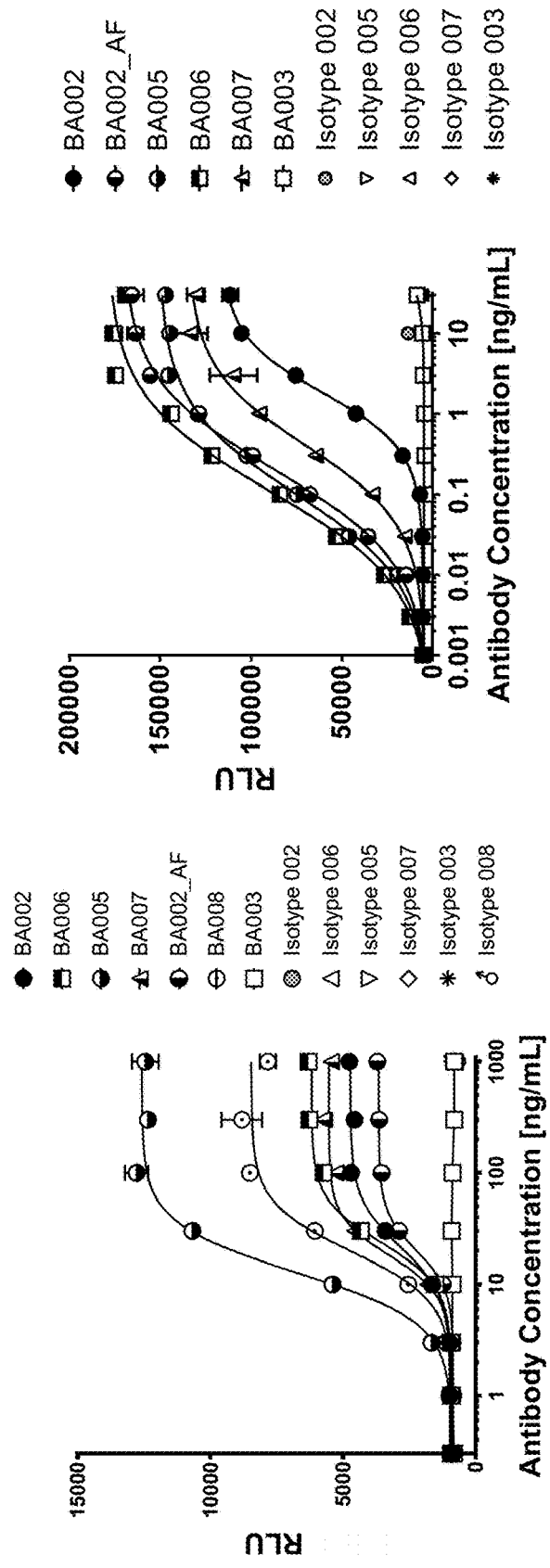
FIG. 12A
FIG. 12B

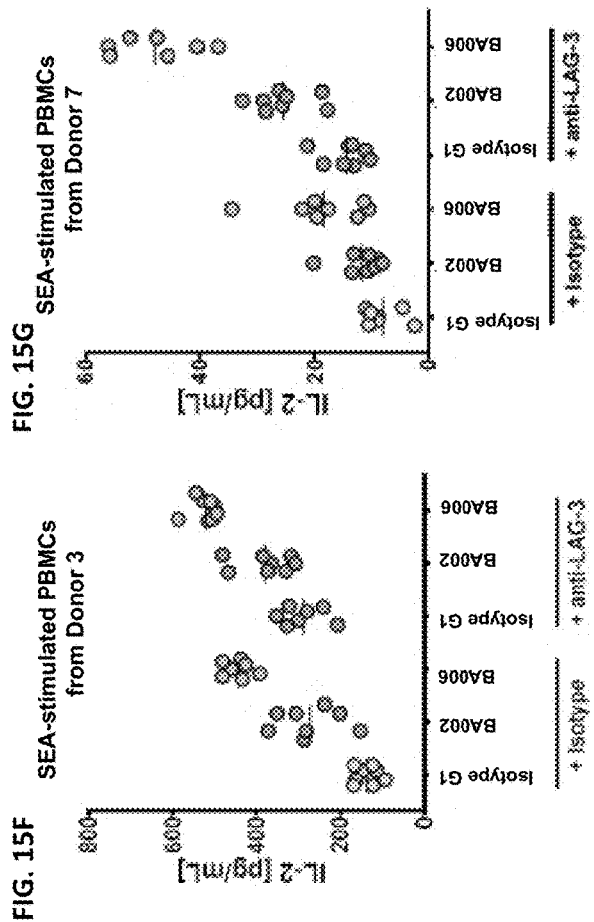
FIG. 15E
FIG. 15F
FIG. 15G
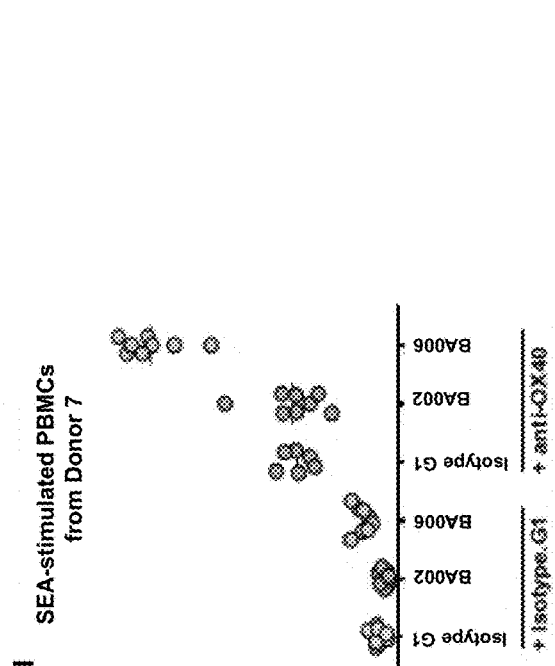
FIG. 15H
FIG. 15I

FIG. 21

*Signal peptide*

| | | |
|---|---|---|
| H. Sapiens | MRWCLLLIWAQGLRQAPLASG MTGTIETTGNISAEKGGSIILQCHLSSTTAQVIQVNWEQQDQ-LLAIC | 69 |
| M. fasicularis | MRWCLFLIWAQGLRQAPLASG MTGTIETTGNISAKKGGSVILQCHLSSTMAQVIQVNWEQHDSLLAIR | 70 |

| | | |
|---|---|---|
| H. Sapiens | NADLGWHISPSFKDRVAPGPGLGLTLQSLTVNDTGEYFCIYHTYPDGTYTGRIFLEVLESSVAEHGARFQ | 139 |
| M. fasicularis | NAELGWHIYPAFKDRVAPGPGLGLTLQSLTMNDTGEYFCTYHTYPDGTYRGRIFLEVLESSVAEHSARFQ | 140 |

*Transmembrane domain*

| | | |
|---|---|---|
| H. Sapiens | IPLLGAMAATLVVICTAVIVVVAL TRKKKALRIHSVEGDLRRKSAGQEEWSPSAPSPPGSCVQAEAAPAG | 209 |
| M. fasicularis | IPLLGAMAMMLVVICIAVIVVVVL ARKKKKSLRIHSVESGLQRKSTGQEEQIPSAPSPPGSCVQAEAAPAG | 210 |

| | | |
|---|---|---|
| H. Sapiens | LCGEQRGEDCAELHDYFNVLSYRSLGNCSFFTETG | 244 |
| M. fasicularis | LCGEQQGDDCAELHDYFNVLSYRSLGSCSFFTETG | 245 |

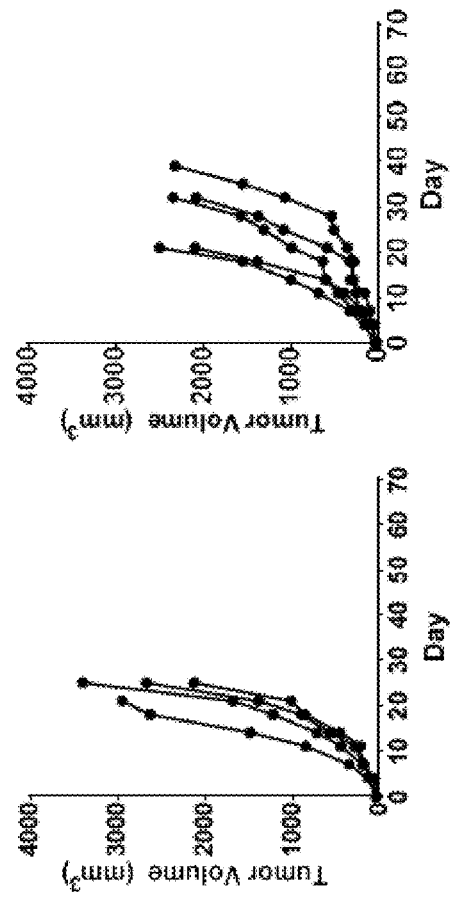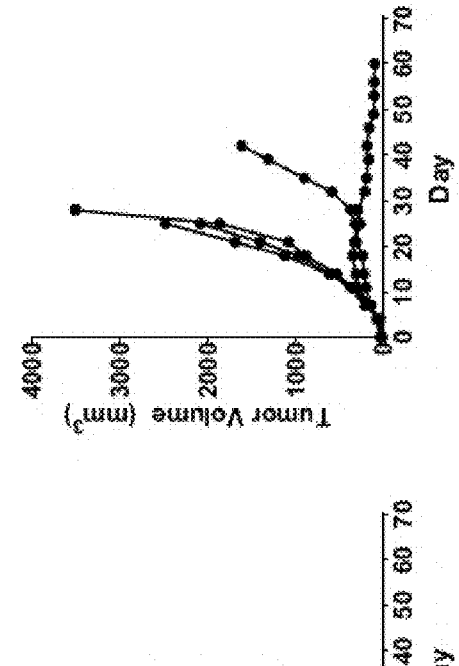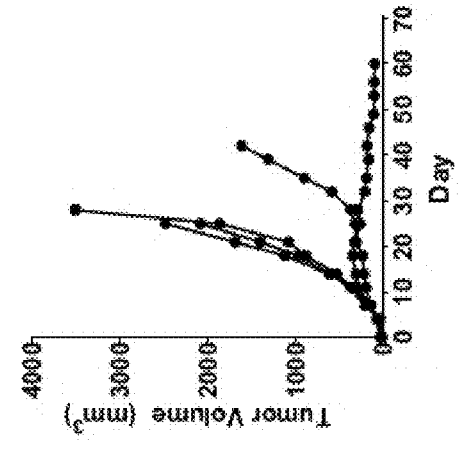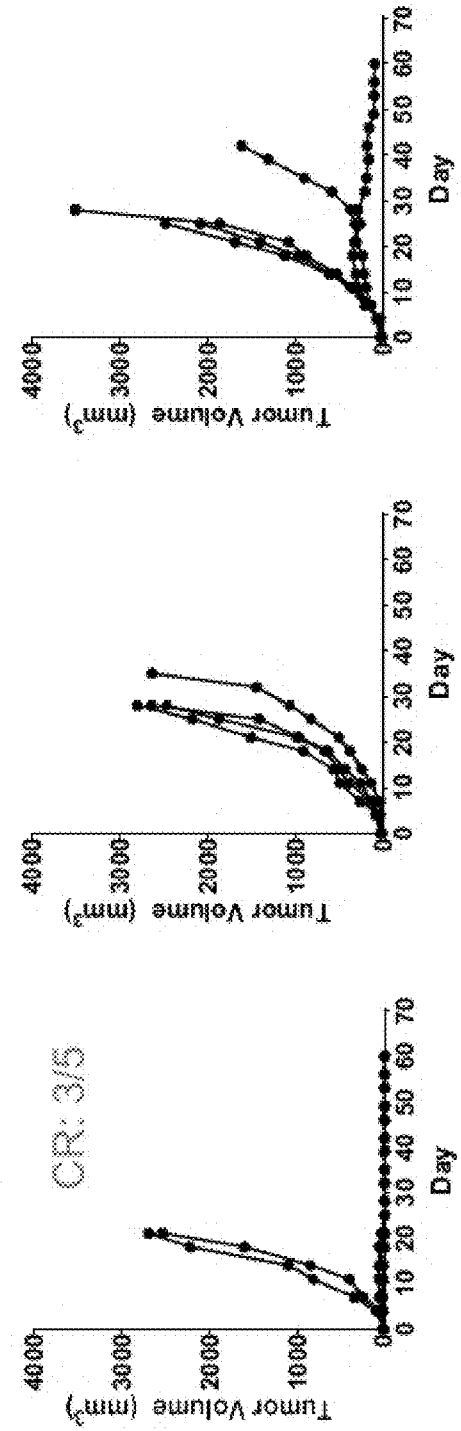

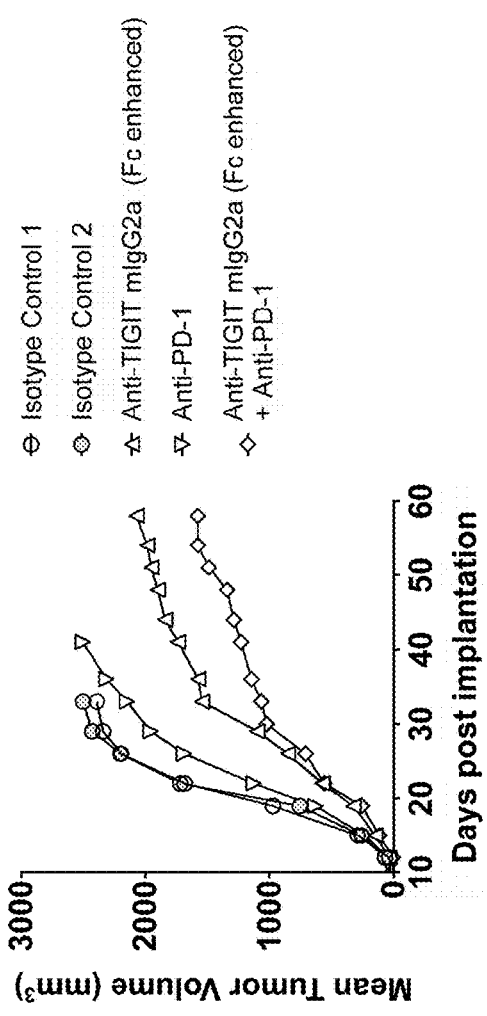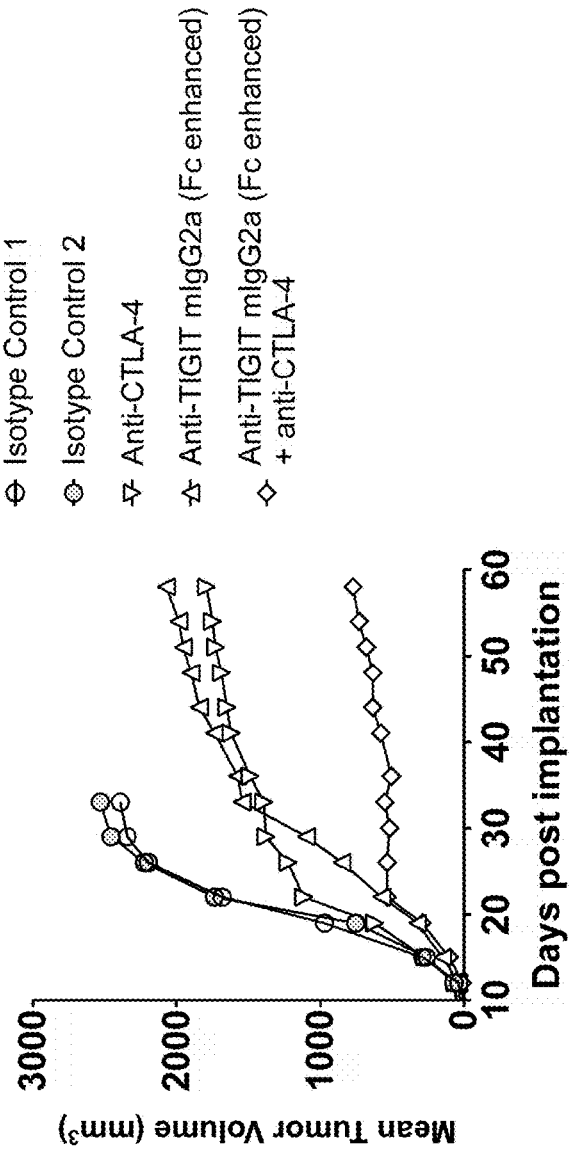
FIG. 26A
FIG. 26B

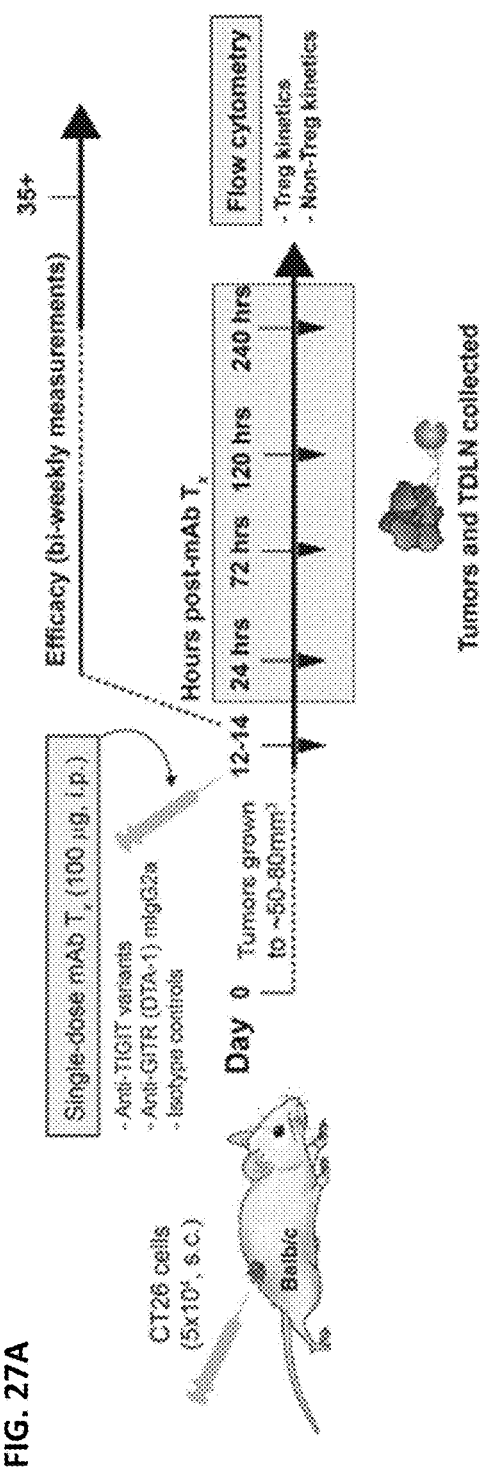
FIG. 27A
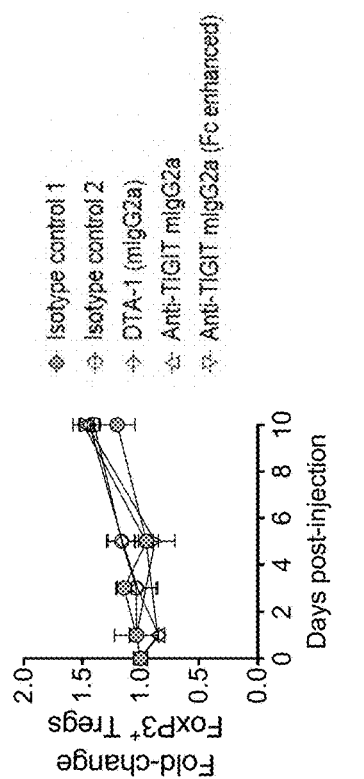
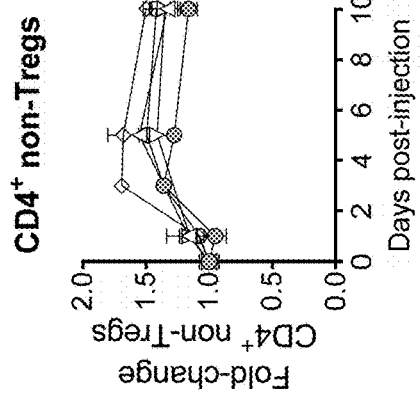
FIG. 27D
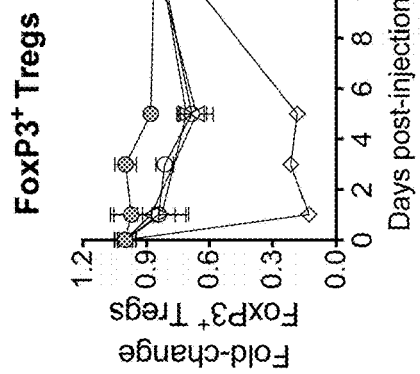
FIG. 27C
FIG. 27B

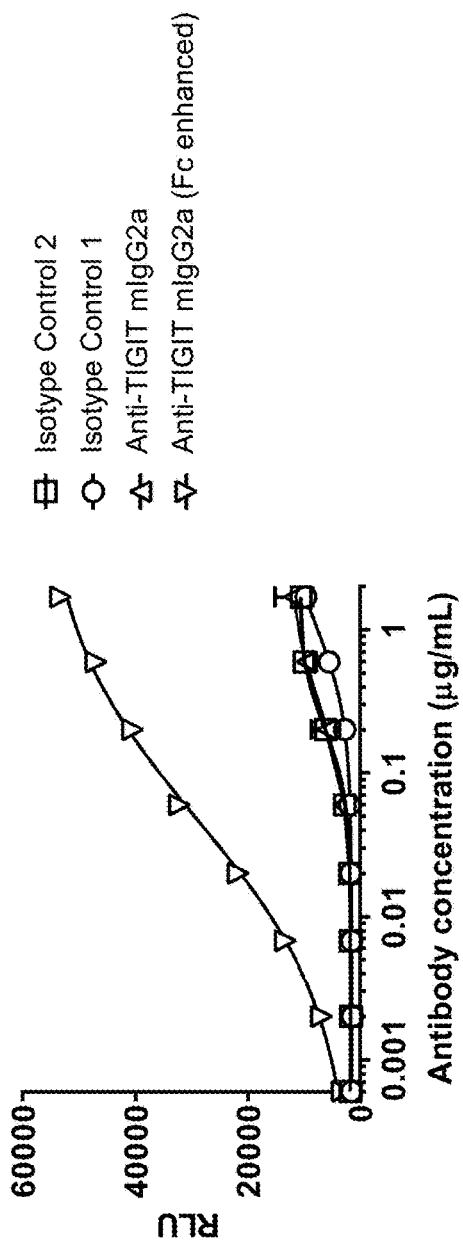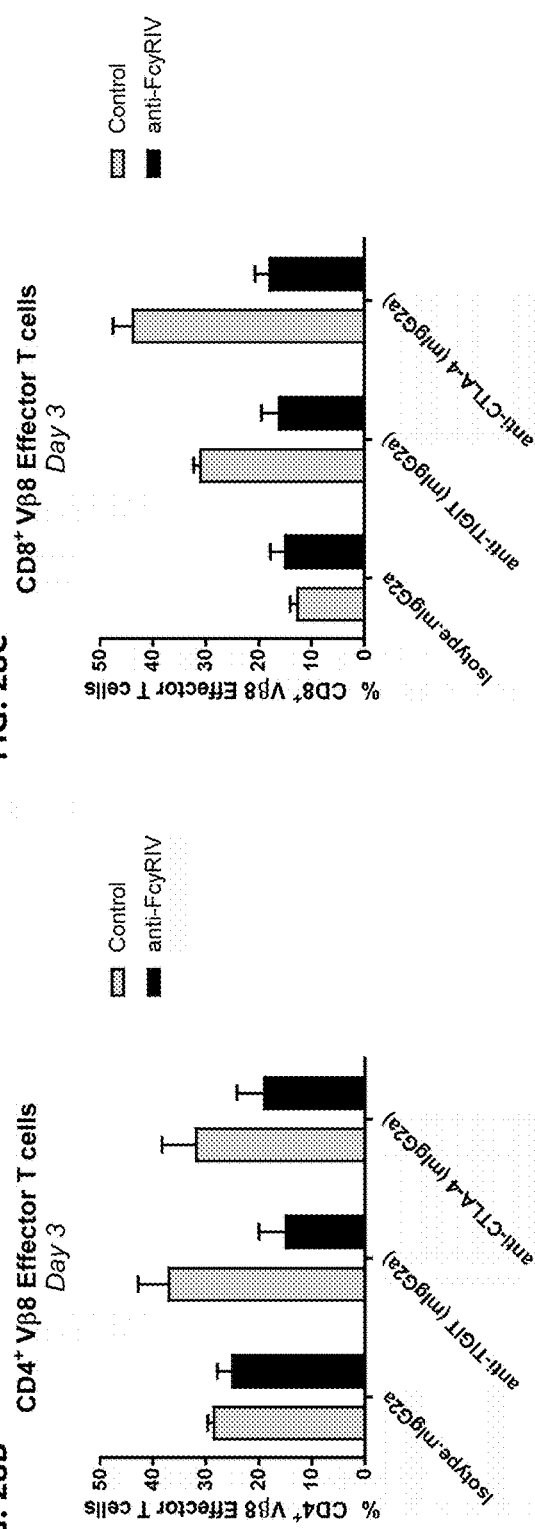
FIG. 28A Co-culture of TIGIT-expressing CHO cells and NFAT-luciferase-expressing Jurkat cells
FIG. 28B CD4+ Vβ8 Effector T cells Day 3
FIG. 28C CD8+ Vβ8 Effector T cells Day 3

US 11,021,537 B2

SEQUENCE LISTING

<160> NUMBER OF SEQ ID NOS: 70

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 1

Ser Tyr Gly Ile Ser
1               5

<210> SEQ ID NO 2
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Gly Tyr Thr Phe Ala Ser Tyr
1               5

<210> SEQ ID NO 3
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gly Ile Thr Pro Phe Phe Asn Arg Val Asp Val Ala Glu Lys Phe Gln
1               5                  10                  15

Gly

<210> SEQ ID NO 4
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Thr Pro Phe Phe Asn Arg
1               5

<210> SEQ ID NO 5
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Asp Leu Arg Arg Gly Gly Val Gly Asp Ala Phe Asp Ile
1               5                  10

<210> SEQ ID NO 6
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Thr Gly Thr Ser Ser Asp Val Gly Ser His Asn Tyr Val Ser
1               5                  10
```

```
<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Glu Val Ser Tyr Arg Pro Ser
1               5

<210> SEQ ID NO 8
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Ser Ser Tyr Thr Pro Ser Ser Ala Thr Val
1               5                   10

<210> SEQ ID NO 9
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Glu or pyro-Glu

<400> SEQUENCE: 9

Xaa Val Gln Leu Val Gln Ser Gly Ala Glu Val Glu Lys Pro Gly Ala
1               5                   10                  15

Ser Val Lys Val Ser Cys Lys Ala Ser Gly Tyr Thr Phe Ala Ser Tyr
            20                  25                  30

Gly Ile Ser Trp Val Arg Gln Ala Pro Gly Gln Gly Leu Glu Trp Met
        35                  40                  45

Gly Gly Ile Thr Pro Phe Phe Asn Arg Val Asp Val Ala Glu Lys Phe
    50                  55                  60

Gln Gly Arg Val Thr Ile Thr Ala Asp Thr Ser Thr Asn Thr Val Tyr
65                  70                  75                  80

Ile Glu Leu Ser Ser Leu Thr Ser Glu Asp Thr Ala Val Tyr Tyr Cys
                85                  90                  95

Ala Arg Asp Leu Arg Arg Gly Gly Val Gly Asp Ala Phe Asp Ile Trp
            100                 105                 110

Gly Arg Gly Thr Leu Val Thr Val Ser Ser
        115                 120

<210> SEQ ID NO 10
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Gln or pyro-Glu
```

<400> SEQUENCE: 10

Xaa Ser Ala Leu Thr Gln Pro Arg Ser Val Ser Gly Ser Pro Gly Gln
1               5                   10                  15

Ser Val Thr Ile Ser Cys Thr Gly Thr Ser Ser Asp Val Gly Ser His
            20                  25                  30

Asn Tyr Val Ser Trp Tyr Gln Gln His Pro Gly Lys Ala Pro Gln Leu
        35                  40                  45

Met Ile Tyr Glu Val Ser Tyr Arg Pro Ser Glu Ile Ser Asn Arg Phe
    50                  55                  60

Ser Gly Ser Lys Ser Gly Asn Thr Ala Ser Leu Thr Ile Ser Gly Leu
65              70                  75                  80

Gln Pro Glu Asp Glu Ala Asp Tyr Tyr Cys Ser Ser Tyr Thr Pro Ser
                85                  90                  95

Ser Ala Thr Val Phe Gly Ala Gly Thr Lys Leu Thr Val Leu
            100                 105                 110

<210> SEQ ID NO 11
<211> LENGTH: 451
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Glu or pyro-Glu

<400> SEQUENCE: 11

Xaa Val Gln Leu Val Gln Ser Gly Ala Glu Val Glu Lys Pro Gly Ala
1               5                   10                  15

Ser Val Lys Val Ser Cys Lys Ala Ser Gly Tyr Thr Phe Ala Ser Tyr
            20                  25                  30

Gly Ile Ser Trp Val Arg Gln Ala Pro Gly Gln Gly Leu Glu Trp Met
        35                  40                  45

Gly Gly Ile Thr Pro Phe Phe Asn Arg Val Asp Val Ala Glu Lys Phe
    50                  55                  60

Gln Gly Arg Val Thr Ile Thr Ala Asp Thr Ser Thr Asn Thr Val Tyr
65              70                  75                  80

Ile Glu Leu Ser Ser Leu Thr Ser Glu Asp Thr Ala Val Tyr Tyr Cys
                85                  90                  95

Ala Arg Asp Leu Arg Arg Gly Val Gly Asp Ala Phe Asp Ile Trp
                100                 105                 110

Gly Arg Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145             150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Arg Val Glu Pro Lys Ser
    210                 215                 220

```
Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
            245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
            275                 280                 285

Val His Asn Ala Lys Thr Lys Pro Arg Glu Glu Gln Tyr Asn Ser Thr
            290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
            325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
            355                 360                 365

Ser Leu Thr Cys Leu Val Lys Gly Phe Tyr Pro Ser Asp Ile Ala Val
370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
            405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
            435                 440                 445

Ser Pro Gly
    450

<210> SEQ ID NO 12
<211> LENGTH: 451
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Glu or pyro-Glu

<400> SEQUENCE: 12

Xaa Val Gln Leu Val Gln Ser Gly Ala Glu Val Glu Lys Pro Gly Ala
1               5                   10                  15

Ser Val Lys Val Ser Cys Lys Ala Ser Gly Tyr Thr Phe Ala Ser Tyr
            20                  25                  30

Gly Ile Ser Trp Val Arg Gln Ala Pro Gly Gln Gly Leu Glu Trp Met
        35                  40                  45

Gly Gly Ile Thr Pro Phe Phe Asn Arg Val Asp Val Ala Glu Lys Phe
50                  55                  60

Gln Gly Arg Val Thr Ile Thr Ala Asp Thr Ser Thr Asn Thr Val Tyr
65                  70                  75                  80

Ile Glu Leu Ser Ser Leu Thr Ser Glu Asp Thr Ala Val Tyr Tyr Cys
                85                  90                  95
```

```
Ala Arg Asp Leu Arg Arg Gly Gly Val Gly Asp Ala Phe Asp Ile Trp
            100                 105                 110

Gly Arg Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Arg Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Ala Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly
    450

<210> SEQ ID NO 13
<211> LENGTH: 451
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
```

```
<222> LOCATION: (1)..(1)
<223> OTHER INFORMATION: Glu or pyro-Glu

<400> SEQUENCE: 13
```

| | | | | | | | | | | | | | | |
|---|---|---|---|---|---|---|---|---|---|---|---|---|---|---|
| Xaa | Val | Gln | Leu | Val | Gln | Ser | Gly | Ala | Glu | Val | Lys | Pro | Gly | Ala |
| 1 | | | | 5 | | | | | 10 | | | | | 15 |
| Ser | Val | Lys | Val | Ser | Cys | Lys | Ala | Ser | Gly | Tyr | Thr | Phe | Ala | Ser |
| | | | 20 | | | | | 25 | | | | | 30 | |
| Tyr | Gly | Ile | Ser | Trp | Val | Arg | Gln | Ala | Pro | Gly | Gln | Gly | Leu | Glu |
| | | | 35 | | | | | 40 | | | | | 45 | |
| Trp | Met | Gly | Gly | Ile | Thr | Pro | Phe | Phe | Asn | Arg | Val | Asp | Val | Ala |
| | | | 50 | | | | | 55 | | | | | 60 | |
| Glu | Lys | Phe | Gln | Gly | Arg | Val | Thr | Ile | Thr | Ala | Asp | Thr | Ser | Thr |
| 65 | | | | | 70 | | | | | 75 | | | | 80 |
| Asn | Thr | Val | Tyr | Ile | Glu | Leu | Ser | Ser | Leu | Thr | Ser | Glu | Asp | Thr |
| | | | | | | | | 85 | | | | | 90 | |
| Ala | Val | Tyr | Tyr | Cys | Ala | Arg | Asp | Leu | Arg | Arg | Gly | Val | Gly | Asp |
| | | | | 95 | | | | 100 | | | | 105 | | |
| Ala | Phe | Asp | Ile | Trp | Gly | Arg | Gly | Thr | Leu | Val | Thr | Val | Ser | Ser |
| | | 110 | | | | | 115 | | | | 120 | | | |
| Ala | Ser | Thr | Lys | Gly | Pro | Ser | Val | Phe | Pro | Leu | Ala | Pro | Ser | Ser |
| 125 | | | | | 130 | | | | | 135 | | | | |
| Lys | Ser | Thr | Ser | Gly | Gly | Thr | Ala | Ala | Leu | Gly | Cys | Leu | Val | Lys |
| 140 | | | | | 145 | | | | | 150 | | | | |
| Asp | Tyr | Phe | Pro | Glu | Pro | Val | Thr | Val | Ser | Trp | Asn | Ser | Gly | Ala |
| | | 155 | | | | | 160 | | | | | 165 | | |
| Leu | Thr | Ser | Gly | Val | His | Thr | Phe | Pro | Ala | Val | Leu | Gln | Ser | Ser |
| 170 | | | | | 175 | | | | | 180 | | | | |
| Gly | Leu | Tyr | Ser | Leu | Ser | Ser | Val | Val | Thr | Val | Pro | Ser | Ser | Ser |
| | | 185 | | | | | 190 | | | | | 195 | | |
| Leu | Gly | Thr | Gln | Thr | Tyr | Ile | Cys | Asn | Val | Asn | His | Lys | Pro | Ser |
| | | 200 | | | | | 205 | | | | | 210 | | |
| Asn | Thr | Lys | Val | Asp | Lys | Arg | Val | Glu | Pro | Lys | Ser | Cys | Asp | Lys |
| | | 215 | | | | | 220 | | | | 225 | | | |
| Thr | His | Thr | Cys | Pro | Pro | Cys | Pro | Ala | Pro | Glu | Phe | Phe | Gly | Gly |
| | 230 | | | | | 235 | | | | | 240 | | | |
| Pro | Ser | Val | Phe | Leu | Phe | Pro | Pro | Lys | Pro | Lys | Asp | Thr | Leu | Met |
| | | 245 | | | | | 250 | | | | | 255 | | |
| Ile | Ser | Arg | Thr | Pro | Glu | Val | Thr | Cys | Val | Val | Val | Asp | Val | Ser |
| | | 260 | | | | | 265 | | | | | 270 | | |
| His | Glu | Asp | Pro | Glu | Val | Lys | Phe | Asn | Trp | Tyr | Val | Asp | Gly | Val |
| | 275 | | | | | 280 | | | | | 285 | | | |
| Glu | Val | His | Asn | Ala | Lys | Thr | Lys | Pro | Arg | Glu | Glu | Gln | Tyr | Ala |
| | 290 | | | | | 295 | | | | | 300 | | | |
| Ser | Thr | Tyr | Arg | Val | Val | Ser | Val | Leu | Thr | Val | Leu | His | Gln | Asp |
| 305 | | | | | 310 | | | | | 315 | | | | |
| Trp | Leu | Asn | Gly | Lys | Glu | Tyr | Lys | Cys | Lys | Val | Ser | Asn | Lys | Ala |
| | | 320 | | | | | 325 | | | | | 330 | | |
| Leu | Pro | Ala | Pro | Ile | Glu | Lys | Thr | Ile | Ser | Lys | Ala | Lys | Gly | Gln |
| | | 335 | | | | | 340 | | | | | 345 | | |
| Pro | Arg | Glu | Pro | Gln | Val | Tyr | Thr | Leu | Pro | Pro | Ser | Arg | Glu | Glu |
| | | 350 | | | | | 355 | | | | | 360 | | |
| Met | Thr | Lys | Asn | Gln | Val | Ser | Leu | Thr | Cys | Leu | Val | Lys | Gly | Phe |
| | | 365 | | | | 370 | | | | | 375 | | | |
| Tyr | Pro | Ser | Asp | Ile | Ala | Val | Glu | Trp | Glu | Ser | Asn | Gly | Gln | Pro |
| | | 380 | | | | 385 | | | | | 390 | | | |
| Glu | Asn | Asn | Tyr | Lys | Thr | Thr | Pro |
| | | 395 | | | | | 400 |

-continued

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly
    450

<210> SEQ ID NO 14
<211> LENGTH: 451
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Glu or pyro-Glu

<400> SEQUENCE: 14

Xaa Val Gln Leu Val Gln Ser Gly Ala Glu Val Glu Lys Pro Gly Ala
1               5                   10                  15

Ser Val Lys Val Ser Cys Lys Ala Ser Gly Tyr Thr Phe Ala Ser Tyr
            20                  25                  30

Gly Ile Ser Trp Val Arg Gln Ala Pro Gly Gln Gly Leu Glu Trp Met
        35                  40                  45

Gly Gly Ile Thr Pro Phe Phe Asn Arg Val Asp Val Ala Glu Lys Phe
    50                  55                  60

Gln Gly Arg Val Thr Ile Thr Ala Asp Thr Ser Thr Asn Thr Val Tyr
65                  70                  75                  80

Ile Glu Leu Ser Ser Leu Thr Ser Glu Asp Thr Ala Val Tyr Tyr Cys
                85                  90                  95

Ala Arg Asp Leu Arg Arg Gly Val Gly Asp Ala Phe Asp Ile Trp
            100                 105                 110

Gly Arg Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Arg Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Asp Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
            275                 280                 285

Val His Asn Ala Lys Thr Lys Pro Arg Glu Glu Gln Tyr Asn Ser Thr
290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
            325                 330                 335

Glu Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
            355                 360                 365

Ser Leu Thr Cys Leu Val Lys Gly Phe Tyr Pro Ser Asp Ile Ala Val
370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
            405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
435                 440                 445

Ser Pro Gly
    450

<210> SEQ ID NO 15
<211> LENGTH: 451
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Glu or pyro-Glu

<400> SEQUENCE: 15

Xaa Val Gln Leu Val Gln Ser Gly Ala Glu Val Glu Lys Pro Gly Ala
1               5                   10                  15

Ser Val Lys Val Ser Cys Lys Ala Ser Gly Tyr Thr Phe Ala Ser Tyr
            20                  25                  30

Gly Ile Ser Trp Val Arg Gln Ala Pro Gly Gln Gly Leu Glu Trp Met
        35                  40                  45

Gly Gly Ile Thr Pro Phe Phe Asn Arg Val Asp Val Ala Glu Lys Phe
    50                  55                  60

Gln Gly Arg Val Thr Ile Thr Ala Asp Thr Ser Thr Asn Thr Val Tyr
65                  70                  75                  80

Ile Glu Leu Ser Ser Leu Thr Ser Glu Asp Thr Ala Val Tyr Tyr Cys
                85                  90                  95

Ala Arg Asp Leu Arg Arg Gly Val Gly Asp Ala Phe Asp Ile Trp
            100                 105                 110

Gly Arg Gly Thr Leu Val Thr Val Ser Ser Ala Ser Thr Lys Gly Pro
            115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr

```
            145                 150                 155                 160
Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
                180                 185                 190

Val Pro Ser Ser Ser Leu Gly Thr Gln Thr Tyr Ile Cys Asn Val Asn
                195                 200                 205

His Lys Pro Ser Asn Thr Lys Val Asp Lys Arg Val Glu Pro Lys Ser
                210                 215                 220

Cys Asp Lys Thr His Thr Cys Pro Pro Cys Pro Ala Pro Glu Leu Leu
225                 230                 235                 240

Gly Gly Pro Asp Val Phe Leu Phe Pro Pro Lys Pro Lys Asp Thr Leu
                245                 250                 255

Met Ile Ser Arg Thr Pro Glu Val Thr Cys Val Val Val Asp Val Ser
                260                 265                 270

His Glu Asp Pro Glu Val Lys Phe Asn Trp Tyr Val Asp Gly Val Glu
                275                 280                 285

Val His Asn Ala Lys Thr Lys Pro Arg Glu Glu Gln Tyr Asn Ser Thr
                290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Leu Pro
                325                 330                 335

Glu Glu Lys Thr Ile Ser Lys Ala Lys Gly Gln Pro Arg Glu Pro Gln
                340                 345                 350

Val Tyr Thr Leu Pro Pro Ser Arg Glu Glu Met Thr Lys Asn Gln Val
                355                 360                 365

Ser Leu Thr Cys Leu Val Lys Gly Phe Tyr Pro Ser Asp Ile Ala Val
                370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
                420                 425                 430

Met His Glu Ala Leu His Asn His Tyr Thr Gln Lys Ser Leu Ser Leu
                435                 440                 445

Ser Pro Gly
    450

<210> SEQ ID NO 16
<211> LENGTH: 451
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Glu or pyro-Glu

<400> SEQUENCE: 16

Xaa Val Gln Leu Val Gln Ser Gly Ala Glu Val Glu Lys Pro Gly Ala
1               5                   10                  15

Ser Val Lys Val Ser Cys Lys Ala Ser Gly Tyr Thr Phe Ala Ser Tyr
                20                  25                  30
```

```
Gly Ile Ser Trp Val Arg Gln Ala Pro Gly Gln Gly Leu Glu Trp Met
         35                  40                  45

Gly Gly Ile Thr Pro Phe Phe Asn Arg Val Asp Val Ala Glu Lys Phe
     50                  55                  60

Gln Gly Arg Val Thr Ile Thr Ala Asp Thr Ser Thr Asn Thr Val Tyr
 65                  70                  75                  80

Ile Glu Leu Ser Ser Leu Thr Ser Glu Asp Thr Ala Val Tyr Tyr Cys
                 85                  90                  95

Ala Arg Asp Leu Arg Arg Gly Val Gly Asp Ala Phe Asp Ile Trp
             100                 105                 110

Gly Arg Gly Thr Leu Val Thr Val Ser Ser Ala Ser Thr Lys Gly Pro
             115                 120                 125

Ser Val Phe Pro Leu Ala Pro Ser Ser Lys Ser Thr Ser Gly Gly Thr
         130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                 165                 170                 175

Ala Val Leu Gln Ser Ser Gly Leu Tyr Ser Leu Ser Ser Val Val Thr
             180                 185                 190

Val Pro Ser Ser Ser Leu Gly Thr Gln Thr Tyr Ile Cys Asn Val Asn
         195                 200                 205

His Lys Pro Ser Asn Thr Lys Val Asp Lys Arg Val Glu Pro Lys Ser
         210                 215                 220

Cys Asp Lys Thr His Thr Cys Pro Pro Cys Pro Ala Pro Glu Leu Val
225                 230                 235                 240

Gly Gly Pro Ser Val Phe Leu Leu Pro Pro Lys Pro Lys Asp Thr Leu
                 245                 250                 255

Met Ile Ser Arg Thr Pro Glu Val Thr Cys Val Val Val Asp Val Ser
             260                 265                 270

His Glu Asp Pro Glu Val Lys Phe Asn Trp Tyr Val Asp Gly Val Glu
         275                 280                 285

Val His Asn Ala Lys Thr Lys Pro Pro Glu Glu Gln Tyr Asn Ser Thr
         290                 295                 300

Leu Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                 325                 330                 335

Ile Glu Lys Thr Ile Ser Lys Ala Lys Gly Gln Pro Arg Glu Pro Gln
             340                 345                 350

Val Tyr Thr Leu Pro Pro Ser Arg Glu Glu Met Thr Lys Asn Gln Val
         355                 360                 365

Ser Leu Thr Cys Leu Val Lys Gly Phe Tyr Pro Ser Asp Ile Ala Val
370                 375                 380

Glu Trp Glu Ser Asn Gly Gln Pro Glu Asn Asn Tyr Lys Thr Thr Pro
385                 390                 395                 400

Leu Val Leu Asp Ser Asp Gly Ser Phe Phe Leu Tyr Ser Lys Leu Thr
                 405                 410                 415

Val Asp Lys Ser Arg Trp Gln Gln Gly Asn Val Phe Ser Cys Ser Val
             420                 425                 430

Met His Glu Ala Leu His Asn His Tyr Thr Gln Lys Ser Leu Ser Leu
             435                 440                 445
```

```
Ser Pro Gly
    450

<210> SEQ ID NO 17
<211> LENGTH: 451
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Glu or pyro-Glu

<400> SEQUENCE: 17

Xaa Val Gln Leu Val Gln Ser Gly Ala Glu Val Glu Lys Pro Gly Ala
1               5                   10                  15

Ser Val Lys Val Ser Cys Lys Ala Ser Gly Tyr Thr Phe Ala Ser Tyr
            20                  25                  30

Gly Ile Ser Trp Val Arg Gln Ala Pro Gly Gln Gly Leu Glu Trp Met
        35                  40                  45

Gly Gly Ile Thr Pro Phe Phe Asn Arg Val Asp Val Ala Glu Lys Phe
    50                  55                  60

Gln Gly Arg Val Thr Ile Thr Ala Asp Thr Ser Thr Asn Thr Val Tyr
65                  70                  75                  80

Ile Glu Leu Ser Ser Leu Thr Ser Glu Asp Thr Ala Val Tyr Tyr Cys
                85                  90                  95

Ala Arg Asp Leu Arg Arg Gly Gly Val Gly Asp Ala Phe Asp Ile Trp
            100                 105                 110

Gly Arg Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Arg Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Glu
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Phe Pro Ala Pro
```

```
              325                 330                 335
Ile Glu Lys Thr Ile Ser Lys Ala Lys Gly Gln Pro Arg Glu Pro Gln
            340                 345                 350
Val Tyr Thr Leu Pro Pro Ser Arg Glu Glu Met Thr Lys Asn Gln Val
            355                 360                 365
Ser Leu Thr Cys Leu Val Lys Gly Phe Tyr Pro Ser Asp Ile Ala Val
            370                 375                 380
Glu Trp Glu Ser Asn Gly Gln Pro Glu Asn Asn Tyr Lys Thr Thr Pro
385                 390                 395                 400
Pro Val Leu Asp Ser Asp Gly Ser Phe Phe Leu Tyr Ser Lys Leu Thr
                405                 410                 415
Val Asp Lys Ser Arg Trp Gln Gln Gly Asn Val Phe Ser Cys Ser Val
                420                 425                 430
Met His Glu Ala Leu His Asn His Tyr Thr Gln Lys Ser Leu Ser Leu
                435                 440                 445
Ser Pro Gly
    450

<210> SEQ ID NO 18
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Glu or pyro-Glu

<400> SEQUENCE: 18

Xaa Val Gln Leu Val Gln Ser Gly Ala Glu Val Glu Lys Pro Gly Ala
1               5                   10                  15
Ser Val Lys Val Ser Cys Lys Ala Ser Gly Tyr Thr Phe Ala Ser Tyr
            20                  25                  30
Gly Ile Ser Trp Val Arg Gln Ala Pro Gly Gln Gly Leu Glu Trp Met
        35                  40                  45
Gly Gly Ile Thr Pro Phe Phe Asn Arg Val Asp Val Ala Glu Lys Phe
    50                  55                  60
Gln Gly Arg Val Thr Ile Thr Ala Asp Thr Ser Thr Asn Thr Val Tyr
65                  70                  75                  80
Ile Glu Leu Ser Ser Leu Thr Ser Glu Asp Thr Ala Val Tyr Tyr Cys
                85                  90                  95
Ala Arg Asp Leu Arg Arg Gly Val Gly Asp Ala Phe Asp Ile Trp
            100                 105                 110
Gly Arg Gly Thr Leu Val Thr Val Ser Ser Ala Ser Thr Lys Gly Pro
        115                 120                 125
Ser Val Phe Pro Leu Ala Pro Cys Ser Arg Ser Thr Ser Glu Ser Thr
    130                 135                 140
Ala Ala Leu Gly Cys Leu Val Lys Asp Tyr Phe Pro Glu Pro Val Thr
145                 150                 155                 160
Val Ser Trp Asn Ser Gly Ala Leu Thr Ser Gly Val His Thr Phe Pro
                165                 170                 175
Ala Val Leu Gln Ser Ser Gly Leu Tyr Ser Leu Ser Ser Val Val Thr
            180                 185                 190
Val Pro Ser Ser Ser Leu Gly Thr Lys Thr Tyr Thr Cys Asn Val Asp
        195                 200                 205
```

```
His Lys Pro Ser Asn Thr Lys Val Asp Lys Arg Val Glu Ser Lys Tyr
    210                 215                 220

Gly Pro Pro Cys Pro Pro Cys Pro Ala Pro Glu Phe Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
        275                 280                 285

Ala Lys Thr Lys Pro Arg Glu Glu Gln Phe Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Gln Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415

Ser Arg Trp Gln Glu Gly Asn Val Phe Ser Cys Ser Val Met His Glu
            420                 425                 430

Ala Leu His Asn His Tyr Thr Gln Lys Ser Leu Ser Leu Ser Leu Gly
        435                 440                 445

<210> SEQ ID NO 19
<211> LENGTH: 329
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
```

```
            115                 120                 125
Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 20
<211> LENGTH: 329
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140
```

```
Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
            165                 170                 175

Glu Gln Tyr Ala Ser Thr Tyr Arg Val Val Ser Val Leu Thr Val Leu
        180                 185                 190

His Gln Asp Trp Leu Asn Gly Lys Glu Tyr Lys Cys Lys Val Ser Asn
    195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 21
<211> LENGTH: 329
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Phe Phe Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
            165                 170                 175
```

```
Glu Gln Tyr Ala Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 22
<211> LENGTH: 329
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Asp Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
```

```
                195                 200                 205
Lys Ala Leu Pro Ala Pro Glu Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 23
<211> LENGTH: 329
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Asp Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Leu Pro Glu Glu Lys Thr Ile Ser Lys Ala Lys Gly
    210                 215                 220
```

```
Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
        260                 265                 270

Asn Tyr Lys Thr Thr Pro Pro Val Leu Asp Ser Asp Gly Ser Phe Phe
    275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325
```

<210> SEQ ID NO 24
<211> LENGTH: 329
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 24

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Val Gly Gly Pro Ser Val Phe Leu Leu Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Pro Glu
                165                 170                 175

Glu Gln Tyr Asn Ser Thr Leu Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255
```

Pro Ser Asp Ile Ala Val Glu Trp Glu Ser Asn Gly Gln Pro Glu Asn
                260                 265                 270

Asn Tyr Lys Thr Thr Pro Leu Val Leu Asp Ser Asp Gly Ser Phe Phe
            275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 25
<211> LENGTH: 329
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Glu His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Phe Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe

```
                275                 280                 285
Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 26
<211> LENGTH: 326
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300
```

Cys Ser Val Met His Glu Ala Leu His Asn His Tyr Thr Gln Lys Ser
305                 310                 315                 320

Leu Ser Leu Ser Leu Gly
            325

<210> SEQ ID NO 27
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Gln or pyro-Glu

<400> SEQUENCE: 27

Xaa Ser Ala Leu Thr Gln Pro Arg Ser Val Ser Gly Ser Pro Gly Gln
1               5                   10                  15

Ser Val Thr Ile Ser Cys Thr Gly Thr Ser Ser Asp Val Gly Ser His
            20                  25                  30

Asn Tyr Val Ser Trp Tyr Gln Gln His Pro Gly Lys Ala Pro Gln Leu
        35                  40                  45

Met Ile Tyr Glu Val Ser Tyr Arg Pro Ser Glu Ile Ser Asn Arg Phe
    50                  55                  60

Ser Gly Ser Lys Ser Gly Asn Thr Ala Ser Leu Thr Ile Ser Gly Leu
65                  70                  75                  80

Gln Pro Glu Asp Glu Ala Asp Tyr Tyr Cys Ser Ser Tyr Thr Pro Ser
                85                  90                  95

Ser Ala Thr Val Phe Gly Ala Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215

<210> SEQ ID NO 28
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
          35                  40                  45

Val Lys Ala Gly Val Glu Thr Thr Thr Pro Ser Lys Gln Ser Asn Asn
 50                  55                  60

Lys Tyr Ala Ala Ser Ser Tyr Leu Ser Leu Thr Pro Glu Gln Trp Lys
 65                  70                  75                  80

Ser His Arg Ser Tyr Ser Cys Gln Val Thr His Glu Gly Ser Thr Val
                 85                  90                  95

Glu Lys Thr Val Ala Pro Thr Glu Cys Ser
            100                 105

<210> SEQ ID NO 29
<211> LENGTH: 244
<212> TYPE: PRT
<213> ORGANISM: Homo sapiens

<400> SEQUENCE: 29

Met Arg Trp Cys Leu Leu Leu Ile Trp Ala Gln Gly Leu Arg Gln Ala
 1               5                  10                  15

Pro Leu Ala Ser Gly Met Met Thr Gly Thr Ile Glu Thr Thr Gly Asn
             20                  25                  30

Ile Ser Ala Glu Lys Gly Gly Ser Ile Ile Leu Gln Cys His Leu Ser
         35                  40                  45

Ser Thr Thr Ala Gln Val Thr Gln Val Asn Trp Glu Gln Gln Asp Gln
 50                  55                  60

Leu Leu Ala Ile Cys Asn Ala Asp Leu Gly Trp His Ile Ser Pro Ser
 65                  70                  75                  80

Phe Lys Asp Arg Val Ala Pro Gly Pro Gly Leu Gly Leu Thr Leu Gln
                 85                  90                  95

Ser Leu Thr Val Asn Asp Thr Gly Glu Tyr Phe Cys Ile Tyr His Thr
            100                 105                 110

Tyr Pro Asp Gly Thr Tyr Thr Gly Arg Ile Phe Leu Glu Val Leu Glu
        115                 120                 125

Ser Ser Val Ala Glu His Gly Ala Arg Phe Gln Ile Pro Leu Leu Gly
130                 135                 140

Ala Met Ala Ala Thr Leu Val Val Ile Cys Thr Ala Val Ile Val Val
145                 150                 155                 160

Val Ala Leu Thr Arg Lys Lys Lys Ala Leu Arg Ile His Ser Val Glu
                165                 170                 175

Gly Asp Leu Arg Arg Lys Ser Ala Gly Gln Glu Glu Trp Ser Pro Ser
            180                 185                 190

Ala Pro Ser Pro Pro Gly Ser Cys Val Gln Ala Glu Ala Ala Pro Ala
        195                 200                 205

Gly Leu Cys Gly Glu Gln Arg Gly Glu Asp Cys Ala Glu Leu His Asp
    210                 215                 220

Tyr Phe Asn Val Leu Ser Tyr Arg Ser Leu Gly Asn Cys Ser Phe Phe
225                 230                 235                 240

Thr Glu Thr Gly

<210> SEQ ID NO 30
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

```
Met Met Thr Gly Thr Ile Glu Thr Gly Asn Ile Ser Ala Glu Lys
1               5                   10                  15

Gly Gly Ser Ile Ile Leu Gln Cys His Leu Ser Ser Thr Thr Ala Gln
            20                  25                  30

Val Thr Gln Val Asn Trp Glu Gln Gln Asp Gln Leu Leu Ala Ile Cys
        35                  40                  45

Asn Ala Asp Leu Gly Trp His Ile Ser Pro Ser Phe Lys Asp Arg Val
    50                  55                  60

Ala Pro Gly Pro Gly Leu Gly Leu Thr Leu Gln Ser Leu Thr Val Asn
65                  70                  75                  80

Asp Thr Gly Glu Tyr Phe Cys Ile Tyr His Thr Tyr Pro Asp Gly Thr
                85                  90                  95

Tyr Thr Gly Arg Ile Phe Leu Glu Val Leu Glu Ser Ser Val Ala Glu
            100                 105                 110

His Gly Ala Arg Phe
        115
```

<210> SEQ ID NO 31
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

```
Tyr His Thr Tyr Pro Asp Gly Thr Tyr Thr Gly Arg Ile Phe Leu Glu
1               5                   10                  15
```

<210> SEQ ID NO 32
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

```
Val Thr Gln Val
1
```

<210> SEQ ID NO 33
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

```
Ile Cys Asn Ala Asp Leu Gly Trp His Ile Ser Pro Ser Phe
1               5                   10
```

<210> SEQ ID NO 34
<211> LENGTH: 98
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Ser Thr Ala Tyr
65                  70                  75                  80

Met Glu Leu Ser Ser Leu Arg Ser Glu Asp Thr Ala Val Tyr Tyr Cys
                85                  90                  95

Ala Arg

<210> SEQ ID NO 35
<211> LENGTH: 98
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg

<210> SEQ ID NO 36
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Met Met Thr Gly Thr Ile Glu Thr Thr Gly Asn Ile Ser Ala Glu Lys
1               5                   10                  15

Gly Gly Ser Ile Ile Leu Gln Cys His Leu Ser Ser Thr Thr Ala Gln
            20                  25                  30

Val Thr Gln Val Asn Trp Glu Gln Gln Asp Gln Leu Leu Ala Ile Cys
        35                  40                  45

Ser Ala Asp Leu Gly Trp His Ile Ser Pro Ser Phe Lys Asp Arg Val
    50                  55                  60

Ala Pro Gly Pro Gly Leu Gly Leu Thr Leu Gln Ser Leu Thr Val Asn
65                  70                  75                  80

Asp Thr Gly Glu Tyr Phe Cys Ile Tyr His Thr Tyr Pro Asp Gly Thr
```

```
                    85                  90                  95

Tyr Thr Gly Arg Ile Phe Leu Glu Val Leu Glu Ser Ser Val Ala Glu
            100                 105                 110

His Gly Ala Arg Phe Gln
        115

<210> SEQ ID NO 37
<211> LENGTH: 99
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Glu Val Ser Asn Arg Pro Ser Gly Val Ser Asn Arg Phe
50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Leu

<210> SEQ ID NO 38
<211> LENGTH: 99
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Ser Tyr
            20                  25                  30

Asn Leu Val Ser Trp Tyr Gln Gln His Pro Gly Lys Ala Pro Lys Leu
        35                  40                  45

Met Ile Tyr Glu Val Ser Lys Arg Pro Ser Gly Val Ser Asn Arg Phe
50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Cys Ser Tyr Ala Gly Ser
                85                  90                  95

Ser Thr Phe

<210> SEQ ID NO 39
<211> LENGTH: 99
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 39

Gln Ser Ala Leu Thr Gln Pro Arg Ser Val Ser Gly Ser Pro Gly Gln
1               5                   10                  15

Ser Val Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Lys Arg Pro Ser Gly Val Pro Asp Arg Phe
50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Cys Ser Tyr Ala Gly Ser
                85                  90                  95

Tyr Thr Phe

<210> SEQ ID NO 40
<211> LENGTH: 223
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Met Met Thr Gly Thr Ile Glu Thr Thr Gly Asn Ile Ser Ala Glu Lys
1               5                   10                  15

Gly Gly Ser Ile Ile Leu Gln Cys His Leu Ser Ser Thr Thr Ala Gln
            20                  25                  30

Val Thr Gln Val Asn Trp Glu Gln Gln Asp Gln Leu Leu Ala Ile Cys
        35                  40                  45

Asn Ala Asp Leu Gly Trp His Ile Ser Pro Ser Phe Lys Asp Arg Val
50                  55                  60

Ala Pro Gly Pro Gly Leu Gly Leu Thr Leu Gln Ser Leu Thr Val Asn
65                  70                  75                  80

Asp Thr Gly Glu Tyr Phe Cys Ile Tyr His Thr Tyr Pro Asp Gly Thr
                85                  90                  95

Tyr Thr Gly Arg Ile Phe Leu Glu Val Leu Glu Ser Ser Val Ala Glu
            100                 105                 110

His Gly Ala Arg Phe Gln Ile Pro Leu Leu Gly Ala Met Ala Ala Thr
        115                 120                 125

Leu Val Val Ile Cys Thr Ala Val Ile Val Val Ala Leu Thr Arg
130                 135                 140

Lys Lys Lys Ala Leu Arg Ile His Ser Val Glu Gly Asp Leu Arg Arg
145                 150                 155                 160

Lys Ser Ala Gly Gln Glu Glu Trp Ser Pro Ser Ala Pro Ser Pro Pro
                165                 170                 175

Gly Ser Cys Val Gln Ala Glu Ala Ala Pro Ala Gly Leu Cys Gly Glu
            180                 185                 190

Gln Arg Gly Glu Asp Cys Ala Glu Leu His Asp Tyr Phe Asn Val Leu
        195                 200                 205

Ser Tyr Arg Ser Leu Gly Asn Cys Ser Phe Phe Thr Glu Thr Gly
    210                 215                 220

<210> SEQ ID NO 41
<211> LENGTH: 120
<212> TYPE: PRT

<213> ORGANISM: Artificial Sequence
<220> FEATURE:
<223> OTHER INFORMATION: Description of Artificial Sequence: Synthetic
      polypeptide

<400> SEQUENCE: 41

Met Met Thr Gly Thr Ile Glu Thr Thr Gly Asn Ile Ser Ala Glu Lys
1               5                   10                  15

Gly Gly Ser Ile Ile Leu Gln Cys His Leu Ser Ser Thr Thr Ala Gln
            20                  25                  30

Val Thr Gln Val Asn Trp Glu Gln Gln Asp Gln Leu Leu Ala Ile Cys
        35                  40                  45

Asn Ala Asp Leu Gly Trp His Ile Ser Pro Ser Phe Lys Asp Arg Val
    50                  55                  60

Ala Pro Gly Pro Gly Leu Gly Leu Thr Leu Gln Ser Leu Thr Val Asn
65                  70                  75                  80

Asp Thr Gly Glu Tyr Phe Cys Ile Tyr His Thr Tyr Pro Asp Gly Thr
                85                  90                  95

Tyr Thr Gly Arg Ile Phe Leu Glu Val Leu Glu Ser Ser Val Ala Glu
            100                 105                 110

His Gly Ala Arg Phe Gln Ile Pro
        115                 120

<210> SEQ ID NO 42
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Met Met Thr Gly Thr Ile Glu Thr Thr Gly Asn Ile Ser Ala Glu Lys
1               5                   10                  15

Gly Gly Ser Ile Ile Leu Gln Cys His Leu Ser Ser Thr Thr Ala Gln
            20                  25                  30

Val Thr Gln Val Asn Trp Glu Gln Gln Asp Gln Leu Leu Ala Ile Cys
        35                  40                  45

Asn Ala Asp Leu Gly Trp His Ile Ser Pro Ser Phe Lys Asp Arg Val
    50                  55                  60

Ala Pro Gly Pro Gly Leu Gly Leu Thr Leu Gln Ser Leu Thr Val Asn
65                  70                  75                  80

Asp Thr Gly Glu Tyr Phe Cys Ile Tyr His Thr Tyr Pro Asp Gly Thr
                85                  90                  95

Tyr Thr Gly Arg Ile Phe Leu Glu Val Leu Glu Ser Ser Val Ala Glu
            100                 105                 110

His Gly Ala Arg Phe Gln
        115

<210> SEQ ID NO 43
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Met Met Thr Gly Thr Ile Glu Thr Thr Gly Asn Ile Ser Ala Glu Lys
1               5                   10                  15

-continued

```
Gly Gly Ser Ile Ile Leu Gln Cys His Leu Ser Ser Thr Thr Ala Gln
            20                  25                  30

Val Ala Gln Val Asn Trp Glu Gln Gln Asp Gln Leu Leu Ala Ile Cys
        35                  40                  45

Asn Ala Asp Leu Gly Trp His Ile Ser Pro Ser Phe Lys Asp Arg Val
 50                  55                  60

Ala Pro Gly Pro Gly Leu Gly Leu Thr Leu Gln Ser Leu Thr Val Asn
65                  70                  75                  80

Asp Thr Gly Glu Tyr Phe Cys Ile Tyr His Thr Tyr Pro Asp Gly Thr
                85                  90                  95

Tyr Thr Gly Arg Ile Phe Leu Glu Val Leu Glu Ser Ser Val Ala Glu
            100                 105                 110

His Gly Ala Arg Phe Gln
        115

<210> SEQ ID NO 44
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Met Met Thr Gly Thr Ile Glu Thr Thr Gly Asn Ile Ser Ala Glu Lys
1               5                   10                  15

Gly Gly Ser Ile Ile Leu Gln Cys His Leu Ser Ser Thr Thr Ala Gln
            20                  25                  30

Val Thr Ala Val Asn Trp Glu Gln Gln Asp Gln Leu Leu Ala Ile Cys
        35                  40                  45

Asn Ala Asp Leu Gly Trp His Ile Ser Pro Ser Phe Lys Asp Arg Val
 50                  55                  60

Ala Pro Gly Pro Gly Leu Gly Leu Thr Leu Gln Ser Leu Thr Val Asn
65                  70                  75                  80

Asp Thr Gly Glu Tyr Phe Cys Ile Tyr His Thr Tyr Pro Asp Gly Thr
                85                  90                  95

Tyr Thr Gly Arg Ile Phe Leu Glu Val Leu Glu Ser Ser Val Ala Glu
            100                 105                 110

His Gly Ala Arg Phe Gln
        115

<210> SEQ ID NO 45
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Met Met Thr Gly Thr Ile Glu Thr Thr Gly Asn Ile Ser Ala Glu Lys
1               5                   10                  15

Gly Gly Ser Ile Ile Leu Gln Cys His Leu Ser Ser Thr Thr Ala Gln
            20                  25                  30

Val Thr Gln Val Asn Trp Glu Gln Gln Asp Gln Leu Leu Ala Glu Cys
        35                  40                  45

Asn Ala Asp Leu Gly Trp His Ile Ser Pro Ser Phe Lys Asp Arg Val
 50                  55                  60
```

```
Ala Pro Gly Pro Gly Leu Gly Leu Thr Leu Gln Ser Leu Thr Val Asn
 65                  70                  75                  80

Asp Thr Gly Glu Tyr Phe Cys Ile Tyr His Thr Tyr Pro Asp Gly Thr
                 85                  90                  95

Tyr Thr Gly Arg Ile Phe Leu Glu Val Leu Glu Ser Ser Val Ala Glu
            100                 105                 110

His Gly Ala Arg Phe Gln
        115

<210> SEQ ID NO 46
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Met Met Thr Gly Thr Ile Glu Thr Thr Gly Asn Ile Ser Ala Glu Lys
  1               5                  10                  15

Gly Gly Ser Ile Ile Leu Gln Cys His Leu Ser Ser Thr Thr Ala Gln
             20                  25                  30

Val Thr Gln Val Asn Trp Glu Gln Gln Asp Gln Leu Leu Ala Ile Cys
         35                  40                  45

Ala Ala Asp Leu Gly Trp His Ile Ser Pro Ser Phe Lys Asp Arg Val
 50                  55                  60

Ala Pro Gly Pro Gly Leu Gly Leu Thr Leu Gln Ser Leu Thr Val Asn
 65                  70                  75                  80

Asp Thr Gly Glu Tyr Phe Cys Ile Tyr His Thr Tyr Pro Asp Gly Thr
                 85                  90                  95

Tyr Thr Gly Arg Ile Phe Leu Glu Val Leu Glu Ser Ser Val Ala Glu
            100                 105                 110

His Gly Ala Arg Phe Gln
        115

<210> SEQ ID NO 47
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Met Met Thr Gly Thr Ile Glu Thr Thr Gly Asn Ile Ser Ala Glu Lys
  1               5                  10                  15

Gly Gly Ser Ile Ile Leu Gln Cys His Leu Ser Ser Thr Thr Ala Gln
             20                  25                  30

Val Thr Gln Val Asn Trp Glu Gln Gln Asp Gln Leu Leu Ala Ile Cys
         35                  40                  45

Asn Ala Asp Ala Gly Trp His Ile Ser Pro Ser Phe Lys Asp Arg Val
 50                  55                  60

Ala Pro Gly Pro Gly Leu Gly Leu Thr Leu Gln Ser Leu Thr Val Asn
 65                  70                  75                  80

Asp Thr Gly Glu Tyr Phe Cys Ile Tyr His Thr Tyr Pro Asp Gly Thr
                 85                  90                  95

Tyr Thr Gly Arg Ile Phe Leu Glu Val Leu Glu Ser Ser Val Ala Glu
            100                 105                 110
```

His Gly Ala Arg Phe Gln
        115

<210> SEQ ID NO 48
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Met Met Thr Gly Thr Ile Glu Thr Thr Gly Asn Ile Ser Ala Glu Lys
1               5                   10                  15

Gly Gly Ser Ile Ile Leu Gln Cys His Leu Ser Ser Thr Thr Ala Gln
            20                  25                  30

Val Thr Gln Val Asn Trp Glu Gln Gln Asp Gln Leu Leu Ala Ile Cys
        35                  40                  45

Asn Ala Asp Glu Gly Trp His Ile Ser Pro Ser Phe Lys Asp Arg Val
    50                  55                  60

Ala Pro Gly Pro Gly Leu Gly Leu Thr Leu Gln Ser Leu Thr Val Asn
65                  70                  75                  80

Asp Thr Gly Glu Tyr Phe Cys Ile Tyr His Thr Tyr Pro Asp Gly Thr
                85                  90                  95

Tyr Thr Gly Arg Ile Phe Leu Glu Val Leu Glu Ser Ser Val Ala Glu
            100                 105                 110

His Gly Ala Arg Phe Gln
        115

<210> SEQ ID NO 49
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Met Met Thr Gly Thr Ile Glu Thr Thr Gly Asn Ile Ser Ala Glu Lys
1               5                   10                  15

Gly Gly Ser Ile Ile Leu Gln Cys His Leu Ser Ser Thr Thr Ala Gln
            20                  25                  30

Val Thr Gln Val Asn Trp Glu Gln Gln Asp Gln Leu Leu Ala Ile Cys
        35                  40                  45

Asn Ala Asp Leu Gly Trp Ala Ile Ser Pro Ser Phe Lys Asp Arg Val
    50                  55                  60

Ala Pro Gly Pro Gly Leu Gly Leu Thr Leu Gln Ser Leu Thr Val Asn
65                  70                  75                  80

Asp Thr Gly Glu Tyr Phe Cys Ile Tyr His Thr Tyr Pro Asp Gly Thr
                85                  90                  95

Tyr Thr Gly Arg Ile Phe Leu Glu Val Leu Glu Ser Ser Val Ala Glu
            100                 105                 110

His Gly Ala Arg Phe Gln
        115

<210> SEQ ID NO 50
<211> LENGTH: 118
<212> TYPE: PRT
<213> ORGANISM: Artificial Sequence -continued

```
<220> FEATURE:
<223> OTHER INFORMATION: Description of Artificial Sequence: Synthetic
      polypeptide

<400> SEQUENCE: 50

Met Met Thr Gly Thr Ile Glu Thr Thr Gly Asn Ile Ser Ala Glu Lys
1               5                   10                  15

Gly Gly Ser Ile Ile Leu Gln Cys His Leu Ser Ser Thr Thr Ala Gln
            20                  25                  30

Val Thr Gln Val Asn Trp Glu Gln Gln Asp Gln Leu Leu Ala Ile Cys
        35                  40                  45

Asn Ala Asp Leu Gly Trp His Ile Ser Ala Ser Phe Lys Asp Arg Val
50                  55                  60

Ala Pro Gly Pro Gly Leu Gly Leu Thr Leu Gln Ser Leu Thr Val Asn
65                  70                  75                  80

Asp Thr Gly Glu Tyr Phe Cys Ile Tyr His Thr Tyr Pro Asp Gly Thr
                85                  90                  95

Tyr Thr Gly Arg Ile Phe Leu Glu Val Leu Glu Ser Ser Val Ala Glu
            100                 105                 110

His Gly Ala Arg Phe Gln
        115

<210> SEQ ID NO 51
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Met Met Thr Gly Thr Ile Glu Thr Thr Gly Asn Ile Ser Ala Glu Lys
1               5                   10                  15

Gly Gly Ser Ile Ile Leu Gln Cys His Leu Ser Ser Thr Thr Ala Gln
            20                  25                  30

Val Thr Gln Val Asn Trp Glu Gln Gln Asp Gln Leu Leu Ala Ile Cys
        35                  40                  45

Asn Ala Asp Leu Gly Trp His Ile Ser Pro Ser Phe Lys Asp Arg Val
50                  55                  60

Ala Pro Gly Pro Gly Leu Gly Leu Thr Leu Gln Ser Leu Thr Val Asn
65                  70                  75                  80

Asp Thr Gly Glu Tyr Phe Cys Ile Tyr Ala Thr Tyr Pro Asp Gly Thr
                85                  90                  95

Tyr Thr Gly Arg Ile Phe Leu Glu Val Leu Glu Ser Ser Val Ala Glu
            100                 105                 110

His Gly Ala Arg Phe Gln
        115

<210> SEQ ID NO 52
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

Met Met Thr Gly Thr Ile Glu Thr Thr Gly Asn Ile Ser Ala Glu Lys
1               5                   10                  15
```

```
Gly Gly Ser Ile Ile Leu Gln Cys His Leu Ser Ser Thr Thr Ala Gln
            20                  25                  30

Val Thr Gln Val Asn Trp Glu Gln Gln Asp Gln Leu Leu Ala Ile Cys
        35                  40                  45

Asn Ala Asp Leu Gly Trp His Ile Ser Pro Ser Phe Lys Asp Arg Val
    50                  55                  60

Ala Pro Gly Pro Gly Leu Gly Leu Thr Leu Gln Ser Leu Thr Val Asn
65                  70                  75                  80

Asp Thr Gly Glu Tyr Phe Cys Ile Tyr His Thr Tyr Pro Asp Gly Ala
                85                  90                  95

Tyr Thr Gly Arg Ile Phe Leu Glu Val Leu Glu Ser Val Ala Glu
            100                 105                 110

His Gly Ala Arg Phe Gln
            115

<210> SEQ ID NO 53
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

Met Met Thr Gly Thr Ile Glu Thr Thr Gly Asn Ile Ser Ala Glu Lys
1               5                   10                  15

Gly Gly Ser Ile Ile Leu Gln Cys His Leu Ser Ser Thr Thr Ala Gln
            20                  25                  30

Val Thr Gln Val Asn Trp Glu Gln Gln Asp Gln Leu Leu Ala Ile Cys
        35                  40                  45

Asn Ala Asp Leu Gly Trp His Ile Ser Pro Ser Phe Lys Asp Arg Val
    50                  55                  60

Ala Pro Gly Pro Gly Leu Gly Leu Thr Leu Gln Ser Leu Thr Val Asn
65                  70                  75                  80

Asp Thr Gly Glu Tyr Phe Cys Ile Tyr His Thr Tyr Pro Asp Gly Ile
                85                  90                  95

Tyr Thr Gly Arg Ile Phe Leu Glu Val Leu Glu Ser Val Ala Glu
            100                 105                 110

His Gly Ala Arg Phe Gln
            115

<210> SEQ ID NO 54
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

Met Met Thr Gly Thr Ile Glu Thr Thr Gly Asn Ile Ser Ala Glu Lys
1               5                   10                  15

Gly Gly Ser Ile Ile Leu Gln Cys His Leu Ser Ser Thr Thr Ala Gln
            20                  25                  30

Val Thr Gln Val Asn Trp Glu Gln Gln Asp Gln Leu Leu Ala Ile Cys
        35                  40                  45

Asn Ala Asp Leu Gly Trp His Ile Ser Pro Ser Phe Lys Asp Arg Val
    50                  55                  60
```

Ala Pro Gly Pro Gly Leu Gly Leu Thr Leu Gln Ser Leu Thr Val Asn
65                  70                  75                  80

Asp Thr Gly Glu Tyr Phe Cys Ile Tyr His Thr Tyr Pro Asp Gly Thr
                85                  90                  95

Tyr Ala Gly Arg Ile Phe Leu Glu Val Leu Glu Ser Ser Val Ala Glu
            100                 105                 110

His Gly Ala Arg Phe Gln
        115

<210> SEQ ID NO 55
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Met Met Thr Gly Thr Ile Glu Thr Gly Asn Ile Ser Ala Glu Lys
1               5                   10                  15

Gly Gly Ser Ile Ile Leu Gln Cys His Leu Ser Ser Thr Thr Ala Gln
            20                  25                  30

Val Thr Gln Val Asn Trp Glu Gln Gln Asp Gln Leu Leu Ala Ile Cys
        35                  40                  45

Asn Ala Asp Leu Gly Trp His Ile Ser Pro Ser Phe Lys Asp Arg Val
    50                  55                  60

Ala Pro Gly Pro Gly Leu Gly Leu Thr Leu Gln Ser Leu Thr Val Asn
65                  70                  75                  80

Asp Thr Gly Glu Tyr Phe Cys Ile Tyr His Thr Tyr Pro Asp Gly Thr
                85                  90                  95

Tyr Thr Gly Ala Ile Phe Leu Glu Val Leu Glu Ser Ser Val Ala Glu
            100                 105                 110

His Gly Ala Arg Phe Gln
        115

<210> SEQ ID NO 56
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

Met Met Thr Gly Thr Ile Glu Thr Gly Asn Ile Ser Ala Glu Lys
1               5                   10                  15

Gly Gly Ser Ile Ile Leu Gln Cys His Leu Ser Ser Thr Thr Ala Gln
            20                  25                  30

Val Thr Gln Val Asn Trp Glu Gln Gln Asp Gln Leu Leu Ala Ile Cys
        35                  40                  45

Asn Ala Asp Leu Gly Trp His Ile Ser Pro Ser Phe Lys Asp Arg Val
    50                  55                  60

Ala Pro Gly Pro Gly Leu Gly Leu Thr Leu Gln Ser Leu Thr Val Asn
65                  70                  75                  80

Asp Thr Gly Glu Tyr Phe Cys Ile Tyr His Thr Tyr Pro Asp Gly Thr
                85                  90                  95

Tyr Thr Gly Arg Ile Ala Leu Glu Val Leu Glu Ser Ser Val Ala Glu
            100                 105                 110

```
His Gly Ala Arg Phe Gln
        115

<210> SEQ ID NO 57
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

Met Met Thr Gly Thr Ile Glu Thr Thr Gly Asn Ile Ser Ala Glu Lys
1               5                   10                  15

Gly Gly Ser Ile Ile Leu Gln Cys His Leu Ser Ser Thr Thr Ala Gln
            20                  25                  30

Val Thr Gln Val Asn Trp Glu Gln Gln Asp Gln Leu Leu Ala Ile Tyr
        35                  40                  45

Ser Val Asp Leu Gly Trp His Ile Ser Pro Ser Phe Lys Asp Arg Val
    50                  55                  60

Ala Pro Gly Pro Gly Leu Gly Leu Thr Leu Gln Ser Leu Thr Val Asn
65                  70                  75                  80

Asp Thr Gly Glu Tyr Phe Cys Ile Tyr His Thr Tyr Pro Asp Gly Thr
                85                  90                  95

Tyr Thr Gly Arg Ile Phe Leu Glu Val Leu Glu Ser Ser Val Ala Glu
            100                 105                 110

His Gly Ala Arg Phe Gln
        115

<210> SEQ ID NO 58
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

Met Met Thr Gly Thr Ile Glu Thr Thr Gly Asn Ile Ser Ala Glu Lys
1               5                   10                  15

Gly Gly Ser Ile Ile Leu Gln Cys His Leu Ser Ser Thr Thr Ala Gln
            20                  25                  30

Val Thr Gln Val Asn Trp Glu Gln Gln Asp Gln Leu Leu Ala Ile Cys
        35                  40                  45

Asn Ala Asp Leu Gly Trp His Val Ala Ser Val Phe Lys Asp Arg Val
    50                  55                  60

Ala Pro Gly Pro Gly Leu Gly Leu Thr Leu Gln Ser Leu Thr Val Asn
65                  70                  75                  80

Asp Thr Gly Glu Tyr Phe Cys Ile Tyr His Thr Tyr Pro Asp Gly Thr
                85                  90                  95

Tyr Thr Gly Arg Ile Phe Leu Glu Val Leu Glu Ser Ser Val Ala Glu
            100                 105                 110

His Gly Ala Arg Phe Gln
        115

<210> SEQ ID NO 59
<211> LENGTH: 118
<212> TYPE: PRT
<213> ORGANISM: Artificial Sequence
<220> FEATURE:
```

<223> OTHER INFORMATION: Description of Artificial Sequence: Synthetic
    polypeptide

<400> SEQUENCE: 59

Met Met Thr Gly Thr Ile Glu Thr Thr Gly Asn Ile Ser Ala Glu Lys
1               5                   10                  15

Gly Gly Ser Ile Ile Leu Gln Cys His Leu Ser Ser Thr Thr Ala Gln
            20                  25                  30

Val Thr Gln Val Asn Trp Glu Gln Gln Asp Gln Leu Leu Ala Ile Cys
        35                  40                  45

Asn Ala Asp Leu Gly Trp His Ile Ser Pro Ser Phe Lys Asp Arg Val
50                  55                  60

Ala Pro Gly Pro Gly Leu Gly Leu Thr Leu Gln Ser Leu Thr Val Asn
65                  70                  75                  80

Asp Thr Gly Glu Tyr Phe Cys Ile Tyr His Thr Tyr Pro Asp Gly Ile
                85                  90                  95

Tyr Lys Gly Arg Ile Phe Leu Glu Val Leu Glu Ser Ser Val Ala Glu
            100                 105                 110

His Gly Ala Arg Phe Gln
        115

<210> SEQ ID NO 60
<211> LENGTH: 99
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 60

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Ser Tyr
            20                  25                  30

Asn Leu Val Ser Trp Tyr Gln Gln His Pro Gly Lys Ala Pro Lys Leu
        35                  40                  45

Met Ile Tyr Glu Gly Ser Lys Arg Pro Ser Gly Val Ser Asn Arg Phe
50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Leu

<210> SEQ ID NO 61
<211> LENGTH: 9
<212> TYPE: PRT
<213> ORGANISM: Cytomegalovirus

<400> SEQUENCE: 61

Asn Leu Val Pro Met Val Ala Thr Val
1               5

<210> SEQ ID NO 62
<211> LENGTH: 119
<212> TYPE: PRT
<213> ORGANISM: Artificial Sequence
<220> FEATURE:
<223> OTHER INFORMATION: Description of Artificial Sequence: Synthetic
    polypeptide

```
<220> FEATURE:
<221> NAME/KEY: MOD_RES
<222> LOCATION: (1)..(1)
<223> OTHER INFORMATION: Glu or pyro-Glu

<400> SEQUENCE: 62

Xaa Val Gln Leu Val Glu Ser Gly Gly Gly Leu Thr Gln Pro Gly Lys
1               5                   10                  15

Ser Leu Lys Leu Ser Cys Glu Ala Ser Gly Phe Thr Phe Ser Ser Phe
            20                  25                  30

Thr Met His Trp Val Arg Gln Ser Pro Gly Lys Gly Leu Glu Trp Val
        35                  40                  45

Ala Phe Ile Arg Ser Gly Ser Gly Ile Val Phe Tyr Ala Asp Ala Val
    50                  55                  60

Arg Gly Arg Phe Thr Ile Ser Arg Asp Asn Ala Lys Asn Leu Leu Phe
65                  70                  75                  80

Leu Gln Met Asn Asp Leu Lys Ser Glu Asp Thr Ala Met Tyr Tyr Cys
                85                  90                  95

Ala Arg Arg Pro Leu Gly His Asn Thr Phe Asp Ser Trp Gly Gln Gly
            100                 105                 110

Thr Leu Val Thr Val Ser Ser
            115

<210> SEQ ID NO 63
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

Asp Ile Val Met Thr Gln Ser Pro Ser Ser Leu Ala Val Ser Pro Gly
1               5                   10                  15

Glu Lys Val Thr Met Thr Cys Lys Ser Ser Gln Ser Leu Tyr Tyr Ser
            20                  25                  30

Gly Val Lys Glu Asn Leu Leu Ala Trp Tyr Gln Gln Lys Pro Gly Gln
        35                  40                  45

Ser Pro Lys Leu Leu Ile Tyr Tyr Ala Ser Ile Arg Phe Thr Gly Val
    50                  55                  60

Pro Asp Arg Phe Thr Gly Ser Gly Ser Gly Thr Asp Tyr Thr Leu Thr
65                  70                  75                  80

Ile Thr Ser Val Gln Ala Glu Asp Met Gly Gln Tyr Phe Cys Gln Gln
                85                  90                  95

Gly Ile Asn Asn Pro Leu Thr Phe Gly Asp Gly Thr Lys Leu Glu Ile
            100                 105                 110

Lys

<210> SEQ ID NO 64
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Glu or pyro-Glu

<400> SEQUENCE: 64
```

-continued

```
Xaa Val Gln Leu Val Glu Ser Gly Gly Gly Leu Thr Gln Pro Gly Lys
1               5                   10                  15

Ser Leu Lys Leu Ser Cys Glu Ala Ser Gly Phe Thr Phe Ser Ser Phe
            20                  25                  30

Thr Met His Trp Val Arg Gln Ser Pro Gly Lys Gly Leu Glu Trp Val
            35                  40                  45

Ala Phe Ile Arg Ser Gly Ser Gly Ile Val Phe Tyr Ala Asp Ala Val
50                  55                  60

Arg Gly Arg Phe Thr Ile Ser Arg Asp Asn Ala Lys Asn Leu Leu Phe
65                  70                  75                  80

Leu Gln Met Asn Asp Leu Lys Ser Glu Asp Thr Ala Met Tyr Tyr Cys
                85                  90                  95

Ala Arg Arg Pro Leu Gly His Asn Thr Phe Asp Ser Trp Gly Gln Gly
                100                 105                 110

Thr Leu Val Thr Val Ser Ser Ala Lys Thr Thr Ala Pro Ser Val Tyr
            115                 120                 125

Pro Leu Ala Pro Val Cys Gly Asp Thr Thr Gly Ser Ser Val Thr Leu
130                 135                 140

Gly Cys Leu Val Lys Gly Tyr Phe Pro Glu Pro Val Thr Leu Thr Trp
145                 150                 155                 160

Asn Ser Gly Ser Leu Ser Ser Gly Val His Thr Phe Pro Ala Val Leu
                165                 170                 175

Gln Ser Asp Leu Tyr Thr Leu Ser Ser Ser Val Thr Val Thr Ser Ser
                180                 185                 190

Thr Trp Pro Ser Gln Ser Ile Thr Cys Asn Val Ala His Pro Ala Ser
            195                 200                 205

Ser Thr Lys Val Asp Lys Lys Ile Glu Pro Arg Gly Pro Thr Ile Lys
            210                 215                 220

Pro Cys Pro Pro Cys Lys Cys Pro Ala Pro Asn Leu Leu Gly Gly Pro
225                 230                 235                 240

Ser Val Phe Ile Phe Pro Pro Lys Ile Lys Asp Val Leu Met Ile Ser
                245                 250                 255

Leu Ser Pro Ile Val Thr Cys Val Val Val Asp Val Ser Glu Asp Asp
            260                 265                 270

Pro Asp Val Gln Ile Ser Trp Phe Val Asn Asn Val Glu Val His Thr
            275                 280                 285

Ala Gln Thr Gln Thr His Arg Glu Asp Tyr Asn Ser Thr Leu Arg Val
            290                 295                 300

Val Ser Ala Leu Pro Ile Gln His Gln Asp Trp Met Ser Gly Lys Glu
305                 310                 315                 320

Phe Lys Cys Lys Val Asn Asn Lys Asp Leu Pro Ala Pro Ile Glu Arg
                325                 330                 335

Thr Ile Ser Lys Pro Lys Gly Ser Val Arg Ala Pro Gln Val Tyr Val
            340                 345                 350

Leu Pro Pro Pro Glu Glu Glu Met Thr Lys Lys Gln Val Thr Leu Thr
            355                 360                 365

Cys Met Val Thr Asp Phe Met Pro Glu Asp Ile Tyr Val Glu Trp Thr
370                 375                 380

Asn Asn Gly Lys Thr Glu Leu Asn Tyr Lys Asn Thr Glu Pro Val Leu
385                 390                 395                 400

Asp Ser Asp Gly Ser Tyr Phe Met Tyr Ser Lys Leu Arg Val Glu Lys
                405                 410                 415
```

```
Lys Asn Trp Val Glu Arg Asn Ser Tyr Ser Cys Ser Val Val His Glu
                420                 425                 430

Gly Leu His Asn His Thr Thr Lys Ser Phe Ser Arg Thr Pro Gly
            435                 440                 445

<210> SEQ ID NO 65
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Glu or pyro-Glu

<400> SEQUENCE: 65

Xaa Val Gln Leu Val Glu Ser Gly Gly Gly Leu Thr Gln Pro Gly Lys
 1               5                  10                  15

Ser Leu Lys Leu Ser Cys Glu Ala Ser Gly Phe Thr Phe Ser Ser Phe
                20                  25                  30

Thr Met His Trp Val Arg Gln Ser Pro Gly Lys Gly Leu Glu Trp Val
            35                  40                  45

Ala Phe Ile Arg Ser Gly Ser Gly Ile Val Phe Tyr Ala Asp Ala Val
        50                  55                  60

Arg Gly Arg Phe Thr Ile Ser Arg Asp Asn Ala Lys Asn Leu Leu Phe
 65                  70                  75                  80

Leu Gln Met Asn Asp Leu Lys Ser Glu Asp Thr Ala Met Tyr Tyr Cys
                85                  90                  95

Ala Arg Arg Pro Leu Gly His Asn Thr Phe Asp Ser Trp Gly Gln Gly
                100                 105                 110

Thr Leu Val Thr Val Ser Ser Ala Lys Thr Thr Ala Pro Ser Val Tyr
            115                 120                 125

Pro Leu Ala Pro Val Cys Gly Asp Thr Thr Gly Ser Ser Val Thr Leu
        130                 135                 140

Gly Cys Leu Val Lys Gly Tyr Phe Pro Glu Pro Val Thr Leu Thr Trp
145                 150                 155                 160

Asn Ser Gly Ser Leu Ser Ser Gly Val His Thr Phe Pro Ala Val Leu
                165                 170                 175

Gln Ser Asp Leu Tyr Thr Leu Ser Ser Ser Val Thr Val Thr Ser Ser
            180                 185                 190

Thr Trp Pro Ser Gln Ser Ile Thr Cys Asn Val Ala His Pro Ala Ser
        195                 200                 205

Ser Thr Lys Val Asp Lys Lys Ile Glu Pro Arg Gly Pro Thr Ile Lys
210                 215                 220

Pro Cys Pro Pro Cys Lys Cys Pro Ala Pro Asn Leu Leu Gly Gly Pro
225                 230                 235                 240

Ser Val Phe Ile Phe Pro Pro Lys Ile Lys Asp Val Leu Met Ile Ser
                245                 250                 255

Leu Ser Pro Ile Val Thr Cys Val Val Val Asp Val Ser Glu Asp Asp
            260                 265                 270

Pro Asp Val Gln Ile Ser Trp Phe Val Asn Asn Val Glu Val His Thr
        275                 280                 285

Ala Gln Thr Gln Thr His Arg Glu Asp Tyr Asn Ser Thr Leu Arg Val
    290                 295                 300

Val Ser Ala Leu Pro Ile Gln His Gln Asp Trp Met Ser Gly Lys Glu
```

```
                305                 310                 315                 320

Phe Lys Cys Lys Val Asn Asn Lys Asp Leu Pro Ala Pro Ile Glu Arg
                       325                 330                 335

Thr Ile Ser Lys Pro Lys Gly Ser Val Arg Ala Pro Gln Val Tyr Val
                       340                 345                 350

Leu Pro Pro Glu Glu Glu Met Thr Lys Lys Gln Val Thr Leu Thr
                       355                 360                 365

Cys Met Val Thr Asp Phe Met Pro Glu Asp Ile Tyr Val Glu Trp Thr
                       370                 375                 380

Asn Asn Gly Lys Thr Glu Leu Asn Tyr Lys Asn Thr Glu Pro Val Leu
       385                 390                 395                 400

Asp Ser Asp Gly Ser Tyr Phe Met Tyr Ser Lys Leu Arg Val Glu Lys
                       405                 410                 415

Lys Asn Trp Val Glu Arg Asn Ser Tyr Ser Cys Ser Val Val His Glu
                       420                 425                 430

Gly Leu His Asn His Thr Thr Lys Ser Phe Ser Arg Thr Pro Gly
                       435                 440                 445

Lys

<210> SEQ ID NO 66
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Glu or pyro-Glu

<400> SEQUENCE: 66

Xaa Val Gln Leu Val Glu Ser Gly Gly Gly Leu Thr Gln Pro Gly Lys
       1               5                   10                  15

Ser Leu Lys Leu Ser Cys Glu Ala Ser Gly Phe Thr Phe Ser Ser Phe
                       20                  25                  30

Thr Met His Trp Val Arg Gln Ser Pro Gly Lys Gly Leu Glu Trp Val
                       35                  40                  45

Ala Phe Ile Arg Ser Gly Ser Gly Ile Val Phe Tyr Ala Asp Ala Val
                       50                  55                  60

Arg Gly Arg Phe Thr Ile Ser Arg Asp Asn Ala Lys Asn Leu Leu Phe
       65                  70                  75                  80

Leu Gln Met Asn Asp Leu Lys Ser Glu Asp Thr Ala Met Tyr Tyr Cys
                       85                  90                  95

Ala Arg Arg Pro Leu Gly His Asn Thr Phe Asp Ser Trp Gly Gln Gly
                       100                 105                 110

Thr Leu Val Thr Val Ser Ser Ala Lys Thr Thr Ala Pro Ser Val Tyr
                       115                 120                 125

Pro Leu Ala Pro Val Cys Gly Asp Thr Thr Gly Ser Ser Val Thr Leu
                       130                 135                 140

Gly Cys Leu Val Lys Gly Tyr Phe Pro Glu Pro Val Thr Leu Thr Trp
       145                 150                 155                 160

Asn Ser Gly Ser Leu Ser Ser Gly Val His Thr Phe Pro Ala Val Leu
                       165                 170                 175

Gln Ser Asp Leu Tyr Thr Leu Ser Ser Ser Val Thr Val Thr Ser Ser
                       180                 185                 190
```

```
Thr Trp Pro Ser Gln Ser Ile Thr Cys Asn Val Ala His Pro Ala Ser
            195                 200                 205

Ser Thr Lys Val Asp Lys Lys Ile Glu Pro Arg Gly Pro Thr Ile Lys
    210                 215                 220

Pro Cys Pro Pro Cys Lys Cys Pro Ala Pro Asn Leu Leu Gly Gly Pro
225                 230                 235                 240

Ser Val Phe Ile Phe Pro Pro Lys Ile Lys Asp Val Leu Met Ile Ser
                245                 250                 255

Leu Ser Pro Ile Val Thr Cys Val Val Asp Val Ser Glu Asp Asp
            260                 265                 270

Pro Asp Val Gln Ile Ser Trp Phe Val Asn Asn Val Glu Val His Thr
    275                 280                 285

Ala Gln Thr Gln Thr His Arg Glu Asp Tyr Gln Ser Thr Leu Arg Val
290                 295                 300

Val Ser Ala Leu Pro Ile Gln His Gln Asp Trp Met Ser Gly Lys Glu
305                 310                 315                 320

Phe Lys Cys Lys Val Asn Asn Lys Asp Leu Pro Ala Pro Ile Glu Arg
                325                 330                 335

Thr Ile Ser Lys Pro Lys Gly Ser Val Arg Ala Pro Gln Val Tyr Val
            340                 345                 350

Leu Pro Pro Pro Glu Glu Glu Met Thr Lys Lys Gln Val Thr Leu Thr
    355                 360                 365

Cys Met Val Thr Asp Phe Met Pro Glu Asp Ile Tyr Val Glu Trp Thr
370                 375                 380

Asn Asn Gly Lys Thr Glu Leu Asn Tyr Lys Asn Thr Glu Pro Val Leu
385                 390                 395                 400

Asp Ser Asp Gly Ser Tyr Phe Met Tyr Ser Lys Leu Arg Val Glu Lys
                405                 410                 415

Lys Asn Trp Val Glu Arg Asn Ser Tyr Ser Cys Ser Val Val His Glu
            420                 425                 430

Gly Leu His Asn His His Thr Thr Lys Ser Phe Ser Arg Thr Pro Gly
    435                 440                 445

Lys

<210> SEQ ID NO 67
<211> LENGTH: 443
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Glu or pyro-Glu

<400> SEQUENCE: 67

Xaa Val Gln Leu Val Glu Ser Gly Gly Gly Leu Thr Gln Pro Gly Lys
1               5                   10                  15

Ser Leu Lys Leu Ser Cys Glu Ala Ser Gly Phe Thr Phe Ser Ser Phe
            20                  25                  30

Thr Met His Trp Val Arg Gln Ser Pro Gly Lys Gly Leu Glu Trp Val
        35                  40                  45

Ala Phe Ile Arg Ser Gly Ser Gly Ile Val Phe Tyr Ala Asp Ala Val
    50                  55                  60

Arg Gly Arg Phe Thr Ile Ser Arg Asp Asn Ala Lys Asn Leu Leu Phe
65                  70                  75                  80
```

Leu Gln Met Asn Asp Leu Lys Ser Glu Asp Thr Ala Met Tyr Tyr Cys
                85                  90                  95

Ala Arg Arg Pro Leu Gly His Asn Thr Phe Asp Ser Trp Gly Gln Gly
            100                 105                 110

Thr Leu Val Thr Val Ser Ser Ala Lys Thr Thr Pro Pro Ser Val Tyr
        115                 120                 125

Pro Leu Ala Pro Gly Ser Ala Ala Gln Thr Asn Ser Met Val Thr Leu
    130                 135                 140

Gly Cys Leu Val Lys Gly Tyr Phe Pro Glu Pro Val Thr Val Thr Trp
145                 150                 155                 160

Asn Ser Gly Ser Leu Ser Ser Gly Val His Thr Phe Pro Ala Val Leu
                165                 170                 175

Gln Ser Asp Leu Tyr Thr Leu Ser Ser Ser Val Thr Val Pro Ser Ser
            180                 185                 190

Thr Trp Pro Ser Glu Thr Val Thr Cys Asn Val Ala His Pro Ala Ser
        195                 200                 205

Ser Thr Lys Val Asp Lys Lys Ile Val Pro Arg Asp Cys Gly Cys Lys
    210                 215                 220

Pro Cys Ile Cys Thr Val Pro Glu Val Ser Ser Val Phe Ile Phe Pro
225                 230                 235                 240

Pro Lys Pro Lys Asp Val Leu Thr Ile Thr Leu Thr Pro Lys Val Thr
                245                 250                 255

Cys Val Val Val Asp Ile Ser Lys Asp Asp Pro Glu Val Gln Phe Ser
            260                 265                 270

Trp Phe Val Asp Asp Val Glu Val His Thr Ala Gln Thr Gln Pro Arg
        275                 280                 285

Glu Glu Gln Phe Asn Ser Thr Phe Arg Ser Val Ser Glu Leu Pro Ile
    290                 295                 300

Met His Gln Asp Trp Leu Asn Gly Lys Glu Phe Lys Cys Arg Val Asn
305                 310                 315                 320

Ser Ala Ala Phe Pro Ala Pro Ile Glu Lys Thr Ile Ser Lys Thr Lys
                325                 330                 335

Gly Arg Pro Lys Ala Pro Gln Val Tyr Thr Ile Pro Pro Pro Lys Glu
            340                 345                 350

Gln Met Ala Lys Asp Lys Val Ser Leu Thr Cys Met Ile Thr Asp Phe
        355                 360                 365

Phe Pro Glu Asp Ile Thr Val Glu Trp Gln Trp Asn Gly Gln Pro Ala
    370                 375                 380

Glu Asn Tyr Lys Asn Thr Gln Pro Ile Met Asp Thr Asp Gly Ser Tyr
385                 390                 395                 400

Phe Val Tyr Ser Lys Leu Asn Val Gln Lys Ser Asn Trp Glu Ala Gly
                405                 410                 415

Asn Thr Phe Thr Cys Ser Val Leu His Glu Gly Leu His Asn His His
            420                 425                 430

Thr Glu Lys Ser Leu Ser His Ser Pro Gly Lys
        435                 440

<210> SEQ ID NO 68
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:

-continued

```
<221> NAME/KEY: MOD_RES
<222> LOCATION: (1)..(1)
<223> OTHER INFORMATION: Glu or pyro-Glu

<400> SEQUENCE: 68

Xaa Val Gln Leu Val Glu Ser Gly Gly Gly Leu Thr Gln Pro Gly Lys
1               5                   10                  15

Ser Leu Lys Leu Ser Cys Glu Ala Ser Gly Phe Thr Phe Ser Ser Phe
            20                  25                  30

Thr Met His Trp Val Arg Gln Ser Pro Gly Lys Gly Leu Glu Trp Val
        35                  40                  45

Ala Phe Ile Arg Ser Gly Ser Gly Ile Val Phe Tyr Ala Asp Ala Val
    50                  55                  60

Arg Gly Arg Phe Thr Ile Ser Arg Asp Asn Ala Lys Asn Leu Leu Phe
65                  70                  75                  80

Leu Gln Met Asn Asp Leu Lys Ser Glu Asp Thr Ala Met Tyr Tyr Cys
                85                  90                  95

Ala Arg Arg Pro Leu Gly His Asn Thr Phe Asp Ser Trp Gly Gln Gly
            100                 105                 110

Thr Leu Val Thr Val Ser Ser Ala Lys Thr Thr Ala Pro Ser Val Tyr
        115                 120                 125

Pro Leu Ala Pro Val Cys Gly Asp Thr Thr Gly Ser Ser Val Thr Leu
130                 135                 140

Gly Cys Leu Val Lys Gly Tyr Phe Pro Glu Pro Val Thr Leu Thr Trp
145                 150                 155                 160

Asn Ser Gly Ser Leu Ser Ser Gly Val His Thr Phe Pro Ala Val Leu
                165                 170                 175

Gln Ser Asp Leu Tyr Thr Leu Ser Ser Ser Val Thr Val Thr Ser Ser
            180                 185                 190

Thr Trp Pro Ser Gln Ser Ile Thr Cys Asn Val Ala His Pro Ala Ser
        195                 200                 205

Ser Thr Lys Val Asp Lys Lys Ile Glu Pro Arg Gly Pro Thr Ile Lys
    210                 215                 220

Pro Cys Pro Pro Cys Lys Cys Pro Ala Pro Asn Leu Leu Gly Gly Pro
225                 230                 235                 240

Asp Val Phe Ile Phe Pro Pro Lys Ile Lys Asp Val Leu Met Ile Ser
                245                 250                 255

Leu Ser Pro Ile Val Thr Cys Val Val Val Asp Val Ser Glu Asp Asp
            260                 265                 270

Pro Asp Val Gln Ile Ser Trp Phe Val Asn Asn Val Glu Val His Thr
        275                 280                 285

Ala Gln Thr Gln Thr His Arg Glu Asp Tyr Asn Ser Thr Leu Arg Val
    290                 295                 300

Val Ser Ala Leu Pro Ile Gln His Gln Asp Trp Met Ser Gly Lys Glu
305                 310                 315                 320

Phe Lys Cys Lys Val Asn Asn Lys Asp Leu Pro Leu Pro Glu Glu Arg
                325                 330                 335

Thr Ile Ser Lys Pro Lys Gly Ser Val Arg Ala Pro Gln Val Tyr Val
            340                 345                 350

Leu Pro Pro Pro Glu Glu Glu Met Thr Lys Lys Gln Val Thr Leu Thr
        355                 360                 365

Cys Met Val Thr Asp Phe Met Pro Glu Asp Ile Tyr Val Glu Trp Thr
    370                 375                 380

Asn Asn Gly Lys Thr Glu Leu Asn Tyr Lys Asn Thr Glu Pro Val Leu
```

```
385                 390                 395                 400
Asp Ser Asp Gly Ser Tyr Phe Met Tyr Ser Lys Leu Arg Val Glu Lys
                405                 410                 415

Lys Asn Trp Val Glu Arg Asn Ser Tyr Ser Cys Ser Val Val His Glu
            420                 425                 430

Gly Leu His Asn His His Thr Thr Lys Ser Phe Ser Arg Thr Pro Gly
            435                 440                 445

<210> SEQ ID NO 69
<211> LENGTH: 220
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 69

Asp Ile Val Met Thr Gln Ser Pro Ser Ser Leu Ala Val Ser Pro Gly
1               5                   10                  15

Glu Lys Val Thr Met Thr Cys Lys Ser Ser Gln Ser Leu Tyr Tyr Ser
            20                  25                  30

Gly Val Lys Glu Asn Leu Leu Ala Trp Tyr Gln Gln Lys Pro Gly Gln
        35                  40                  45

Ser Pro Lys Leu Leu Ile Tyr Tyr Ala Ser Ile Arg Phe Thr Gly Val
50                  55                  60

Pro Asp Arg Phe Thr Gly Ser Gly Ser Gly Thr Asp Tyr Thr Leu Thr
65                  70                  75                  80

Ile Thr Ser Val Gln Ala Glu Asp Met Gly Gln Tyr Phe Cys Gln Gln
                85                  90                  95

Gly Ile Asn Asn Pro Leu Thr Phe Gly Asp Gly Thr Lys Leu Glu Ile
            100                 105                 110

Lys Arg Ala Asp Ala Ala Pro Thr Val Ser Ile Phe Pro Pro Ser Ser
        115                 120                 125

Glu Gln Leu Thr Ser Gly Gly Ala Ser Val Val Cys Phe Leu Asn Asn
130                 135                 140

Phe Tyr Pro Lys Asp Ile Asn Val Lys Trp Lys Ile Asp Gly Ser Glu
145                 150                 155                 160

Arg Gln Asn Gly Val Leu Asn Ser Trp Thr Asp Gln Asp Ser Lys Asp
                165                 170                 175

Ser Thr Tyr Ser Met Ser Ser Thr Leu Thr Leu Thr Lys Asp Glu Tyr
            180                 185                 190

Glu Arg His Asn Ser Tyr Thr Cys Glu Ala Thr His Lys Thr Ser Thr
        195                 200                 205

Ser Pro Ile Val Lys Ser Phe Asn Arg Asn Glu Cys
210                 215                 220

<210> SEQ ID NO 70
<211> LENGTH: 245
<212> TYPE: PRT
<213> ORGANISM: Macaca fascicularis

<400> SEQUENCE: 70

Met Arg Trp Cys Leu Phe Leu Ile Trp Ala Gln Gly Leu Arg Gln Ala
1               5                   10                  15

Pro Leu Ala Ser Gly Met Met Thr Gly Thr Ile Glu Thr Thr Gly Asn
            20                  25                  30

Ile Ser Ala Lys Lys Gly Gly Ser Val Ile Leu Gln Cys His Leu Ser
```

-continued

```
                35                  40                  45
Ser Thr Met Ala Gln Val Thr Gln Val Asn Trp Glu Gln His Asp His
        50                  55                  60

Ser Leu Leu Ala Ile Arg Asn Ala Glu Leu Gly Trp His Ile Tyr Pro
65                  70                  75                  80

Ala Phe Lys Asp Arg Val Ala Pro Gly Pro Gly Leu Gly Leu Thr Leu
                85                  90                  95

Gln Ser Leu Thr Met Asn Asp Thr Gly Glu Tyr Phe Cys Thr Tyr His
                100                 105                 110

Thr Tyr Pro Asp Gly Thr Tyr Arg Gly Arg Ile Phe Leu Glu Val Leu
            115                 120                 125

Glu Ser Ser Val Ala Glu His Ser Ala Arg Phe Gln Ile Pro Leu Leu
            130                 135                 140

Gly Ala Met Ala Met Met Leu Val Val Ile Cys Ile Ala Val Ile Val
145                 150                 155                 160

Val Val Val Leu Ala Arg Lys Lys Ser Leu Arg Ile His Ser Val
                165                 170                 175

Glu Ser Gly Leu Gln Arg Lys Ser Thr Gly Gln Glu Gln Ile Pro
                180                 185                 190

Ser Ala Pro Ser Pro Pro Gly Ser Cys Val Gln Ala Glu Ala Ala Pro
            195                 200                 205

Ala Gly Leu Cys Gly Glu Gln Gln Gly Asp Asp Cys Ala Glu Leu His
            210                 215                 220

Asp Tyr Phe Asn Val Leu Ser Tyr Arg Ser Leu Gly Ser Cys Ser Phe
225                 230                 235                 240

Phe Thr Glu Thr Gly
                245
```

ANTI-TIGIT ANTIBODIES AND METHODS OF USE THEREOF

RELATED APPLICATIONS

This application claims the benefit of U.S. Provisional Application Nos. 62/492,829, filed May 1, 2017; and 62/500,345, filed May 2, 2017, each of which is incorporated by reference herein in its entirety.

1. FIELD

The instant disclosure relates to antibodies that specifically bind to TIGIT (e.g., human TIGIT) and methods of using the same.

2. BACKGROUND

The protein T-cell immunoreceptor with Ig and ITIM domains (TIGIT), also known as VSIG9 or VSTM3, is a type I transmembrane protein in the immunoglobulin (Ig) superfamily. It has a single Ig domain, a type I transmembrane domain, a single intracellular immunoreceptor tyrosine-based inhibitory motif (ITIM) and a single immunoglobulin tail tyrosine (ITT)-like phosphorylation motif and is expressed on activated CD4-positive/CD25-positive regulatory T cells (Tregs), memory CD45RO-positive T cells, and natural killer (NK) cells, but not naïve T cells.

Poliovirus receptor (PVR, also known as CD155) is highly expressed on monocytes and dendritic cells, and is capable of activating effector T cells and NK cells, as well as attenuating the activity of Tregs, through binding to its two receptors CD226 and CD96. TIGIT binds to PVR and has been shown to antagonize the interaction of PVR with CD226 and CD96, thereby suppressing T cell- and NK cell-mediated immune activity.

Given the apparent role of human TIGIT in modulating immune responses, therapeutic agents designed to antagonize TIGIT signaling hold great promise for the treatment of diseases that involve immune suppression.

3. SUMMARY

The instant disclosure provides antibodies that specifically bind to TIGIT (e.g., human TIGIT) and antagonize TIGIT function, e.g., TIGIT-mediated immune suppression. Also provided are pharmaceutical compositions comprising these antibodies, nucleic acids encoding these antibodies, expression vectors and host cells for making these antibodies, and methods of treating a subject using these antibodies. The antibodies disclosed herein are particularly useful for increasing T cell and NK cell activation in response to an antigen (e.g., a tumor antigen or an infectious disease antigen) and/or decreasing Treg-mediated immune suppression, and hence, are useful for treating cancer in a subject or treating or preventing an infectious disease in a subject.

Accordingly, in one aspect, the instant disclosure provides an antibody or isolated antibody comprising a heavy chain variable region (VH) comprising complementarity determining regions (CDRs) CDRH1, CDRH2 and CDRH3 and a light chain variable region (VL) comprising complementarity determining regions CDRL1, CDRL2 and CDRL3, wherein:
(a) CDRH1 comprises the amino acid sequence of SYGIS (SEQ ID NO: 1) or GYTFASY (SEQ ID NO: 2);

(b) CDRH2 comprises the amino acid sequence of GITPFFNRVDVAEKFQG (SEQ ID NO: 3) or TPFFNR (SEQ ID NO: 4);
(c) CDRH3 comprises the amino acid sequence of CDRH3 comprises the amino acid sequence of DLRRGGVGDAFDI (SEQ ID NO: 5);
(d) CDRL1 comprises the amino acid sequence of CDRL1 comprises the amino acid sequence of TGTSSDVGSHNYVS (SEQ ID NO: 6);
(e) CDRL2 comprises the amino acid sequence of EVSYRPS (SEQ ID NO: 7); and/or
(f) CDRL3 comprises the amino acid sequence of SSYTPSSATV (SEQ ID NO: 8).

In certain embodiments, the CDRH1, CDRH2, CDRH3, CDRL1, CDRL2, and CDRL3 comprise the amino acid sequences set forth in SEQ ID NOs: 1, 3, 5, 6, 7, and 8, respectively. In certain embodiments, the CDRH1, CDRH2, CDRH3, CDRL1, CDRL2, and CDRL3 comprise the amino acid sequences set forth in SEQ ID NOs: 2, 4, 5, 6, 7, and 8, respectively.

In certain embodiments, the antibody comprises a heavy chain variable region comprising an amino acid sequence that is at least 75%, 80%, 85%, 90%, 95%, 96%, 97%, 98%, 99%, or 100% identical to the amino acid sequence of SEQ ID NO: 9. In certain embodiments, the heavy chain variable region comprises the amino acid sequence of SEQ ID NO: 9. In certain embodiments, the amino acid sequence of the heavy chain variable region consists of the amino acid sequence of SEQ ID NO: 9. In certain embodiments, X in SEQ ID NO: 9 is glutamate (E). In certain embodiments, X in SEQ ID NO: 9 is pyroglutamate (pE).

In certain embodiments, the antibody comprises a light chain variable region comprising an amino acid sequence that is at least 75%, 80%, 85%, 90%, 95%, 96%, 97%, 98%, 99%, or 100% identical to the amino acid sequence of SEQ ID NO: 10. In certain embodiments, the light chain variable region comprises the amino acid sequence of SEQ ID NO: 10. In certain embodiments, the amino acid sequence of the light chain variable region consists of the amino acid sequence of SEQ ID NO: 10. In certain embodiments, X in SEQ ID NO: 10 is glutamine (Q). In certain embodiments, X in SEQ ID NO: 10 is pyroglutamate (pE).

In another aspect, the instant disclosure provides an isolated antibody that specifically binds to human TIGIT, the antibody comprising a heavy chain variable region comprising the amino acid sequence of SEQ ID NO: 9. In certain embodiments, the amino acid sequence of the heavy chain variable region consists of the amino acid sequence of SEQ ID NO: 9. In certain embodiments, X in SEQ ID NO: 9 is glutamate (E). In certain embodiments, X in SEQ ID NO: 9 is pyroglutamate (pE).

In another aspect, the instant disclosure provides an isolated antibody that specifically binds to human TIGIT, the antibody comprising a light chain variable region comprising the amino acid sequence of SEQ ID NO: 10. In certain embodiments, the amino acid sequence of the light chain variable region consists of the amino acid sequence of SEQ ID NO: 10. In certain embodiments, X in SEQ ID NO: 10 is glutamine (Q). In certain embodiments, X in SEQ ID NO: 10 is pyroglutamate (pE).

In another aspect, the instant disclosure provides an isolated antibody that specifically binds to human TIGIT, the antibody comprising a heavy chain variable region comprising the amino acid sequence of SEQ ID NO: 9 and a light chain variable region comprising the amino acid sequence of SEQ ID NO: 10. In certain embodiments, the amino acid sequence of the heavy chain variable region consists of the amino acid sequence of SEQ ID NO: 9 the amino acid sequence of the light chain variable region consists of the amino acid sequence of SEQ ID NO: 10. In certain embodiments, X in SEQ ID NO: 9 is glutamate (E). In certain embodiments, X in SEQ ID NO: 9 is pyroglutamate (pE). In certain embodiments, X in SEQ ID NO: 10 is glutamine (Q). In certain embodiments, X in SEQ ID NO: 10 is pyroglutamate (pE).

In another aspect, the instant disclosure provides an isolated antibody that specifically binds to human TIGIT, the antibody comprising a heavy chain variable region having an amino acid sequence derived from a human IGHV1-69*01 germline sequence. In another aspect, the instant disclosure provides an isolated antibody that specifically binds to human TIGIT, the antibody comprising a heavy chain variable region having an amino acid sequence derived from a human IGHV1-69*06 germline sequence. In another aspect, the instant disclosure provides an isolated antibody that specifically binds to human TIGIT, the antibody comprising a heavy chain variable region having an amino acid sequence derived from a human IGHV1-69*12 germline sequence.

In another aspect, the instant disclosure provides an isolated antibody that specifically binds to human TIGIT, the antibody comprising a light chain variable region having an amino acid sequence derived from a human IGLV2-14*01 germline sequence. In another aspect, the instant disclosure provides an isolated antibody that specifically binds to human TIGIT, the antibody comprising a light chain variable region having an amino acid sequence derived from a human IGLV2-23*02 germline sequence. In another aspect, the instant disclosure provides an isolated antibody that specifically binds to human TIGIT, the antibody comprising a light chain variable region having an amino acid sequence derived from a human IGLV2-11*01 germline sequence.

In another aspect, the instant disclosure provides an isolated antibody that specifically binds to human TIGIT, the antibody comprising a heavy chain variable region comprising an amino acid region that is at least 75%, 80%, 85%, 90%, 95%, 96%, 97%, 98%, 99%, or 100% identical to the amino acid sequence of SEQ ID NO: 34 or 35. In another aspect, the instant disclosure provides an isolated antibody that specifically binds to human TIGIT, the antibody comprising a light chain variable region comprising an amino acid region that is at least 75%, 80%, 85%, 90%, 95%, 96%, 97%, 98%, 99%, or 100% identical to the amino acid sequence of any one of SEQ ID NOs: 37-39 and 60.

In certain embodiments, the antibody binds to the same epitope of human TIGIT as an antibody comprising a heavy chain variable region comprising the amino acid sequence of SEQ ID NO: 9 and a light chain variable region comprising the amino acid sequence of SEQ ID NO: 10.

In certain embodiments, the instant disclosure provides an isolated antibody that specifically binds to human TIGIT, wherein the antibody binds to the same epitope of human TIGIT as an antibody comprising a heavy chain variable region comprising the amino acid sequence of SEQ ID NO: 9 and a light chain variable region comprising the amino acid sequence of SEQ ID NO: 10.

In certain embodiments, the antibody binds to an epitope located within a region of human TIGIT, the amino acid sequence of the region consisting of the amino acid sequence of any one of SEQ ID NOs: 31-33.

In certain embodiments, the instant disclosure provides an isolated antibody that specifically binds to human TIGIT, wherein the antibody binds to an epitope located within a region of human TIGIT, wherein the amino acid sequence of the region consists of the amino acid sequence of any one of SEQ ID NOs: 31-33.

In certain embodiments, the antibody binds to one or more amino acid residues of human TIGIT selected from the group consisting of Q35, I47, N49, H90, and T96, numbered according to the amino acid sequence of SEQ ID NO: 40. In certain embodiments, the antibody binds to one or more amino acid residues of human TIGIT selected from the group consisting of Q35, I47, and T96, numbered according to the amino acid sequence of SEQ ID NO: 40. In certain embodiments, the antibody binds to amino acid residue T96 of human TIGIT, numbered according to the amino acid sequence of SEQ ID NO: 40. In certain embodiments, the binding between the antibody and a protein comprising the amino acid sequence of SEQ ID NO: 52 is substantially weakened (e.g., reduced by at least 30%, 35%, 40%, 45%, 50%, 55%, 60%, 65%, 70%, 75%, 80%, 85%, or 90%) relative to the binding of the antibody to a protein comprising the amino acid sequence of SEQ ID NO: 42. In certain embodiments, the binding between the antibody and a protein comprising the amino acid sequence of SEQ ID NO: 53 is substantially weakened (e.g., reduced by at least 30%, 35%, 40%, 45%, 50%, 55%, 60%, 65%, 70%, 75%, 80%, 85%, or 90%) relative to the binding of the antibody to a protein comprising the amino acid sequence of SEQ ID NO: 42. In certain embodiments, the antibody binds to amino acid residue Q35 of human TIGIT, numbered according to the amino acid sequence of SEQ ID NO: 40. In certain embodiments, the binding between the antibody and a protein comprising the amino acid sequence of SEQ ID NO: 44 is substantially weakened (e.g., reduced by at least 30%, 35%, 40%, 45%, 50%, 55%, 60%, 65%, 70%, 75%, 80%, 85%, or 90%) relative to the binding of the antibody to a protein comprising the amino acid sequence of SEQ ID NO: 42. In certain embodiments, the antibody binds to amino acid residue I47 of human TIGIT, numbered according to the amino acid sequence of SEQ ID NO: 40. In certain embodiments, the binding between the antibody and a protein comprising the amino acid sequence of SEQ ID NO: 45 is substantially weakened (e.g., reduced by at least 30%, 35%, 40%, 45%, 50%, 55%, 60%, 65%, 70%, 75%, 80%, 85%, or 90%) relative to the binding of the antibody to a protein comprising the amino acid sequence of SEQ ID NO: 42. In certain embodiments, the antibody binds to amino acid residue N49 of human TIGIT, numbered according to the amino acid sequence of SEQ ID NO: 40. In certain embodiments, the binding between the antibody and a protein comprising the amino acid sequence of SEQ ID NO: 46 is substantially weakened (e.g., reduced by at least 30%, 35%, 40%, 45%, 50%, 55%, 60%, 65%, 70%, 75%, 80%, 85%, or 90%) relative to the binding of the antibody to a protein comprising the amino acid sequence of SEQ ID NO: 42. In certain embodiments, the binding between the antibody and a protein comprising the amino acid sequence of SEQ ID NO: 36 is substantially weakened (e.g., reduced by at least 30%, 35%, 40%, 45%, 50%, 55%, 60%, 65%, 70%, 75%, 80%, 85%, or 90%) relative to the binding of the antibody to a protein comprising the amino acid sequence of SEQ ID NO: 42. In certain embodiments, the antibody binds to amino acid residue H90 of human TIGIT, numbered according to the amino acid sequence of SEQ ID NO: 40. In certain embodiments, the binding between the antibody and a protein comprising the amino acid sequence of SEQ ID NO: 51 is substantially weakened (e.g., reduced by at least 30%, 35%, 40%, 45%, 50%, 55%, 60%, 65%, 70%, 75%, 80%, 85%, or 90%) relative to the binding of the antibody to a protein comprising the amino acid sequence of SEQ ID NO: 42. In certain embodiments, the binding between the antibody and a protein comprising the amino acid sequence of SEQ ID NO: 57 is substantially weakened (e.g., reduced by at least 30%, 35%, 40%, 45%, 50%, 55%, 60%, 65%, 70%, 75%, 80%, 85%, or 90%) relative to the binding of the antibody to a protein comprising the amino acid sequence of SEQ ID NO: 42. In certain embodiments, the binding between the antibody and a protein comprising the amino acid sequence of SEQ ID NO: 59 is substantially weakened (e.g., reduced by at least 30%, 35%, 40%, 45%, 50%, 55%, 60%, 65%, 70%, 75%, 80%, 85%, or 90%) relative to the binding of the antibody to a protein comprising the amino acid sequence of SEQ ID NO: 42. In certain embodiments, the binding between the antibody and a protein comprising the amino acid sequence of SEQ ID NO: 48 is substantially weakened (e.g., reduced by at least 30%, 35%, 40%, 45%, 50%, 55%, 60%, 65%, 70%, 75%, 80%, 85%, or 90%) relative to the binding of the antibody to a protein comprising the amino acid sequence of SEQ ID NO: 42.

In certain embodiments, the antibody does not bind to one or more of the amino acid residues of human TIGIT selected from the group consisting of T34, L52, H55, I56, S57, P58, S59, T98, R100, and F102, numbered according to the amino acid sequence of SEQ ID NO: 40. In certain embodiments, the antibody does not bind to amino acid residue T34 of human TIGIT, numbered according to the amino acid sequence of SEQ ID NO: 40. In certain embodiments, the binding of the antibody to a protein comprising the amino acid sequence of SEQ ID NO: 43 is not substantially weakened (e.g., not reduced by more than 30%, 35%, 40%, 45%, 50%, 55%, 60%, 65%, 70%, 75%, 80%, 85%, or 90%) relative to the binding of the antibody to a protein comprising the amino acid sequence of SEQ ID NO: 42. In certain embodiments, the antibody does not bind to amino acid residue L52 of human TIGIT, numbered according to the amino acid sequence of SEQ ID NO: 40. In certain embodiments, the binding of the antibody to a protein comprising the amino acid sequence of SEQ ID NO: 47 is not substantially weakened (e.g., not reduced by more than 30%, 35%, 40%, 45%, 50%, 55%, 60%, 65%, 70%, 75%, 80%, 85%, or 90%) relative to the binding of the antibody to a protein comprising the amino acid sequence of SEQ ID NO: 42. In certain embodiments, the antibody does not bind to amino acid residue H55 of human TIGIT, numbered according to the amino acid sequence of SEQ ID NO: 40. In certain embodiments, the binding of the antibody to a protein comprising the amino acid sequence of SEQ ID NO: 49 is not substantially weakened (e.g., not reduced by more than 30%, 35%, 40%, 45%, 50%, 55%, 60%, 65%, 70%, 75%, 80%, 85%, or 90%) relative to the binding of the antibody to a protein comprising the amino acid sequence of SEQ ID NO: 42. In certain embodiments, the antibody does not bind to amino acid residue I56 of human TIGIT, numbered according to the amino acid sequence of SEQ ID NO: 40. In certain embodiments, the antibody does not bind to amino acid residue S57 of human TIGIT, numbered according to the amino acid sequence of SEQ ID NO: 40. In certain embodiments, the antibody does not bind to amino acid residue P58 of human TIGIT, numbered according to the amino acid sequence of SEQ ID NO: 40. In certain embodiments, the antibody does not bind to amino acid residue S59 of human TIGIT, numbered according to the amino acid sequence of SEQ ID NO: 40. In certain embodiments, the binding of the antibody to a protein comprising the amino acid sequence of SEQ ID NO: 58 is not substantially weakened (e.g., not reduced by more than 30%, 35%, 40%, 45%, 50%, 55%, 60%, 65%, 70%, 75%, 80%, 85%, or 90%) relative to the binding of the antibody to a protein comprising the amino acid sequence of SEQ ID NO: 42. In certain embodiments, the antibody does not bind to amino acid residue T98 of human TIGIT, numbered according to the amino acid sequence of SEQ ID NO: 40. In certain embodiments, the binding of the antibody to a protein comprising the amino acid sequence of SEQ ID NO: 54 is not substantially weakened (e.g., not reduced by more than 30%, 35%, 40%, 45%, 50%, 55%, 60%, 65%, 70%, 75%, 80%, 85%, or 90%) relative to the binding of the antibody to a protein comprising the amino acid sequence of SEQ ID NO: 42. In certain embodiments, the antibody does not bind to amino acid residue R100 of human TIGIT, numbered according to the amino acid sequence of SEQ ID NO: 40. In certain embodiments, the binding of the antibody to a protein comprising the amino acid sequence of SEQ ID NO: 55 is not substantially weakened (e.g., not reduced by more than 30%, 35%, 40%, 45%, 50%, 55%, 60%, 65%, 70%, 75%, 80%, 85%, or 90%) relative to the binding of the antibody to a protein comprising the amino acid sequence of SEQ ID NO: 42.

In another aspect the instant disclosure provides, an isolated antibody that specifically binds to human TIGIT, wherein the antibody binds to one or more amino acid residues of human TIGIT selected from the group consisting of Q35, I47, N49, H90, and T96, numbered according to the amino acid sequence of SEQ ID NO: 40.

In another aspect the instant disclosure provides, an isolated antibody that specifically binds to human TIGIT, wherein the antibody binds to one or more amino acid residues of human TIGIT selected from the group consisting of Q35, I47, and T96, numbered according to the amino acid sequence of SEQ ID NO: 40.

In another aspect the instant disclosure provides, an isolated antibody that specifically binds to human TIGIT, wherein the antibody binds to amino acid residue T96 of human TIGIT, numbered according to the amino acid sequence of SEQ ID NO: 40.

In another aspect the instant disclosure provides, an isolated antibody that specifically binds to human TIGIT, wherein the binding between the antibody and a protein comprising the amino acid sequence of SEQ ID NO: 52 is substantially weakened (e.g., reduced by at least 30%, 35%, 40%, 45%, 50%, 55%, 60%, 65%, 70%, 75%, 80%, 85%, or 90%) relative to the binding of the antibody to a protein comprising the amino acid sequence of SEQ ID NO: 42.

In another aspect the instant disclosure provides, an isolated antibody that specifically binds to human TIGIT, wherein the binding between the antibody and a protein comprising the amino acid sequence of SEQ ID NO: 53 is substantially weakened (e.g., reduced by at least 30%, 35%, 40%, 45%, 50%, 55%, 60%, 65%, 70%, 75%, 80%, 85%, or 90%) relative to the binding of the antibody to a protein comprising the amino acid sequence of SEQ ID NO: 42.

In another aspect the instant disclosure provides, an isolated antibody that specifically binds to human TIGIT, wherein the antibody binds to amino acid residue Q35 of human TIGIT, numbered according to the amino acid sequence of SEQ ID NO: 40.

In another aspect the instant disclosure provides, an isolated antibody that specifically binds to human TIGIT, wherein the binding between the antibody and a protein comprising the amino acid sequence of SEQ ID NO: 44 is substantially weakened (e.g., reduced by at least 30%, 35%, 40%, 45%, 50%, 55%, 60%, 65%, 70%, 75%, 80%, 85%, or 90%) relative to the binding of the antibody to a protein comprising the amino acid sequence of SEQ ID NO: 42.

In another aspect the instant disclosure provides, an isolated antibody that specifically binds to human TIGIT, wherein the antibody binds to amino acid residue I47 of human TIGIT, numbered according to the amino acid sequence of SEQ ID NO: 40.

In another aspect the instant disclosure provides, an isolated antibody that specifically binds to human TIGIT, wherein the binding between the antibody and a protein comprising the amino acid sequence of SEQ ID NO: 45 is substantially weakened (e.g., reduced by at least 30%, 35%, 40%, 45%, 50%, 55%, 60%, 65%, 70%, 75%, 80%, 85%, or 90%) relative to the binding of the antibody to a protein comprising the amino acid sequence of SEQ ID NO: 42.

In another aspect the instant disclosure provides, an isolated antibody that specifically binds to human TIGIT, wherein the antibody binds to amino acid residue N49 of human TIGIT, numbered according to the amino acid sequence of SEQ ID NO: 40.

In another aspect the instant disclosure provides, an isolated antibody that specifically binds to human TIGIT, wherein the binding between the antibody and a protein comprising the amino acid sequence of SEQ ID NO: 46 is substantially weakened (e.g., reduced by at least 30%, 35%, 40%, 45%, 50%, 55%, 60%, 65%, 70%, 75%, 80%, 85%, or 90%) relative to the binding of the antibody to a protein comprising the amino acid sequence of SEQ ID NO: 42.

In another aspect the instant disclosure provides, an isolated antibody that specifically binds to human TIGIT, wherein the binding between the antibody and a protein comprising the amino acid sequence of SEQ ID NO: 36 is substantially weakened (e.g., reduced by at least 30%, 35%, 40%, 45%, 50%, 55%, 60%, 65%, 70%, 75%, 80%, 85%, or 90%) relative to the binding of the antibody to a protein comprising the amino acid sequence of SEQ ID NO: 42.

In another aspect the instant disclosure provides, an isolated antibody that specifically binds to human TIGIT, wherein the antibody binds to amino acid residue H90 of human TIGIT, numbered according to the amino acid sequence of SEQ ID NO: 40.

In another aspect the instant disclosure provides, an isolated antibody that specifically binds to human TIGIT, wherein the binding between the antibody and a protein comprising the amino acid sequence of SEQ ID NO: 51 is substantially weakened (e.g., reduced by at least 30%, 35%, 40%, 45%, 50%, 55%, 60%, 65%, 70%, 75%, 80%, 85%, or 90%) relative to the binding of the antibody to a protein comprising the amino acid sequence of SEQ ID NO: 42.

In another aspect the instant disclosure provides, an isolated antibody that specifically binds to human TIGIT, wherein the binding between the antibody and a protein comprising the amino acid sequence of SEQ ID NO: 57 is substantially weakened (e.g., reduced by at least 30%, 35%, 40%, 45%, 50%, 55%, 60%, 65%, 70%, 75%, 80%, 85%, or 90%) relative to the binding of the antibody to a protein comprising the amino acid sequence of SEQ ID NO: 42.

In another aspect the instant disclosure provides, an isolated antibody that specifically binds to human TIGIT, wherein the binding between the antibody and a protein comprising the amino acid sequence of SEQ ID NO: 59 is substantially weakened (e.g., reduced by at least 30%, 35%, 40%, 45%, 50%, 55%, 60%, 65%, 70%, 75%, 80%, 85%, or 90%) relative to the binding of the antibody to a protein comprising the amino acid sequence of SEQ ID NO: 42.

In another aspect the instant disclosure provides, an isolated antibody that specifically binds to human TIGIT, wherein the binding between the antibody and a protein comprising the amino acid sequence of SEQ ID NO: 48 is substantially weakened (e.g., reduced by at least 30%, 35%, 40%, 45%, 50%, 55%, 60%, 65%, 70%, 75%, 80%, 85%, or 90%) relative to the binding of the antibody to a protein comprising the amino acid sequence of SEQ ID NO: 42.

In another aspect the instant disclosure provides, an isolated antibody that specifically binds to human TIGIT, wherein the antibody does not bind to one or more of the amino acid residues selected from the group consisting of T34, L52, H55, I56, S57, P58, S59, T98, R100, and F102 of human TIGIT, numbered according to the amino acid sequence of SEQ ID NO: 40.

In another aspect the instant disclosure provides, an isolated antibody that specifically binds to human TIGIT, wherein the antibody does not bind to amino acid residue T34 of human TIGIT, numbered according to the amino acid sequence of SEQ ID NO: 40.

In another aspect the instant disclosure provides, an isolated antibody that specifically binds to human TIGIT, wherein the binding of the antibody to a protein comprising the amino acid sequence of SEQ ID NO: 43 is not substantially weakened (e.g., not reduced by more than 30%, 35%, 40%, 45%, 50%, 55%, 60%, 65%, 70%, 75%, 80%, 85%, or 90%) relative to the binding of the antibody to a protein comprising the amino acid sequence of SEQ ID NO: 42.

In another aspect the instant disclosure provides, an isolated antibody that specifically binds to human TIGIT, wherein the antibody does not bind to amino acid residue L52 of human TIGIT, numbered according to the amino acid sequence of SEQ ID NO: 40.

In another aspect the instant disclosure provides, an isolated antibody that specifically binds to human TIGIT, wherein the binding of the antibody to a protein comprising the amino acid sequence of SEQ ID NO: 47 is not substantially weakened (e.g., not reduced by more than 30%, 35%, 40%, 45%, 50%, 55%, 60%, 65%, 70%, 75%, 80%, 85%, or 90%) relative to the binding of the antibody to a protein comprising the amino acid sequence of SEQ ID NO: 42.

In another aspect the instant disclosure provides, an isolated antibody that specifically binds to human TIGIT, wherein the antibody does not bind to amino acid residue H55 of human TIGIT, numbered according to the amino acid sequence of SEQ ID NO: 40.

In another aspect the instant disclosure provides, an isolated antibody that specifically binds to human TIGIT, wherein the binding of the antibody to a protein comprising the amino acid sequence of SEQ ID NO: 49 is not substantially weakened (e.g., not reduced by more than 30%, 35%, 40%, 45%, 50%, 55%, 60%, 65%, 70%, 75%, 80%, 85%, or 90%) relative to the binding of the antibody to a protein comprising the amino acid sequence of SEQ ID NO: 42.

In another aspect the instant disclosure provides, an isolated antibody that specifically binds to human TIGIT, wherein the antibody does not bind to amino acid residue I56 of human TIGIT, numbered according to the amino acid sequence of SEQ ID NO: 40.

In another aspect the instant disclosure provides, an isolated antibody that specifically binds to human TIGIT, wherein the antibody does not bind to amino acid residue S57 of human TIGIT, numbered according to the amino acid sequence of SEQ ID NO: 40.

In another aspect the instant disclosure provides, an isolated antibody that specifically binds to human TIGIT, wherein the antibody does not bind to amino acid residue P58 of human TIGIT, numbered according to the amino acid sequence of SEQ ID NO: 40.

In another aspect the instant disclosure provides, an isolated antibody that specifically binds to human TIGIT, wherein the antibody does not bind to amino acid residue S59 of human TIGIT, numbered according to the amino acid sequence of SEQ ID NO: 40.

In another aspect the instant disclosure provides, an isolated antibody that specifically binds to human TIGIT, wherein the binding of the antibody to a protein comprising the amino acid sequence of SEQ ID NO: 58 is not substantially weakened (e.g., not reduced by more than 30%, 35%, 40%, 45%, 50%, 55%, 60%, 65%, 70%, 75%, 80%, 85%, or 90%) relative to the binding of the antibody to a protein comprising the amino acid sequence of SEQ ID NO: 42.

In another aspect the instant disclosure provides, an isolated antibody that specifically binds to human TIGIT, wherein the antibody does not bind to amino acid residue T98 of human TIGIT, numbered according to the amino acid sequence of SEQ ID NO: 40.

In another aspect the instant disclosure provides, an isolated antibody that specifically binds to human TIGIT, wherein the binding of the antibody to a protein comprising the amino acid sequence of SEQ ID NO: 54 is not substantially weakened (e.g., not reduced by more than 30%, 35%, 40%, 45%, 50%, 55%, 60%, 65%, 70%, 75%, 80%, 85%, or 90%) relative to the binding of the antibody to a protein comprising the amino acid sequence of SEQ ID NO: 42.

In another aspect the instant disclosure provides, an isolated antibody that specifically binds to human TIGIT, wherein the antibody does not bind to amino acid residue R100 of human TIGIT, numbered according to the amino acid sequence of SEQ ID NO: 40.

In another aspect the instant disclosure provides, an isolated antibody that specifically binds to human TIGIT, wherein the binding of the antibody to a protein comprising the amino acid sequence of SEQ ID NO: 55 is not substantially weakened (e.g., not reduced by more than 30%, 35%, 40%, 45%, 50%, 55%, 60%, 65%, 70%, 75%, 80%, 85%, or 90%) relative to the binding of the antibody to a protein comprising the amino acid sequence of SEQ ID NO: 42.

In another aspect the instant disclosure provides, an isolated antibody that specifically binds to human TIGIT, wherein the antibody does not bind to amino acid residue F102 of human TIGIT, numbered according to the amino acid sequence of SEQ ID NO: 40.

In another aspect the instant disclosure provides, an isolated antibody that specifically binds to human TIGIT, wherein the binding of the antibody to a protein comprising the amino acid sequence of SEQ ID NO: 56 is not substantially weakened (e.g., not reduced by more than 30%, 35%, 40%, 45%, 50%, 55%, 60%, 65%, 70%, 75%, 80%, 85%, or 90%) relative to the binding of the antibody to a protein comprising the amino acid sequence of SEQ ID NO: 42.

In another aspect the instant disclosure provides, an isolated antibody that specifically binds to human TIGIT, wherein the antibody does not bind to any of amino acid residues T34, L52, H55, I56, S57, P58, S59, T98, R100, and F102 of human TIGIT, numbered according to the amino acid sequence of SEQ ID NO: 40.

In certain embodiments, the antibody further comprises a heavy chain constant region selected from the group consisting of human $IgG_1$, $IgG_2$, $IgG_3$, $IgG_4$, $IgA_1$, and $IgA_2$.

In certain embodiments, the antibody comprises an $IgG_1$ heavy chain constant region.

In certain embodiments, the antibody comprises a heavy chain constant region comprising the amino acid sequence of SEQ ID NO: 19. In certain embodiments, the amino acid sequence of the $IgG_1$ heavy chain constant region comprises an N297A mutation, numbered according to the EU numbering system. In certain embodiments, the antibody comprises a heavy chain constant region comprising the amino acid sequence of SEQ ID NO: 20.

In certain embodiments, the amino acid sequence of the $IgG_1$ heavy chain constant region comprises L234F, L235F, and N297A mutations, numbered according to the EU numbering system. In certain embodiments, the antibody comprises a heavy chain constant region comprising the amino acid sequence of SEQ ID NO: 21.

In certain embodiments, the amino acid sequence of the $IgG_1$ heavy chain constant region comprises S239D and I332E mutations, numbered according to the EU numbering system. In certain embodiments, the antibody comprises a heavy chain constant region comprising the amino acid sequence of SEQ ID NO: 22.

In certain embodiments, the amino acid sequence of the $IgG_1$ heavy chain constant region comprises S239D, A330L, and I332E mutations, numbered according to the EU numbering system. In certain embodiments, the antibody comprises a heavy chain constant region comprising the amino acid sequence of SEQ ID NO: 23.

In certain embodiments, the amino acid sequence of the $IgG_1$ heavy chain constant region comprises L235V, F243L, R292P, Y300L, and P396L mutations, numbered according to the EU numbering system. In certain embodiments, the antibody comprises a heavy chain constant region comprising the amino acid sequence of SEQ ID NO: 24.

In certain embodiments, the $IgG_1$ heavy chain constant region is afucosylated.

In certain embodiments, the amino acid sequence of the $IgG_1$ heavy chain constant region comprises S267E and L328F mutations, numbered according to the EU numbering system. In certain embodiments, the antibody comprises a heavy chain constant region comprising the amino acid sequence of SEQ ID NO: 25.

In certain embodiments, the increase of FcγRIIIA and/or FcγRIIA activity in a first cytotoxic cell contacted with the antibody is greater than the increase of FcγRIIIA and/or FcγRIIA activity in a second cytotoxic cell contacted with a reference antibody comprising the same heavy chain variable region as the antibody, and a heavy chain constant region comprising the amino acid sequence of SEQ ID NO: 19. In certain embodiments, the cytotoxic cell is a natural killer cell.

In certain embodiments, the antibody comprises an $IgG_4$ heavy chain constant region. In certain embodiments, the amino acid sequence of the $IgG_4$ heavy chain constant region comprises an S228P mutation, numbered according to the EU numbering system.

In certain embodiments, the antibody comprises a heavy chain constant region comprising the amino acid sequence of SEQ ID NO: 26. In certain embodiments, the antibody comprises a light chain constant region comprising the amino acid sequence of SEQ ID NO: 28.

In another aspect, the instant disclosure provides an isolated antibody that specifically binds to human TIGIT, the antibody comprising:

(a) a heavy chain comprising an amino acid sequence selected from the group consisting of SEQ ID NOs: 11-18; and/or (b) a light chain comprising the amino acid sequence of SEQ ID NO: 27.

In certain embodiments, the amino acid sequence of the heavy chain consists of an amino acid sequence selected from the group consisting of SEQ ID NOs: 11-18; and/or the amino acid sequence of the light chain consists of the amino acid sequence of SEQ ID NO: 27.

In certain embodiments, the antibody is a human antibody. In certain embodiments, the antibody is a bispecific antibody. In certain embodiments, the antibody is antagonistic to human TIGIT.

In certain embodiments, the antibody preferentially kills regulatory T cells over effector T cells in a population of peripheral blood mononuclear cells (PBMCs) in vitro. In certain embodiments, the antibody decreases or inhibits binding of human TIGIT to PVR or PVRL2 relative to the level of binding in the absence of the antibody. In certain embodiments, the antibody induces IL-2 and/or IFNγ production by PBMCs stimulated with staphylococcal enterotoxin A (SEA).

In certain embodiments, the antibody is conjugated to a cytotoxic agent, cytostatic agent, toxin, radionuclide, or detectable label. In certain embodiments, the antibody is cross-linked to a second antibody or a fragment thereof.

In another aspect, the instant disclosure provides an isolated antigen-binding fragment of the antibody disclosed herein, wherein the antigen-binding fragment specifically binds to human TIGIT.

In another aspect, the instant disclosure provides a pharmaceutical composition comprising an antibody or antigen-binding fragment as disclosed herein, and a pharmaceutically acceptable carrier or excipient.

In another aspect, the instant disclosure provides an isolated polynucleotide encoding a heavy chain and/or light chain of the antibody or antigen-binding fragment as disclosed herein.

In another aspect, the instant disclosure provides a vector comprising a polynucleotide as disclosed herein.

In another aspect, the instant disclosure provides a recombinant host cell comprising a polynucleotide or vector as disclosed herein.

In another aspect, the instant disclosure provides a method of producing an antibody that specifically binds to human TIGIT, or an antigen-binding fragment thereof, the method comprising culturing a host cell as disclosed herein such that the polynucleotide is expressed and the antibody, or antigen-binding fragment, is produced.

In another aspect, the instant disclosure provides a method of increasing T cell activation in response to an antigen in a subject, the method comprising administering to the subject an effective amount of an antibody, antigen-binding fragment, or pharmaceutical composition as disclosed herein. In another aspect, the instant disclosure provides a method of decreasing or inhibiting Treg activity in response to an antigen in a subject, the method comprising administering to the subject an effective amount of an antibody, antigen-binding fragment, or pharmaceutical composition as disclosed herein. In another aspect, the instant disclosure provides a method of increasing NK cell activation in response to an antigen in a subject, the method comprising administering to the subject an effective amount of an antibody, antigen-binding fragment, or pharmaceutical composition as disclosed herein. In another aspect, the instant disclosure provides a method of treating cancer in a subject, the method comprising administering to the subject an effective amount of an antibody, antigen-binding fragment, or pharmaceutical composition as disclosed herein.

In certain embodiments, the antibody, antigen-binding fragment, or pharmaceutical composition is administered intravenously. In certain embodiments, the antibody, antigen-binding fragment, or pharmaceutical composition is administered intravenously at 0.1 mg/kg, 0.3 mg/kg, 1 mg/kg, 3 mg/kg, 6 mg/kg, 10 mg/kg, 15 mg/kg, 20 mg/kg, or more, optionally at an interval of once every three weeks.

In certain embodiments, the antibody, antigen-binding fragment, or pharmaceutical composition is administered intratumorally. In certain embodiments, the antibody, antigen-binding fragment, or pharmaceutical composition is administered intratumorally at 0.03 mg/kg, 0.1 mg/kg, 0.3 mg/kg, 1 mg/kg, 3 mg/kg, 6 mg/kg, 10 mg/kg, 15 mg/kg, 20 mg/kg, or more, optionally at an interval of once every three weeks.

In certain embodiments, the antibody, antigen-binding fragment, or pharmaceutical composition is administered subcutaneously. In certain embodiments, the antibody, antigen-binding fragment, or pharmaceutical composition is delivered to a tumor draining lymph node.

In certain embodiments, a method disclosed herein further comprises administering an additional therapeutic agent to the subject. In certain embodiments, the additional therapeutic agent is administered systemically.

In certain embodiments, the subject has a solid tumor and the additional therapeutic agent comprises an anti-PD-1 antibody, optionally wherein the anti-PD-1 antibody is pembrolizumab or nivolumab.

In certain embodiments, the subject has head and neck squamous cell carcinoma and wherein the additional therapeutic agent is an anti-EGFR antibody, optionally wherein the anti-EGFR antibody is cetuximab, optionally wherein the method further comprises administering a chemotherapeutic agent to the subject, optionally wherein the chemotherapeutic agent is administered systemically, and optionally wherein the chemotherapeutic agent is gemcitabine.

In certain embodiments, the subject has HER2+ breast cancer and wherein the additional therapeutic agent is an anti-HER2 antibody, optionally wherein the anti-HER2 antibody is trastuzumab, optionally wherein the method further comprises administering a chemotherapeutic agent to the subject, optionally wherein the chemotherapeutic agent is administered systemically, optionally wherein the chemotherapeutic agent is gemcitabine.

In certain embodiments, the additional therapeutic agent is a chemotherapeutic or a checkpoint targeting agent. In certain embodiments, the checkpoint targeting agent is selected from the group consisting of an antagonist anti-PD-1 antibody, an antagonist anti-PD-L1 antibody, an antagonist anti-PD-L2 antibody, an antagonist anti-CTLA-4 antibody, an antagonist anti-TIM-3 antibody, an antagonist anti-LAG-3 antibody, an antagonist VISTA antibody, an antagonist CD96 antibody, an antagonist anti-CEACAM1 antibody, an agonist anti-CD137 antibody, an agonist anti-GITR antibody, and an agonist anti-OX40 antibody.

In certain embodiments, the additional therapeutic agent is an inhibitor of indoleamine-2,3-dioxygenase (IDO). In certain embodiments, the inhibitor is selected from the group consisting of epacadostat, F001287, indoximod, and NLG919.

In certain embodiments, the additional therapeutic agent is a vaccine. In certain embodiments, the vaccine comprises a heat shock protein peptide complex (HSPPC) comprising a heat shock protein complexed with an antigenic peptide. In certain embodiments, the heat shock protein is hsc70 and is complexed with a tumor-associated antigenic peptide. In certain embodiments, the heat shock protein is gp96 protein and is complexed with a tumor-associated antigenic peptide, wherein the HSPPC is derived from a tumor obtained from a subject.

In another aspect, the instant disclosure provides a method of treating an infectious disease in a subject, the method comprising administering to the subject an effective amount of an antibody, antigen-binding fragment, or pharmaceutical composition as disclosed herein.

4. BRIEF DESCRIPTION OF THE DRAWINGS

FIGS. 1A-1D are a series of surface plasmon resonance (SPR) sensorgrams showing the binding of the anti-TIGIT antibody BA002 to purified TIGIT protein. FIGS. 1A, 1B and 1C show the binding of human dimeric TIGIT-Fc, cynomolgus dimeric TIGIT-Fc, and human monomeric TIGIT-His, respectively, to captured BA002. FIG. 1D shows the binding of BA002 (in Fab format) to captured human dimeric TIGIT-Fc protein. In each sensorgram, response units (RU) are plotted against time after protein injection.

FIGS. 2A-2D are a series of graphs showing the binding of the anti-TIGIT antibody BA002 or an IgG1 isotype control antibody to cells expressing cell surface human TIGIT or cynomolgus monkey TIGIT. The levels of binding of BA002 or an IgG1 isotype control antibody to Jurkat cells engineered to express human TIGIT (FIG. 2A), activated primary CD4+CD25+ T cells (FIG. 2B), activated primary CD8+CD25+ T cells (FIG. 2C), or CHO cells engineered to express cynomolgus TIGIT (FIG. 2D), as assessed by median fluorescence intensity (MFI), are plotted against the concentrations of BA002 incubated with the cells.

FIGS. 3A-3B are a series of histograms and graphs showing that BA002 exhibited no binding to TIGIT-related family members CD96 and CD226. The levels of binding of BA002 or an IgG1 isotype control antibody to Jurkat cells engineered to express human TIGIT, CD96, and CD226 (FIG. 3A) or CD96 and CD226 only (FIG. 3B), as assessed by median fluorescence intensity (MFI), are plotted against the concentrations of BA002 incubated with the cells.

FIGS. 4A-4F are a series of graphs showing that BA002 disrupted binding between TIGIT and its ligand, CD155/PVR, at levels comparable to or greater than a panel of reference anti-TIGIT antibodies.

FIGS. 5A-5F are a series of graphs showing that BA002 disrupted binding between TIGIT and its ligand, CD112/PVRL2, at levels comparable or greater than a panel of reference anti-TIGIT antibodies.

Figure 6:
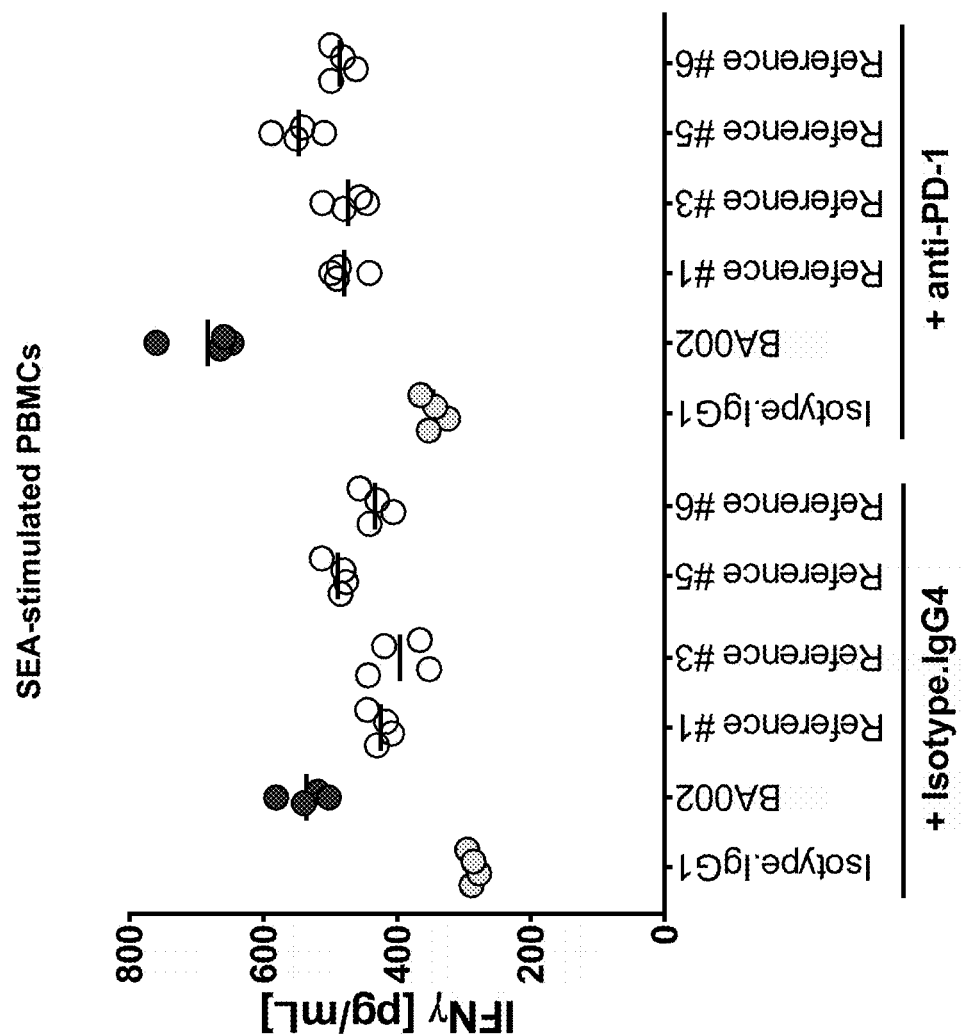

FIG. 6 is a graph showing that BA002 enhanced interferon-γ (IFNγ) secretion by SEA-stimulated PBMCs to a greater degree than reference anti-TIGIT antibodies, and that the combination of BA002 and an anti-PD-1 antibody further enhanced IFNγ secretion by SEA-stimulated PBMCs beyond that observed for BA002 alone. The degree of enhancement observed in the anti-PD-1 combination was also greater for BA002 than for the reference anti-TIGIT antibodies.

Figure 7A:
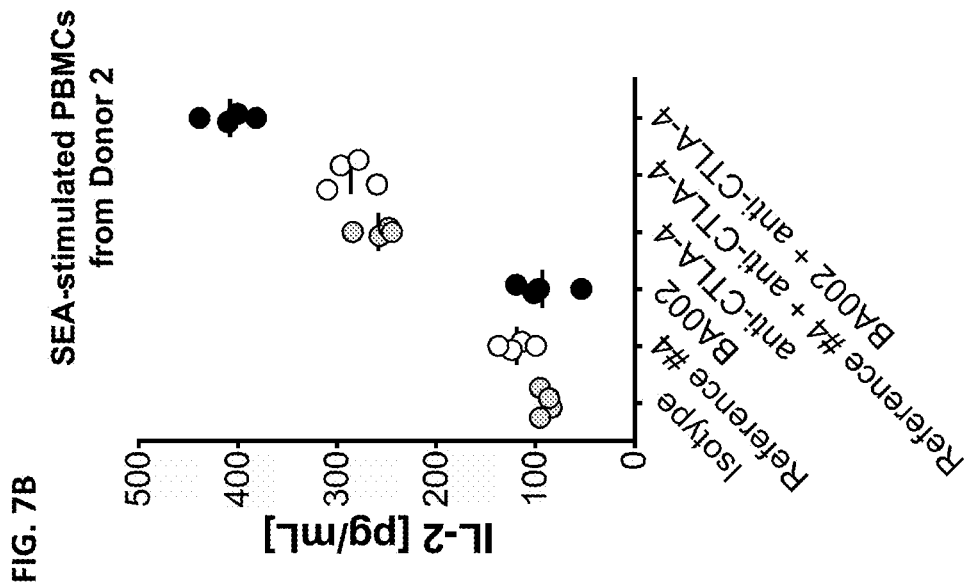
Figure 7B:
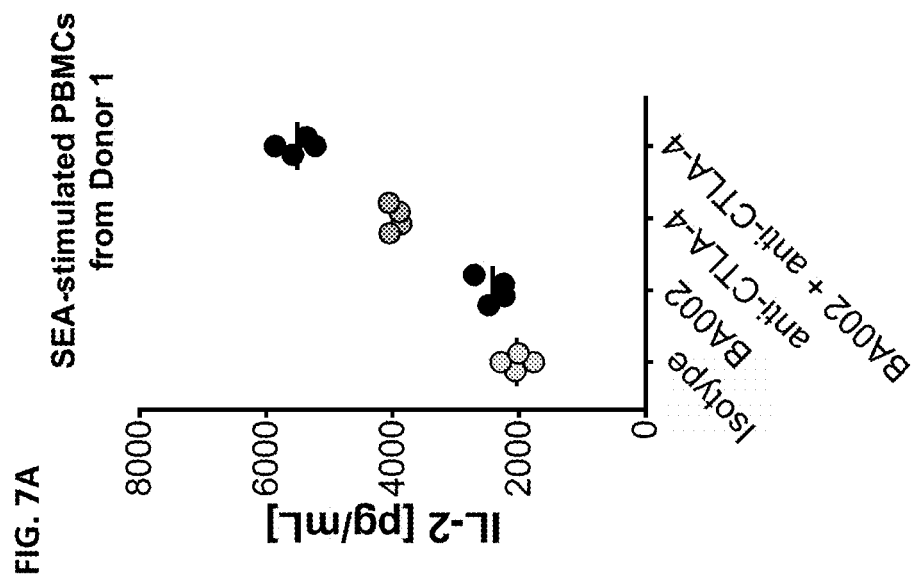

FIGS. 7A-7B are a series of graphs showing that the combination of BA002 with an anti-CTLA-4 antibody enhanced interleukin-2 (IL-2) secretion by SEA-stimulated PBMCs from two different donors, compared to isotype controls.

Figure 8B:
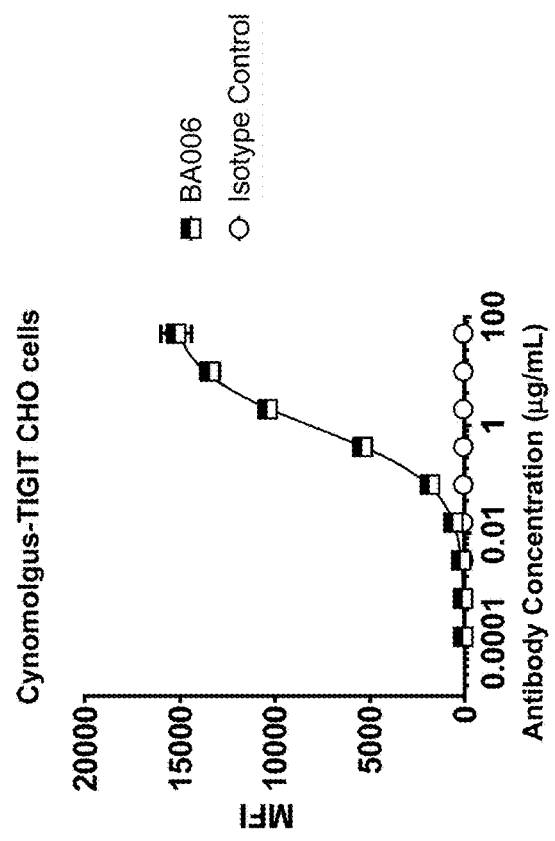
Figure 8A:
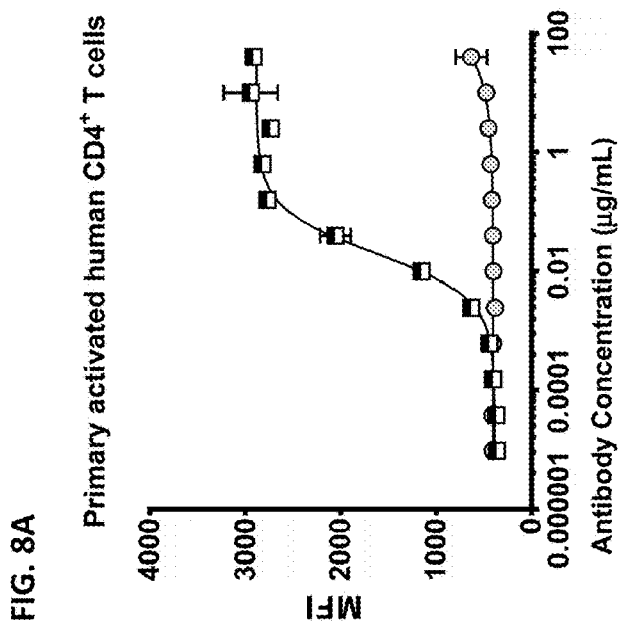
Figure 8D:
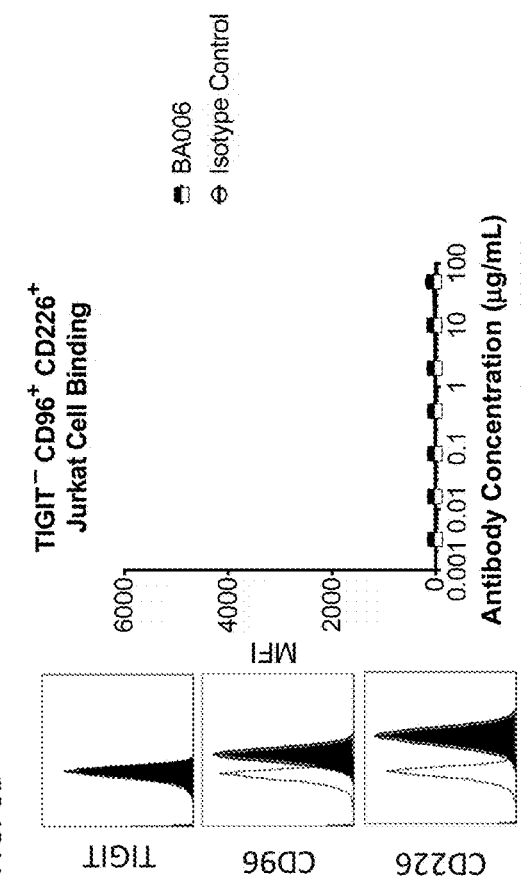
Figure 8C:
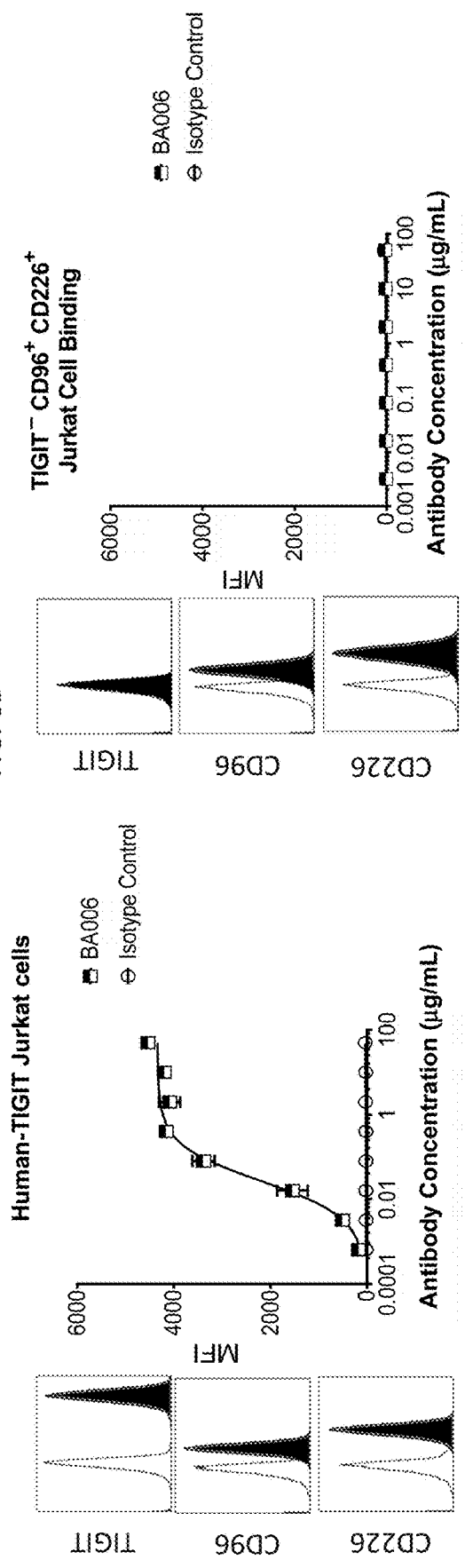

FIGS. 8A-8D are a series of graphs showing that BA006 bound to cells expressing human TIGIT and cynomolgus monkey TIGIT, and that BA006 did not bind to the related family members CD96 and CD226. BA006 bound to activated primary human CD4+ T cells (FIG. 8A) and to CHO cells engineered to express cynomolgus TIGIT (FIG. 8B). BA006 bound to Jurkat cells expressing TIGIT, CD96, and CD226 (FIG. 8C), but did not bind to Jurkat cells expressing CD96 and CD226 alone (FIG. 8D). In each graph, the median fluorescence intensity (MFI) is plotted against antibody concentration.

FIGS. 9A-9D are a series of graphs showing that Fc variants of BA002 further enhanced PBMC cytokine secretion (FIGS. 9A-9B) and T cell activation, as measured by upregulation of CD25 (FIGS. 9C-9D). The Fc variants of BA002 also showed further enhancement of cytokine secretion and T cell activation when combined with an anti-PD-1 antibody.

Figure 10A:
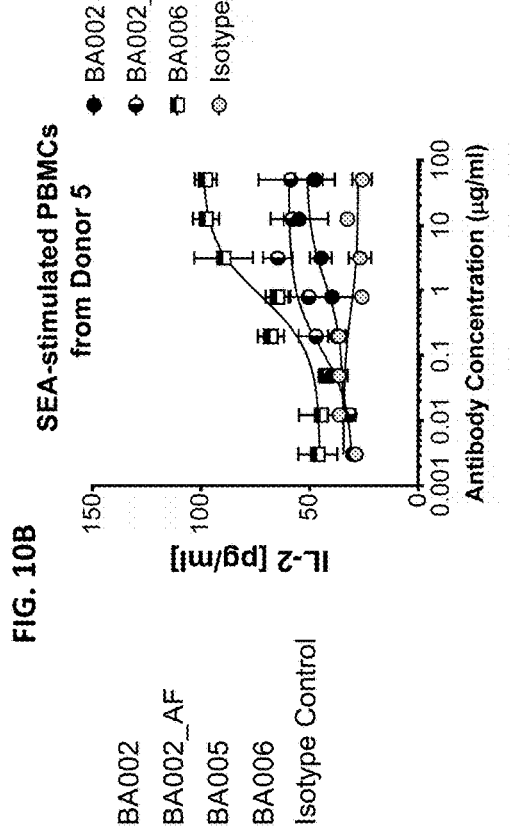
Figure 10B:
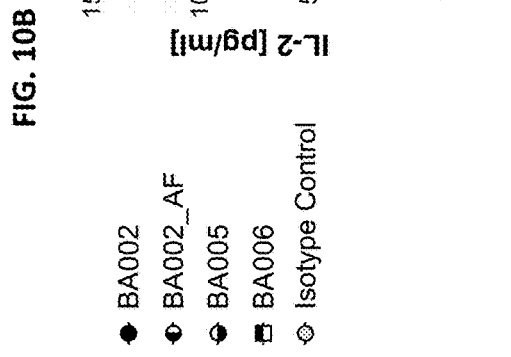
Figure 10C:
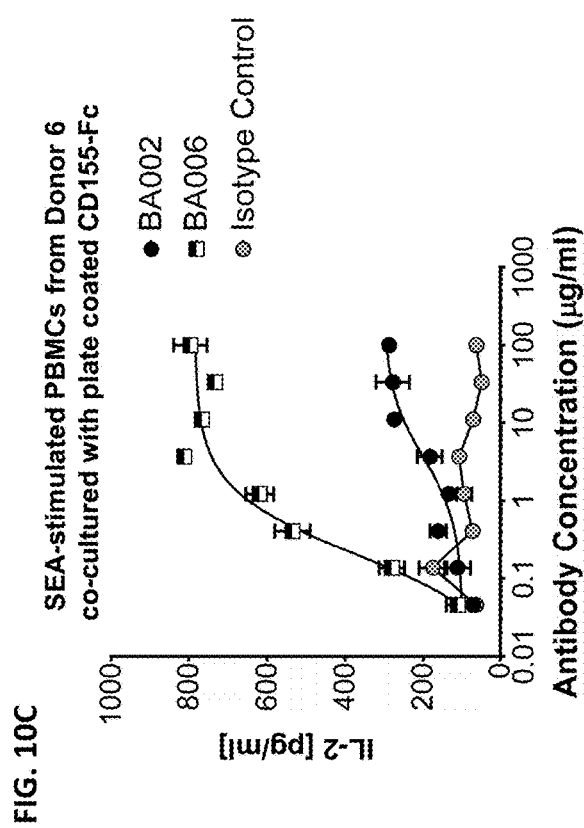
Figure 10E:
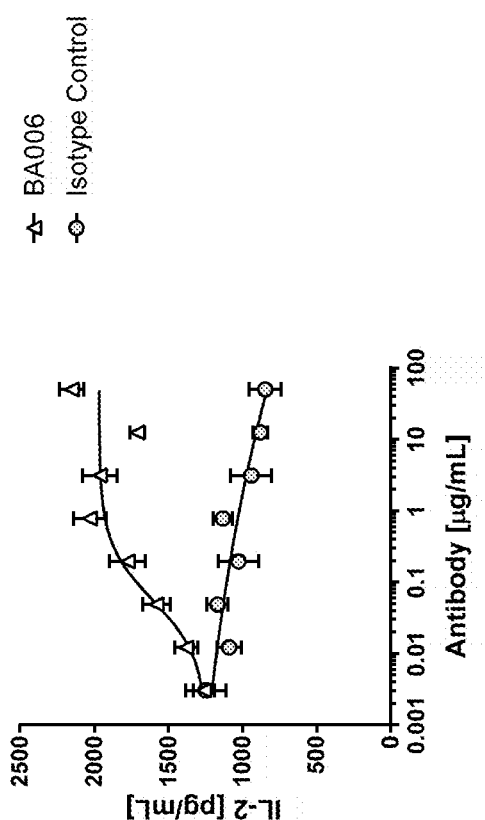
Figure 10D:
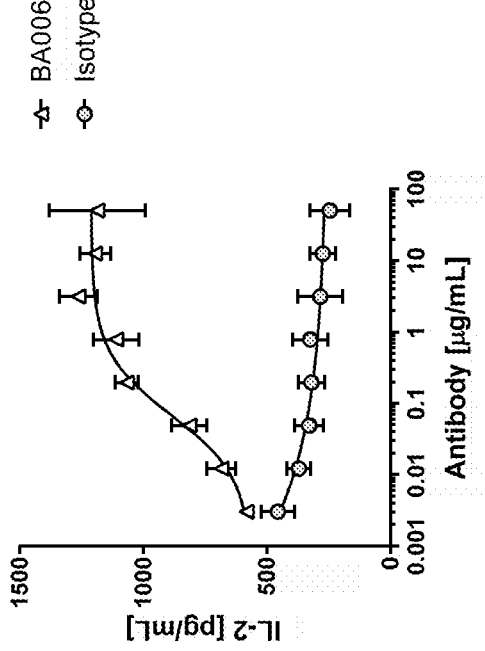

FIGS. 10A-10E are a series of graphs showing that BA002 and Fc variants thereof enhanced IL-2 secretion in SEA-stimulated PBMCs from five separate donors in a dose-dependent manner. In one donor, BA002, the Fc variants BA006 and BA005, and an afucosylated form of BA002 (BA002_AF) enhanced IL-2 secretion by SEA-stimulated PBMCs (FIG. 10A). In a second donor, the combination of BA002 or a variant thereof with an anti-PD-1 antibody also enhanced IL-2 secretion by SEA-stimulated PBMCs (FIG. 10B). BA006 and BA002 enhanced IL-2 secretion by SEA-stimulated PBMCs from a third donor in the presence of CD155-Fc (FIG. 10C). FIGS. 10D and 10E show dose-dependent activation by BA006 of PBMCs from two different donors in the presence of a low concentration (10 ng/mL) of SEA.

Figure 11A:
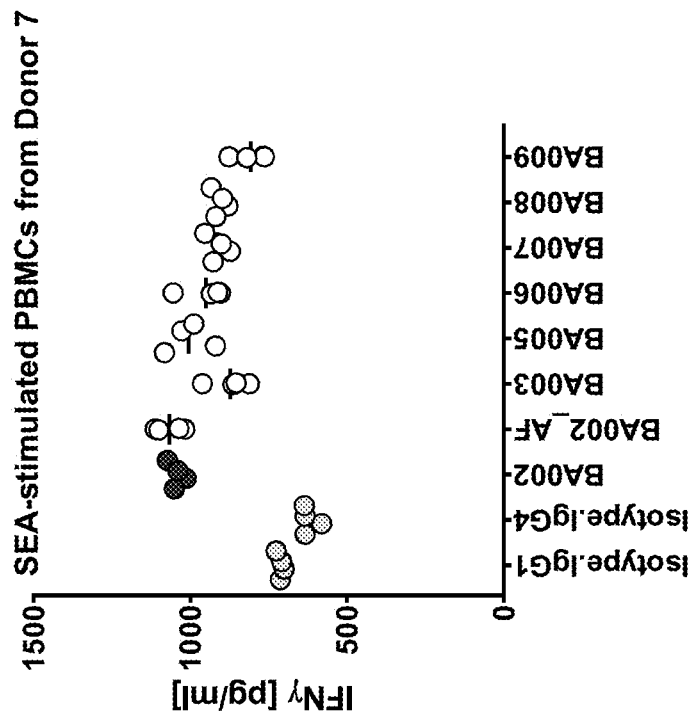
Figure 11B:
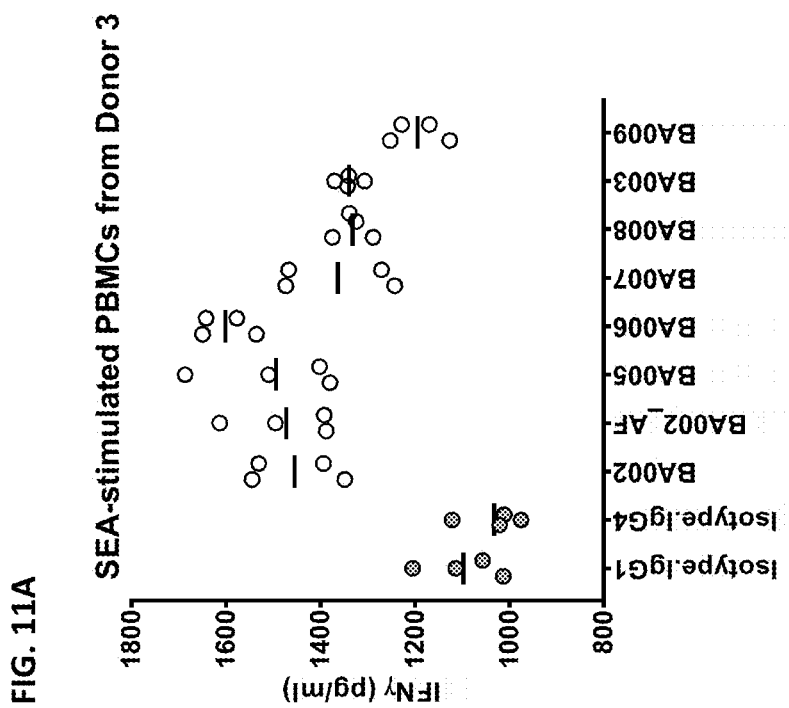

FIGS. 11A-11B are a series of graphs showing that BA002 and variants thereof enhanced IFNγ secretion by SEA-stimulated PBMCs from two different donors, relative to isotype control antibodies.

FIGS. 12A-12B are a series of graphs showing the capacity of various Fc variants of the anti-TIGIT antibody BA002 to signal through FcγRIIA (FIG. 12A) or FcγRIIIA (FIG. 12B) when co-engaged with TIGIT expressing target cells (Jurkat cells engineered to express human TIGIT). In FIG. 12A, isotype controls for BA002 (i.e., isotype 002) and each variant (i.e., isotype 003, isotype 005, isotype 006, and isotype 007) were only tested at the highest antibody concentration (i.e., 1000 ng/mL). In FIG. 12B, the isotype controls were only tested at the two highest antibody concentrations (i.e., 30 and 10 ng/mL).

Figure 13A:
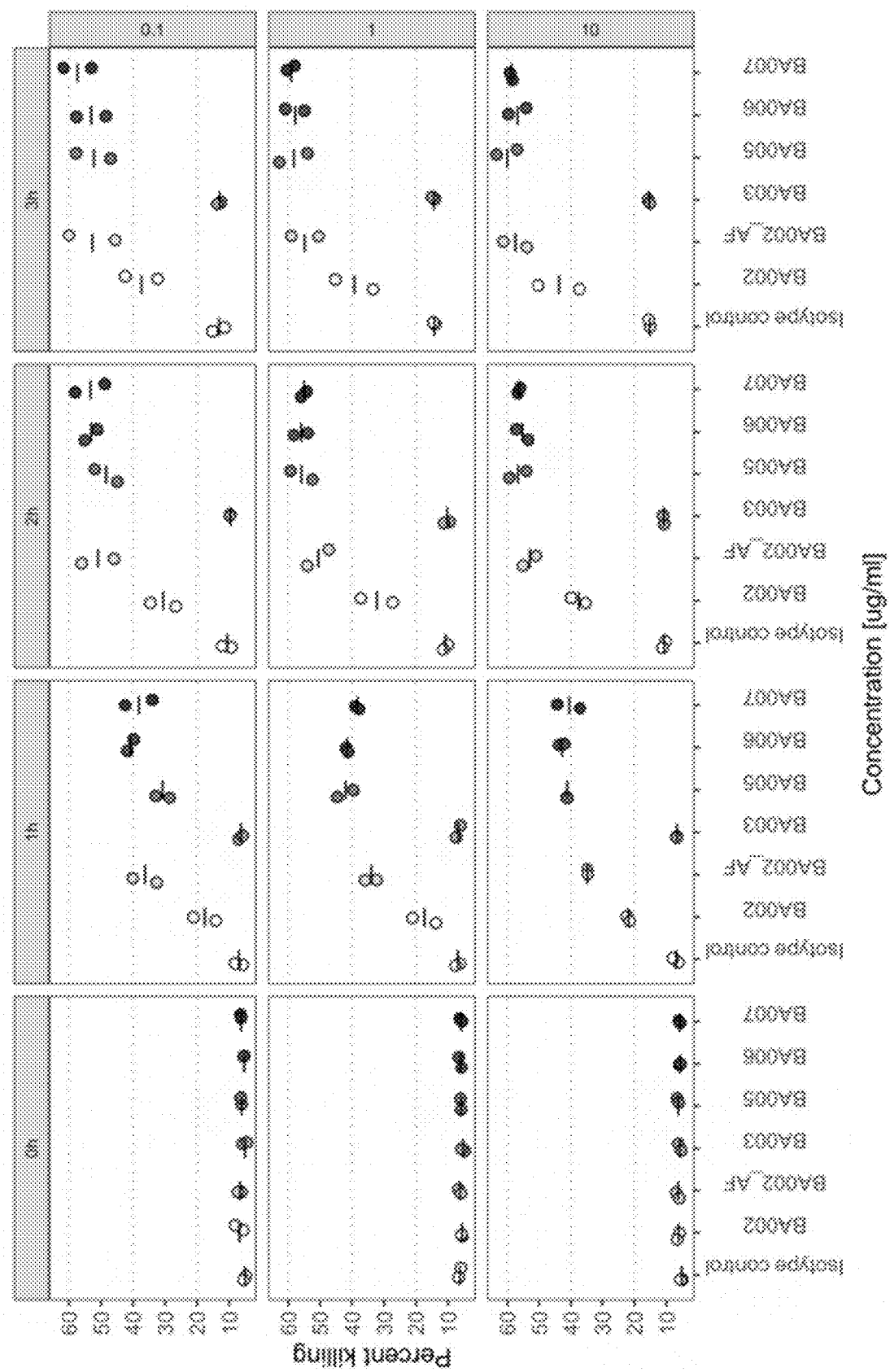
Figure 13B:
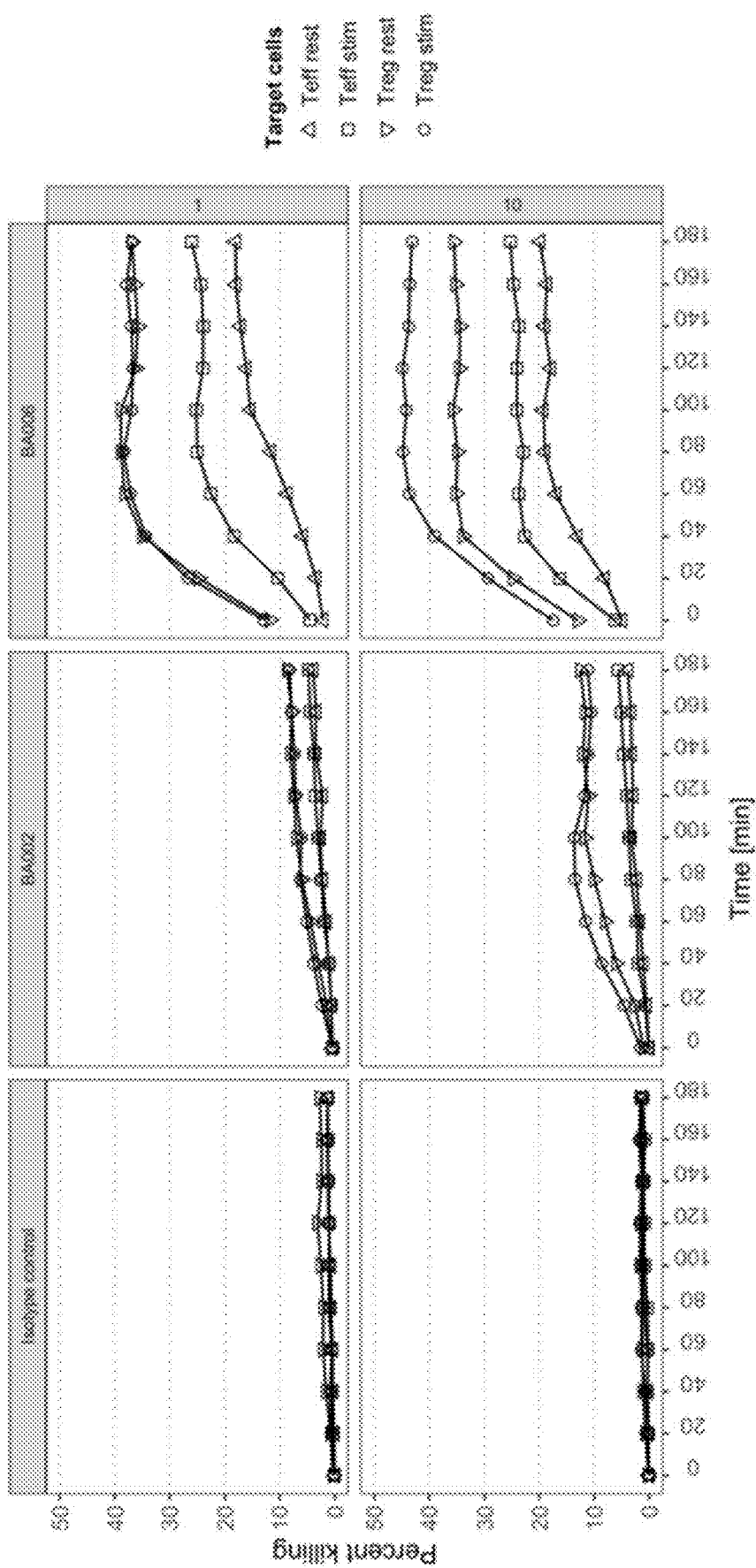

FIGS. 13A-13B are two series of graphs showing that BA002 and variants thereof promoted antibody-dependent cell-mediated cytotoxicity (ADCC) of TIGIT-expressing cells. Percent cell killing of TIGIT-expressing Jurkat cells at four time points (0 hours, 1 hour, 2 hours, and 3 hours) after incubation with antibodies at three different concentrations (0.1 μg/mL, 1 μg/mL, and 10 μg/mL) is shown in FIG. 13A. Preferential targeting of regulatory T cells by BA002 and BA006 for NK cell-mediated ADCC in a co-culture setting, as compared with activated effector T cells, is shown in FIG. 13B.

Figure 14:
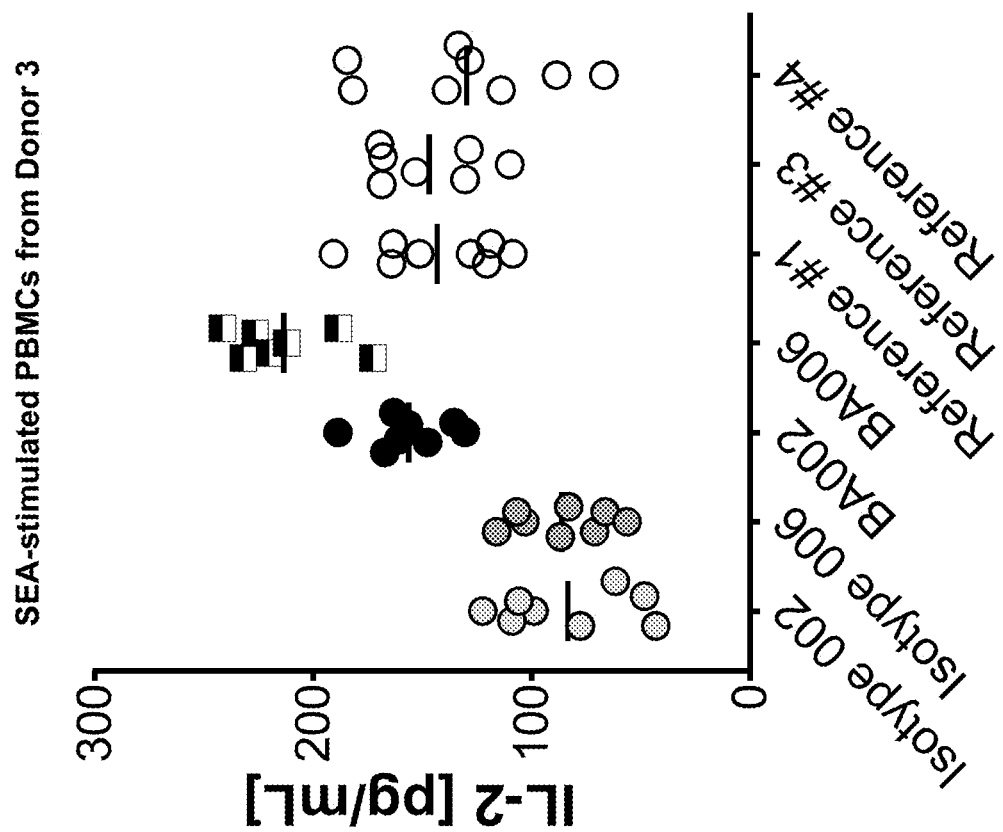

FIG. 14 is a graph showing that the anti-TIGIT antibodies BA002 and BA006 enhanced IL-2 secretion by SEA-stimulated PBMCs, with BA006 exhibiting substantially greater enhancement of IL-2 secretion than reference anti-TIGIT antibodies.

FIGS. 15A-15I are a series of graphs showing that the anti-TIGIT antibodies BA002 and BA006 can effectively combine with an antagonistic anti-PD-1 antibody (FIG. 15A), an antagonistic anti-PD-L1 antibody (FIGS. 15B and 15C), an agonistic anti-CD137 antibody (FIG. 15D), an antagonistic anti-CTLA-4 antibody (FIG. 15E), an antagonistic anti-LAG-3 antibody (FIGS. 15F and 15G), or an agonistic anti-OX40 antibody (FIGS. 15H and 15I) to promote IL-2 secretion by SEA-stimulated PBMCs.

Figure 16B:
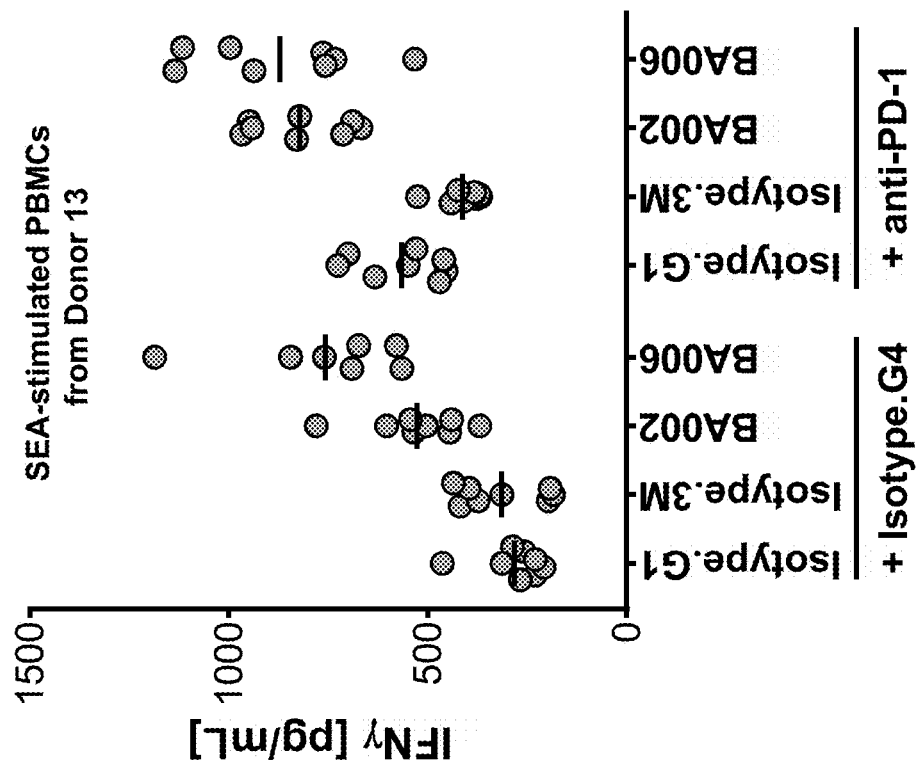
Figure 16A:
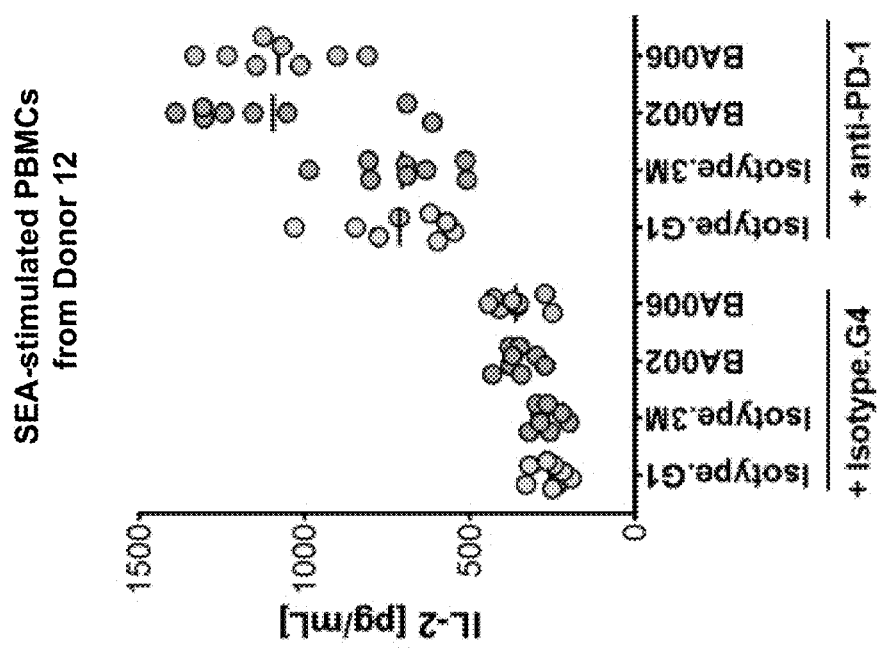

FIGS. 16A-16B are a series of graphs showing production of IL-2 (FIG. 16A) and IFNγ (FIG. 16B) from cynomolgus PBMCs after incubation with BA002 or BA006 in the presence or absence of an anti-PD-1 antibody. The isotype control antibodies for BA002 and BA006 are "Isotype.G1"

and "Isotype.3M," respectively. The isotype control antibody for the anti-PD-1 antibody is "Isotype.G4."

Figure 17A:
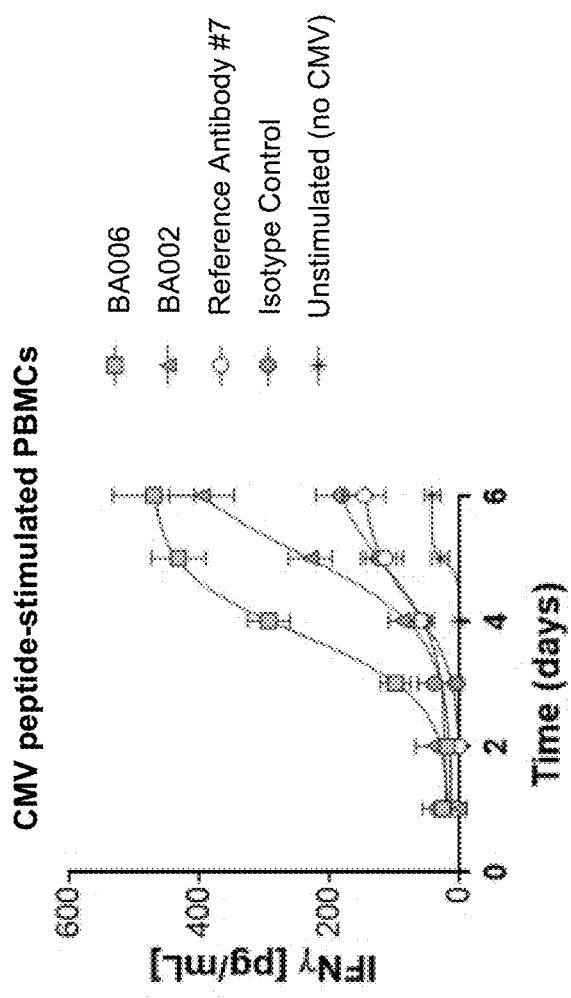
Figure 17B:
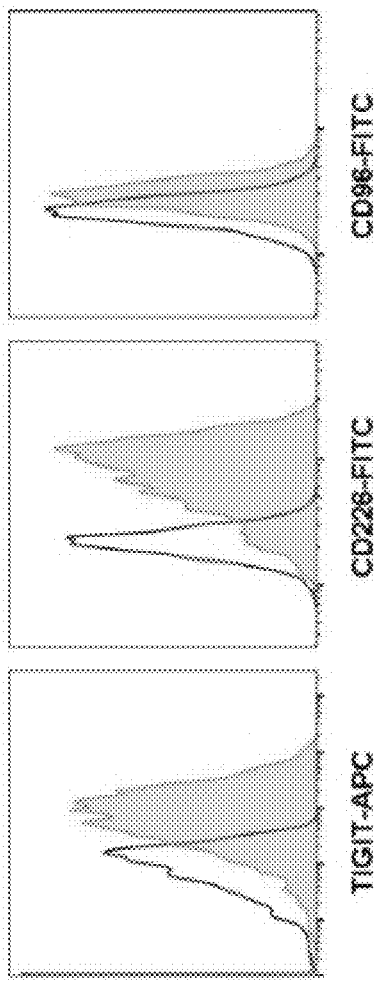
Figure 17C:
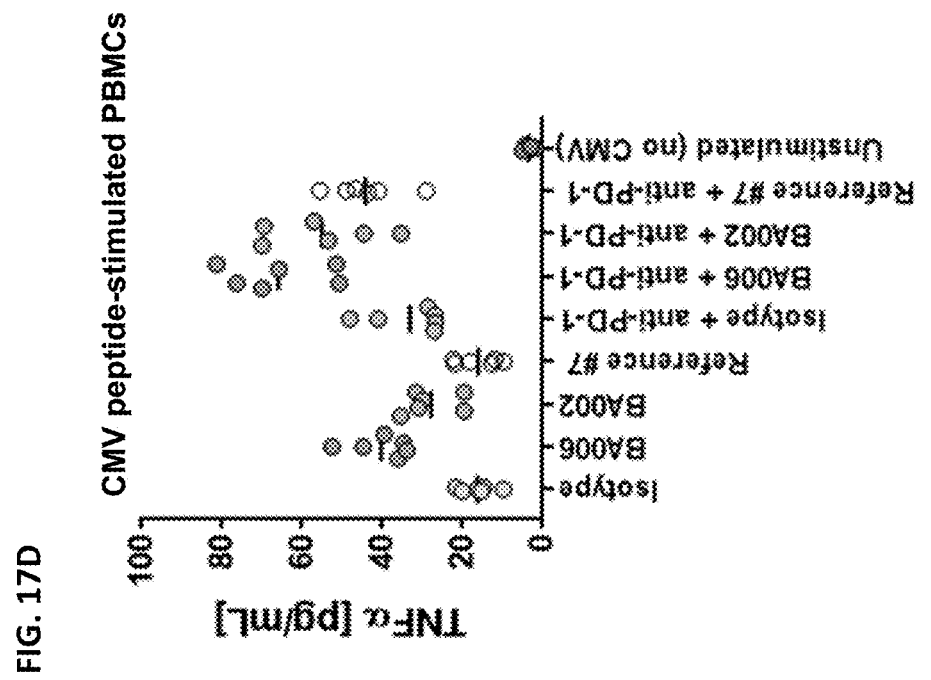
Figure 17D:
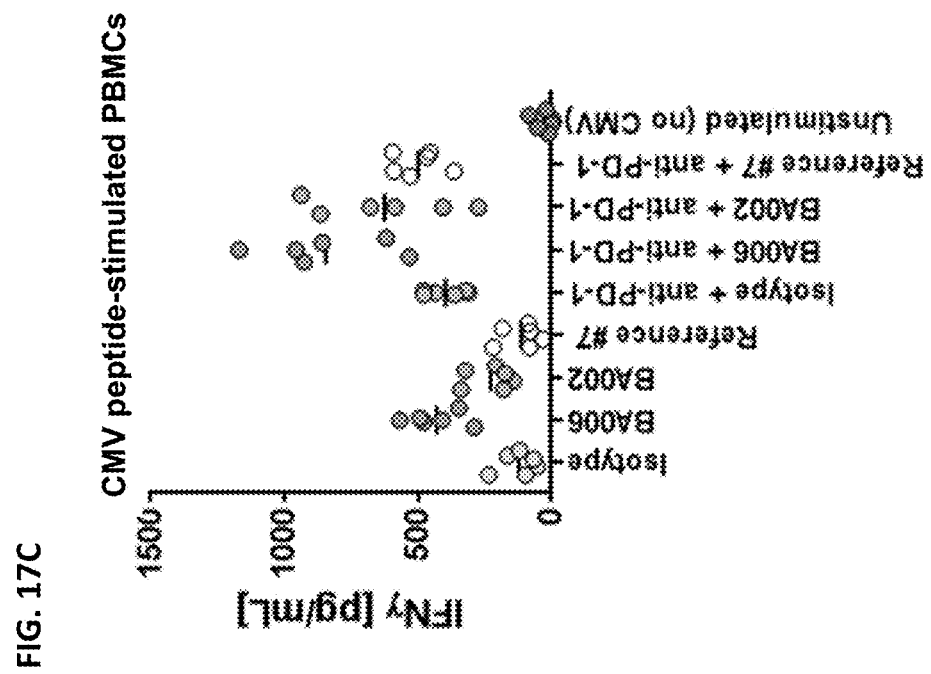
Figure 17E:
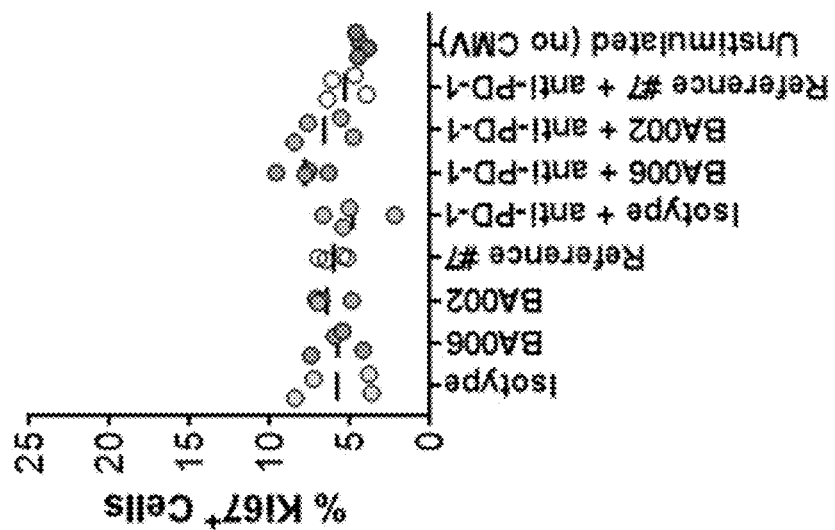
Figure 17F:
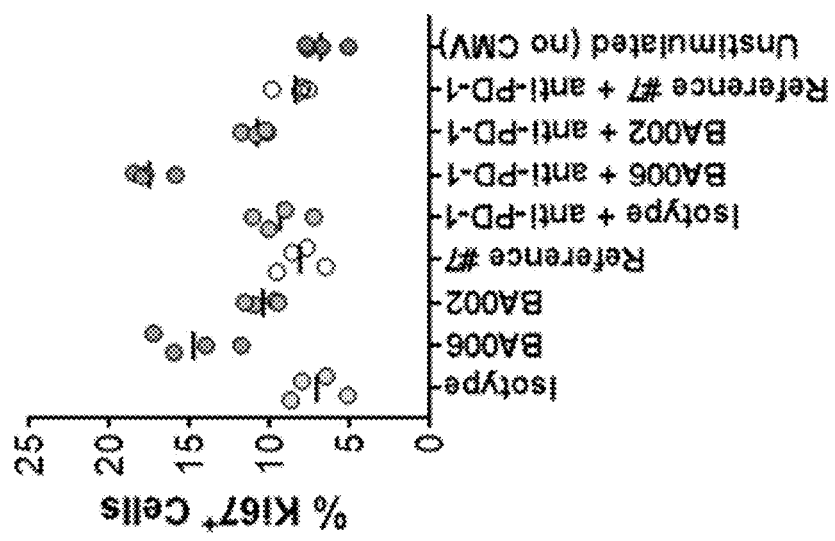

FIGS. 17A-17F are a series of graphs and histograms showing the effect of anti-TIGIT antibodies on MHC class I-mediated memory T cell recall. FIG. 17A is a graph showing interferon gamma (IFNγ) production over time by CMV-reactive PBMCs stimulated with CMV pp65 peptide and BA002 or BA006. FIG. 17B is a set of representative histograms showing the expression of TIGIT, CD226, and CD96 on activated CD8 effector memory T cells (grey area; the black lines with white fills indicate staining of cells with isotype control antibodies). FIGS. 17C and 17D show the production of IFNγ and TNFα, respectively, from the stimulated PBMCs. FIGS. 17E and 17F show the percentage of proliferating cells, as indicated by Ki67 positive staining, in the CD8 effector memory T cell population and CD4 effector memory T cell population from stimulated PBMCs.

Figure 18A:
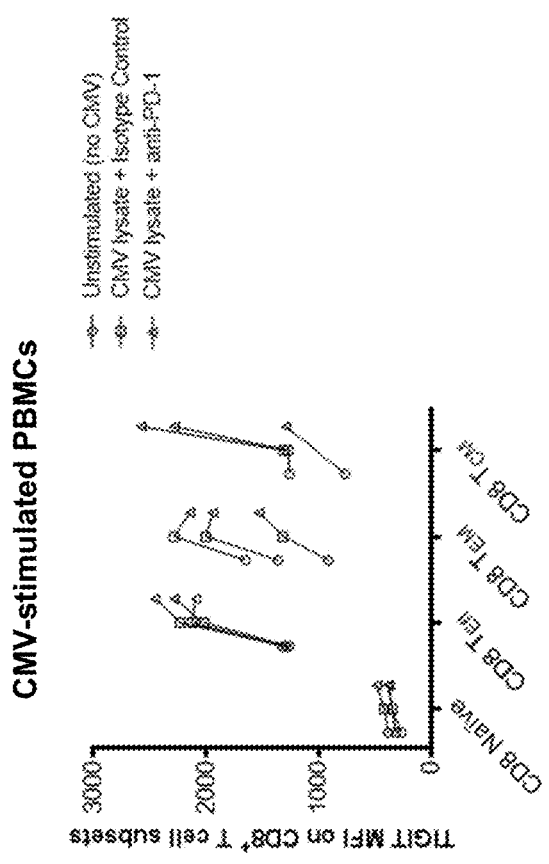
Figure 18B:
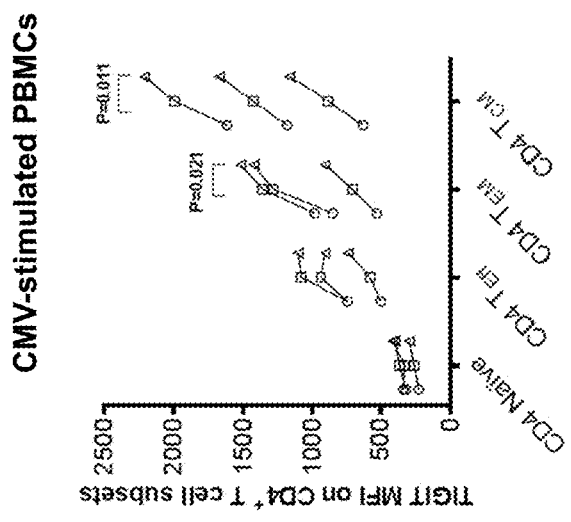
Figure 18C:
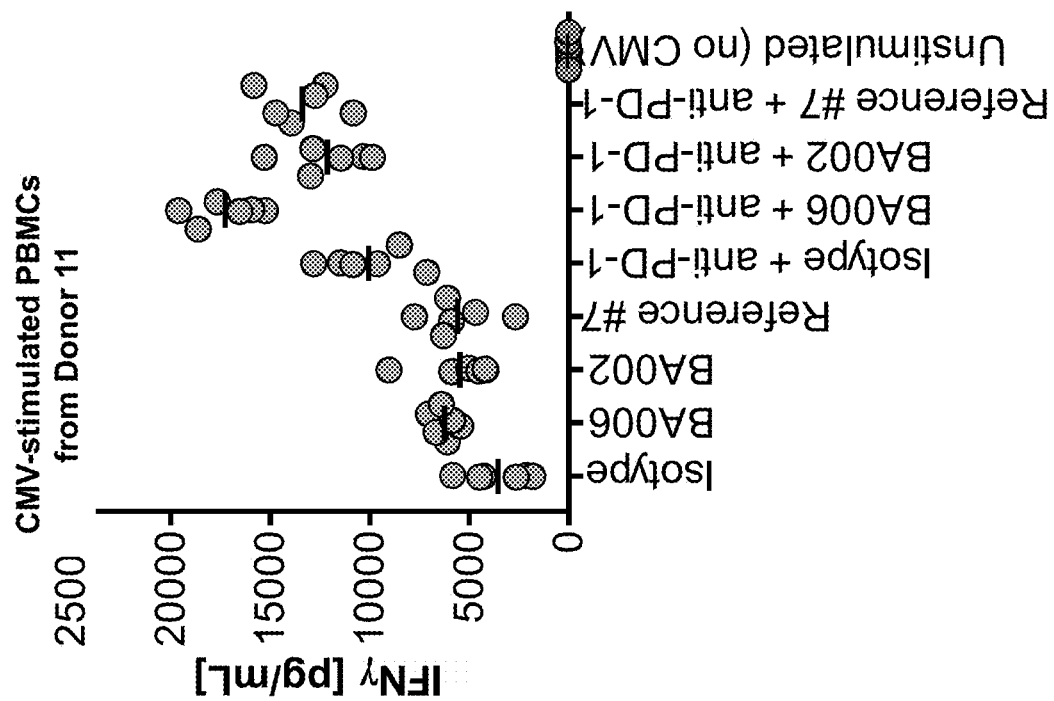
Figure 18D:
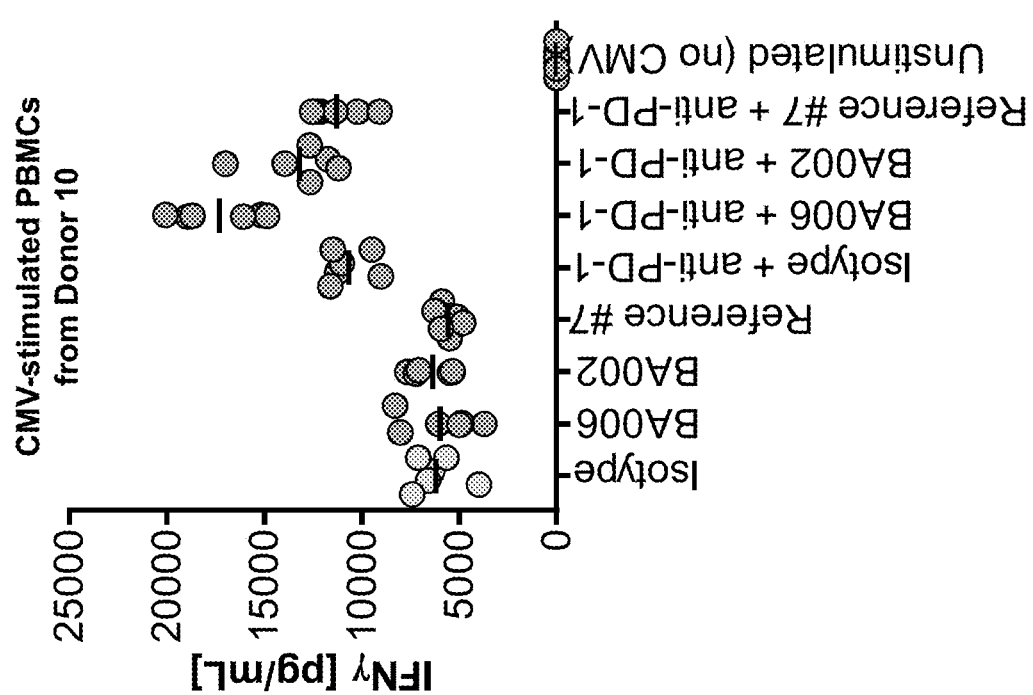

FIGS. 18A-18D are a series of graphs showing the effect of anti-TIGIT antibodies on MHC class II-mediated memory T cell recall. FIGS. 18A and 18B are representative graphs from three CMV seropositive donors showing the levels of TIGIT expression on subsets of CD4 T cells and CD8 T cells from CMV-reactive PBMCs stimulated with CMV whole antigen, which were known to be primarily processed and presented on MHC class II. FIGS. 18C and 18D show the production of IFNγ by PBMCs from two different donors in the presence or absence of BA002, BA006, an anti-TIGIT reference antibody, and/or an anti-PD-1 antibody.

Figure 19:
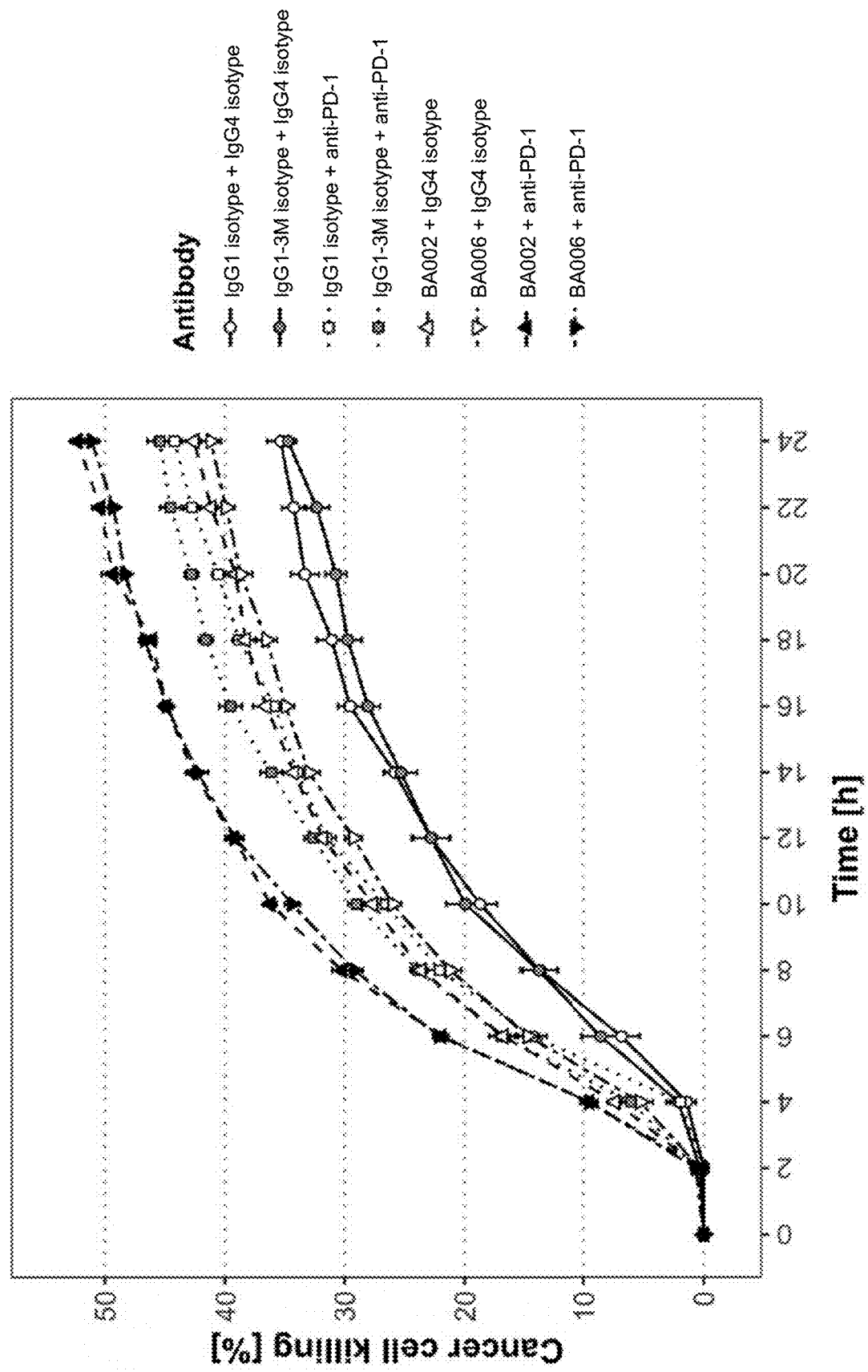

FIG. 19 is a graph showing the percentage of killing of NY-ESO-1 expressing tumor cells over time by co-cultured primary human T cells expressing a NY-ESO-1 TCR in the presence or absence of BA002 or its isotype control antibody ("IgG1 isotype"), BA006 or its isotype control antibody ("IgG1-3M isotype"), or an anti-PD-1 antibody or its isotype control antibody ("IgG4 isotype"), either alone or in combination, as measured by live cell imaging, relative to the number of the tumor cells at the time of addition of the T cells.

Figure 20A:
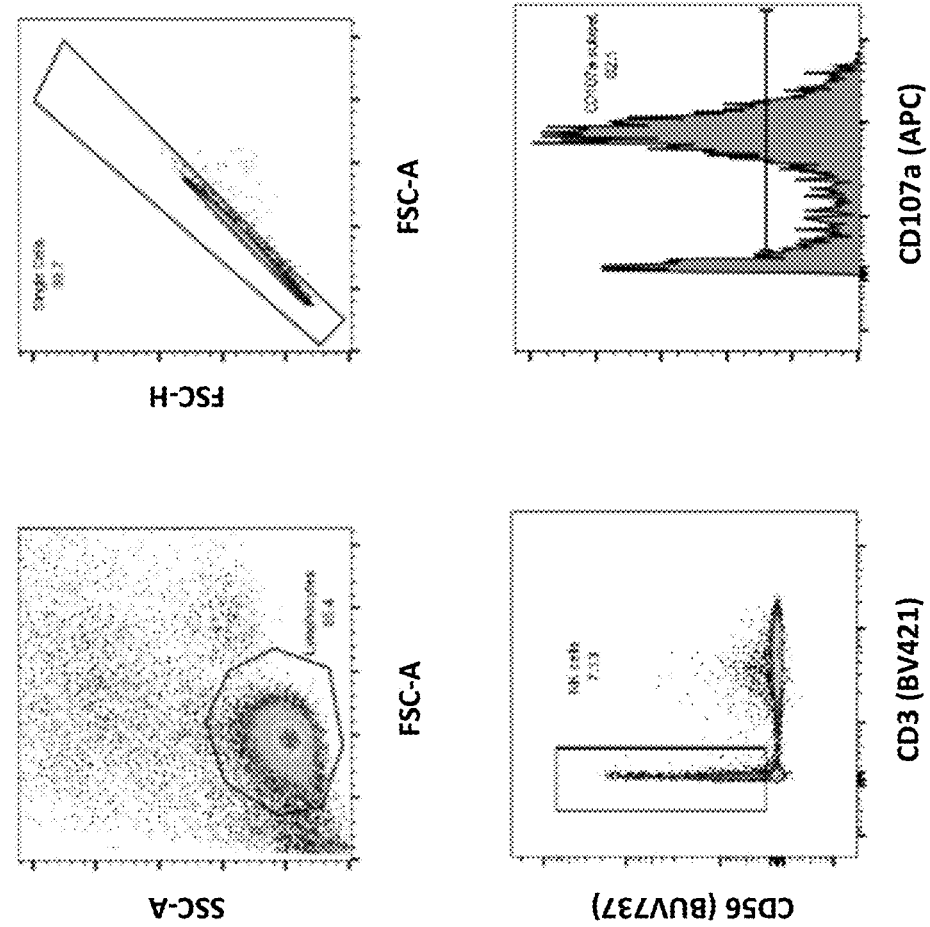
Figure 20D:
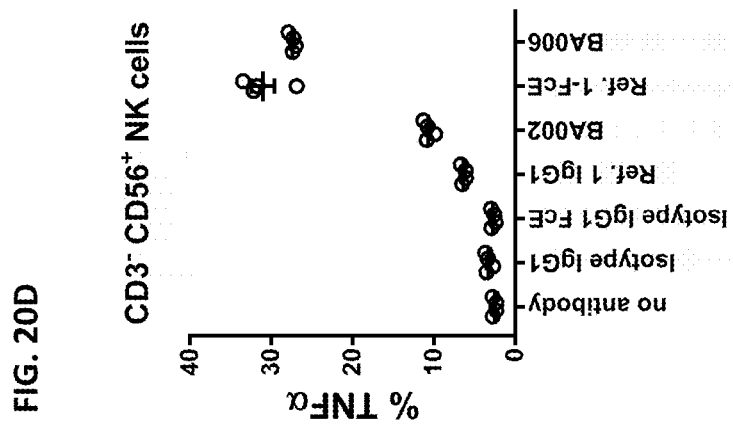
Figure 20C:
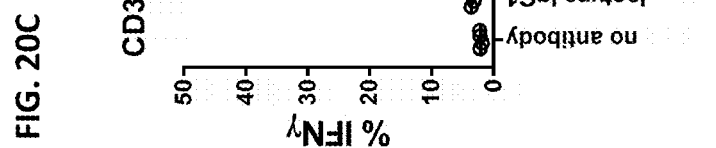
Figure 20B:
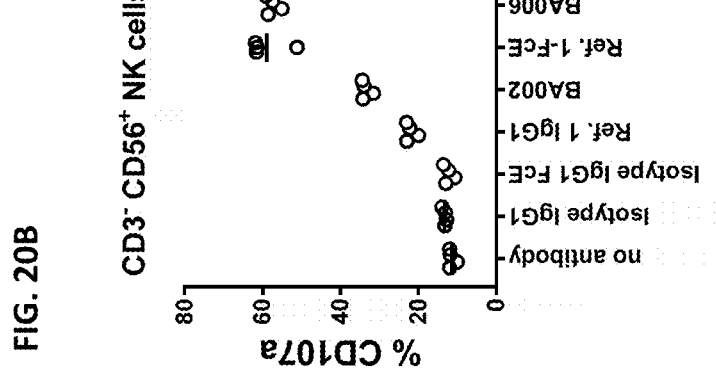
Figure 20E:
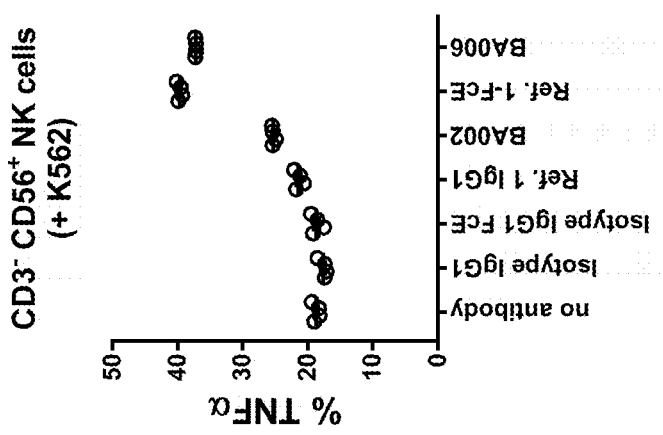
Figure 20F:
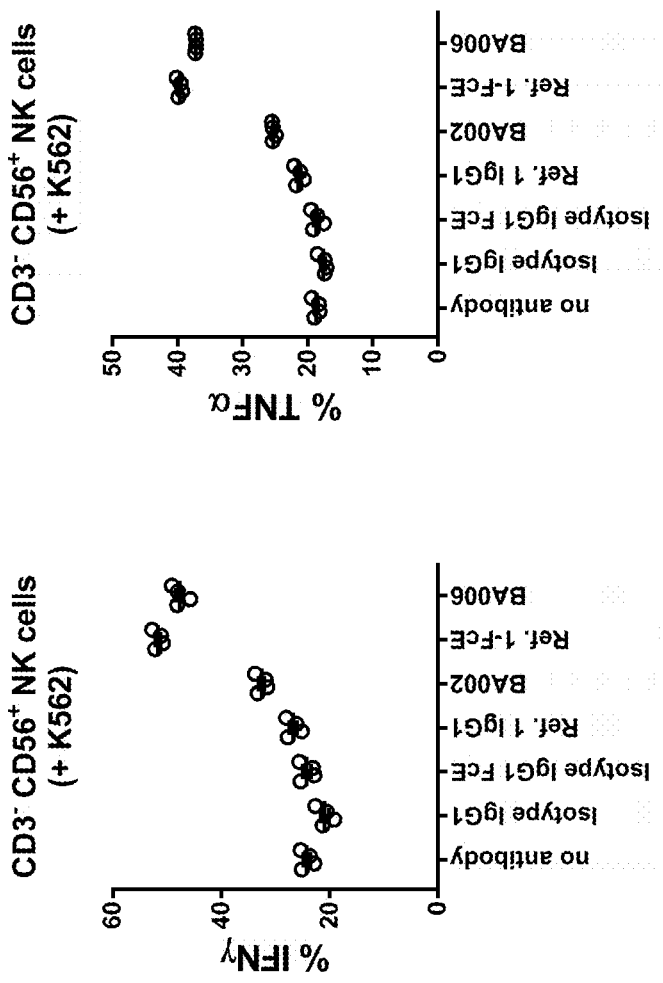
Figure 20G:
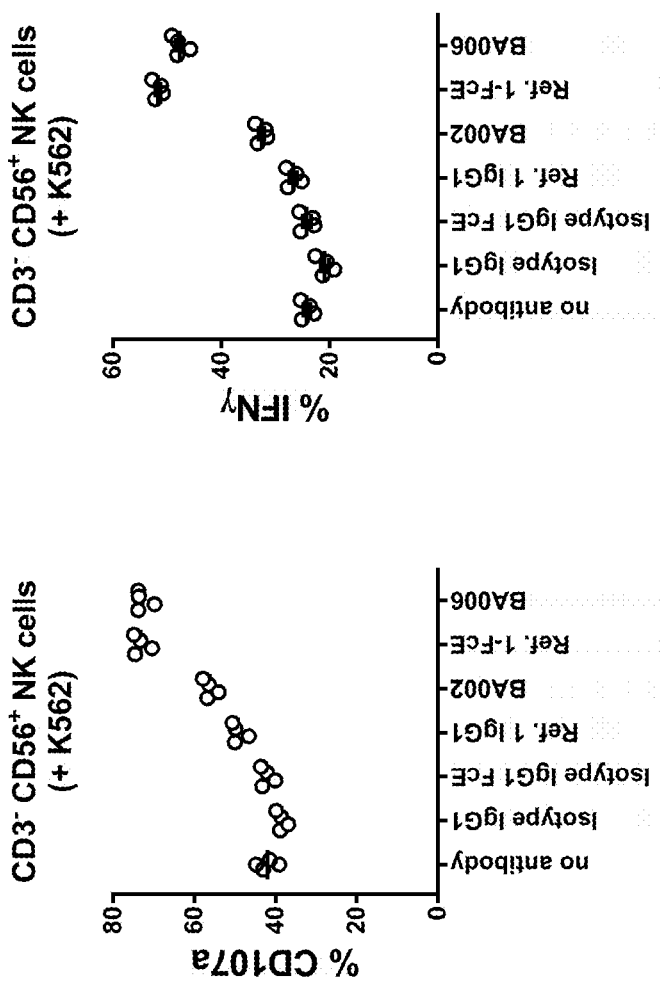

FIGS. 20A-20G show the effects of anti-TIGIT antibodies on NK cell activation. FIG. 20A is a series of graphs showing the gating parameters for identifying NK cells from the PBMC population, and a histogram showing the distribution of the CD107a activation marker. FIGS. 20B-20G are a series of graphs showing the percentage of cells positive for CD107a (FIGS. 20B and 20E), IFNγ (FIGS. 20C and 20F), and TNFα (FIGS. 20D and 20G) out of all the NK cells in the PBMC population, after incubation of the PBMC population with the indicated antibodies either alone (FIGS. 20B-20D) or in a co-culture with K562 cells (FIGS. 20E-20G). "Ref. 1 IgG1" refers to reference antibody #1 in the IgG1 format, and "Ref. 1-FcE" refers to a variant of reference antibody #1 comprising the S239D/A330L/I332E substitutions in the Fc region.

FIG. 21 is a sequence alignment of human TIGIT (SEQ ID NO: 29) and cynomolgus monkey TIGIT (SEQ ID NO: 70). The BA002 epitope regions identified by hydrogen-deuterium exchange (HDX)-mass spectrometry are indicated in bold and underlining, with differences between the human and cynomolgus sequences in these regions shown without underlining. The signal peptide and transmembrane domains of TIGIT are indicated with boxes.

Figure 22B:
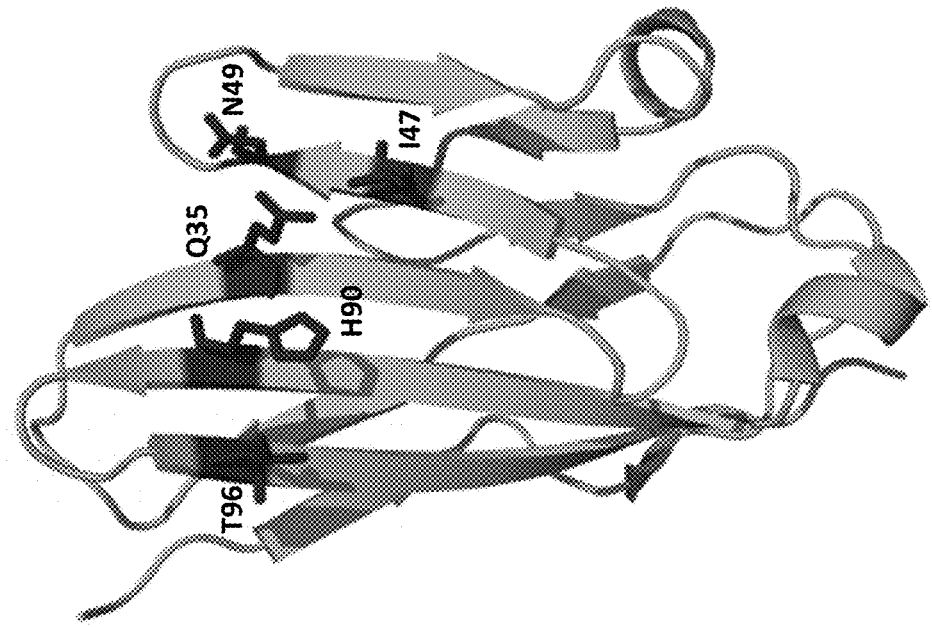
Figure 22A:
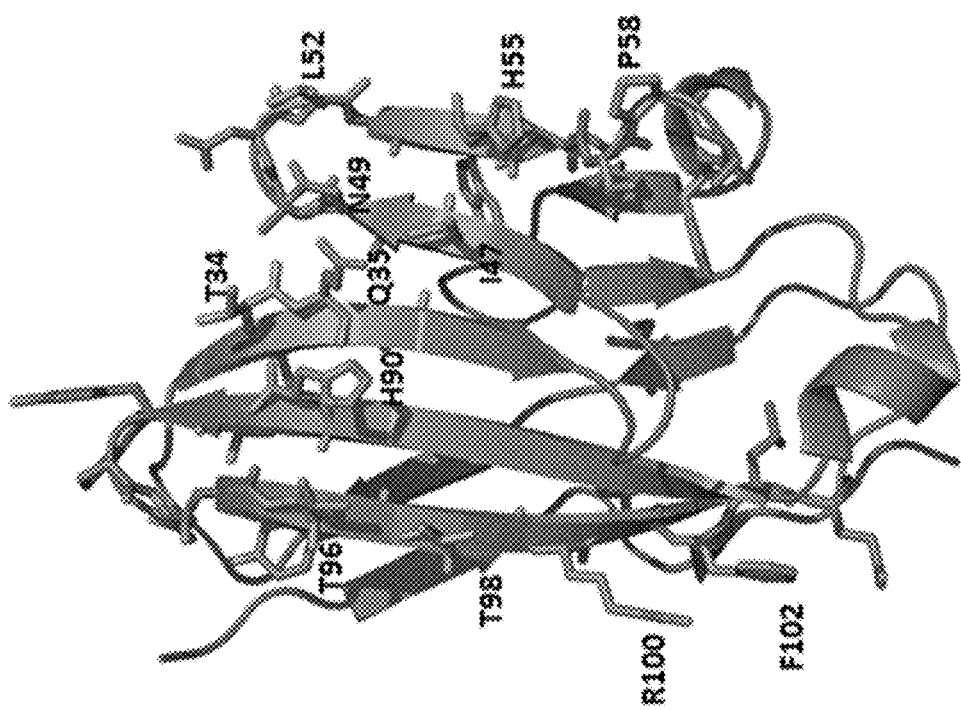
Figure 23A:
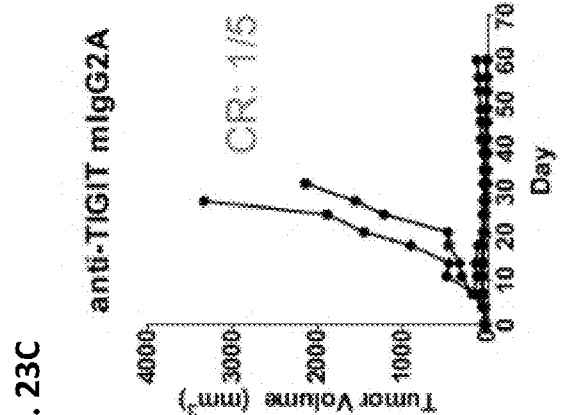
Figures 23B, 23C:
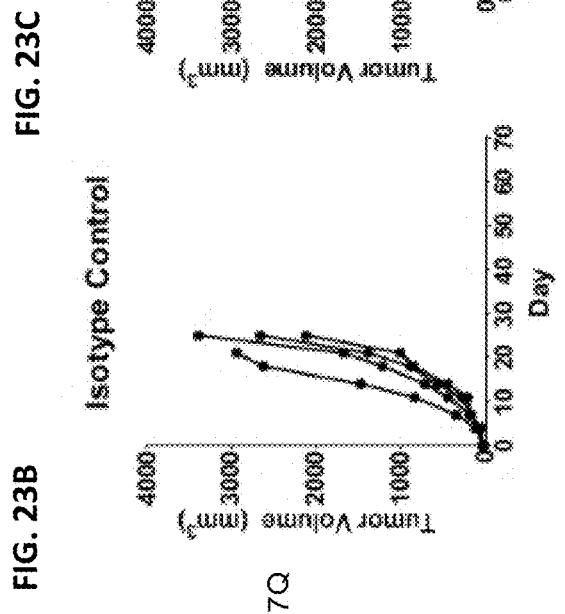
Figure 23D:
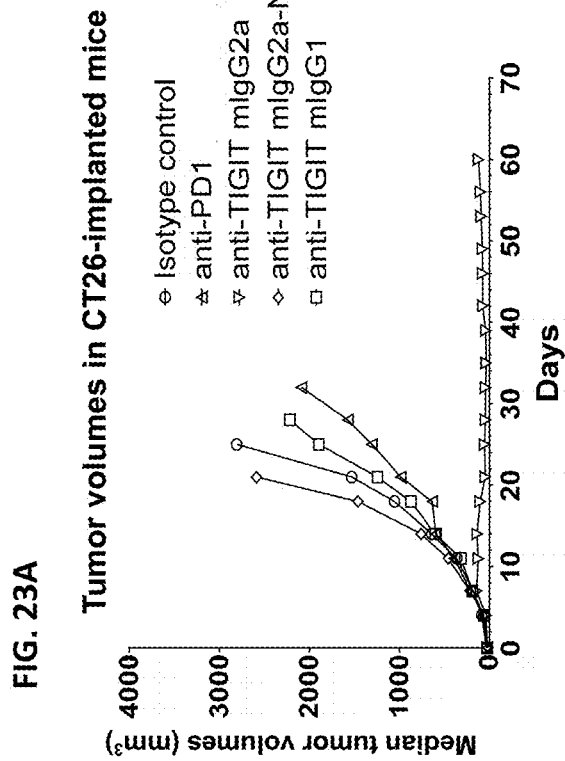
Figures 23E, 23F:
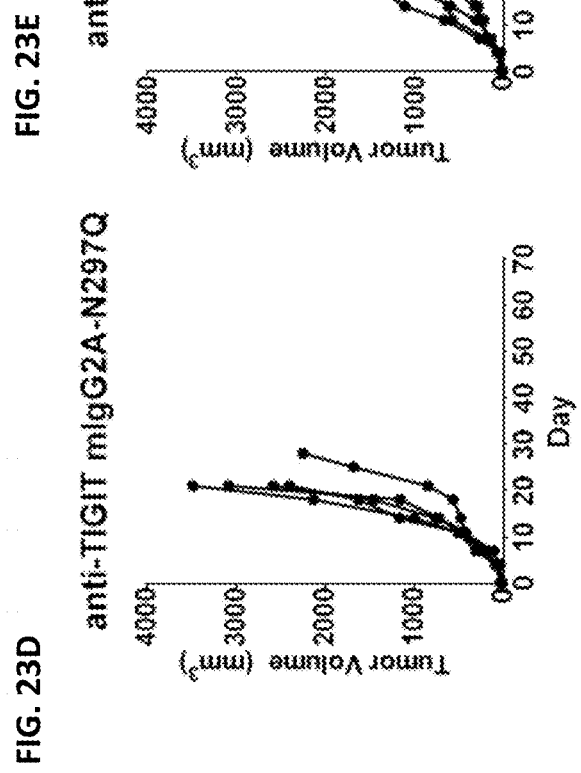
Figure 24A:
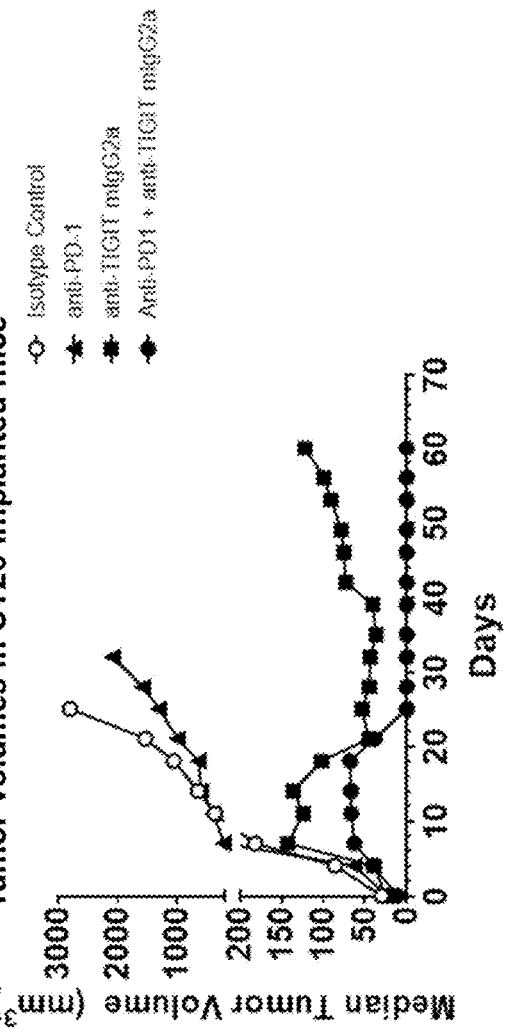
Figure 24B:
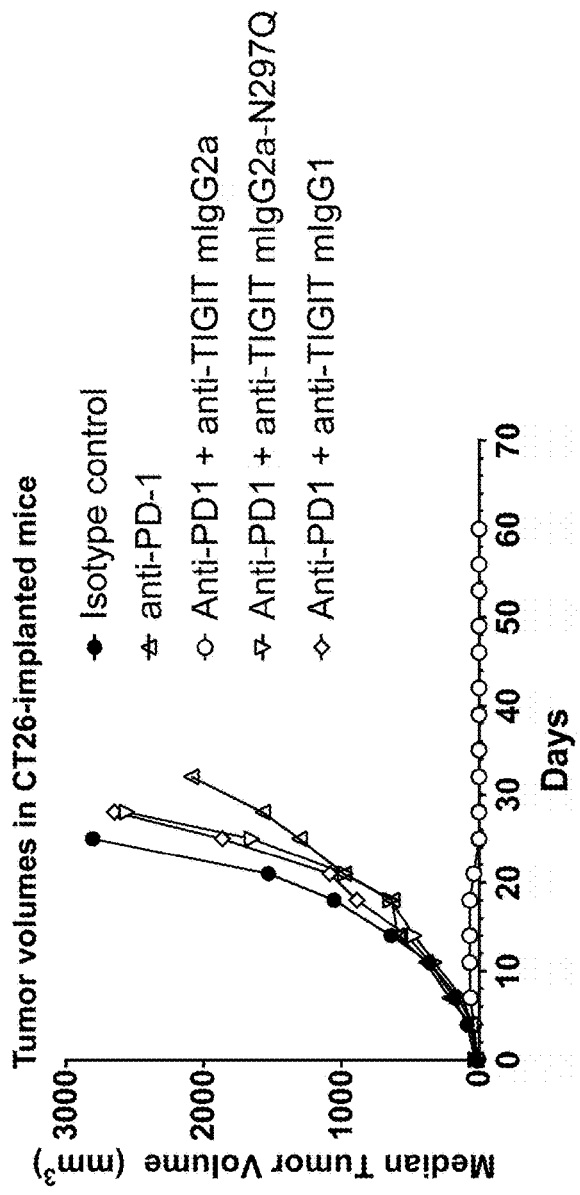
Figure 25A:
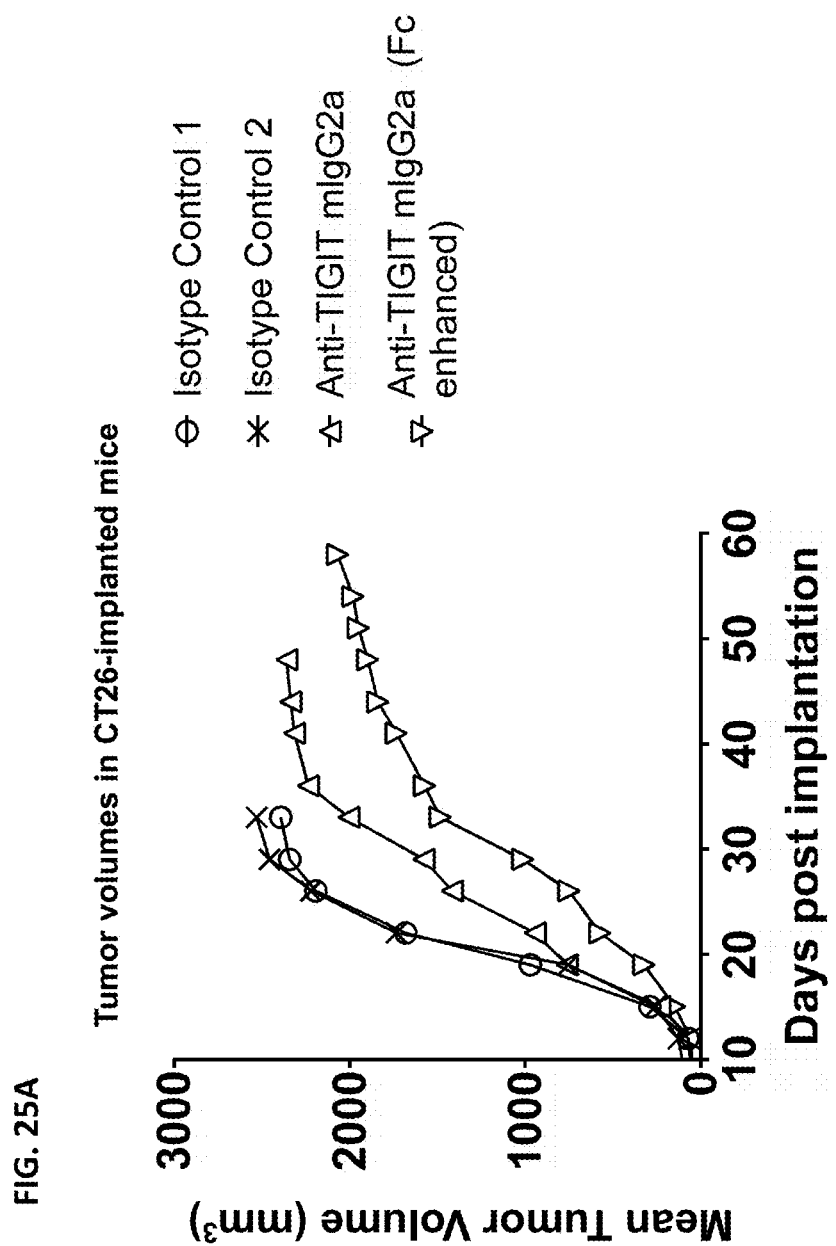
Figure 25B:
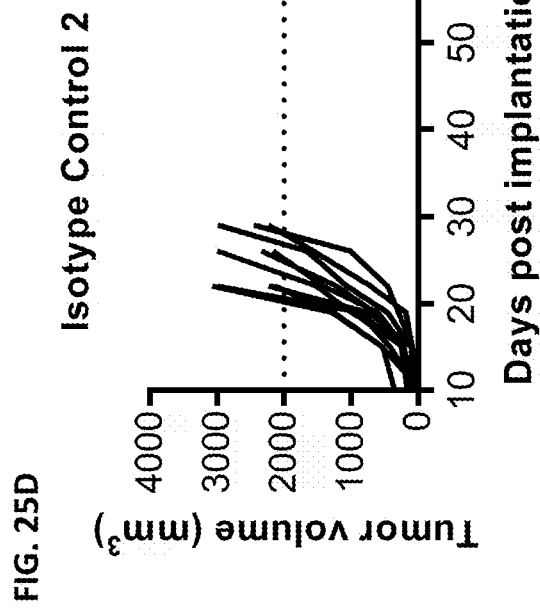
Figure 25D:
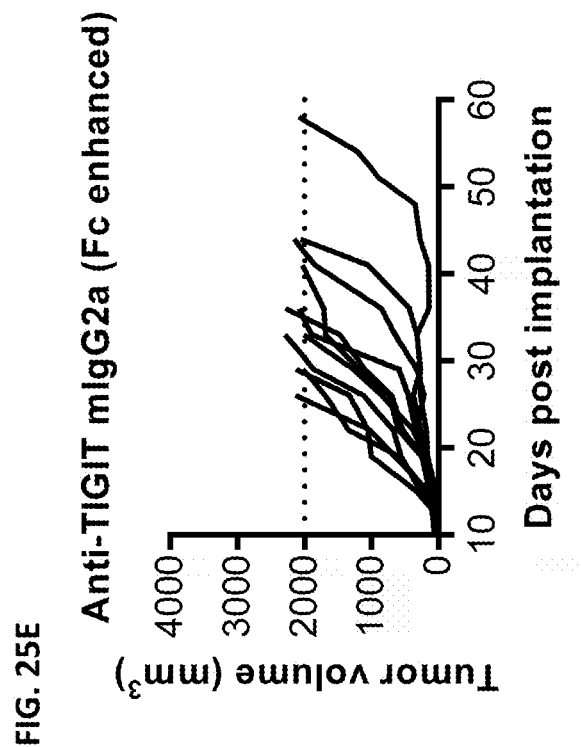
Figure 25C:
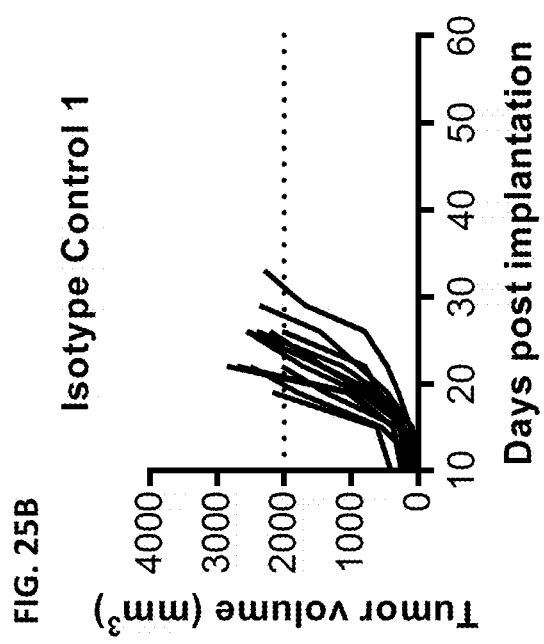
Figure 25E:
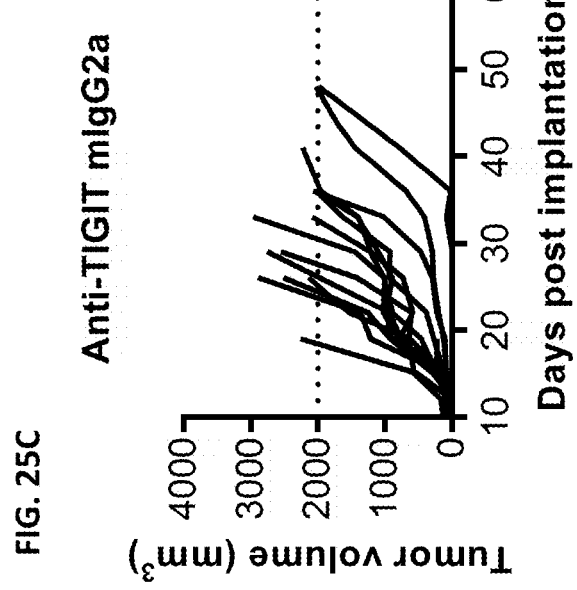

FIGS. 22A-22B are ribbon diagrams showing the structure of human TIGIT protein with specific amino acid residues highlighted. FIG. 22A shows the amino acid residues in the BA002 epitope regions of TIGIT, as identified by HDX, facing the PVR-binding surface of the protein. FIG. 22B shows Q35, I47, H90, T96, and N49, which may constitute a conformational epitope bound by BA006.

FIGS. 23A-23F are a series of graphs showing inhibition of tumor progression by an anti-TIGIT antibody in a xenograft mouse model in which the test antibodies were administered at an early stage of tumor progression. The median tumor volumes are plotted against time in FIG. 23A, and the tumor volumes of each individual mouse are plotted against time in FIGS. 23B-23F (n=5 per treatment group).

FIGS. 24A-24G are a series of graphs showing inhibition of tumor progression by various surrogate anti-TIGIT antibodies in combination with an anti-PD-1 antibody in a xenograft mouse model in which the test antibodies were administered at an early stage of tumor progression. The median tumor volumes are plotted against time in FIGS. 24A and 24B (with different y-axis scales), and the tumor volumes of each individual mouse are plotted against time in FIGS. 24C-24G (n=5 per treatment group). Surrogate antibodies "anti-TIGIT mIgG2a," "anti-TIGIT mIgG2a-N297Q," "anti-TIGIT mIgG1," and "anti-TIGIT mIgG2 (Fc enhanced)" differ only in their Fc regions in accordance with their names.

FIGS. 25A-25E are a series of graphs showing inhibition of tumor progression by anti-TIGIT surrogate antibody mIgG2a ("anti-TIGIT mIgG2a") or its isotype control antibody ("Isotype Control 1"), or surrogate antibody mIgG2a (Fc enhanced) ("anti-TIGIT mIgG2 (Fc enhanced)") or its isotype control antibody ("Isotype Control 2"), in a xenograft mouse model in which the test antibodies were administered at a late stage of tumor progression. The mean tumor volumes are plotted against time in FIG. 25A, and the tumor volumes of each individual mouse are plotted against time in FIGS. 25B-25E (n=10 per treatment group). The dotted line in FIGS. 25B-25E represents a standard to euthanize mice having tumor volumes exceeding 2000 mm$^3$.

FIGS. 26A-26B are a series of graphs showing inhibition of tumor progression by anti-TIGIT surrogate antibody mIgG2a ("anti-TIGIT mIgG2a") or its isotype control antibody ("Isotype Control 1"), or surrogate antibody mIgG2a (Fc enhanced) ("anti-TIGIT mIgG2 (Fc enhanced)") or its isotype control antibody ("Isotype Control 2"), in combination with another checkpoint modulating antibody in a xenograft mouse model in which the test antibodies were administered at a late stage of tumor progression. The mean tumor volumes of mice treated with an anti-TIGIT antibody and an anti-PD-1 antibody (FIG. 26A) or an anti-CTLA-4 antibody (FIG. 26B) are plotted against time (n=10 per treatment group for each figure).

Figure 27E:
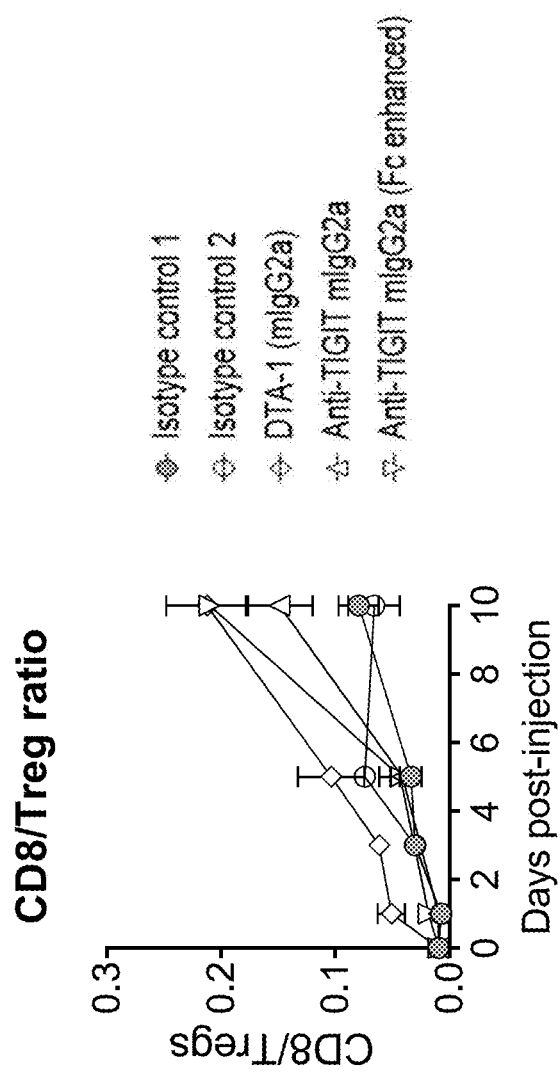
Figure 27F:
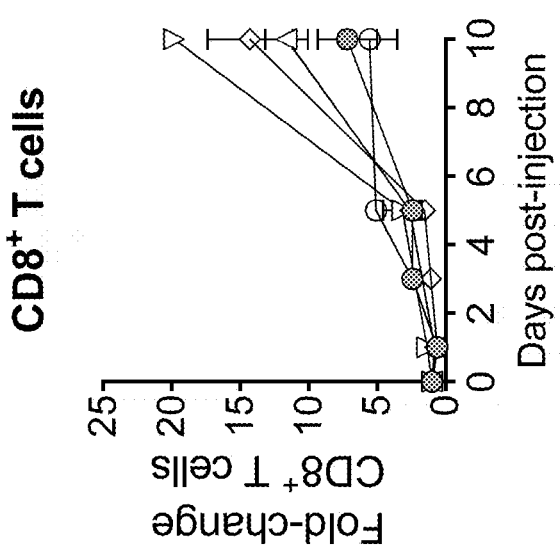

FIGS. 27A-27F are a series of graphs showing a study design and comparisons of the amounts of T cell subsets in tumors and tumor-draining lymph nodes (TDLNs) in a mouse xenograft model after administration of anti-TIGIT surrogate antibody mIgG2a ("anti-TIGIT mIgG2a") or its isotype control antibody ("Isotype Control 1"), or surrogate antibody mIgG2a (Fc enhanced) ("anti-TIGIT mIgG2 (Fc enhanced)") or its isotype control antibody ("Isotype Control 2"). An agonistic anti-GITR antibody ("DTA-1 (mIgG2a)") was used as a positive control for regulatory T cell depletion. FIG. 27A illustrates the study design. The relative changes in the amounts of intratumoral FoxP3$^+$ regulatory T cells (Tregs) (FIG. 27B), intratumoral CD4$^+$ non-Tregs (FIG. 27C), FoxP3$^+$ Tregs in tumor-draining lymph nodes (TDLNs) (FIG. 27D), and intratumoral CD8$^+$ T cells (FIG. 27E) are plotted against time post injection of anti-TIGIT antibody. The ratios of intratumoral CD8$^+$ T cells to intratumoral Tregs are shown in FIG. 27F (n=4 per treatment group and time point).

FIGS. 28A-28C are a series of graphs showing the involvement of FcγRIV in anti-TIGIT antibody-mediated T cell activation. FIG. 28A shows the results of cell-based luciferase reporter assays that examined the effect of various concentrations of anti-TIGIT surrogate antibody mIgG2a ("anti-TIGIT mIgG2a") or its isotype control antibody ("Isotype Control 1"), or surrogate antibody mIgG2a (Fc enhanced) ("anti-TIGIT mIgG2 (Fc enhanced)") or its isotype control antibody ("Isotype Control 2") on effector T cell activation in a co-culture of FcγRIV-expressing effector T cells and murine TIGIT-expressing CHO cells. The relative luciferase activity (RLU) is plotted against antibody concentration. FIGS. 28B and 28C show the results of a murine in vivo immune activation assay that examined the effect of anti-TIGIT mIgG2a or an mIgG2 anti-CTLA-4 antibody ("anti-CLTA-4 mIgG2a") on $CD4^+$ (FIG. 28B) and $CD8^+$ (FIG. 28C) T cell proliferation in response to SEB superantigen in the presence or absence of an anti-FcγRIV antibody (n=4 mice per group, data representative of at least two independent experiments). Proliferation was determined by assaying the percentage of $Ki67^+$ T cells using flow cytometry.

5. DETAILED DESCRIPTION

The instant disclosure provides antibodies that specifically bind to TIGIT (e.g., human TIGIT or cynomolgus TIGIT) and antagonize TIGIT function, e.g., TIGIT-mediated immune suppression. Also provided are pharmaceutical compositions comprising these antibodies, nucleic acids encoding these antibodies, expression vectors and host cells for making these antibodies, and methods of treating a subject using these antibodies. The antibodies disclosed herein are particularly useful for increasing T cell and NK cell activation in response to an antigen (e.g., a tumor antigen or an infectious disease antigen), and hence, are useful for treating cancer in a subject or treating or preventing an infectious disease in a subject. All instances of "isolated antibodies" described herein are additionally contemplated as antibodies that may be, but need not be, isolated. All instances of "isolated polynucleotides" described herein are additionally contemplated as polynucleotides that may be, but need not be, isolated. All instances of "antibodies" described herein are additionally contemplated as antibodies that may be, but need not be, isolated. All instances of "polynucleotides" described herein are additionally contemplated as polynucleotides that may be, but need not be, isolated.

5.1 Definitions

As used herein, the terms "about" and "approximately," when used to modify a numeric value or numeric range, indicate that deviations of 5% to 10% above (e.g., up to 5% to 10% above) and 5% to 10% below (e.g., up to 5% to 10% below) the value or range remain within the intended meaning of the recited value or range.

As used herein, the term "TIGIT" refers to T-cell immunoreceptor with Ig and ITIM domains (also known as VSIG9 or VSTM3) that in humans is encoded by the TIGIT gene. As used herein, the term "human TIGIT" refers to a TIGIT protein encoded by a wild-type human TIGIT gene (e.g., GenBank™ accession number NM_173799.3) or an extracellular domain of such a protein. An exemplary amino acid sequence of an immature human TIGIT protein is provided as SEQ ID NO: 29. An exemplary amino acid sequence of a mature human TIGIT protein is provided as SEQ ID NO: 40. Exemplary amino acid sequences of an extracellular domain of a mature human TIGIT protein are provided as SEQ ID NOs: 30, 41, and 42.

As used herein, the terms "antibody" and "antibodies" include full length antibodies, antigen-binding fragments of full length antibodies, and molecules comprising antibody CDRs, VH regions, and/or VL regions. Examples of antibodies include, without limitation, monoclonal antibodies, recombinantly produced antibodies, monospecific antibodies, multispecific antibodies (including bispecific antibodies), human antibodies, humanized antibodies, chimeric antibodies, immunoglobulins, synthetic antibodies, tetrameric antibodies comprising two heavy chain and two light chain molecules, an antibody light chain monomer, an antibody heavy chain monomer, an antibody light chain dimer, an antibody heavy chain dimer, an antibody light chain-antibody heavy chain pair, intrabodies, heteroconjugate antibodies, antibody-drug conjugates, single domain antibodies, monovalent antibodies, single chain antibodies or single-chain Fvs (scFv), camelized antibodies, affybodies, Fab fragments, F(ab')₂ fragments, disulfide-linked Fvs (sdFv), anti-idiotypic (anti-Id) antibodies (including, e.g., anti-anti-Id antibodies), and antigen-binding fragments of any of the above. In certain embodiments, antibodies described herein refer to polyclonal antibody populations. Antibodies can be of any type (e.g., IgG, IgE, IgM, IgD, IgA or IgY), any class (e.g., $IgG_1$, $IgG_2$, $IgG_3$, $IgG_4$, $IgA_1$ or $IgA_2$), or any subclass (e.g., $IgG_{2a}$ or $IgG_{2b}$) of immunoglobulin molecule. In certain embodiments, antibodies described herein are IgG antibodies, or a class (e.g., human $IgG_1$ or $IgG_4$) or subclass thereof. In a specific embodiment, the antibody is a humanized monoclonal antibody. In another specific embodiment, the antibody is a human monoclonal antibody.

As used herein, the terms "VH region" and "VL region" refer, respectively, to single antibody heavy and light chain variable regions, comprising FR (Framework Regions) 1, 2, 3 and 4 and CDR (Complementarity Determining Regions) 1, 2 and 3 (see Kabat et al., (1991) Sequences of Proteins of Immunological Interest (NIH Publication No. 91-3242, Bethesda), which is herein incorporated by reference in its entirety).

As used herein, the term "CDR" or "complementarity determining region" means the noncontiguous antigen combining sites found within the variable region of both heavy and light chain polypeptides. These particular regions have been described by Kabat et al., J. Biol. Chem. 252, 6609-6616 (1977) and Kabat et al., Sequences of protein of immunological interest. (1991), by Chothia et al., J. Mol. Biol. 196:901-917 (1987), and by MacCallum et al., J. Mol. Biol. 262:732-745 (1996), all of which are herein incorporated by reference in their entireties, where the definitions include overlapping or subsets of amino acid residues when compared against each other. In certain embodiments, the term "CDR" is a CDR as defined by MacCallum et al., J. Mol. Biol. 262:732-745 (1996) and Martin A. "Protein Sequence and Structure Analysis of Antibody Variable Domains," in *Antibody Engineering*, Kontermann and Dübel, eds., Chapter 31, pp. 422-439, Springer-Verlag, Berlin (2001). In certain embodiments, the term "CDR" is a CDR as defined by Kabat et al., J. Biol. Chem. 252, 6609-6616 (1977) and Kabat et al., Sequences of protein of immunological interest. (1991). In certain embodiments, heavy chain CDRs and light chain CDRs of an antibody are defined using different conventions. In certain embodiments, heavy chain CDRs and/or light chain CDRs are defined by performing structural analysis of an antibody and identifying residues in the variable region(s) predicted to make contact with an epitope region of a target molecule (e.g., human and/or cynomolgus TIGIT). CDRH1, CDRH2 and CDRH3 denote the heavy chain CDRs, and CDRL1, CDRL2 and CDRL3 denote the light chain CDRs.

As used herein, the term "framework (FR) amino acid residues" refers to those amino acids in the framework region of an immunoglobulin chain. The term "framework region" or "FR region" as used herein, includes the amino acid residues that are part of the variable region, but are not part of the CDRs (e.g., using the Kabat or MacCallum definition of CDRs).

As used herein, the terms "variable region" and "variable domain" are used interchangeably and are common in the art. The variable region typically refers to a portion of an antibody, generally, a portion of a light or heavy chain, typically about the amino-terminal 110 to 120 amino acids or 110 to 125 amino acids in the mature heavy chain and about 90 to 115 amino acids in the mature light chain, which differ extensively in sequence among antibodies and are used in the binding and specificity of a particular antibody for its particular antigen. The variability in sequence is concentrated in those regions called complementarity determining regions (CDRs) while the more highly conserved regions in the variable domain are called framework regions (FR). Without wishing to be bound by any particular mechanism or theory, it is believed that the CDRs of the light and heavy chains are primarily responsible for the interaction and specificity of the antibody with antigen. In certain embodiments, the variable region is a human variable region. In certain embodiments, the variable region comprises rodent or murine CDRs and human framework regions (FRs). In particular embodiments, the variable region is a primate (e.g., non-human primate) variable region. In certain embodiments, the variable region comprises rodent or murine CDRs and primate (e.g., non-human primate) framework regions (FRs).

The terms "VL" and "VL domain" are used interchangeably to refer to the light chain variable region of an antibody.

The terms "VH" and "VH domain" are used interchangeably to refer to the heavy chain variable region of an antibody.

As used herein, the terms "constant region" and "constant domain" are interchangeable and are common in the art. The constant region is an antibody portion, e.g., a carboxyl terminal portion of a light and/or heavy chain which is not directly involved in binding of an antibody to antigen but which can exhibit various effector functions, such as interaction with an Fc receptor (e.g., Fc gamma receptor). The constant region of an immunoglobulin molecule generally has a more conserved amino acid sequence relative to an immunoglobulin variable domain.

As used herein, the term "heavy chain" when used in reference to an antibody can refer to any distinct type, e.g., alpha (α), delta (δ), epsilon (ε), gamma (γ), and mu (μ), based on the amino acid sequence of the constant domain, which give rise to IgA, IgD, IgE, IgG, and IgM classes of antibodies, respectively, including subclasses of IgG, e.g., IgG$_1$, IgG$_2$, IgG$_3$, and IgG$_4$.

As used herein, the term "light chain" when used in reference to an antibody can refer to any distinct type, e.g., kappa (κ) or lambda (λ) based on the amino acid sequence of the constant domains. Light chain amino acid sequences are well known in the art. In specific embodiments, the light chain is a human light chain.

As used herein, the term "EU numbering system" refers to the EU numbering convention for the constant regions of an antibody, as described in Edelman, G. M. et al., Proc. Natl. Acad. USA, 63, 78-85 (1969) and Kabat et al, Sequences of Proteins of Immunological Interest, U.S. Dept. Health and Human Services, 5th edition, 1991, each of which is herein incorporated by reference in its entirety.

"Binding affinity" generally refers to the strength of the sum total of non-covalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant ($K_D$). Affinity can be measured and/or expressed in a number of ways known in the art, including, but not limited to, equilibrium dissociation constant ($K_D$), and equilibrium association constant ($K_A$). The $K_D$ is calculated from the quotient of $k_{off}/k_{on}$, whereas $K_A$ is calculated from the quotient of $k_{on}/k_{off}$. $k_{on}$ refers to the association rate constant of, e.g., an antibody to an antigen, and $k_{off}$ refers to the dissociation rate constant of, e.g., an antibody to an antigen. The $k_{on}$ and $k_{off}$ can be determined by techniques known to one of ordinary skill in the art, such as BIAcore® or KinExA. As used herein, a "lower affinity" refers to a larger $K_D$.

As used herein, the terms "specifically binds," "specifically recognizes," "immunospecifically binds," and "immunospecifically recognizes" are analogous terms in the context of antibodies and refer to molecules that bind to an antigen (e.g., epitope or immune complex) as such binding is understood by one skilled in the art. For example, a molecule that specifically binds to an antigen can bind to other peptides or polypeptides, generally with lower affinity as determined by, e.g., immunoassays, BIAcore®, KinExA 3000 instrument (Sapidyne Instruments, Boise, Id.), or other assays known in the art. In a specific embodiment, molecules that specifically bind to an antigen bind to the antigen with a $K_A$ that is at least 2 logs (e.g., factors of 10), 2.5 logs, 3 logs, 4 logs or greater than the $K_A$ when the molecules bind non-specifically to another antigen.

In another specific embodiment, molecules that specifically bind to an antigen do not cross react with other proteins under similar binding conditions. In another specific embodiment, molecules that specifically bind to TIGIT do not cross react with other non-TIGIT proteins. In a specific embodiment, provided herein is an antibody that binds to TIGIT (e.g., human TIGIT) with higher affinity than to another unrelated antigen. In certain embodiments, provided herein is an antibody that binds to TIGIT (e.g., human TIGIT) with a 20%, 25%, 30%, 35%, 40%, 45%, 50%, 55%, 60%, 65%, 70%, 75%, 80%, 85%, 90%, 95% or higher affinity than to another, unrelated antigen as measured by, e.g., a radioimmunoassay, surface plasmon resonance, or kinetic exclusion assay. In a specific embodiment, the extent of binding of an anti-TIGIT antibody described herein to an unrelated, non-TIGIT protein is less than 10%, 15%, or 20% of the binding of the antibody to TIGIT protein as measured by, e.g., a radioimmunoassay.

As used herein, an "epitope" is a term in the art and refers to a localized region of an antigen to which an antibody can specifically bind. An epitope can be, for example, contiguous amino acids of a polypeptide (linear or contiguous epitope) or an epitope can, for example, come together from two or more non-contiguous regions of a polypeptide or polypeptides (conformational, non-linear, discontinuous, or non-contiguous epitope). In certain embodiments, the epitope to which an antibody binds can be determined by, e.g., NMR spectroscopy, X-ray diffraction crystallography studies, ELISA assays, hydrogen/deuterium exchange coupled with mass spectrometry (e.g., liquid chromatography electrospray mass spectrometry), array-based oligo-peptide scanning assays (e.g., constraining peptides using CLIPS (Chemical Linkage of Peptides onto Scaffolds) to map discontinuous or conformational epitopes), and/or mutagenesis mapping (e.g., site-directed mutagenesis mapping). For X-ray crystallography, crystallization may be accomplished using any of the known methods in the art (e.g., Giegé R et al., (1994) Acta Crystallogr D Biol Crystallogr 50(Pt 4): 339-350; McPherson A (1990) Eur J Biochem 189: 1-23; Chayen N E (1997) Structure 5: 1269-1274; McPherson A (1976) J Biol Chem 251: 6300-6303, each of which is herein incorporated by reference in its entirety). Antibody:antigen crystals may be studied using well known X-ray diffraction techniques and may be refined using computer software such as X-PLOR (Yale University, 1992, distributed by Molecular Simulations, Inc.; see, e.g., Meth Enzymol (1985) volumes 114 & 115, eds Wyckoff H W et al., U.S. 2004/0014194), and BUSTER (Bricogne G (1993) Acta Crystallogr D Biol Crystallogr 49(Pt 1): 37-60; Bricogne G (1997) Meth Enzymol 276A: 361-423, ed Carter C W; Roversi P et al., (2000) Acta Crystallogr D Biol Crystallogr 56(Pt 10): 1316-1323), each of which is herein incorporated by reference in its entirety. Mutagenesis mapping studies may be accomplished using any method known to one of skill in the art. See, e.g., Champe M et al., (1995) J Biol Chem 270: 1388-1394 and Cunningham B C & Wells J A (1989) Science 244: 1081-1085, each of which is herein incorporated by reference in its entirety, for a description of mutagenesis techniques, including alanine scanning mutagenesis techniques. CLIPS (Chemical Linkage of Peptides onto Scaffolds) is a technology to present one or more peptides in a structurally constrained configuration to behave as functional mimics of complex protein domains. See, e.g., U.S. Publication Nos. US 2008/0139407 A1 and US 2007/099240 A1, and U.S. Pat. No. 7,972,993, each of which is herein incorporated by reference in its entirety. In a specific embodiment, the epitope of an antibody is determined using alanine scanning mutagenesis studies. In a specific embodiment, the epitope of an antibody is determined using hydrogen/deuterium exchange coupled with mass spectrometry. In a specific embodiment, the epitope of an antibody is determined using CLIPS Epitope Mapping Technology from Pepscan Therapeutics. In a specific embodiment, the epitope of an antibody is determined by protein mutagenesis, e.g., by generating switch mutants of an antigen with portions of its ortholog from another species and then testing the switch mutants for loss of antibody binding (e.g., by a FACS-based cell binding assay, as described herein).

As used herein, the term "an epitope located within" a region of human TIGIT refers to an epitope comprising one or more of the amino acid residues of the specified region. In certain embodiments, the epitope comprises each one of the amino acid residues located within the specified region. In certain embodiments, the epitope consists of each one of the amino acid residues located within the specified region. In certain embodiments, one or more additional amino acid residues of human TIGIT outside the specified region bind to an antibody together with an epitope located within the specified region.

As used herein, the binding between a test antibody and a first antigen is "substantially weakened" relative to the binding between the test antibody and a second antigen if the binding between the test antibody and the first antigen is reduced by at least 30%, 40%, 50%, 60%, 70%, 80% or 90% relative to the binding between the test antibody and the second antigen, e.g., in a given experiment, or using mean values from multiple experiments, as assessed by, e.g., a binding assay disclosed herein.

As used herein, the terms "T cell receptor" and "TCR" are used interchangeably and refer to full length heterodimeric αβ or γδ TCRs, antigen-binding fragments of full length TCRs, and molecules comprising TCR CDRs or variable regions. Examples of TCRs include, but are not limited to, full length TCRs, antigen-binding fragments of full length TCRs, soluble TCRs lacking transmembrane and cytoplasmic regions, single-chain TCRs containing variable regions of TCRs attached by a flexible linker, TCR chains linked by an engineered disulfide bond, monospecific TCRs, multi-specific TCRs (including bispecific TCRs), TCR fusions, human TCRs, humanized TCRs, chimeric TCRs, recombinantly produced TCRs, and synthetic TCRs. The term encompasses wild-type TCRs and genetically engineered TCRs (e.g., a chimeric TCR comprising a chimeric TCR chain which includes a first portion from a TCR of a first species and a second portion from a TCR of a second species).

As used herein, the terms "major histocompatibility complex" and "MHC" are used interchangeably and refer to an MHC class I molecule and/or an MHC class II molecule.

As used herein, the term "peptide-MHC complex" refers to an MHC molecule (MHC class I or MHC class II) with a peptide bound in the art-recognized peptide binding pocket of the MHC.

As used herein, the term "treat," "treating," and "treatment" refer to therapeutic or preventative measures described herein. The methods of "treatment" employ administration of an antibody to a subject having a disease or disorder, or predisposed to having such a disease or disorder, in order to prevent, cure, delay, reduce the severity of, or ameliorate one or more symptoms of the disease or disorder or recurring disease or disorder, or in order to prolong the survival of a subject beyond that expected in the absence of such treatment.

As used herein, the term "effective amount" in the context of the administration of a therapy to a subject refers to the amount of a therapy that achieves a desired prophylactic or therapeutic effect.

As used herein, the term "subject" includes any human or non-human animal. In one embodiment, the subject is a human or non-human mammal. In one embodiment, the subject is a human.

The determination of "percent identity" between two sequences (e.g., amino acid sequences or nucleic acid sequences) can be accomplished using a mathematical algorithm. A specific, non-limiting example of a mathematical algorithm utilized for the comparison of two sequences is the algorithm of Karlin S & Altschul S F (1990) PNAS 87: 2264-2268, modified as in Karlin S & Altschul S F (1993) PNAS 90: 5873-5877, each of which is herein incorporated by reference in its entirety. Such an algorithm is incorporated into the NBLAST and XBLAST programs of Altschul S F et al., (1990) J Mol Biol 215: 403, which is herein incorporated by reference in its entirety. BLAST nucleotide searches can be performed with the NBLAST nucleotide program parameters set, e.g., for score=100, wordlength=12 to obtain nucleotide sequences homologous to a nucleic acid molecules described herein. BLAST protein searches can be performed with the XBLAST program parameters set, e.g., to score 50, wordlength=3 to obtain amino acid sequences homologous to a protein molecule described herein. To obtain gapped alignments for comparison purposes, Gapped BLAST can be utilized as described in Altschul S F et al., (1997) Nuc Acids Res 25: 3389-3402, which is herein incorporated by reference in its entirety. Alternatively, PSI BLAST can be used to perform an iterated search which detects distant relationships between molecules (Id.). When utilizing BLAST, Gapped BLAST, and PSI Blast programs, the default parameters of the respective programs (e.g., of XBLAST and NBLAST) can be used (see, e.g., National Center for Biotechnology Information (NCBI) on the worldwide web, ncbi.nlm.nih.gov). Another specific, non-limiting example of a mathematical algorithm utilized for the comparison of sequences is the algorithm of Myers and Miller, 1988, CABIOS 4:11-17, which is herein incorporated by reference in its entirety. Such an algorithm is incorporated in the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

The percent identity between two sequences can be determined using techniques similar to those described above, with or without allowing gaps. In calculating percent identity, typically only exact matches are counted.

5.2 Anti-TIGIT Antibodies

In one aspect, the instant disclosure provides antibodies that specifically bind to TIGIT (e.g., human TIGIT or cynomolgus TIGIT) and antagonize TIGIT function. The amino acid sequences of exemplary antibodies are set forth in Table 1, herein.

TABLE 1

Amino acid sequences of exemplary anti-TIGIT antibodies.

| Description | Amino Acid Sequence | SEQ ID NO: |
|---|---|---|
| BA002 Kabat CDRH1 | SYGIS | 1 |
| BA002 Alternate CDRH1 | GYTFASY | 2 |
| BA002 Kabat CDRH2 | GITPFFNRVDVAEKFQG | 3 |
| BA002 Alternate CDRH2 | TPFFNR | 4 |
| BA002 Kabat CDRH3 | DLRRGGVGDAFDI | 5 |
| BA002 Kabat CDRL1 | TGTSSDVGSHNYVS | 6 |
| BA002 Kabat CDRL2 | EVSYRPS | 7 |
| BA002 Kabat CDRL3 | SSYTPSSATV | 8 |
| BA002 VH | XVQLVQSGAEVEKPGASVKVSCKASGYTFASYGIS WVRQAPGQGLEWMGGITPFFNRVDVAEKFQGRVTI TADTSTNTVYIELSSLTSEDTAVYYCARDLRRGGVG DAFDIWGRGTLVTVSS, wherein X is glutamate (E) or pyroglutamate (pE) | 9 |
| BA002 VL | XSALTQPRSVSGSPGQSVTISCTGTSSDVGSHNYVS WYQQHPGKAPQLMIYEVSYRPSEISNRFSGSKSGNT ASLTISGLQPEDEADYYCSSYTPSSATVFGAGTKLTV L, wherein X is glutamine (Q) or pyroglutamate (pE) | 10 |
| BA002 full length heavy chain (IgG1) | XVQLVQSGAEVEKPGASVKVSCKASGYTFASYGIS WVRQAPGQGLEWMGGITPFFNRVDVAEKFQGRVTI TADTSTNTVYIELSSLTSEDTAVYYCARDLRRGGVG DAFDIWGRGTLVTVSSASTKGPSVFPLAPSSKSTSGG TAALGCLVKDYFPEPVTVSWNSGALTSGVHTFPAV LQSSGLYSLSSVVTVPSSSLGTQTYICNVNHKPSNTK VDKRVEPKSCDKTHTCPPCPAPELLGGPSVFLFPPKP KDTLMISRTPEVTCVVVDVSHEDPEVKFNWYVDGV EVHNAKTKPREEQYNSTYRVVSVLTVLHQDWLNG KEYKCKVSNKALPAPIEKTISKAKGQPREPQVYTLPP SREEMTKNQVSLTCLVKGFYPSDIAVEWESNGQPEN NYKTTPPVLDSDGSFFLYSKLTVDKSRWQQGNVFSC SVMHEALHNHYTQKSLSLSPG, wherein X is glutamate (E) or pyroglutamate (pE) | 11 |
| BA003 full length heavy chain (N297A variant of BA002, numbered according to the EU numbering system) | XVQLVQSGAEVEKPGASVKVSCKASGYTFASYGIS WVRQAPGQGLEWMGGITPFFNRVDVAEKFQGRVTI TADTSTNTVYIELSSLTSEDTAVYYCARDLRRGGVG DAFDIWGRGTLVTVSSASTKGPSVFPLAPSSKSTSGG TAALGCLVKDYFPEPVTVSWNSGALTSGVHTFPAV LQSSGLYSLSSVVTVPSSSLGTQTYICNVNHKPSNTK VDKRVEPKSCDKTHTCPPCPAPELLGGPSVFLFPPKP KDTLMISRTPEVTCVVVDVSHEDPEVKFNWYVDGV EVHNAKTKPREEQYASTYRVVSVLTVLHQDWLNG KEYKCKVSNKALPAPIEKTISKAKGQPREPQVYTLPP SREEMTKNQVSLTCLVKGFYPSDIAVEWESNGQPEN NYKTTPPVLDSDGSFFLYSKLTVDKSRWQQGNVFSC SVMHEALHNHYTQKSLSLSPG, wherein X is glutamate (E) or pyroglutamate (pE) | 12 |
| BA004 full length heavy chain (L234F/L235F/N297A variant of BA002, numbered according to the EU numbering system) | XVQLVQSGAEVEKPGASVKVSCKASGYTFASYGIS WVRQAPGQGLEWMGGITPFFNRVDVAEKFQGRVTI TADTSTNTVYIELSSLTSEDTAVYYCARDLRRGGVG DAFDIWGRGTLVTVSSASTKGPSVFPLAPSSKSTSGG TAALGCLVKDYFPEPVTVSWNSGALTSGVHTFPAV LQSSGLYSLSSVVTVPSSSLGTQTYICNVNHKPSNTK VDKRVEPKSCDKTHTCPPCPAPEFFGGPSVFLFPPKP KDTLMISRTPEVTCVVVDVSHEDPEVKFNWYVDGV EVHNAKTKPREEQYASTYRVVSVLTVLHQDWLNG KEYKCKVSNKALPAPIEKTISKAKGQPREPQVYTLPP SREEMTKNQVSLTCLVKGFYPSDIAVEWESNGQPEN NYKTTPPVLDSDGSFFLYSKLTVDKSRWQQGNVFSC SVMHEALHNHYTQKSLSLSPG, wherein X is glutamate (E) or pyroglutamate (pE) | 13 |
| BA005 full length heavy chain (S239D/I332E variant of BA002, numbered | XVQLVQSGAEVEKPGASVKVSCKASGYTFASYGIS WVRQAPGQGLEWMGGITPFFNRVDVAEKFQGRVTI TADTSTNTVYIELSSLTSEDTAVYYCARDLRRGGVG DAFDIWGRGTLVTVSSASTKGPSVFPLAPSSKSTSGG TAALGCLVKDYFPEPVTVSWNSGALTSGVHTFPAV LQSSGLYSLSSVVTVPSSSLGTQTYICNVNHKPSNTK VDKRVEPKSCDKTHTCPPCPAPELLGGPDVFLFPPKP KDTLMISRTPEVTCVVVDVSHEDPEVKFNWYVDGV EVHNAKTKPREEQYNSTYRVVSVLTVLHQDWLNG KEYKCKVSNKALPAPEEKTISKAKGQPREPQVYTLP | 14 |

TABLE 1-continued

Amino acid sequences of exemplary anti-TIGIT antibodies.

| Description | Amino Acid Sequence | SEQ ID NO: |
|---|---|---|
| according to the EU numbering system) | PSREEMTKNQVSLTCLVKGFYPSDIAVEWESNGQPE NNYKTTPPVLDSDGSFFLYSKLTVDKSRWQQGNVF SCSVMHEALHNHYTQKSLSLSPG, wherein X is glutamate (E) or pyroglutamate (pE) | |
| BA006 full length heavy chain (S239D/ A330L/ I332E variant of BA002, numbered according to the EU numbering system) | XVQLVQSGAEVEKPGASVKVSCKASGYTFASYGIS WVRQAPGQGLEWMGGITPFFNRVDVAEKFQGRVTI TADTSTNTVYIELSSLTSEDTAVYYCARDLRRGGVG DAFDIWGRGTLVTVSSASTKGPSVFPLAPSSKSTSGG TAALGCLVKDYFPEPVTVSWNSGALTSGVHTFPAV LQSSGLYSLSSVVTVPSSSLGTQTYICNVNHKPSNTK VDKRVEPKSCDKTHTCPPCPAPELLGGPDVFLFPPKP KDTLMISRTPEVTCVVVDVSHEDPEVKFNWYVDGV EVHNAKTKPREEQYNSTYRVVSVLTVLHQDWLNG KEYKCKVSNKALPLPEEKTISKAKGQPREPQVYTLP PSREEMTKNQVSLTCLVKGFYPSDIAVEWESNGQPE NNYKTTPPVLDSDGSFFLYSKLTVDKSRWQQGNVF SCSVMHEALHNHYTQKSLSLSPG, wherein X is glutamate (E) or pyroglutamate (pE) | 15 |
| BA007 full length heavy chain (L235V/ F243L/ R292P/ Y300L/ P396L variant of BA002, numbered according to the EU numbering system) | XVQLVQSGAEVEKPGASVKVSCKASGYTFASYGIS WVRQAPGQGLEWMGGITPFFNRVDVAEKFQGRVTI TADTSTNTVYIELSSLTSEDTAVYYCARDLRRGGVG DAFDIWGRGTLVTVSSASTKGPSVFPLAPSSKSTSGG TAALGCLVKDYFPEPVTVSWNSGALTSGVHTFPAV LQSSGLYSLSSVVTVPSSSLGTQTYICNVNHKPSNTK VDKRVEPKSCDKTHTCPPCPAPELVGGPSVFLLPPKP KDTLMISRTPEVTCVVVDVSHEDPEVKFNWYVDGV EVHNAKTPPEEQYNSTLRVVSVLTVLHQDWLNGK EYKCKVSNKALPAPIEKTISKAKGQPREPQVYTLPPS REEMTKNQVSLTCLVKGFYPSDIAVEWESNGQPEN NYKTTPVLDSDGSFFLYSKLTVDKSRWQQGNVFS CSVMHEALHNHYTQKSLSLSPG, wherein X is glutamate (E) or pyroglutamate (pE) | 16 |
| BA008 full length heavy chain (S267E/ L328F variant of BA002, numbered according to the EU numbering system) | XVQLVQSGAEVEKPGASVKVSCKASGYTFASYGIS WVRQAPGQGLEWMGGITPFFNRVDVAEKFQGRVTI TADTSTNTVYIELSSLTSEDTAVYYCARDLRRGGVG DAFDIWGRGTLVTVSSASTKGPSVFPLAPSSKSTSGG TAALGCLVKDYFPEPVTVSWNSGALTSGVHTFPAV LQSSGLYSLSSVVTVPSSSLGTQTYICNVNHKPSNTK VDKRVEPKSCDKTHTCPPCPAPELLGGPSVFLFPPKP KDTLMISRTPEVTCVVVDVEHEDPEVKFNWYVDGV EVHNAKTKPREEQYNSTYRVVSVLTVLHQDWLNG KEYKCKVSNKAFPAPIEKTISKAKGQPREPQVYTLPP SREEMTKNQVSLTCLVKGFYPSDIAVEWESNGQPEN NYKTTPPVLDSDGSFFLYSKLTVDKSRWQQGNVFSC SVMHEALHNHYTQKSLSLSPG, wherein X is glutamate (E) or pyroglutamate (pE) | 17 |
| BA009 full length heavy chain (IgG4 S228P variant of BA002, numbered according to the EU numbering system) | XVQLVQSGAEVEKPGASVKVSCKASGYTFASYGIS WVRQAPGQGLEWMGGITPFFNRVDVAEKFQGRVTI TADTSTNTVYIELSSLTSEDTAVYYCARDLRRGGVG DAFDIWGRGTLVTVSSASTKGPSVFPLAPCSRSTSES TAALGCLVKDYFPEPVTVSWNSGALTSGVHTFPAV LQSSGLYSLSSVVTVPSSSLGTKTYTCNVDHKPSNT KVDKRVESKYGPPCPPCPAPEFLGGPSVFLFPPKPKD TLMISRTPEVTCVVVDVSQEDPEVQFNWYVDGVEV HNAKTKPREEQFNSTYRVVSVLTVLHQDWLNGKEY KCKVSNKGLPSSIEKTISKAKGQPREPQVYTLPPSQE EMTKNQVSLTCLVKGFYPSDIAVEWESNGQPENNY KTTPPVLDSDGSFFLYSRLTVDKSRWQEGNVFSCSV MHEALHNHYTQKSLSLSLG, wherein X is glutamate (E) or pyroglutamate (pE) | 18 |
| BA002 heavy chain constant region | ASTKGPSVFPLAPSSKSTSGGTAALGCLVKDYFPEPV TVSWNSGALTSGVHTFPAVLQSSGLYSLSSVVTVPS SSLGTQTYICNVNHKPSNTKVDKRVEPKSCDKTHTC PPCPAPELLGGPSVFLFPPKPKDTLMISRTPEVTCVV VDVSHEDPEVKFNWYVDGVEVHNAKTKPREEQYN STYRVVSVLTVLHQDWLNGKEYKCKVSNKALPAPI EKTISKAKGQPREPQVYTLPPSREEMTKNQVSLTCL VKGFYPSDIAVEWESNGQPENNYKTTPPVLDSDGSF FLYSKLTVDKSRWQQGNVFSCSVMHEALHNHYTQ KSLSLSPG | 19 |
| BA003 heavy chain constant region | ASTKGPSVFPLAPSSKSTSGGTAALGCLVKDYFPEPV TVSWNSGALTSGVHTFPAVLQSSGLYSLSSVVTVPS SSLGTQTYICNVNHKPSNTKVDKRVEPKSCDKTHTC PPCPAPELLGGPSVFLFPPKPKDTLMISRTPEVTCVV VDVSHEDPEVKFNWYVDGVEVHNAKTKPREEQYA STYRVVSVLTVLHQDWLNGKEYKCKVSNKALPAPI EKTISKAKGQPREPQVYTLPPSREEMTKNQVSLTCL VKGFYPSDIAVEWESNGQPENNYKTTPPVLDSDGSF FLYSKLTVDKSRWQQGNVFSCSVMHEALHNHYTQ KSLSLSPG | 20 |
| BA004 heavy chain constant region | ASTKGPSVFPLAPSSKSTSGGTAALGCLVKDYFPEPV TVSWNSGALTSGVHTFPAVLQSSGLYSLSSVVTVPS SSLGTQTYICNVNHKPSNTKVDKRVEPKSCDKTHTC PPCPAPEFFGGPSVFLFPPKPKDTLMISRTPEVTCVVV DVSHEDPEVKFNWYVDGVEVHNAKTKPREEQYAS TYRVVSVLTVLHQDWLNGKEYKCKVSNKALPAPIE KTISKAKGQPREPQVYTLPPSREEMTKNQVSLTCLV KGFYPSDIAVEWESNGQPENNYKTTPPVLDSDGSFF LYSKLTVDKSRWQQGNVFSCSVMHEALHNHYTQK SLSLSPG | 21 |
| BA005 heavy chain constant region | ASTKGPSVFPLAPSSKSTSGGTAALGCLVKDYFPEPV TVSWNSGALTSGVHTFPAVLQSSGLYSLSSVVTVPS SSLGTQTYICNVNHKPSNTKVDKRVEPKSCDKTHTC PPCPAPELLGGPDVFLFPPKPKDTLMISRTPEVTCVV VDVSHEDPEVKFNWYVDGVEVHNAKTKPREEQYN STYRVVSVLTVLHQDWLNGKEYKCKVSNKALPAPE EKTISKAKGQPREPQVYTLPPSREEMTKNQVSLTCL VKGFYPSDIAVEWESNGQPENNYKTTPPVLDSDGSF FLYSKLTVDKSRWQQGNVFSCSVMHEALHNHYTQ KSLSLSPG | 22 |
| BA006 heavy chain constant region | ASTKGPSVFPLAPSSKSTSGGTAALGCLVKDYFPEPV TVSWNSGALTSGVHTFPAVLQSSGLYSLSSVVTVPS SSLGTQTYICNVNHKPSNTKVDKRVEPKSCDKTHTC PPCPAPELLGGPDVFLFPPKPKDTLMISRTPEVTCVV VDVSHEDPEVKFNWYVDGVEVHNAKTKPREEQYN STYRVVSVLTVLHQDWLNGKEYKCKVSNKALPLPE EKTISKAKGQPREPQVYTLPPSREEMTKNQVSLTCL VKGFYPSDIAVEWESNGQPENNYKTTPPVLDSDGSF FLYSKLTVDKSRWQQGNVFSCSVMHEALHNHYTQ KSLSLSPG | 23 |
| BA007 heavy chain constant region | ASTKGPSVFPLAPSSKSTSGGTAALGCLVKDYFPEPV TVSWNSGALTSGVHTFPAVLQSSGLYSLSSVVTVPS SSLGTQTYICNVNHKPSNTKVDKRVEPKSCDKTHTC PPCPAPELVGGPSVFLLPPKPKDTLMISRTPEVTCVV VDVSHEDPEVKFNWYVDGVEVHNAKTKPPEEQYN STLRVVSVLTVLHQDWLNGKEYKCKVSNKALPAPI EKTISKAKGQPREPQVYTLPPSREEMTKNQVSLTCL VKGFYPSDIAVEWESNGQPENNYKTTPLVLDSDGSF FLYSKLTVDKSRWQQGNVFSCSVMHEALHNHYTQ KSLSLSPG | 24 |
| BA008 heavy chain constant region | ASTKGPSVFPLAPSSKSTSGGTAALGCLVKDYFPEPV TVSWNSGALTSGVHTFPAVLQSSGLYSLSSVVTVPS SSLGTQTYICNVNHKPSNTKVDKRVEPKSCDKTHTC PPCPAPELLGGPSVFLFPPKPKDTLMISRTPEVTCVV VDVEHEDPEVKFNWYVDGVEVHNAKTKPREEQYN STYRVVSVLTVLHQDWLNGKEYKCKVSNKAFPAPI EKTISKAKGQPREPQVYTLPPSREEMTKNQVSLTCL VKGFYPSDIAVEWESNGQPENNYKTTPPVLDSDGSF FLYSKLTVDKSRWQQGNVFSCSVMHEALHNHYTQ KSLSLSPG | 25 |

TABLE 1-continued

Amino acid sequences of exemplary anti-TIGIT antibodies.

| Description | Amino Acid Sequence | SEQ ID NO: |
|---|---|---|
| BA009 heavy chain constant region | ASTKGPSVFPLAPCSRSTSESTAALGCLVKDYFPEPVTVSWNSGALTSGVHTFPAVLQSSGLYSLSSVVTVPSSSLGTKTYTCNVDHKPSNTKVDKRVESKYGPPCPPCPAPEFLGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLTCLVKGFYPSDIAVEWESNGQPENNYKTTPPVLDSDGSFFLYSRLTVDKSRWQEGNVFSCSVMHEALHNHYTQKSLSLSLG | 26 |
| BA002 full length light chain | XSALTQPRSVSGSPGQSVTISCTGTSSDVGSHNYVSWYQQHPGKAPQLMIYEVSYRPSEISNRFSGSKSGNTASLTISGLQPEDEADYYCSSYTPSSATVFGAGTKLTVLGQPKAAPSVTLFPPSSEELQANKATLVCLISDFYPGAVTVAWKADSSPVKAGVETTTPSKQSNNKYAASSYLSLTPEQWKSHRSYSCQVTHEGSTVEKTVAPTECS, wherein X is glutamine (Q) or pyroglutamate (pE) | 27 |
| BA002 light chain constant region | GQPKAAPSVTLFPPSSEELQANKATLVCLISDFYPGAVTVAWKADSSPVKAGVETTTPSKQSNNKYAASSYLSLTPEQWKSHRSYSCQVTHEGSTVEKTVAPTECS | 28 |

TABLE 2

Closest germline genes to the exemplary anti-TIGIT antibodies.

| Closest germline gene | Amino Acid Sequence | SEQ ID NO: |
|---|---|---|
| IGHV1-69*01 heavy chain variable region | QVQLVQSGAEVKKPGSSVKVSCKASGGTFSSYAISWVRQAPGQGLEWMGGIIPIFGTANYAQKFQGRVTITADESTSTAYMELSSLRSEDTAVYYCAR | 34 |
| IGHV1-69*06 heavy chain variable region | QVQLVQSGAEVKKPGSSVKVSCKASGGTFSSYAISWVRQAPGQGLEWMGGIIPIFGTANYAQKFQGRVTITADKSTSTAYMELSSLRSEDTAVYYCAR | 35 |
| IGLV2-14*01 light chain variable region | QSALTQPASVSGSPGQSITISCTGTSSDVGGYNYVSWYQQHPGKAPKLMIYEVSNRPSGVSNRFSGSKSGNTASLTISGLQAEDEADYYCSSYTSSSTL | 37 |
| IGLV2-14*02 light chain variable region | QSALTQPASVSGSPGQSITISCTGTSSDVGSYNLVSWYQQHPGKAPKLMIYEGSKRPSGVSNRFSGSKSGNTASLTISGLQAEDEADYYCSSYTSSSTL | 60 |

TABLE 2-continued

Closest germline genes to the exemplary anti-TIGIT antibodies.

| Closest germline gene | Amino Acid Sequence | SEQ ID NO: |
|---|---|---|
| IGLV2-23*02 light chain variable region | QSALTQPASVSGSPGQSITISCTGTSSDVGSYNLVSWYQQHPGKAPKLMIYEVSKRPSGVSNRFSGSKSGNTASLTISGLQAEDEADYYCCSYAGSSTF | 38 |
| IGLV2-11*01 light chain variable region | QSALTQPRSVSGSPGQSVTISCTGTSSDVGGYNYVSWYQQHPGKAPKLMIYDVSKRPSGVPDRFSGSKSGNTASLTISGLQAEDEADYYCCSYAGSYTF | 39 |

TABLE 3

Exemplary sequences of TIGIT.

| Description | Amino Acid Sequence | SEQ ID NO: |
|---|---|---|
| Exemplary immature TIGIT full length sequence | MRWCLLLIWAQGLRQAPLASGMMTGTIETTGNISAEKGGSIILQCHLSSTTAQVTQVNWEQQDQLLAICNADLGWHISPSFKDRVAPGPGLGLTLQSLTVNDTGEYFCIYHTYPDGTYTGRIFLEVLESSVAEHGARFQIPLLGAMAATLVVICTAVIVVVALTRKKKALRIHSVEGDLRRKSAGQEEWSPSAPSPPGSCVQAEAAPAGLCGEQRGEDCAELHDYFNVLSYRSLGNCSFFTETG | 29 |
| Exemplary TIGIT extracellular domain sequence (epitope sequences indicated in bold) | MMTGTIETTGNISAEKGGSIILQCHLSSTTAQVTQVNWEQQDQLLAICNADLGWHISPSFKDRVAPGPGLGLTLQSLTVNDTGEYFCIYHTYPDGTYTGRIFLEVLESSVAEHGARF | 30 |
| TIGIT epitope sequence #1 (Residues 89-104 of mature TIGIT sequence) | YHTYPDGTYTGRIFLE | 31 |
| TIGIT epitope sequence #2 (Residues 33-36 of mature TIGIT sequence) | VTQV | 32 |
| TIGIT epitope sequence #3 | ICNADLGWHISPSF | 33 |

TABLE 3-continued

Exemplary sequences of TIGIT.

| Description | Amino Acid Sequence | SEQ ID NO: |
|---|---|---|
| (Residues 47-60 of mature TIGIT sequence) | | |
| Exemplary mature TIGIT full length sequence | MMTGTIETTGNISAEKGGSIILQCHLSSTTAQVTQVNW EQQDQLLAICNADLGWHISPSFKDRVAPGPGLGLTLQS LTVNDTGEYFCIYHTYPDGTYTGRIFLEVLESSVAEHG ARFQIPLLGAMAATLVVICTAVIVVVALTRKKKALRIH SVEGDLRRKSAGQEEWSPSAPSPPGSCVQAEAAPAGLC GEQRGEDCAELHDYFNVLSYRSLGNCSFFTETG | 40 |
| Exemplary TIGIT extracellular domain sequence | MMTGTIETTGNISAEKGGSIILQCHLSSTTAQVTQVNW EQQDQLLAICNADLGWHISPSFKDRVAPGPGLGLTLQS LTVNDTGEYFCIYHTYPDGTYTGRIFLEVLESSVAEHG ARFQIP | 41 |
| Exemplary TIGIT extracellular domain sequence | MMTGTIETTGNISAEKGGSIILQCHLSSTTAQVTQVNW EQQDQLLAICNADLGWHISPSFKDRVAPGPGLGLTLQS LTVNDTGEYFCIYHTYPDGTYTGRIFLEVLESSVAEHG ARFQ | 42 |
| Exemplary TIGIT extracellular domain T34A | MMTGTIETTGNISAEKGGSIILQCHLSSTTAQVAQVNW EQQDQLLAICNADLGWHISPSFKDRVAPGPGLGLTLQS LTVNDTGEYFCIYHTYPDGTYTGRIFLEVLESSVAEHG ARFQ | 43 |
| Exemplary TIGIT extracellular domain Q35A | MMTGTIETTGNISAEKGGSIILQCHLSSTTAQVTAVNW EQQDQLLAICNADLGWHISPSFKDRVAPGPGLGLTLQS LTVNDTGEYFCIYHTYPDGTYTGRIFLEVLESSVAEHG ARFQ | 44 |
| Exemplary TIGIT extracellular domain I47E | MMTGTIETTGNISAEKGGSIILQCHLSSTTAQVTQVNW EQQDQLLAECNADLGWHISPSFKDRVAPGPGLGLTLQ SLTVNDTGEYFCIYHTYPDGTYTGRIFLEVLESSVAEH GARFQ | 45 |
| Exemplary TIGIT extracellular domain N49A | MMTGTIETTGNISAEKGGSIILQCHLSSTTAQVTQVNW EQQDQLLAICAADLGWHISPSFKDRVAPGPGLGLTLQS LTVNDTGEYFCIYHTYPDGTYTGRIFLEVLESSVAEHG ARFQ | 46 |
| Exemplary TIGIT extracellular domain L52A | MMTGTIETTGNISAEKGGSIILQCHLSSTTAQVTQVNW EQQDQLLAICNADAGWHISPSFKDRVAPGPGLGLTLQS LTVNDTGEYFCIYHTYPDGTYTGRIFLEVLESSVAEHG ARFQ | 47 |
| Exemplary TIGIT extracellular domain L52E | MMTGTIETTGNISAEKGGSIILQCHLSSTTAQVTQVNW EQQDQLLAICNADEGWHISPSFKDRVAPGPGLGLTLQS LTVNDTGEYFCIYHTYPDGTYTGRIFLEVLESSVAEHG ARFQ | 48 |
| Exemplary TIGIT extracellular domain H55A | MMTGTIETTGNISAEKGGSIILQCHLSSTTAQVTQVNW EQQDQLLAICNADLGWAISPSFKDRVAPGPGLGLTLQS LTVNDTGEYFCIYHTYPDGTYTGRIFLEVLESSVAEHG ARFQ | 49 |
| Exemplary TIGIT extracellular domain P58A | MMTGTIETTGNISAEKGGSIILQCHLSSTTAQVTQVNW EQQDQLLAICNADLGWHISASFKDRVAPGPGLGLTLQS LTVNDTGEYFCIYHTYPDGTYTGRIFLEVLESSVAEHG ARFQ | 50 |
| Exemplary TIGIT extracellular domain H90A | MMTGTIETTGNISAEKGGSIILQCHLSSTTAQVTQVNW EQQDQLLAICNADLGWHISPSFKDRVAPGPGLGLTLQS LTVNDTGEYFCIYATYPDGTYTGRIFLEVLESSVAEHG ARFQ | 51 |
| Exemplary TIGIT extracellular domain T96A | MMTGTIETTGNISAEKGGSIILQCHLSSTTAQVTQVNW EQQDQLLAICNADLGWHISPSFKDRVAPGPGLGLTLQS LTVNDTGEYFCIYHTYPDGAYTGRIFLEVLESSVAEHG ARFQ | 52 |
| Exemplary TIGIT extracellular domain T96I | MMTGTIETTGNISAEKGGSIILQCHLSSTTAQVTQVNW EQQDQLLAICNADLGWHISPSFKDRVAPGPGLGLTLQS LTVNDTGEYFCIYHTYPDGIYTGRIFLEVLESSVAEHG ARFQ | 53 |
| Exemplary TIGIT extracellular domain T98A | MMTGTIETTGNISAEKGGSIILQCHLSSTTAQVTQVNW EQQDQLLAICNADLGWHISPSFKDRVAPGPGLGLTLQS LTVNDTGEYFCIYHTYPDGTYAGRIFLEVLESSVAEHG ARFQ | 54 |
| Exemplary TIGIT extracellular domain R100A | MMTGTIETTGNISAEKGGSIILQCHLSSTTAQVTQVNW EQQDQLLAICNADLGWHISPSFKDRVAPGPGLGLTLQS LTVNDTGEYFCIYHTYPDGTYTGAIFLEVLESSVAEHG ARFQ | 55 |
| Exemplary TIGIT extracellular domain F102A | MMTGTIETTGNISAEKGGSIILQCHLSSTTAQVTQVNW EQQDQLLAICNADLGWHISPSFKDRVAPGPGLGLTLQS LTVNDTGEYFCIYHTYPDGTYTGRIALEVLESSVAEHG ARFQ | 56 |
| Exemplary TIGIT extracellular domain C48Y, N49S, A50V | MMTGTIETTGNISAEKGGSIILQCHLSSTTAQVTQVNW EQQDQLLAIYSVDLGWHISPSFKDRVAPGPGLGLTLQS LTVNDTGEYFCIYHTYPDGTYTGRIFLEVLESSVAEHG ARFQ | 57 |
| Exemplary TIGIT extracellular domain N49S | MMTGTIETTGNISAEKGGSIILQCHLSSTTAQVTQVNW EQQDQLLAICSADLGWHISPSFKDRVAPGPGLGLTLQS LTVNDTGEYFCIYHTYPDGTYTGRIFLEVLESSVAEHG ARFQ | 36 |

TABLE 3-continued

Exemplary sequences of TIGIT.

| Description | Amino Acid Sequence | SEQ ID NO: |
|---|---|---|
| Exemplary TIGIT extracellular domain I56V, S57A, P58S, S59V | MMTGTIETTGNISAEKGGSIILQCHLSSTTAQVTQVNW EQQDQLLAICNADLGWHVASVFKDRVAPGPGLGLTLQ SLTVNDTGEYFCIYHTYPDGTYTGRIFLEVLESSVAEH GARFQ | 58 |
| Exemplary TIGIT extracellular domain T96I, T98K | MMTGTIETTGNISAEKGGSIILQCHLSSTTAQVTQVNW EQQDQLLAICNADLGWHISPSFKDRVAPGPGLGLTLQS LTVNDTGEYFCIYHTYPDGIYKGRIFLEVLESSVAEHG ARFQ | 59 |

In certain embodiments, the instant disclosure provides an isolated antibody that specifically binds to TIGIT (e.g., human TIGIT or cynomolgus TIGIT), the antibody comprising a VH domain comprising one, two, or all three of the CDRs of a VH domain set forth in Table 1 herein. In certain embodiments, the antibody comprises the CDRH1 of a VH domain set forth in Table 1. In certain embodiments, the antibody comprises the CDRH2 of a VH domain set forth in Table 1. In certain embodiments, the antibody comprises the CDRH3 of a VH domain set forth in Table 1.

In certain embodiments, the instant disclosure provides an isolated antibody that specifically binds to TIGIT (e.g., human TIGIT or cynomolgus TIGIT), the antibody comprising a VL domain comprising one, two, or all three of the CDRs of a VL domain disclosed in Table 1 herein. In certain embodiments, the antibody comprises the CDRL1 of a VL domain set forth in Table 1. In certain embodiments, the antibody comprises the CDRL2 of a VL domain set forth in Table 1. In certain embodiments, the antibody comprises the CDRL3 of a VL domain set forth in Table 1.

In certain embodiments, the CDRs of an antibody can be determined according to Kabat et al., J. Biol. Chem. 252, 6609-6616 (1977) and Kabat et al., Sequences of protein of immunological interest (1991), each of which is herein incorporated by reference in its entirety. In certain embodiments, the light chain CDRs of an antibody are determined according to Kabat and the heavy chain CDRs of an antibody are determined according to MacCallum (supra). In certain embodiments, heavy chain CDRs and/or light chain CDRs are defined by performing structural analysis of an antibody and identifying residues in the variable region(s) predicted to make contact with an epitope region of a target molecule (e.g., human and/or cynomolgus TIGIT).

In certain embodiments, the CDRs of an antibody can be determined according to the Chothia numbering scheme, which refers to the location of immunoglobulin structural loops (see, e.g., Chothia C & Lesk A M, (1987), J Mol Biol 196: 901-917; Al-Lazikani B et al., (1997) J Mol Biol 273: 927-948; Chothia C et al., (1992) J Mol Biol 227: 799-817; Tramontano A et al., (1990) J Mol Biol 215(1): 175-82; and U.S. Pat. No. 7,709,226, all of which are herein incorporated by reference in their entireties). Typically, when using the Kabat numbering convention, the Chothia CDRH1 loop is present at heavy chain amino acids 26 to 32, 33, or 34, the Chothia CDRH2 loop is present at heavy chain amino acids 52 to 56, and the Chothia CDRH3 loop is present at heavy chain amino acids 95 to 102, while the Chothia CDRL1 loop is present at light chain amino acids 24 to 34, the Chothia CDRL2 loop is present at light chain amino acids 50 to 56, and the Chothia CDRL3 loop is present at light chain amino acids 89 to 97. The end of the Chothia CDRH1 loop when numbered using the Kabat numbering convention varies between H32 and H34 depending on the length of the loop (this is because the Kabat numbering scheme places the insertions at H35A and H35B; if neither 35A nor 35B is present, the loop ends at 32; if only 35A is present, the loop ends at 33; if both 35A and 35B are present, the loop ends at 34).

In certain embodiments, the CDRs of an antibody can be determined according to MacCallum R M et al., (1996) J Mol Biol 262: 732-745, herein incorporated by reference in its entirety. See also, e.g., Martin A. "Protein Sequence and Structure Analysis of Antibody Variable Domains," in *Antibody Engineering*, Kontermann and Dübel, eds., Chapter 31, pp. 422-439, Springer-Verlag, Berlin (2001), herein incorporated by reference in its entirety.

In certain embodiments, the instant disclosure provides an isolated antibody that specifically binds to TIGIT (e.g., human TIGIT or cynomolgus TIGIT), the antibody comprising the Chothia VH CDRs of a VH disclosed in Table 1 herein. In certain embodiments, the instant disclosure provides an isolated antibody that specifically binds to TIGIT (e.g., human TIGIT or cynomolgus TIGIT), the antibody comprising the Chothia VL CDRs of a VL disclosed in Table 1 herein. In certain embodiments, the instant disclosure provides an isolated antibody that specifically binds to TIGIT (e.g., human TIGIT or cynomolgus TIGIT), the antibody comprising the Chothia VH CDRs and Chothia VL CDRs of an antibody disclosed in Table 1 herein. In certain embodiments, antibodies that specifically bind to TIGIT (e.g., human TIGIT or cynomolgus TIGIT) comprise one or more CDRs, in which the Chothia and Kabat CDRs have the same amino acid sequence. In certain embodiments, the instant disclosure provides an isolated antibody that specifically binds to TIGIT (e.g., human TIGIT or cynomolgus TIGIT) and comprises combinations of Kabat CDRs and Chothia CDRs.

In certain embodiments, the CDRs of an antibody can be determined according to the IMGT numbering system as described in Lefranc M-P, (1999) The Immunologist 7: 132-136 and Lefranc M-P et al., (1999) Nucleic Acids Res 27: 209-212, each of which is herein incorporated by reference in its entirety. According to the IMGT numbering scheme, CDRH1 is at positions 26 to 35, CDRH2 is at positions 51 to 57, CDRH3 is at positions 93 to 102, CDRL1 is at positions 27 to 32, CDRL2 is at positions 50 to 52, and CDRL3 is at positions 89 to 97.

In certain embodiments, the instant disclosure provides antibodies that specifically bind to TIGIT (e.g., human TIGIT or cynomolgus TIGIT) and comprise CDRs of an antibody disclosed in Table 1 herein, as determined by the IMGT numbering system, for example, as described in Lefranc M-P (1999) supra and Lefranc M-P et al., (1999) supra.

In certain embodiments, the CDRs of an antibody can be determined according to the AbM numbering scheme, which refers to AbM hypervariable regions, which represent a compromise between the Kabat CDRs and Chothia structural loops, and are used by Oxford Molecular's AbM antibody modeling software (Oxford Molecular Group, Inc.), herein incorporated by reference in its entirety. In a particular embodiment, the instant disclosure provides antibodies that specifically bind to TIGIT (e.g., human TIGIT or cynomolgus TIGIT) and comprise CDRs of an antibody disclosed in Table 1 herein as determined by the AbM numbering scheme.

In certain embodiments, the instant disclosure provides an isolated antibody that specifically binds to TIGIT (e.g., human TIGIT or cynomolgus TIGIT), wherein the antibody comprises a heavy chain variable region comprising the CDRH1, CDRH2, and CDRH3 region amino acid sequences of a VH domain set forth in SEQ ID NO: 9, and a light chain variable region comprising the CDRL1, CDRL2, and CDRL3 region amino acid sequences of a VL domain set forth in SEQ ID NO: 10, wherein each CDR is defined in accordance with the MacCallum definition, the Kabat definition, the Chothia definition, the IMGT numbering system, the AbM definition of CDR, structural analysis, or a combination thereof, wherein the structural analysis identifies residues in the variable region(s) predicted to make contact with an epitope region of TIGIT (e.g., human TIGIT or cynomolgus TIGIT). In certain embodiments, the instant disclosure provides an isolated antibody that specifically binds to TIGIT (e.g., human TIGIT or cynomolgus TIGIT) and comprises a combination of CDRs defined by the Kabat definition and CDRs defined by structural analysis of the antibody, wherein the structural analysis identifies residues in the variable region(s) predicted to make contact with an epitope region of TIGIT (e.g., human TIGIT or cynomolgus TIGIT).

In certain embodiments, the instant disclosure provides an isolated antibody that specifically binds to TIGIT (e.g., human TIGIT or cynomolgus TIGIT), the antibody comprising:
(a) a CDRH1 comprises the amino acid sequence of SYGIS (SEQ ID NO: 1) or GYTFASY (SEQ ID NO: 2);
(b) a CDRH2 comprises the amino acid sequence of GITPFFNRVDVAEKFQG (SEQ ID NO: 3) or TPFFNR (SEQ ID NO: 4);
(c) a CDRH3 comprises the amino acid sequence of DLRRGGVGDAFDI (SEQ ID NO: 5);
(d) a CDRL1 comprises the amino acid sequence of TGTSSDVGSHNYVS (SEQ ID NO: 6);
(e) a CDRL2 comprises the amino acid sequence of EVSYRPS (SEQ ID NO: 7); and/or
(f) a CDRL3 comprises the amino acid sequence of SSYTPSSATV (SEQ ID NO: 8).

In certain embodiments, the instant disclosure provides an isolated antibody that specifically binds to TIGIT (e.g., human TIGIT or cynomolgus TIGIT), the antibody comprising:
(a) a CDRH1 comprises the amino acid sequence of SYGIS (SEQ ID NO: 1) or GYTFASY (SEQ ID NO: 2);
(b) a CDRH2 comprises the amino acid sequence of GITPFFNRVDVAEKFQG (SEQ ID NO: 3) or TPFFNR (SEQ ID NO: 4);
(c) a CDRH3 comprises the amino acid sequence of DLRRGGVGDAFDI (SEQ ID NO: 5);
(d) a CDRL1 comprises the amino acid sequence of TGTSSDVGSHNYVS (SEQ ID NO: 6);
(e) a CDRL2 comprises the amino acid sequence of EVSYRPS (SEQ ID NO: 7); and
(f) a CDRL3 comprises the amino acid sequence of SSYTPSSATV (SEQ ID NO: 8).

In certain embodiments, the instant disclosure provides an isolated antibody that specifically binds to TIGIT (e.g., human TIGIT or cynomolgus TIGIT), wherein the antibody comprises a VH domain comprising the CDRH1, CDRH2 and CDRH3 amino acid sequences set forth in SEQ ID NOs: 1, 3, and 5, respectively. In certain embodiments, the instant disclosure provides an isolated antibody that specifically binds to TIGIT (e.g., human TIGIT or cynomolgus TIGIT), wherein the antibody comprises a VH domain comprising the CDRH1, CDRH2 and CDRH3 amino acid sequences set forth in SEQ ID NOs: 2, 4, and 5, respectively. In certain embodiments, the instant disclosure provides an isolated antibody that specifically binds to TIGIT (e.g., human TIGIT or cynomolgus TIGIT), wherein the antibody comprises a VL domain comprising the CDRL1, CDRL2 and CDRL3 amino acid sequences set forth in SEQ ID NOs: 6, 7, and 8, respectively.

In certain embodiments, the instant disclosure provides an isolated antibody that specifically binds to TIGIT (e.g., human TIGIT or cynomolgus TIGIT), wherein the antibody comprises a heavy chain variable region comprising CDRH1, CDRH2, and CDRH3 regions, and a light chain variable region comprising CDRL1, CDRL2, and CDRL3 regions, wherein the CDRH1, CDRH2, CDRH3, CDRL1, CDRL2, and CDRL3 regions comprise the amino acid sequences set forth in SEQ ID NOs: 1, 3, 5, 6, 7, and 8, respectively. In certain embodiments, the instant disclosure provides an isolated antibody that specifically binds to TIGIT (e.g., human TIGIT or cynomolgus TIGIT), wherein the antibody comprises a heavy chain variable region comprising CDRH1, CDRH2, and CDRH3 regions, and a light chain variable region comprising CDRL1, CDRL2, and CDRL3 regions, wherein the CDRH1, CDRH2, CDRH3, CDRL1, CDRL2, and CDRL3 regions comprise the amino acid sequences set forth in SEQ ID NOs: 2, 4, 5, 6, 7, and 8, respectively.

In certain embodiments, the instant disclosure provides an isolated antibody that specifically binds to TIGIT (e.g., human TIGIT or cynomolgus TIGIT), comprising a heavy chain variable region comprising an amino acid sequence of SEQ ID NO: 9. In certain embodiments, the instant disclosure provides an isolated antibody that specifically binds to TIGIT (e.g., human TIGIT or cynomolgus TIGIT), comprising a heavy chain variable region comprising an amino acid sequence that is at least 75%, 80%, 85%, 90%, 95%, or 100% (e.g., at least 86, 87, 88, 89, 90, 91, 92, 93, 94, 95, 96, 97, 98 or 99%) identical to the amino acid sequence set forth in SEQ ID NO: 9. In certain embodiments, the instant disclosure provides an isolated antibody that specifically binds to TIGIT (e.g., human TIGIT or cynomolgus TIGIT), comprising a light chain variable region comprising an amino acid sequence of SEQ ID NO: 10. In certain embodiments, the instant disclosure provides an isolated antibody that specifically binds to TIGIT (e.g., human TIGIT or cynomolgus TIGIT), comprising a light chain variable region comprising an amino acid sequence that is at least 75%, 80%, 85%, 90%, 95%, or 100% (e.g., at least 86, 87, 88, 89, 90, 91, 92, 93, 94, 95, 96, 97, 98 or 99%) identical to the amino acid sequence set forth in SEQ ID NO: 10.

In certain embodiments, the instant disclosure provides an isolated antibody that specifically binds to TIGIT (e.g., human TIGIT or cynomolgus TIGIT), comprising a heavy chain variable region comprising an amino acid sequence of SEQ ID NO: 9, and a light chain variable region comprising an amino acid sequence of SEQ ID NO: 10. In certain embodiments, the instant disclosure provides an isolated antibody that specifically binds to TIGIT (e.g., human TIGIT or cynomolgus TIGIT), comprising a heavy chain variable region comprising an amino acid sequence that is at least 75%, 80%, 85%, 90%, 95%, or 100% (e.g., at least 86, 87, 88, 89, 90, 91, 92, 93, 94, 95, 96, 97, 98 or 99%) identical to the amino acid sequence set forth in SEQ ID NO: 9, and a light chain variable region comprising an amino acid sequence that is at least 75%, 80%, 85%, 90%, 95%, or 100% (e.g., at least 86, 87, 88, 89, 90, 91, 92, 93, 94, 95, 96, 97, 98 or 99%) identical to the amino acid sequence set forth in SEQ ID NO: 10.

In certain embodiments, the instant disclosure provides an isolated antibody that specifically binds to TIGIT (e.g., human TIGIT or cynomolgus TIGIT), comprising a heavy chain variable region having an amino acid sequence derived from a human IGHV1-69 germline sequence. In certain embodiments, the human IGHV1-69 germline sequence is selected from the group consisting of a human IGHV1-69*01 germline sequence (e.g., having the amino acid sequence of SEQ ID NO: 34), a human IGHV1-69*06 germline sequence (e.g., having the amino acid sequence of SEQ ID NO: 35), and a human IGHV1-69*12 germline sequence. One or more regions selected from framework 1, framework 2, framework 3, CDRH1, and CDRH2 (e.g., two, three, four or five of these regions) can be derived from a human IGHV1-69 germline sequence. In one embodiment, framework 1, framework 2, framework 3, CDRH1, and CDRH2 are all derived from a human IGHV1-69 germline sequence. In certain embodiments, the heavy chain variable region comprises a CDRH3 comprising the amino acid sequence set forth in SEQ ID NO: 5.

In certain embodiments, the instant disclosure provides an isolated antibody that specifically binds to TIGIT (e.g., human TIGIT or cynomolgus TIGIT), comprising a light chain variable region having an amino acid sequence derived from a human germline sequence selected from the group consisting of IGLV2-14 (e.g., IGLV2-14*01, e.g., having the amino acid sequence of SEQ ID NO: 37, or IGLV2-14*02, e.g., having the amino acid sequence of SEQ ID NO: 60), IGLV2-23 (e.g., IGLV2-23*02, e.g., having the amino acid sequence of SEQ ID NO: 38), and IGLV2-11 (e.g., IGLV2-11*01, e.g., having the amino acid sequence of SEQ ID NO: 39). One or more regions selected from framework 1, framework 2, framework 3, CDRL1, and CDRL2 (e.g., two, three, four or five of these regions) can be derived from a human germline sequence selected from the group consisting of IGLV2-14 (e.g., IGLV2-14*01, e.g., having the amino acid sequence of SEQ ID NO: 37, or IGLV2-14*02, e.g., having the amino acid sequence of SEQ ID NO: 60), IGLV2-23 (e.g., IGLV2-23*02, e.g., having the amino acid sequence of SEQ ID NO: 38), and IGLV2-11 (e.g., IGLV2-11*01, e.g., having the amino acid sequence of SEQ ID NO: 39). In one embodiment, framework 1, framework 2, framework 3, CDRL1, and CDRL2 are all derived from a human germline sequence selected from the group consisting of IGLV2-14 (e.g., IGLV2-14*01, e.g., having the amino acid sequence of SEQ ID NO: 37, or IGLV2-14*02, e.g., having the amino acid sequence of SEQ ID NO: 60), IGLV2-23 (e.g., IGLV2-23*02, e.g., having the amino acid sequence of SEQ ID NO: 38), and IGLV2-11 (e.g., IGLV2-11*01, e.g., having the amino acid sequence of SEQ ID NO: 39). In certain embodiments, the light chain variable region comprises a CDRL3 comprising the amino acid sequence set forth in SEQ ID NO: 8.

In certain embodiments, the instant disclosure provides an isolated antibody that specifically binds to TIGIT (e.g., human TIGIT or cynomolgus TIGIT), comprising a heavy chain variable region having an amino acid sequence derived from a human IGHV1-69 germline sequence (e.g., a human IGHV1-69*01 germline sequence (e.g., having the amino acid sequence of SEQ ID NO: 34), a human IGHV1-69*06 germline sequence (e.g., having the amino acid sequence of SEQ ID NO: 35), or a human IGHV1-69*12 germline sequence); and a light chain variable region having an amino acid sequence derived from a human germline sequence selected from the group consisting of IGLV2-14 (e.g., IGLV2-14*01, e.g., having the amino acid sequence of SEQ ID NO: 37, or IGLV2-14*02, e.g., having the amino acid sequence of SEQ ID NO: 60), IGLV2-23 (e.g., IGLV2-23*02, e.g., having the amino acid sequence of SEQ ID NO: 38), and IGLV2-11 (e.g., IGLV2-11*01, e.g., having the amino acid sequence of SEQ ID NO: 39). In certain embodiments, the heavy chain variable region comprises a CDRH3 comprising the amino acid sequence set forth in SEQ ID NO: 5, and the light chain variable region comprises a CDRL3 comprising the amino acid sequence set forth in SEQ ID NO: 8.

In certain embodiments, the instant disclosure provides an isolated antibody that specifically binds to human TIGIT, the antibody comprising a heavy chain variable region comprising an amino acid region that is at least 75%, 80%, 85%, 90%, 95%, 96%, 97%, 98%, 99%, or 100% identical to the amino acid sequence of SEQ ID NO: 34 or 35. In certain embodiments, the instant disclosure provides an isolated antibody that specifically binds to human TIGIT, the antibody comprising a light chain variable region comprising an amino acid region that is at least 75%, 80%, 85%, 90%, 95%, 96%, 97%, 98%, 99%, or 100% identical to the amino acid sequence of any one of SEQ ID NOs: 37-39 and 60.

In certain embodiments, the instant disclosure provides an isolated antibody that cross-competes for binding to TIGIT (e.g., human TIGIT or cynomolgus TIGIT) with an antibody comprising the heavy and light chain variable region amino acid sequences set forth in SEQ ID NOs: 9 and 10, respectively.

In another aspect, the instant disclosure provides an antibody or isolated antibody that binds, e.g., specifically binds, to the same epitope of human TIGIT as an antibody of the present invention. In certain embodiments, the epitope is determined by hydrogen-deuterium exchange (HDX), for example as described in the examples, or by protein mutagenesis, for example as described in the examples.

In certain embodiments, the instant disclosure provides an isolated antibody that binds to the same or an overlapping epitope of TIGIT (e.g., an epitope of human TIGIT or an epitope of cynomolgus TIGIT) as an antibody described herein, e.g., an antibody comprising the heavy and light chain variable region amino acid sequences set forth in SEQ ID NOs: 9 and 10, respectively. In certain embodiments, the epitope of an antibody can be determined by, e.g., NMR spectroscopy, surface plasmon resonance (BIAcore®), X-ray diffraction crystallography studies, ELISA assays, hydrogen/deuterium exchange coupled with mass spectrometry (e.g., liquid chromatography electrospray mass spectrometry), array-based oligo-peptide scanning assays, and/or mutagenesis mapping (e.g., site-directed mutagenesis mapping). For X-ray crystallography, crystallization may be accomplished using any of the known methods in the art (e.g., Giegé R et al., (1994) Acta Crystallogr D Biol Crystallogr 50(Pt 4): 339-350; McPherson A (1990) Eur J Biochem 189: 1-23; Chayen N E (1997) Structure 5: 1269-1274; McPherson A (1976) J Biol Chem 251: 6300-6303, all of which are herein incorporated by reference in their entireties). Antibody:antigen crystals may be studied using well known X-ray diffraction techniques and may be refined using computer software such as X-PLOR (Yale University, 1992, distributed by Molecular Simulations, Inc.; see, e.g., Meth Enzymol (1985) volumes 114 & 115, eds Wyckoff H W et al.; U.S. Patent Application No. 2004/0014194), and BUSTER (Bricogne G (1993) Acta Crystallogr D Biol Crystallogr 49(Pt 1): 37-60; Bricogne G (1997) Meth Enzymol 276A: 361-423, ed Carter C W; Roversi P et al., (2000) Acta Crystallogr D Biol Crystallogr 56(Pt 10): 1316-1323, all of which are herein incorporated by reference in their entireties). Mutagenesis mapping studies may be accomplished using any method known to one of skill in the art. See, e.g., Champe M et al., (1995) supra and Cunningham B C & Wells J A (1989) supra for a description of mutagenesis techniques, including alanine scanning mutagenesis techniques. In a specific embodiment, the epitope of an antibody is determined using alanine scanning mutagenesis studies. In addition, antibodies that recognize and bind to the same or overlapping epitopes of TIGIT (e.g., human TIGIT or cynomolgus TIGIT) can be identified using routine techniques such as an immunoassay, for example, by showing the ability of one antibody to block the binding of another antibody to a target antigen, i.e., a competitive binding assay. Competition binding assays also can be used to determine whether two antibodies have similar binding specificity for an epitope. Competitive binding can be determined in an assay in which the immunoglobulin under test inhibits specific binding of a reference antibody to a common antigen, such as TIGIT (e.g., human TIGIT or cynomolgus TIGIT). Numerous types of competitive binding assays are known, for example: solid phase direct or indirect radioimmunoassay (RIA), solid phase direct or indirect enzyme immunoassay (EIA), sandwich competition assay (see Stahli C et al., (1983) Methods Enzymol 9: 242-253); solid phase direct biotin-avidin EIA (see Kirkland T N et al., (1986) J Immunol 137: 3614-9); solid phase direct labeled assay, solid phase direct labeled sandwich assay (see Harlow E & Lane D, (1988) Antibodies: A Laboratory Manual, Cold Spring Harbor Press); solid phase direct label RIA using 1-125 label (see Morel G A et al., (1988) Mol Immunol 25(1): 7-15); solid phase direct biotin-avidin EIA (see Cheung R C et al., (1990) Virology 176: 546-52); and direct labeled RIA (see Moldenhauer G et al., (1990) Scand J Immunol 32: 77-82), all of which are herein incorporated by reference in their entireties. Typically, such an assay involves the use of purified antigen (e.g., TIGIT, such as human TIGIT or cynomolgus TIGIT) bound to a solid surface or cells bearing either of these, an unlabeled test immunoglobulin and a labeled reference immunoglobulin. Competitive inhibition can be measured by determining the amount of label bound to the solid surface or cells in the presence of the test immunoglobulin. Usually the test immunoglobulin is present in excess. Usually, when a competing antibody is present in excess, it will inhibit specific binding of a reference antibody to a common antigen by at least 50-55%, 55-60%, 60-65%, 65-70%, 70-75% or more. A competition binding assay can be configured in a large number of different formats using either labeled antigen or labeled antibody. In a common version of this assay, the antigen is immobilized on a 96-well plate. The ability of unlabeled antibodies to block the binding of labeled antibodies to the antigen is then measured using radioactive or enzyme labels. For further details see, for example, Wagener C et al., (1983) J Immunol 130: 2308-2315; Wagener C et al., (1984) J Immunol Methods 68: 269-274; Kuroki M et al., (1990) Cancer Res 50: 4872-4879; Kuroki M et al., (1992) Immunol Invest 21: 523-538; Kuroki M et al., (1992) Hybridoma 11: 391-407 and Antibodies: A Laboratory Manual, Ed Harlow E & Lane D editors supra, pp. 386-389, all of which are herein incorporated by reference in their entireties.

In certain embodiments, the instant disclosure provides an isolated antibody that binds to an epitope located within a region of human TIGIT comprising the amino acid sequence set forth in SEQ ID NO: 31, 32, or 33. In certain embodiments, the isolated antibody binds to an epitope located within a region of human TIGIT consisting essentially of the amino acid sequence set forth in SEQ ID NO: 31, 32, or 33. In certain embodiments, the isolated antibody binds to an epitope located within a region of human TIGIT, the amino acid sequence of the region consisting of the amino acid sequence set forth in SEQ ID NO: 31, 32, or 33. In certain embodiments, the isolated antibody binds to a discontinuous epitope located within a region of human TIGIT comprising a plurality of amino acid sequences, each of the plurality of amino acid sequences consisting of, consisting essentially of, or comprising the amino acid sequence set forth in SEQ ID NO: 31, 32, or 33 (e.g., SEQ ID NOs: 31 and 32, SEQ ID NOs: 31 and 33, SEQ ID NOs: 32 and 33, or SEQ ID NOs: 31, 32, and 33).

In certain embodiments, the isolated antibody binds to an epitope located within a region of human TIGIT comprising, consisting essentially of, or consisting of the amino acid sequence set forth in SEQ ID NO: 31. In another aspect, the instant disclosure provides an antibody that, when bound to a human TIGIT protein or fragment thereof, reduces hydrogen/deuterium exchange in a region consisting of the amino acid sequence set forth in SEQ ID NO: 31 relative to hydrogen/deuterium exchange in the region consisting of the amino acid sequence set forth in SEQ ID NO: 31 in the absence of the antibody, as determined by a hydrogen/deuterium exchange assay. In certain embodiments, the reduction in hydrogen/deuterium exchange is measured using hydrogen-deuterium exchange (HDX), for example as described herein in the examples.

In certain embodiments, the isolated antibody binds to an epitope located within a region of human TIGIT comprising, consisting essentially of, or consisting of the amino acid sequence set forth in SEQ ID NO: 32. In another aspect, the instant disclosure provides an antibody that, when bound to a human TIGIT protein or fragment thereof, reduces hydrogen/deuterium exchange in a region consisting of the amino acid sequence set forth in SEQ ID NO: 32 relative to hydrogen/deuterium exchange in the region consisting of the amino acid sequence set forth in SEQ ID NO: 32 in the absence of the antibody, as determined by a hydrogen/deuterium exchange assay. In certain embodiments, the reduction in hydrogen/deuterium exchange is measured using hydrogen-deuterium exchange (HDX), for example as described herein in the examples.

In certain embodiments, the isolated antibody binds to an epitope located within a region of human TIGIT comprising, consisting essentially of, or consisting of the amino acid sequence set forth in SEQ ID NO: 33. In another aspect, the instant disclosure provides an antibody that, when bound to a human TIGIT protein or fragment thereof, reduces hydrogen/deuterium exchange in a region consisting of the amino acid sequence set forth in SEQ ID NO: 33 relative to hydrogen/deuterium exchange in the region consisting of the amino acid sequence set forth in SEQ ID NO: 33 in the absence of the antibody, as determined by a hydrogen/deuterium exchange assay. In certain embodiments, the reduction in hydrogen/deuterium exchange is measured using hydrogen-deuterium exchange (HDX), for example as described herein in the examples.

In certain embodiments, the antibody binds to a conformational epitope located within the amino acid sequences of SEQ ID NOs: 31 and 32; 31 and 33; or 32 and 33. In certain embodiments, the antibody binds to a conformational epitope located within the amino acid sequences of 31, 32, and 33.

In certain embodiments, the antibody binds to an epitope (e.g., conformational epitope) comprising one or more amino acid residues selected from the group consisting of Q35, I47, N49, H90, and T96, numbered according to the amino acid sequence of SEQ ID NO: 40. In certain embodiments, the antibody binds to an epitope (e.g., conformational epitope) comprising the amino acid residue of Q35, numbered according to the amino acid sequence of SEQ ID NO: 40. In certain embodiments, the antibody binds to an epitope (e.g., conformational epitope) comprising the amino acid residue of I47, numbered according to the amino acid sequence of SEQ ID NO: 40. In certain embodiments, the antibody binds to an epitope (e.g., conformational epitope) comprising the amino acid residue of N49, numbered according to the amino acid sequence of SEQ ID NO: 40. In certain embodiments, the antibody binds to an epitope (e.g., conformational epitope) comprising the amino acid residue of H90, numbered according to the amino acid sequence of SEQ ID NO: 40. In certain embodiments, the antibody binds to an epitope (e.g., conformational epitope) comprising the amino acid residue of T96, numbered according to the amino acid sequence of SEQ ID NO: 40. In certain embodiments, the antibody binds to an epitope (e.g., conformational epitope) comprising two or more, three or more, or four or more amino acid residues selected from the group consisting of Q35, I47, N49, H90, and T96, numbered according to the amino acid sequence of SEQ ID NO: 40. In certain embodiments, the antibody binds to an epitope (e.g., conformational epitope) comprising the amino acid residues of Q35, I47, N49, H90, and T96, numbered according to the amino acid sequence of SEQ ID NO: 40.

In certain embodiments, the antibody binds to an epitope (e.g., conformational epitope) comprising one or more amino acid residues selected from the group consisting of Q35, I47, and T96, numbered according to the amino acid sequence of SEQ ID NO: 40. In certain embodiments, the antibody binds to an epitope (e.g., conformational epitope) comprising two or more amino acid residues selected from the group consisting of Q35, I47, and T96, numbered according to the amino acid sequence of SEQ ID NO: 40. In certain embodiments, the antibody binds to an epitope (e.g., conformational epitope) comprising the amino acid residues of Q35, I47, and T96, numbered according to the amino acid sequence of SEQ ID NO: 40.

In certain embodiments, the epitope (e.g., conformational epitope) of the antibody does not comprise at least one of the amino acid residues selected from the group consisting of T34, L52, H55, I56, S57, P58, S59, T98, R100, and F102, numbered according to the amino acid sequence of SEQ ID NO: 40. In certain embodiments, the epitope (e.g., conformational epitope) of the antibody does not comprise the amino acid residue of T34, numbered according to the amino acid sequence of SEQ ID NO: 40. In certain embodiments, the epitope (e.g., conformational epitope) of the antibody does not comprise the amino acid residue of L52, numbered according to the amino acid sequence of SEQ ID NO: 40. In certain embodiments, the epitope (e.g., conformational epitope) of the antibody does not comprise the amino acid residue of H55, numbered according to the amino acid sequence of SEQ ID NO: 40. In certain embodiments, the epitope (e.g., conformational epitope) of the antibody does not comprise the amino acid residue of I56, numbered according to the amino acid sequence of SEQ ID NO: 40. In certain embodiments, the epitope (e.g., conformational epitope) of the antibody does not comprise the amino acid residue of S57, numbered according to the amino acid sequence of SEQ ID NO: 40. In certain embodiments, the epitope (e.g., conformational epitope) of the antibody does not comprise the amino acid residue of P58, numbered according to the amino acid sequence of SEQ ID NO: 40. In certain embodiments, the epitope (e.g., conformational epitope) of the antibody does not comprise the amino acid residue of S59, numbered according to the amino acid sequence of SEQ ID NO: 40. In certain embodiments, the epitope (e.g., conformational epitope) of the antibody does not comprise the amino acid residue of T98, numbered according to the amino acid sequence of SEQ ID NO: 40. In certain embodiments, the epitope (e.g., conformational epitope) of the antibody does not comprise the amino acid residue of R100, numbered according to the amino acid sequence of SEQ ID NO: 40. In certain embodiments, the epitope (e.g., conformational epitope) of the antibody does not comprise the amino acid residue of F102, numbered according to the amino acid sequence of SEQ ID NO: 40. In certain embodiments, the epitope (e.g., conformational epitope) of the antibody does not comprise at least two, at least three, at least four, at least five, at least six, at least seven, at least eight, or at least nine of the amino acid residues selected from the group consisting of T34, L52, H55, I56, S57, P58, S59, T98, R100, and F102, numbered according to the amino acid sequence of SEQ ID NO: 40. In certain embodiments, the epitope (e.g., conformational epitope) of the antibody does not comprise any one of the amino acid residues of T34, L52, H55, I56, S57, P58, S59, T98, R100, and F102, numbered according to the amino acid sequence of SEQ ID NO: 40.

In certain embodiments, the epitope (e.g., conformational epitope) of the antibody does not comprise at least one of the amino acid residues selected from the group consisting of L52, H55, I56, S57, P58, S59, and F102, numbered according to the amino acid sequence of SEQ ID NO: 40. In certain embodiments, the epitope (e.g., conformational epitope) of the antibody does not comprise at least two, at least three, at least four, at least five, or at least six of the amino acid residues selected from the group consisting of L52, H55, I56, S57, P58, S59, and F102, numbered according to the amino acid sequence of SEQ ID NO: 40. In certain embodiments, the epitope of the antibody does not comprise any one of the amino acid residues of L52, H55, I56, S57, P58, S59, and F102, numbered according to the amino acid sequence of SEQ ID NO: 40.

In certain embodiments, the epitope (e.g., conformational epitope) of the antibody does not comprise at least one of the amino acid residues selected from the group consisting of L52, H55, and F102, numbered according to the amino acid sequence of SEQ ID NO: 40. In certain embodiments, the epitope (e.g., conformational epitope) of the antibody does not comprise at least two of the amino acid residues selected from the group consisting of L52, H55, and F102, numbered according to the amino acid sequence of SEQ ID NO: 40. In certain embodiments, the epitope of the antibody does not comprise any one of the amino acid residues of L52, H55, and F102, numbered according to the amino acid sequence of SEQ ID NO: 40.

In certain embodiments, the instant disclosure provides an isolated antibody that specifically binds to TIGIT (e.g., human TIGIT or cynomolgus TIGIT), wherein the antibody does not substantially bind to a TIGIT protein or an extracellular domain thereof comprising an amino acid mutation selected from the group consisting of Q35A, I47E, N49A, L52E, H90A, T96A, T96I, C48Y/N49S/A50V, and T96I/

T98K. The binding affinity can be assessed by any method known in the art (e.g., the method disclosed in the Example 5 herein). In certain embodiments, the antibody does not substantially bind to a TIGIT protein or an extracellular domain thereof comprising a Q35A mutation. In certain embodiments, the binding affinity of the antibody to the TIGIT protein or the extracellular domain thereof comprising a Q35A mutation is at least 30%, 35%, 40%, 45%, 50%, 55%, 60%, 65%, 70%, 75%, 80%, 85%, or 90% lower than the binding affinity of the antibody to a wild-type TIGIT protein (e.g., comprising the amino acid sequence of SEQ ID NO: 40) or a corresponding extracellular domain thereof. In certain embodiments, the amino acid sequence of the extracellular domain of the TIGIT protein comprising a Q35A mutation consists of or consists essentially of the amino acid sequence of SEQ ID NO: 44, and the amino acid sequence of the corresponding extracellular domain of the wild-type TIGIT protein consists of or consists essentially of the amino acid sequence of SEQ ID NO: 42. In certain embodiments, the antibody does not substantially bind to a TIGIT protein comprising an I47E mutation. In certain embodiments, the binding affinity of the antibody to the TIGIT protein or the extracellular domain thereof comprising a I47E mutation is at least 30%, 35%, 40%, 45%, 50%, 55%, 60%, 65%, 70%, 75%, 80%, 85%, or 90% lower than the binding affinity of the antibody to a wild-type TIGIT protein (e.g., comprising the amino acid sequence of SEQ ID NO: 40) or a corresponding extracellular domain thereof. In certain embodiments, the amino acid sequence of the extracellular domain of the TIGIT protein comprising an I47E mutation consists of or consists essentially of the amino acid sequence of SEQ ID NO: 45, and the amino acid sequence of the corresponding extracellular domain of the wild-type TIGIT protein consists of or consists essentially of the amino acid sequence of SEQ ID NO: 42. In certain embodiments, the antibody does not substantially bind to a TIGIT protein comprising an N49A mutation. In certain embodiments, the binding affinity of the antibody to the TIGIT protein or the extracellular domain thereof comprising an N49A mutation is at least 30%, 35%, 40%, 45%, 50%, 55%, 60%, 65%, 70%, 75%, 80%, 85%, or 90% lower than the binding affinity of the antibody to a wild-type TIGIT protein (e.g., comprising the amino acid sequence of SEQ ID NO: 40) or a corresponding extracellular domain thereof. In certain embodiments, the amino acid sequence of the extracellular domain of the TIGIT protein comprising an N49A mutation consists of or consists essentially of the amino acid sequence of SEQ ID NO: 46, and the amino acid sequence of the corresponding extracellular domain of the wild-type TIGIT protein consists of or consists essentially of the amino acid sequence of SEQ ID NO: 42. In certain embodiments, the antibody does not substantially bind to a TIGIT protein comprising an L52E mutation. In certain embodiments, the binding affinity of the antibody to the TIGIT protein or the extracellular domain thereof comprising an L52E mutation is at least 30%, 35%, 40%, 45%, 50%, 55%, 60%, 65%, 70%, 75%, 80%, 85%, or 90% lower than the binding affinity of the antibody to a wild-type TIGIT protein (e.g., comprising the amino acid sequence of SEQ ID NO: 40) or a corresponding extracellular domain thereof. In certain embodiments, the amino acid sequence of the extracellular domain of the TIGIT protein comprising an L52E mutation consists of or consists essentially of the amino acid sequence of SEQ ID NO: 48, and the amino acid sequence of the corresponding extracellular domain of the wild-type TIGIT protein consists of or consists essentially of the amino acid sequence of SEQ ID NO: 42. In certain embodiments, the antibody does not substantially bind to a TIGIT protein comprising an H90A mutation. In certain embodiments, the binding affinity of the antibody to the TIGIT protein or the extracellular domain thereof comprising an H90A mutation is at least 30%, 35%, 40%, 45%, 50%, 55%, 60%, 65%, 70%, 75%, 80%, 85%, or 90% lower than the binding affinity of the antibody to a wild-type TIGIT protein (e.g., comprising the amino acid sequence of SEQ ID NO: 40) or a corresponding extracellular domain thereof. In certain embodiments, the amino acid sequence of the extracellular domain of the TIGIT protein comprising an H90A mutation consists of or consists essentially of the amino acid sequence of SEQ ID NO: 51, and the amino acid sequence of the corresponding extracellular domain of the wild-type TIGIT protein consists of or consists essentially of the amino acid sequence of SEQ ID NO: 42. In certain embodiments, the antibody does not substantially bind to a TIGIT protein comprising a T96A mutation. In certain embodiments, the binding affinity of the antibody to the TIGIT protein or the extracellular domain thereof comprising a T96A mutation is at least 30%, 35%, 40%, 45%, 50%, 55%, 60%, 65%, 70%, 75%, 80%, 85%, or 90% lower than the binding affinity of the antibody to a wild-type TIGIT protein (e.g., comprising the amino acid sequence of SEQ ID NO: 40) or a corresponding extracellular domain thereof. In certain embodiments, the amino acid sequence of the extracellular domain of the TIGIT protein comprising a T96A mutation consists of or consists essentially of the amino acid sequence of SEQ ID NO: 52, and the amino acid sequence of the corresponding extracellular domain of the wild-type TIGIT protein consists of or consists essentially of the amino acid sequence of SEQ ID NO: 42. In certain embodiments, the antibody does not substantially bind to a TIGIT protein comprising a T96I mutation. In certain embodiments, the binding affinity of the antibody to the TIGIT protein or the extracellular domain thereof comprising a T96I mutation is at least 30%, 35%, 40%, 45%, 50%, 55%, 60%, 65%, 70%, 75%, 80%, 85%, or 90% lower than the binding affinity of the antibody to a wild-type TIGIT protein (e.g., comprising the amino acid sequence of SEQ ID NO: 40) or a corresponding extracellular domain thereof. In certain embodiments, the amino acid sequence of the extracellular domain of the TIGIT protein comprising a T96I mutation consists of or consists essentially of the amino acid sequence of SEQ ID NO: 53, and the amino acid sequence of the corresponding extracellular domain of the wild-type TIGIT protein consists of or consists essentially of the amino acid sequence of SEQ ID NO: 42. In certain embodiments, the antibody does not substantially bind to a TIGIT protein comprising a C48Y/N49S/A50V mutation. In certain embodiments, the binding affinity of the antibody to the TIGIT protein or the extracellular domain thereof comprising a C48Y/N49S/A50V mutation is at least 30%, 35%, 40%, 45%, 50%, 55%, 60%, 65%, 70%, 75%, 80%, 85%, or 90% lower than the binding affinity of the antibody to a wild-type TIGIT protein (e.g., comprising the amino acid sequence of SEQ ID NO: 40) or a corresponding extracellular domain thereof. In certain embodiments, the amino acid sequence of the extracellular domain of the TIGIT protein comprising a C48Y/N49S/A50V mutation consists of or consists essentially of the amino acid sequence of SEQ ID NO: 57, and the amino acid sequence of the corresponding extracellular domain of the wild-type TIGIT protein consists of or consists essentially of the amino acid sequence of SEQ ID NO: 42. In certain embodiments, the antibody does not substantially bind to a TIGIT protein comprising a T96I/T98K mutation. In certain embodiments, the binding affinity of the antibody to the TIGIT protein or the extracellular domain thereof comprising a T96I/T98K mutation is at least 30%, 35%, 40%, 45%, 50%, 55%, 60%, 65%, 70%, 75%, 80%, 85%, or 90% lower than the binding affinity of the antibody to a wild-type TIGIT protein (e.g., comprising the amino acid sequence of SEQ ID NO: 40) or a corresponding extracellular domain thereof. In certain embodiments, the amino acid sequence of the extracellular domain of the TIGIT protein comprising a T96I/T98K mutation consists of or consists essentially of the amino acid sequence of SEQ ID NO: 59, and the amino acid sequence of the corresponding extracellular domain of the wild-type TIGIT protein consists of or consists essentially of the amino acid sequence of SEQ ID NO: 42. In certain embodiments, the amino acid sequence of the TIGIT protein comprising a T96I/T98K mutation consists of or consists essentially of the amino acid sequence of SEQ ID NO: 59.

In certain embodiments, the antibody specifically and/or substantially binds to a TIGIT protein comprising an amino acid mutation selected from the group consisting of T34A, L52A, H55A, P58A, T98A, R100A, F102A, and I56V/S57A/P58S/S59V. The binding affinity can be assessed by any method known in the art (e.g., the method disclosed in the Example 5 herein). In certain embodiments, the antibody specifically and/or substantially binds to a TIGIT protein comprising a T34A mutation. In certain embodiments, the binding affinity of the antibody to the TIGIT protein or the extracellular domain thereof comprising a T34A mutation is greater than or equal to 70%, 75%, 80%, 85%, 90%, or 95% of the binding affinity of the antibody to a wild-type TIGIT protein (e.g., comprising the amino acid sequence of SEQ ID NO: 40) or a corresponding extracellular domain thereof. In certain embodiments, the amino acid sequence of the extracellular domain of a TIGIT protein comprising a T34A mutation consists of or consists essentially of the amino acid sequence of SEQ ID NO: 43, and the amino acid sequence of the corresponding extracellular domain of the wild-type TIGIT protein consists of or consists essentially of the amino acid sequence of SEQ ID NO: 42. In certain embodiments, the antibody specifically and/or substantially binds to a TIGIT protein comprising an L52A mutation. In certain embodiments, the binding affinity of the antibody to the TIGIT protein or the extracellular domain thereof comprising an L52A mutation is greater than or equal to 70%, 75%, 80%, 85%, 90%, or 95% of the binding affinity of the antibody to a wild-type TIGIT protein (e.g., comprising the amino acid sequence of SEQ ID NO: 40) or a corresponding extracellular domain thereof. In certain embodiments, the amino acid sequence of the extracellular domain of a TIGIT protein comprising an L52A mutation consists of or consists essentially of the amino acid sequence of SEQ ID NO: 47, and the amino acid sequence of the corresponding extracellular domain of the wild-type TIGIT protein consists of or consists essentially of the amino acid sequence of SEQ ID NO: 42. In certain embodiments, the antibody specifically and/or substantially binds to a TIGIT protein comprising an H55A mutation. In certain embodiments, the binding affinity of the antibody to the TIGIT protein or the extracellular domain thereof comprising an H55A mutation is greater than or equal to 70%, 75%, 80%, 85%, 90%, or 95% of the binding affinity of the antibody to a wild-type TIGIT protein (e.g., comprising the amino acid sequence of SEQ ID NO: 40) or a corresponding extracellular domain thereof. In certain embodiments, the amino acid sequence of the extracellular domain of a TIGIT protein comprising an H55A mutation consists of or consists essentially of the amino acid sequence of SEQ ID NO: 49, and the amino acid sequence of the corresponding extracellular domain of the wild-type TIGIT protein consists of or consists essentially of the amino acid sequence of SEQ ID NO: 42. In certain embodiments, the antibody specifically and/or substantially binds to a TIGIT protein comprising a P58A mutation. In certain embodiments, the binding affinity of the antibody to the TIGIT protein or the extracellular domain thereof comprising a P58A mutation is greater than or equal to 70%, 75%, 80%, 85%, 90%, or 95% of the binding affinity of the antibody to a wild-type TIGIT protein (e.g., comprising the amino acid sequence of SEQ ID NO: 40) or a corresponding extracellular domain thereof. In certain embodiments, the amino acid sequence of the extracellular domain of a TIGIT protein comprising a P58A mutation consists of or consists essentially of the amino acid sequence of SEQ ID NO: 50, and the amino acid sequence of the corresponding extracellular domain of the wild-type TIGIT protein consists of or consists essentially of the amino acid sequence of SEQ ID NO: 42. In certain embodiments, the antibody specifically and/or substantially binds to a TIGIT protein comprising a T98A mutation. In certain embodiments, the binding affinity of the antibody to the TIGIT protein or the extracellular domain thereof comprising a T98A mutation is greater than or equal to 70%, 75%, 80%, 85%, 90%, or 95% of the binding affinity of the antibody to a wild-type TIGIT protein (e.g., comprising the amino acid sequence of SEQ ID NO: 40) or a corresponding extracellular domain thereof. In certain embodiments, the amino acid sequence of the extracellular domain of a TIGIT protein comprising a T98A mutation consists of or consists essentially of the amino acid sequence of SEQ ID NO: 54, and the amino acid sequence of the corresponding extracellular domain of the wild-type TIGIT protein consists of or consists essentially of the amino acid sequence of SEQ ID NO: 42. In certain embodiments, the antibody specifically and/or substantially binds to a TIGIT protein comprising an R100A mutation. In certain embodiments, the binding affinity of the antibody to the TIGIT protein or the extracellular domain thereof comprising an R100A mutation is greater than or equal to 70%, 75%, 80%, 85%, 90%, or 95% of the binding affinity of the antibody to a wild-type TIGIT protein (e.g., comprising the amino acid sequence of SEQ ID NO: 40) or a corresponding extracellular domain thereof. In certain embodiments, the amino acid sequence of the extracellular domain of a TIGIT protein comprising an R100A mutation consists of or consists essentially of the amino acid sequence of SEQ ID NO: 55, and the amino acid sequence of the corresponding extracellular domain of the wild-type TIGIT protein consists of or consists essentially of the amino acid sequence of SEQ ID NO: 42. In certain embodiments, the antibody specifically and/or substantially binds to a TIGIT protein comprising an F102A mutation. In certain embodiments, the binding affinity of the antibody to the TIGIT protein or the extracellular domain thereof comprising an F102A mutation is greater than or equal to 70%, 75%, 80%, 85%, 90%, or 95% of the binding affinity of the antibody to a wild-type TIGIT protein (e.g., comprising the amino acid sequence of SEQ ID NO: 40) or a corresponding extracellular domain thereof. In certain embodiments, the amino acid sequence of the extracellular domain of a TIGIT protein comprising an F102A mutation consists of or consists essentially of the amino acid sequence of SEQ ID NO: 56, and the amino acid sequence of the corresponding extracellular domain of the wild-type TIGIT protein consists of or consists essentially of the amino acid sequence of SEQ ID NO: 42. In certain embodiments, the antibody specifically and/or substantially binds to a TIGIT protein comprising an I56V/S57A/P58S/S59V mutation. In certain embodiments, the binding affinity of the antibody to the TIGIT protein or the extracellular domain thereof comprising an I56V/S57A/P58S/S59V mutation is greater than or equal to 70%, 75%, 80%, 85%, 90%, or 95% of the binding affinity of the antibody to a wild-type TIGIT protein (e.g., comprising the amino acid sequence of SEQ ID NO: 40) or a corresponding extracellular domain thereof. In certain embodiments, the amino acid sequence of the extracellular domain of a TIGIT protein comprising an I56V/S57A/P58S/S59V mutation consists of or consists essentially of the amino acid sequence of SEQ ID NO: 58, and the amino acid sequence of the corresponding extracellular domain of the wild-type TIGIT protein consists of or consists essentially of the amino acid sequence of SEQ ID NO: 42.

In certain embodiments, the antibody inhibits the binding of human TIGIT to human PVR, PVRL2, and/or PVRL3. In certain embodiments, the binding of human TIGIT to human PVR is reduced by more than 50%, 55%, 60%, 65%, 70%, 75%, 80%, 85%, 90%, 95%, 96%, 97%, 98%, or 99% in the presence of the antibody relative to the binding of human TIGIT to human PVR in the absence of the antibody. In certain embodiments, the binding of human TIGIT to human PVRL2 is reduced by more than 50%, 55%, 60%, 65%, 70%, 75%, 80%, 85%, 90%, 95%, 96%, 97%, 98%, or 99% in the presence of the antibody relative to the binding of human TIGIT to human PVRL2 in the absence of the antibody.

In certain embodiments, the antibody inhibits a soluble fragment of human TIGIT from binding to a soluble fragment of human PVR, PVRL2, and/or PVRL3. In certain embodiments, the binding of a soluble fragment of human TIGIT to a soluble fragment of human PVR is reduced by more than 50%, 55%, 60%, 65%, 70%, 75%, 80%, 85%, 90%, 95%, 96%, 97%, 98%, or 99% in the presence of the antibody relative to the binding of a soluble fragment of human TIGIT to a soluble fragment of human PVR in the absence of the antibody. In certain embodiments, the binding of a soluble fragment of human TIGIT to a soluble fragment of human PVRL2 is reduced by more than 50%, 55%, 60%, 65%, 70%, 75%, 80%, 85%, 90%, 95%, 96%, 97%, 98%, or 99% in the presence of the antibody relative to the binding of a soluble fragment of human TIGIT to a soluble fragment of human PVRL2 in the absence of the antibody.

In certain embodiments, the antibody inhibits a TIGIT-expressing cell from binding to a soluble fragment of human PVR, PVRL2, and/or PVRL3. In certain embodiments, the binding of a TIGIT-expressing cell to a soluble fragment of human PVR is reduced by more than 50%, 55%, 60%, 65%, 70%, 75%, 80%, 85%, 90%, 95%, 96%, 97%, 98%, or 99% in the presence of the antibody relative to the binding of a TIGIT-expressing cell to a soluble fragment of human PVR in the absence of the antibody. In certain embodiments, the binding of a TIGIT-expressing cell to a soluble fragment of human PVRL2 is reduced by more than 50%, 55%, 60%, 65%, 70%, 75%, 80%, 85%, 90%, 95%, 96%, 97%, 98%, or 99% in the presence of the antibody relative to the binding of a TIGIT-expressing cell to a soluble fragment of human PVRL2 in the absence of the antibody.

In certain embodiments, the antibody inhibits a TIGIT-expressing cell from binding to a cell expressing human PVR, PVRL2, and/or PVRL3. In certain embodiments, the binding of a TIGIT-expressing cell to a PVR-expressing cell is reduced by more than 50%, 55%, 60%, 65%, 70%, 75%, 80%, 85%, 90%, 95%, 96%, 97%, 98%, or 99% in the presence of the antibody relative to the binding of a TIGIT-expressing cell to a PVR-expressing cell in the absence of the antibody. In certain embodiments, the binding of a TIGIT-expressing cell to a PVRL2-expressing cell is reduced by more than 50%, 55%, 60%, 65%, 70%, 75%, 80%, 85%, 90%, 95%, 96%, 97%, 98%, or 99% in the presence of the antibody relative to the binding of a TIGIT-expressing cell to a PVRL2-expressing cell in the absence of the antibody.

In certain embodiments, the antibody does not bind specifically to CD226 (e.g., human CD226). In certain embodiments, the binding affinity of the antibody to TIGIT is stronger by at least 5%, 10%, 15%, 20%, 25%, 30%, 35%, 40%, 45%, 50%, 55%, 60%, 65%, 70%, 75%, 80%, 85%, 90%, 95%, 98%, or 99% than the binding affinity of the antibody to CD226, as assessed by methods described herein and/or known to one of skill in the art. In certain embodiments, the binding affinity of the antibody to TIGIT is stronger by at least 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, 100 fold, or more, than the binding affinity of the antibody to CD226, as assessed by methods described herein and/or known to one of skill in the art. In certain embodiments, the $K_D$ that represents the affinity of the antibody to CD226 is higher than 1, 2, 5, 10, 20, 50, or 100 µg/ml.

In certain embodiments, the antibody does not bind specifically to CD96 (e.g., human CD96). In certain embodiments, the binding affinity of the antibody to TIGIT is stronger by at least 5%, 10%, 15%, 20%, 25%, 30%, 35%, 40%, 45%, 50%, 55%, 60%, 65%, 70%, 75%, 80%, 85%, 90%, 95%, 98%, or 99% than the binding affinity of the antibody to CD96, as assessed by methods described herein and/or known to one of skill in the art. In certain embodiments, the binding affinity of the antibody to TIGIT is stronger by at least 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, 100 fold, or more, than the binding affinity of the antibody to CD96, as assessed by methods described herein and/or known to one of skill in the art. In certain embodiments, the $K_D$ that represents the affinity of the antibody to CD96 is higher than 1, 2, 5, 10, 20, 50, or 100 µg/mL.

In certain embodiments, the instant disclosure provides an isolated antibody that specifically binds to TIGIT (e.g., human TIGIT or cynomolgus TIGIT), the antibody comprising a heavy chain comprising the amino acid sequence set forth in SEQ ID NO: 11, 12, 13, 14, 15, 16, 17, or 18. In certain embodiments, the antibody comprises a heavy chain comprising the amino acid sequence set forth in SEQ ID NO: 11. In certain embodiments, the antibody comprises a heavy chain comprising the amino acid sequence set forth in SEQ ID NO: 12. In certain embodiments, the antibody comprises a heavy chain comprising the amino acid sequence set forth in SEQ ID NO: 13. In certain embodiments, the antibody comprises a heavy chain comprising the amino acid sequence set forth in SEQ ID NO: 14. In certain embodiments, the antibody comprises a heavy chain comprising the amino acid sequence set forth in SEQ ID NO: 15. In certain embodiments, the antibody comprises a heavy chain comprising the amino acid sequence set forth in SEQ ID NO: 16. In certain embodiments, the antibody comprises a heavy chain comprising the amino acid sequence set forth in SEQ ID NO: 17. In certain embodiments, the antibody comprises a heavy chain comprising the amino acid sequence set forth in SEQ ID NO: 18. In certain embodiments, the amino acid sequence of the heavy chain consists of the amino acid sequence set forth in SEQ ID NO: 11. In certain embodiments, the amino acid sequence of the heavy chain consists of the amino acid sequence set forth in SEQ ID NO: 12. In certain embodiments, the amino acid sequence of the heavy chain consists of the amino acid sequence set forth in SEQ ID NO: 13. In certain embodiments, the amino acid sequence of the heavy chain consists of the amino acid sequence set forth in SEQ ID NO: 14. In certain embodiments, the amino acid sequence of the heavy chain consists of the amino acid sequence set forth in SEQ ID NO: 15. In certain embodiments, the amino acid sequence of the heavy chain consists of the amino acid sequence set forth in SEQ ID NO: 16. In certain embodiments, the amino acid sequence of the heavy chain consists of the amino acid sequence set forth in SEQ ID NO: 17. In certain embodiments, the amino acid sequence of the heavy chain consists of the amino acid sequence set forth in SEQ ID NO: 18.

In certain embodiments, the instant disclosure provides an isolated antibody that specifically binds to TIGIT (e.g., human TIGIT or cynomolgus TIGIT), the antibody comprising a light chain comprising the amino acid sequence set forth in SEQ ID NO: 27. In certain embodiments, the amino acid sequence of the light chain consists of the amino acid sequence set forth in SEQ ID NO: 27.

In certain embodiments, the instant disclosure provides an isolated antibody that specifically binds to TIGIT (e.g., human TIGIT or cynomolgus TIGIT), the antibody comprising a heavy chain comprising the amino acid sequence of SEQ ID NO: 11; and a light chain comprising the amino acid sequence of SEQ ID NO: 27. In certain embodiments, the instant disclosure provides an isolated antibody that specifically binds to TIGIT (e.g., human TIGIT or cynomolgus TIGIT), the antibody comprising a heavy chain comprising the amino acid sequence of SEQ ID NO: 12; and a light chain comprising the amino acid sequence of SEQ ID NO: 27. In certain embodiments, the instant disclosure provides an isolated antibody that specifically binds to TIGIT (e.g., human TIGIT or cynomolgus TIGIT), the antibody comprising a heavy chain comprising the amino acid sequence of SEQ ID NO: 13; and a light chain comprising the amino acid sequence of SEQ ID NO: 27. In certain embodiments, the instant disclosure provides an isolated antibody that specifically binds to TIGIT (e.g., human TIGIT or cynomolgus TIGIT), the antibody comprising a heavy chain comprising the amino acid sequence of SEQ ID NO: 14; and a light chain comprising the amino acid sequence of SEQ ID NO: 27. In certain embodiments, the instant disclosure provides an isolated antibody that specifically binds to TIGIT (e.g., human TIGIT or cynomolgus TIGIT), the antibody comprising a heavy chain comprising the amino acid sequence of SEQ ID NO: 15; and a light chain comprising the amino acid sequence of SEQ ID NO: 27. In certain embodiments, the instant disclosure provides an isolated antibody that specifically binds to TIGIT (e.g., human TIGIT or cynomolgus TIGIT), the antibody comprising a heavy chain comprising the amino acid sequence of SEQ ID NO: 16; and a light chain comprising the amino acid sequence of SEQ ID NO: 27. In certain embodiments, the instant disclosure provides an isolated antibody that specifically binds to TIGIT (e.g., human TIGIT or cynomolgus TIGIT), the antibody comprising a heavy chain comprising the amino acid sequence of SEQ ID NO: 17; and a light chain comprising the amino acid sequence of SEQ ID NO: 27. In certain embodiments, the instant disclosure provides an isolated antibody that specifically binds to TIGIT (e.g., human TIGIT or cynomolgus TIGIT), the antibody comprising a heavy chain comprising the amino acid sequence of SEQ ID NO: 18; and a light chain comprising the amino acid sequence of SEQ ID NO: 27.

In certain embodiments, the amino acid sequences of the heavy chain and light chain consist of the amino acid sequences of SEQ ID NOs: 11 and 27, respectively. In certain embodiments, the amino acid sequences of the heavy chain and light chain consist of the amino acid sequences of SEQ ID NOs: 12 and 27, respectively. In certain embodiments, the amino acid sequences of the heavy chain and light chain consist of the amino acid sequences of SEQ ID NOs: 13 and 27, respectively. In certain embodiments, the amino acid sequences of the heavy chain and light chain consist of the amino acid sequences of SEQ ID NOs: 14 and 27, respectively. In certain embodiments, the amino acid sequences of the heavy chain and light chain consist of the amino acid sequences of SEQ ID NOs: 15 and 27, respectively. In certain embodiments, the amino acid sequences of the heavy chain and light chain consist of the amino acid sequences of SEQ ID NOs: 16 and 27, respectively. In certain embodiments, the amino acid sequences of the heavy chain and light chain consist of the amino acid sequences of SEQ ID NOs: 17 and 27, respectively. In certain embodiments, the amino acid sequences of the heavy chain and light chain consist of the amino acid sequences of SEQ ID NOs: 18 and 27, respectively.

Any antibody format can be used in the antibodies disclosed herein. In certain embodiments, the antibody is a single chain antibody or single-chain Fv (scFv). In certain embodiments, the antibody is a scFv fused with an Fc region (scFv-Fc). In certain embodiments, the antibody is a Fab fragment. In certain embodiments, the antibody is a F(ab')$_2$ fragment.

In certain embodiments, the antibody disclosed herein is a multispecific antibody (e.g., a bispecific antibody) which specifically binds to TIGIT (e.g., human TIGIT or cynomolgus TIGIT) and a second antigen.

In certain embodiments, the antibody disclosed herein is conjugated to a second antibody that specifically binds to a second antigen. In certain embodiments, the antibody disclosed herein is covalently conjugated to a second antibody. In certain embodiments, the antibody disclosed herein is non-covalently conjugated to a second antibody. In certain embodiments, the antibody disclosed herein is cross-linked to a second antibody. In certain embodiments, the second antigen is a tumor-associated antigen (e.g., a polypeptide overexpressed in a tumor, a polypeptide derived from an oncovirus, a polypeptide comprising a post-translational modification specific to a tumor, a polypeptide specifically mutated in a tumor). In certain embodiments, the tumor-associated antigen is EGFR (e.g., human EGFR), optionally wherein the second antibody is cetuximab. In certain embodiments, the tumor-associated antigen is Her2 (e.g., human Her2), optionally wherein the second antibody is trastuzumab. In certain embodiments, the tumor-associated antigen is CD20 (e.g., human CD20).

In certain embodiments, the antibody disclosed herein is conjugated to a cytotoxic agent, cytostatic agent, toxin, radionuclide, or detectable label. In certain embodiments, the cytotoxic agent is able to induce death or destruction of a cell in contact therewith. In certain embodiments, the cytostatic agent is able to prevent or substantially reduce proliferation and/or inhibits the activity or function of a cell in contact therewith. In certain embodiments, the cytotoxic agent or cytostatic agent is a chemotherapeutic agent. In certain embodiments, the radionuclide is selected from the group consisting of the isotopes $^3$H, $^{14}$C, $^{32}$P, $^{35}$S, $^{36}$Cl, $^{51}$Cr, $^{57}$Co, $^{58}$Co, $^{59}$Fe, $^{67}$Cu, $^{90}$Y, $^{99}$Tc, $^{111}$In, $^{117}$Lu, $^{121}$I, $^{124}$I, $^{125}$I, $^{131}$I, $^{198}$Au, $^{211}$At, $^{213}$Bi, $^{225}$Ac and $^{186}$Re. In certain embodiments, the detectable label comprises a fluorescent moiety or a click chemistry handle.

Any immunoglobulin (Ig) constant region can be used in the antibodies disclosed herein. In certain embodiments, the Ig region is a human IgG, IgE, IgM, IgD, IgA, or IgY immunoglobulin molecule, any class (e.g., IgG$_1$, IgG$_2$, IgG$_3$, IgG$_4$, IgA$_1$, and IgA$_2$), or any subclass (e.g., IgG$_{2a}$ and IgG$_{2b}$) of immunoglobulin molecule.

In certain embodiments, the instant disclosure provides an isolated antibody that specifically binds to TIGIT (e.g., human TIGIT or cynomolgus TIGIT), the antibody comprising a heavy chain constant region comprising the amino acid sequence of SEQ ID NO: 19, 20, 21, 22, 23, 24, 25, or 26. In certain embodiments, the instant disclosure provides an isolated antibody that specifically binds to TIGIT (e.g., human TIGIT or cynomolgus TIGIT), the antibody comprising a light chain constant region comprising the amino acid sequence of SEQ ID NO: 28.

In certain embodiments, one, two, or more mutations (e.g., amino acid substitutions) are introduced into the Fc region of an antibody described herein (e.g., CH2 domain (residues 231-340 of human IgG$_1$) and/or CH3 domain (residues 341-447 of human IgG$_1$) and/or the hinge region, numbered according to the EU numbering system, to alter one or more functional properties of the antibody, such as serum half-life, complement fixation, Fc receptor binding, and/or antigen-dependent cellular cytotoxicity.

In certain embodiments, one, two, or more mutations (e.g., amino acid substitutions) are introduced into the hinge region of the Fc region (CH1 domain) such that the number of cysteine residues in the hinge region are altered (e.g., increased or decreased) as described in, e.g., U.S. Pat. No. 5,677,425, herein incorporated by reference in its entirety. The number of cysteine residues in the hinge region of the CH1 domain may be altered to, e.g., facilitate assembly of the light and heavy chains, or to alter (e.g., increase or decrease) the stability of the antibody.

In a specific embodiment, one, two, or more amino acid mutations (e.g., substitutions, insertions or deletions) are introduced into an IgG constant domain, or FcRn-binding fragment thereof (preferably an Fc or hinge-Fc domain fragment) to alter (e.g., decrease or increase) half-life of the antibody in vivo. See, e.g., International Publication Nos. WO 02/060919; WO 98/23289; and WO 97/34631; and U.S. Pat. Nos. 5,869,046, 6,121,022, 6,277,375 and 6,165,745, all of which are herein incorporated by reference in their entireties, for examples of mutations that will alter (e.g., decrease or increase) the half-life of an antibody in vivo. In certain embodiments, one, two or more amino acid mutations (e.g., substitutions, insertions, or deletions) are introduced into an IgG constant domain, or FcRn-binding fragment thereof (preferably an Fc or hinge-Fc domain fragment) to decrease the half-life of the antibody in vivo. In other embodiments, one, two or more amino acid mutations (e.g., substitutions, insertions or deletions) are introduced into an IgG constant domain, or FcRn-binding fragment thereof (preferably an Fc or hinge-Fc domain fragment) to increase the half-life of the antibody in vivo. In a specific embodiment, the antibodies may have one or more amino acid mutations (e.g., substitutions) in the second constant (CH2) domain (residues 231-340 of human IgG$_1$) and/or the third constant (CH3) domain (residues 341-447 of human IgG$_1$), numbered according to the EU numbering system. In a specific embodiment, the constant region of the IgG$_1$ of an antibody described herein comprises a methionine (M) to tyrosine (Y) substitution in position 252, a serine (S) to threonine (T) substitution in position 254, and a threonine (T) to glutamic acid (E) substitution in position 256, numbered according to the EU numbering system. See U.S. Pat. No. 7,658,921, which is herein incorporated by reference in its entirety. This type of mutant IgG, referred to as "YTE mutant" has been shown to display fourfold increased half-life as compared to wild-type versions of the same antibody (see Dall'Acqua W F et al., (2006) J Biol Chem 281: 23514-24, which is herein incorporated by reference in its entirety). In certain embodiments, an antibody comprises an IgG constant domain comprising one, two, three or more amino acid substitutions of amino acid residues at positions 251-257, 285-290, 308-314, 385-389, and 428-436, numbered according to the EU numbering system.

In certain embodiments, one, two, or more mutations (e.g., amino acid substitutions) are introduced into the Fc region of an antibody described herein (e.g., CH2 domain (residues 231-340 of human IgG$_1$) and/or CH3 domain (residues 341-447 of human IgG$_1$) and/or the hinge region, numbered according to the EU numbering system, to increase or decrease the affinity of the antibody for an Fc receptor (e.g., an activated Fc receptor) on the surface of an effector cell. Mutations in the Fc region of an antibody that decrease or increase the affinity of an antibody for an Fc receptor and techniques for introducing such mutations into the Fc receptor or fragment thereof are known to one of skill in the art. Examples of mutations in the Fc receptor of an antibody that can be made to alter the affinity of the antibody for an Fc receptor are described in, e.g., Smith P et al., (2012) PNAS 109: 6181-6186, U.S. Pat. No. 6,737,056, and International Publication Nos. WO 02/060919; WO 98/23289; and WO 97/34631, all of which are herein incorporated by reference in their entireties.

In certain embodiments, the antibody comprises a heavy chain constant region that is a variant of a wild type heavy chain constant region, wherein the variant heavy chain constant region binds to FcγRIIB with higher affinity than the wild type heavy chain constant region binds to FcγRIIB In certain embodiments, the variant heavy chain constant region is a variant human heavy chain constant region, e.g., a variant human IgG1, a variant human IgG2, or a variant human IgG4 heavy chain constant region. In certain embodiments, the variant human IgG heavy chain constant region comprises one or more of the following amino acid mutations, according to the EU numbering system: G236D, P238D, S239D, S267E, L328F, and L328E. In certain embodiments, the variant human IgG heavy chain constant region comprises a set of amino acid mutations selected from the group consisting of: S267E and L328F; P238D and L328E; P238D and one or more substitutions selected from the group consisting of E233D, G237D, H268D, P271G, and A330R; P238D, E233D, G237D, H268D, P271G, and A330R; G236D and S267E; S239D and S267E; V262E, S267E, and L328F; and V264E, S267E, and L328F, according to the EU numbering system. In certain embodiments, the FcγRIIB is expressed on a cell selected from the group consisting of macrophages, monocytes, B cells, dendritic cells, endothelial cells, and activated T cells.

In a further embodiment, one, two, or more amino acid substitutions are introduced into an IgG constant domain Fc region to alter the effector function(s) of the antibody. For example, one or more amino acids selected from amino acid residues 234, 235, 236, 237, 239, 243, 267, 292, 297, 300, 318, 320, 322, 328, 330, 332, and 396, numbered according to the EU numbering system, can be replaced with a different amino acid residue such that the antibody has an altered affinity for an effector ligand but retains the antigen-binding ability of the parent antibody. The effector ligand to which affinity is altered can be, for example, an Fc receptor or the C1 component of complement. This approach is described in further detail in U.S. Pat. Nos. 5,624,821 and 5,648,260, each of which is herein incorporated by reference in its entirety. In certain embodiments, the deletion or inactivation (through point mutations or other means) of a constant region domain may reduce Fc receptor binding of the circulating antibody thereby increasing tumor localization. See, e.g., U.S. Pat. Nos. 5,585,097 and 8,591,886, each of which is herein incorporated by reference in its entirety, for a description of mutations that delete or inactivate the constant domain and thereby increase tumor localization. In certain embodiments, one or more amino acid substitutions may be introduced into the Fc region of an antibody described herein to remove potential glycosylation sites on the Fc region, which may reduce Fc receptor binding (see, e.g., Shields R L et al., (2001) J Biol Chem 276: 6591-604, which is herein incorporated by reference in its entirety). In various embodiments, one or more of the following mutations in the constant region of an antibody described herein may be made: an N297A substitution; an N297Q substitution; an L234A substitution; an L234F substitution; an L235A substitution; an L235F substitution; an L235V substitution; an L237A substitution; an S239D substitution; an E233P substitution; an L234V substitution; an L235A substitution; a C236 deletion; a P238A substitution; an S239D substitution; an F243L substitution; a D265A substitution; an S267E substitution; an L328F substitution; an R292P substitution; a Y300L substitution; an A327Q substitution; a P329A substitution; an A332L substitution; an I332E substitution; or a P396L substitution, numbered according to the EU numbering system.

In certain embodiments, a mutation selected from the group consisting of D265A, P329A, and a combination thereof, numbered according to the EU numbering system, may be made in the constant region of an antibody described herein. In certain embodiments, a mutation selected from the group consisting of L235A, L237A, and a combination thereof, numbered according to the EU numbering system, may be made in the constant region of an antibody described herein. In certain embodiments, a mutation selected from the group consisting of S267E, L328F, and a combination thereof, numbered according to the EU numbering system, may be made in the constant region of an antibody described herein. In certain embodiments, a mutation selected from the group consisting of S239D, I332E, optionally A330L, and a combination thereof, numbered according to the EU numbering system, may be made in the constant region of an antibody described herein. In certain embodiments, a mutation selected from the group consisting of L235V, F243L, R292P, Y300L, P396L, and a combination thereof, numbered according to the EU numbering system, may be made in the constant region of an antibody described herein. In certain embodiments, a mutation selected from the group consisting of S267E, L328F, and a combination thereof, numbered according to the EU numbering system, may be made in the constant region of an antibody described herein.

In a specific embodiment, an antibody described herein comprises the constant domain of an $IgG_1$ with an N297Q or N297A amino acid substitution, numbered according to the EU numbering system. In one embodiment, an antibody described herein comprises the constant domain of an $IgG_1$ with a mutation selected from the group consisting of D265A, P329A, and a combination thereof, numbered according to the EU numbering system. In another embodiment, an antibody described herein comprises the constant domain of an $IgG_1$ with a mutation selected from the group consisting of L234A, L235A, and a combination thereof, numbered according to the EU numbering system. In another embodiment, an antibody described herein comprises the constant domain of an $IgG_1$ with a mutation selected from the group consisting of L234F, L235F, N297A, and a combination thereof, numbered according to the EU numbering system. In certain embodiments, amino acid residues in the constant region of an antibody described herein in the positions corresponding to positions L234, L235, and D265 in a human $IgG_1$ heavy chain, numbered according to the EU numbering system, are not L, L, and D, respectively. This approach is described in detail in International Publication No. WO 14/108483, which is herein incorporated by reference in its entirety. In a particular embodiment, the amino acids corresponding to positions L234, L235, and D265 in a human $IgG_1$ heavy chain are F, E, and A; or A, A, and A, respectively, numbered according to the EU numbering system.

In certain embodiments, one or more amino acids selected from amino acid residues 329, 331, and 322 in the constant region of an antibody described herein, numbered according to the EU numbering system, can be replaced with a different amino acid residue such that the antibody has altered C1q binding and/or reduced or abolished complement dependent cytotoxicity (CDC). This approach is described in further detail in U.S. Pat. No. 6,194,551 (Idusogie et al.), which is herein incorporated by reference in its entirety. In certain embodiments, one or more amino acid residues within amino acid positions 231 to 238 in the N-terminal region of the CH2 domain of an antibody described herein are altered to thereby alter the ability of the antibody to fix complement, numbered according to the EU numbering system. This approach is described further in International Publication No. WO 94/29351, which is herein incorporated by reference in its entirety. In certain embodiments, the Fc region of an antibody described herein is modified to increase the ability of the antibody to mediate antibody dependent cellular cytotoxicity (ADCC) and/or to increase the affinity of the antibody for an Fcγ receptor by mutating one or more amino acids (e.g., introducing amino acid substitutions) at the following positions: 238, 239, 248, 249, 252, 254, 255, 256, 258, 265, 267, 268, 269, 270, 272, 276, 278, 280, 283, 285, 286, 289, 290, 292, 293, 294, 295, 296, 298, 301, 303, 305, 307, 309, 312, 315, 320, 322, 324, 326, 327, 328, 329, 330, 331, 333, 334, 335, 337, 338, 340, 360, 373, 376, 378, 382, 388, 389, 398, 414, 416, 419, 430, 434, 435, 437, 438, or 439, numbered according to the EU numbering system. This approach is described further in International Publication No. WO 00/42072, which is herein incorporated by reference in its entirety.

In certain embodiments, an antibody described herein comprises a modified constant domain of an $IgG_1$, wherein the modification increases the ability of the antibody to mediate antibody dependent cellular cytotoxicity (ADCC). In certain embodiments, 0.1, 1, or 10 μg/mL of the antibody is capable of inducing cell death of at least 20%, 25%, 30%, 35%, 40%, 45%, 50%, 55%, or 60% of TIGIT-expressing cells within 1, 2, or 3 hours, as assessed by methods described herein and/or known to a person of skill in the art. In certain embodiments, the modified constant domain of an $IgG_1$ comprises S239D and I332E substitutions, numbered according to the EU numbering system. In certain embodiments, the modified constant domain of an $IgG_1$ comprises S239D, A330L, and I332E substitutions, numbered according to the EU numbering system. In certain embodiments, the modified constant domain of an IgG$_1$ comprises L235V, F243L, R292P, Y300L, and P396L substitutions, numbered according to the EU numbering system. In certain embodiments, the antibody is capable of inducing cell death in effector T cells and Tregs, wherein the percentage of Tregs that undergo cell death is higher than the percentage of effector T cells that undergo cell death by at least 1.2 fold, 1.3 fold, 1.4 fold, 1.5 fold, 1.6 fold, 1.7 fold, 1.8 fold, 1.9 fold, 2 fold, 2.5 fold, 3 fold, 3.5 fold, 4 fold, 4.5 fold, or 5 fold.

In certain embodiments, an antibody described herein comprises the constant region of an IgG$_4$ antibody and the serine at amino acid residue 228 of the heavy chain, numbered according to the EU numbering system, is substituted for proline. In certain embodiments, the instant disclosure provides an isolated antibody that specifically binds to TIGIT (e.g., human TIGIT or cynomolgus TIGIT), the antibody comprising a heavy chain constant region comprising the amino acid sequence of SEQ ID NO: 26.

In certain embodiments, any of the constant region mutations or modifications described herein can be introduced into one or both heavy chain constant regions of an antibody described herein having two heavy chain constant regions.

In certain embodiments, the instant disclosure provides an isolated antibody that specifically binds to TIGIT (e.g., human TIGIT or cynomolgus TIGIT) and functions as an antagonist (e.g., decreases or inhibits TIGIT activity).

In certain embodiments, the instant disclosure provides an isolated antibody that specifically binds to TIGIT (e.g., human TIGIT or cynomolgus TIGIT) and decreases or inhibits TIGIT (e.g., human TIGIT or cynomolgus TIGIT) activity by at least 5%, 10%, 15%, 20%, 25%, 30%, 35%, 40%, 45%, 50%, 55%, 60%, 65%, 70%, 75%, 80%, 85%, 90%, 95%, 98%, or 99%, as assessed by methods described herein and/or known to one of skill in the art, relative to TIGIT (e.g., human TIGIT or cynomolgus TIGIT) activity without any antibody or with an unrelated antibody (e.g., an antibody that does not specifically bind to TIGIT (e.g., human TIGIT or cynomolgus TIGIT)). In certain embodiments, the instant disclosure provides an isolated antibody that specifically binds to TIGIT (e.g., human TIGIT or cynomolgus TIGIT) and decreases or inhibits TIGIT (e.g., human TIGIT or cynomolgus TIGIT) activity by at least about 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, 100 fold, or more, as assessed by methods described herein and/or known to one of skill in the art, relative to TIGIT (e.g., human TIGIT or cynomolgus TIGIT) activity without any antibody or with an unrelated antibody (e.g., an antibody that does not specifically bind to TIGIT (e.g., human TIGIT)). Non-limiting examples of TIGIT (e.g., human TIGIT or cynomolgus TIGIT) activity can include TIGIT (e.g., human TIGIT or cynomolgus TIGIT) signaling; TIGIT (e.g., human TIGIT or cynomolgus TIGIT) binding to its ligand (e.g., PVR (e.g., human or cynomolgus PVR), PVRL2 (e.g., human or cynomolgus PVRL2), PVRL3 (e.g., human or cynomolgus PVRL3), or a fragment and/or fusion protein thereof); activation of a T cell (e.g., a T cell expressing human TIGIT); activation of a natural killer (NK) cell; decrease or inhibition of a Treg; increase of cytokine (e.g., IL-2, IFN-γ, and/or TNF-α) production; increase of the activity of PVR (e.g., human PVR), PVRL2 (e.g., human PVRL2), and/or PVRL3 (e.g., human PVRL3); and activation of an antigen-presenting cell (APC) expressing PVR (e.g., human PVR), PVRL2 (e.g., human PVRL2), and/or PVRL3 (e.g., human PVRL3). In specific embodiments, an increase in a TIGIT (e.g., human TIGIT or cynomolgus TIGIT) activity is assessed as described in the Examples, infra.

In specific embodiments, the instant disclosure provides an isolated antibody that specifically binds to TIGIT (e.g., human TIGIT or cynomolgus TIGIT) and decreases or inhibits TIGIT (e.g., human or cynomolgus TIGIT) binding to its ligand (e.g., PVR (e.g., human or cynomolgus PVR), PVRL2 (e.g., human or cynomolgus PVRL2), PVRL3 (e.g., human or cynomolgus PVRL3), or a fragment and/or fusion protein thereof) by at least about 5%, 10%, 15%, 20%, 25%, 30%, 35%, 40%, 45%, 50%, 55%, 60%, 65%, 70%, 75%, 80%, 85%, 90%, 95%, 98%, or 99%, as assessed by methods described herein (see the Examples, infra) or known to one of skill in the art, relative to TIGIT (e.g., human TIGIT or cynomolgus TIGIT) binding to this ligand without any antibody or with an unrelated antibody (e.g., an antibody that does not specifically bind to TIGIT (e.g., human or cynomolgus TIGIT)). In specific embodiments, the instant disclosure provides an isolated antibody that specifically binds to TIGIT (e.g., human or cynomolgus TIGIT) and increases TIGIT (e.g., human or cynomolgus TIGIT) binding to its ligand (e.g., PVR (e.g., human or cynomolgus PVR), PVRL2 (e.g., human or cynomolgus PVRL2), PVRL3 (e.g., human or cynomolgus PVRL3), or a fragment and/or fusion protein thereof) by at least about 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold, as assessed by methods described herein (see the Examples, infra) or known to one of skill in the art, relative to TIGIT (e.g., human TIGIT) binding to this ligand without any antibody or with an unrelated antibody (e.g., an antibody that does not specifically bind to TIGIT (e.g., human or cynomolgus TIGIT)).

In specific embodiments, the instant disclosure provides an isolated antibody that specifically binds to TIGIT (e.g., human TIGIT or cynomolgus TIGIT) and activates a T cell (e.g., a T cell expressing human TIGIT). In certain embodiments, the T cell is a memory T cell. In certain embodiments, the T cell is a TIGIT-expressing Jurkat cell. In certain embodiments, the antibody disclosed herein increases the activity of Nuclear factor of activated T-cells (NFAT) by at least about 5%, 10%, 15%, 20%, 25%, 30%, 35%, 40%, 45%, 50%, 55%, 60%, 65%, 70%, 75%, 80%, 85%, 90%, 95%, 98%, or 99%, as assessed by methods described herein (see the Examples, infra) or known to one of skill in the art, relative to NFAT activity without any antibody or with an unrelated antibody (e.g., an antibody that does not specifically bind to TIGIT (e.g., human TIGIT or cynomolgus TIGIT)). In certain embodiments, the antibody disclosed herein increases the activity of NFAT by at least about 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold, or more, as assessed by methods described herein (see the Examples, infra) or known to one of skill in the art, relative to NFAT activity without any antibody or with an unrelated antibody (e.g., an antibody that does not specifically bind to TIGIT (e.g., human TIGIT or cynomolgus TIGIT)). In certain embodiments, the antibody increases NFAT activity in the presence of a ligand of TIGIT (e.g., PVR (e.g., human or cynomolgus PVR), PVRL2 (e.g., human or cynomolgus PVRL2), PVRL3 (e.g., human or cynomolgus PVRL3), a fragment and/or fusion protein thereof), and/or a cell expressing a ligand of TIGIT (e.g., a monocyte, a dendritic cell).

In specific embodiments, the instant disclosure provides an isolated antibody that specifically binds to TIGIT (e.g., human TIGIT or cynomolgus TIGIT) and increases cytokine production (e.g., IL-2, IFN-γ and/or TNF-α) by at least about 5%, 10%, 15%, 20%, 25%, 30%, 35%, 40%, 45%, 50%, 55%, 60%, 65%, 70%, 75%, 80%, 85%, 90%, 95%, 98%, or 99%, as assessed by methods described herein (see the Examples, infra) or known to one of skill in the art, relative to cytokine production without any antibody or with an unrelated antibody (e.g., an antibody that does not specifically bind to TIGIT (e.g., human TIGIT or cynomolgus TIGIT)). In specific embodiments, the instant disclosure provides an isolated antibody that specifically binds to TIGIT (e.g., human TIGIT or cynomolgus TIGIT) and increases cytokine production (e.g., IL-2, IFN-γ and/or TNF-α) by at least about 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold, or more, as assessed by methods described herein (see the Examples, infra) or known to one of skill in the art, relative to cytokine production without any antibody or with an unrelated antibody (e.g., an antibody that does not specifically bind to TIGIT (e.g., human TIGIT or cynomolgus TIGIT)). In certain embodiments, the antibody increases cytokine production (e.g., IL-2, IFN-γ and/or TNF-α) in the presence of a ligand of TIGIT (e.g., PVR (e.g., human or cynomolgus PVR), PVRL2 (e.g., human or cynomolgus PVRL2), PVRL3 (e.g., human or cynomolgus PVRL3), a fragment and/or fusion protein thereof), and/or a cell expressing a ligand of TIGIT (e.g., a monocyte, a dendritic cell). In certain embodiments, the antibody increases the production of IL-2 relative to IL-2 production without any antibody or with an unrelated antibody (e.g., an antibody that does not specifically bind to TIGIT (e.g., human TIGIT or cynomolgus TIGIT)) to a greater degree than the antibody increases the production of IFN-γ relative to IFN-γ production without any antibody or with an unrelated antibody (e.g., an antibody that does not specifically bind to TIGIT (e.g., human TIGIT or cynomolgus TIGIT)).

In certain embodiments, the instant disclosure provides an isolated antibody that specifically binds to TIGIT (e.g., human TIGIT or cynomolgus TIGIT) and which either alone or in combination with an anti-PD-1 antibody (e.g., pembrolizumab or nivolumab), increases IFNγ and/or IL-2 production in human peripheral blood mononuclear cells (PBMCs) in response to *Staphylococcus* Enterotoxin A (SEA) stimulation by at least about 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold, as assessed by methods described herein (see the Examples, infra) or known to one of skill in the art, relative to IFNγ and/or IL-2 production without any antibody or with an unrelated antibody (e.g., an antibody that does not specifically bind to TIGIT (e.g., human TIGIT or cynomolgus TIGIT)).

In certain embodiments, the instant disclosure provides an isolated antibody that specifically binds to TIGIT (e.g., human TIGIT or cynomolgus TIGIT) and which either alone or in combination with an anti-CTLA-4 antibody (e.g., ipilimumab), increases IFNγ and/or IL-2 production in human peripheral blood mononuclear cells (PBMCs) in response to *Staphylococcus* Enterotoxin A (SEA) stimulation by at least about 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold, as assessed by methods described herein (see the Examples, infra) or known to one of skill in the art, relative to IFNγ and/or IL-2 production without any antibody or with an unrelated antibody (e.g., an antibody that does not specifically bind to TIGIT (e.g., human TIGIT or cynomolgus TIGIT)).

In certain embodiments, human peripheral blood mononuclear cells (PBMCs) stimulated with *Staphylococcus* Enterotoxin A (SEA) in the presence of an antibody described herein, which specifically binds to TIGIT (e.g., human TIGIT or cynomolgus TIGIT), have increased IFNγ and/or IL-2 production by at least about 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold, relative to IFNγ and/or IL-2 production from PBMCs only stimulated with SEA without any antibody or with an unrelated antibody (e.g., an antibody that does not specifically bind to TIGIT (e.g., human TIGIT or cynomolgus TIGIT)), as assessed by methods described herein (see the Examples, infra) or known to one of skill in the art.

In certain embodiments, the instant disclosure provides an isolated antibody that specifically binds to TIGIT (e.g., human TIGIT or cynomolgus TIGIT) and increases or promotes memory recall of a memory T cell. In certain embodiments, the memory T cell is a CD8 effector memory T cell. In certain embodiments, the memory T cell is a CD4 effector memory T cell. In certain embodiments, the antibody increases the number of proliferating memory T cells when the memory T cells are in contact with their cognate antigen(s) by at least about 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold, as assessed by methods described herein (see the Examples, infra) or known to one of skill in the art, relative to the number of proliferating memory T cells when the memory T cells are in contact with their cognate antigen(s) in the absence of any antibody or in the presence of an unrelated antibody (e.g., an antibody that does not specifically bind to TIGIT (e.g., human TIGIT or cynomolgus TIGIT)). In certain embodiments, the antibody increases the production of a cytokine (e.g., IFNγ, TNFα) from a memory T cell when the memory T cell is in contact with its cognate antigen by at least about 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold, as assessed by methods described herein (see the Examples, infra) or known to one of skill in the art, relative to the production of the cytokine from a memory T cell when the memory T cell is in contact with its cognate antigen in the absence of any antibody or in the presence of an unrelated antibody (e.g., an antibody that does not specifically bind to TIGIT (e.g., human TIGIT or cynomolgus TIGIT)).

In certain embodiments, the instant disclosure provides an isolated antibody that specifically binds to TIGIT (e.g., human TIGIT or cynomolgus TIGIT) and activates an NK cell. In certain embodiments, the NK cells are isolated. In certain embodiments, the NK cells are in a mixed culture of PBMCs. In certain embodiments, the antibody disclosed herein increases the expression level of CD107a in NK cells by at least about 5%, 10%, 15%, 20%, 25%, 30%, 35%, 40%, 45%, 50%, 55%, 60%, 65%, 70%, 75%, 80%, 85%, 90%, 95%, 98%, or 99%, as assessed by methods described herein (see the Examples, infra) or known to one of skill in the art, relative to the expression level of CD107a in NK cells without any antibody or with an unrelated antibody (e.g., an antibody that does not specifically bind to TIGIT (e.g., human TIGIT or cynomolgus TIGIT)). In certain embodiments, the antibody disclosed herein increases the expression level of CD107a in NK cells by at least about 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold, or more, as assessed by methods described herein (see the Examples, infra) or known to one of skill in the art, relative to the expression level of CD107a in NK cells without any antibody or with an unrelated antibody (e.g., an antibody that does not specifically bind to TIGIT (e.g., human TIGIT or cynomolgus TIGIT)). In certain embodiments, the antibody disclosed herein increases cytokine production (e.g., IFNγ and/or TNFα) from NK cells by at least about 5%, 10%, 15%, 20%, 25%, 30%, 35%, 40%, 45%, 50%, 55%, 60%, 65%, 70%, 75%, 80%, 85%, 90%, 95%, 98%, or 99%, as assessed by methods described herein (see the Examples, infra) or known to one of skill in the art, relative to cytokine production (e.g., IFNγ and/or TNFα) from NK cells without any antibody or with an unrelated antibody (e.g., an antibody that does not specifically bind to TIGIT (e.g., human TIGIT or cynomolgus TIGIT)). In certain embodiments, the antibody disclosed herein increases cytokine production (e.g., IFNγ and/or TNFα) from NK cells by at least about 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold, or more, as assessed by methods described herein (see the Examples, infra) or known to one of skill in the art, relative to cytokine production (e.g., IFNγ and/or TNFα) from NK cells without any antibody or with an unrelated antibody (e.g., an antibody that does not specifically bind to TIGIT (e.g., human TIGIT or cynomolgus TIGIT)).

5.3 Pharmaceutical Compositions

Provided herein are compositions comprising an anti-TIGIT (e.g., human TIGIT or cynomolgus TIGIT) antibody disclosed herein having the desired degree of purity in a physiologically acceptable carrier, excipient or stabilizer (see, e.g., Remington's Pharmaceutical Sciences (1990) Mack Publishing Co., Easton, Pa.). Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

In a specific embodiment, pharmaceutical compositions comprise an anti-TIGIT (e.g., human TIGIT or cynomolgus TIGIT) antibody disclosed herein, and optionally one or more additional prophylactic or therapeutic agents, in a pharmaceutically acceptable carrier. In a specific embodiment, pharmaceutical compositions comprise an effective amount of an antibody described herein, and optionally one or more additional prophylactic or therapeutic agents, in a pharmaceutically acceptable carrier. In certain embodiments, the antibody is the only active ingredient included in the pharmaceutical composition. Pharmaceutical compositions described herein can be useful in increasing or promoting TIGIT (e.g., human TIGIT or cynomolgus TIGIT) activity and treating a condition, such as cancer or an infectious disease. In one embodiment, the present invention relates to a pharmaceutical composition of the present invention comprising an anti-TIGIT antibody of the present invention for use as a medicament. In another embodiment, the present invention relates to a pharmaceutical composition of the present invention for use in a method for the treatment of cancer or an infectious disease.

Pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances. Examples of aqueous vehicles include Sodium Chloride Injection, Ringers Injection, Isotonic Dextrose Injection, Sterile Water Injection, Dextrose and Lactated Ringers Injection. Nonaqueous parenteral vehicles include fixed oils of vegetable origin, cottonseed oil, corn oil, sesame oil and peanut oil. Antimicrobial agents in bacteriostatic or fungistatic concentrations can be added to parenteral preparations packaged in multiple-dose containers which include phenols or cresols, mercurials, benzyl alcohol, chlorobutanol, methyl and propyl p-hydroxybenzoic acid esters, thimerosal, benzalkonium chloride and benzethonium chloride. Isotonic agents include sodium chloride and dextrose. Buffers include phosphate and citrate. Antioxidants include sodium bisulfate. Local anesthetics include procaine hydrochloride. Suspending and dispersing agents include sodium carboxymethylcelluose, hydroxypropyl methylcellulose and polyvinylpyrrolidone. Emulsifying agents include Polysorbate 80 (TWEEN® 80). A sequestering or chelating agent of metal ions includes EDTA. Pharmaceutical carriers also include ethyl alcohol, polyethylene glycol and propylene glycol for water miscible vehicles; and sodium hydroxide, hydrochloric acid, citric acid or lactic acid for pH adjustment.

A pharmaceutical composition may be formulated for any route of administration to a subject. Specific examples of routes of administration include intranasal, oral, pulmonary, transdermal, intradermal, and parenteral. Parenteral administration, characterized by either subcutaneous, intramuscular or intravenous injection, is also contemplated herein. Injectables can be prepared in conventional forms, either as liquid solutions or suspensions, solid forms suitable for solution or suspension in liquid prior to injection, or as emulsions. The injectables, solutions and emulsions also contain one or more excipients. Suitable excipients are, for example, water, saline, dextrose, glycerol or ethanol. In addition, if desired, the pharmaceutical compositions to be administered can also contain minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins.

Preparations for parenteral administration of an antibody include sterile solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use and sterile emulsions. The solutions may be either aqueous or nonaqueous.

If administered intravenously, suitable carriers include physiological saline or phosphate buffered saline (PBS), and solutions containing thickening and solubilizing agents, such as glucose, polyethylene glycol, and polypropylene glycol and mixtures thereof.

Topical mixtures comprising an antibody are prepared as described for the local and systemic administration. The resulting mixture can be a solution, suspension, emulsions or the like and can be formulated as creams, gels, ointments, emulsions, solutions, elixirs, lotions, suspensions, tinctures, pastes, foams, aerosols, irrigations, sprays, suppositories, bandages, dermal patches or any other formulations suitable for topical administration.

An anti-TIGIT (e.g., human TIGIT or cynomolgus TIGIT) antibody disclosed herein can be formulated as an aerosol for topical application, such as by inhalation (see, e.g., U.S. Pat. Nos. 4,044,126, 4,414,209 and 4,364,923, which describe aerosols for delivery of a steroid useful for treatment of inflammatory diseases, particularly asthma and are herein incorporated by reference in their entireties). These formulations for administration to the respiratory tract can be in the form of an aerosol or solution for a nebulizer, or as a microfine powder for insufflations, alone or in combination with an inert carrier such as lactose. In such a case, the particles of the formulation will, in one embodiment, have diameters of less than 50 microns, in one embodiment less than 10 microns.

An anti-TIGIT (e.g., human TIGIT or cynomolgus TIGIT) antibody disclosed herein can be formulated for local or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the antibody alone or in combination with other pharmaceutically acceptable excipients can also be administered.

Transdermal patches, including iontophoretic and electrophoretic devices, are well known to those of skill in the art, and can be used to administer an antibody. For example, such patches are disclosed in U.S. Pat. Nos. 6,267,983, 6,261,595, 6,256,533, 6,167,301, 6,024,975, 6,010715, 5,985,317, 5,983,134, 5,948,433, and 5,860,957, all of which are herein incorporated by reference in their entireties.

In certain embodiments, a pharmaceutical composition comprising an antibody described herein is a lyophilized powder, which can be reconstituted for administration as solutions, emulsions and other mixtures. It may also be reconstituted and formulated as solids or gels. The lyophilized powder is prepared by dissolving an antibody described herein, or a pharmaceutically acceptable derivative thereof, in a suitable solvent. In certain embodiments, the lyophilized powder is sterile. The solvent may contain an excipient which improves the stability or other pharmacological component of the powder or reconstituted solution, prepared from the powder. Excipients that may be used include, but are not limited to, dextrose, sorbitol, fructose, corn syrup, xylitol, glycerin, glucose, sucrose or other suitable agent. The solvent may also contain a buffer, such as citrate, sodium or potassium phosphate or other such buffer known to those of skill in the art at, in one embodiment, about neutral pH. Subsequent sterile filtration of the solution followed by lyophilization under standard conditions known to those of skill in the art provides the desired formulation. In one embodiment, the resulting solution will be apportioned into vials for lyophilization. Each vial will contain a single dosage or multiple dosages of the compound. The lyophilized powder can be stored under appropriate conditions, such as at about 4° C. to room temperature. Reconstitution of this lyophilized powder with water for injection provides a formulation for use in parenteral administration. For reconstitution, the lyophilized powder is added to sterile water or other suitable carrier. The precise amount depends upon the selected compound. Such amount can be empirically determined.

The anti-TIGIT (e.g., human TIGIT or cynomolgus TIGIT) antibodies disclosed herein and other compositions provided herein can also be formulated to be targeted to a particular tissue, receptor, or other area of the body of the subject to be treated. Many such targeting methods are well known to those of skill in the art. All such targeting methods are contemplated herein for use in the instant compositions. For non-limiting examples of targeting methods, see, e.g., U.S. Pat. Nos. 6,316,652, 6,274,552, 6,271,359, 6,253,872, 6,139,865, 6,131,570, 6,120,751, 6,071,495, 6,060,082, 6,048,736, 6,039,975, 6,004,534, 5,985,307, 5,972,366, 5,900,252, 5,840,674, 5,759,542 and 5,709,874, all of which are herein incorporated by reference in their entireties. In a specific embodiment, an antibody described herein is targeted to a tumor.

The compositions to be used for in vivo administration can be sterile. This is readily accomplished by filtration through, e.g., sterile filtration membranes.

5.4 Methods of Use and Uses

In another aspect, the instant disclosure provides a method of treating a subject using the anti-TIGIT (e.g., human TIGIT or cynomolgus TIGIT) antibodies disclosed herein. Any disease or disorder in a subject that would benefit from decrease of TIGIT (e.g., human TIGIT or cynomolgus TIGIT) function can be treated using the anti-TIGIT (e.g., human TIGIT or cynomolgus TIGIT) antibodies disclosed herein. In certain embodiments, the disease or disorder is resistant to a checkpoint targeting agent (e.g., an antagonist anti-CTLA-4 antibody, an antagonist anti-PD-L1 antibody, an antagonist anti-PD-L2 antibody, or an antagonist anti-PD-1 antibody). In certain embodiments, the disease or disorder is recurrent after treatment with a checkpoint targeting agent (e.g., an antagonist anti-CTLA-4 antibody, an antagonist anti-PD-L1 antibody, an antagonist anti-PD-L2 antibody, or an antagonist anti-PD-1 antibody).

The anti-TIGIT (e.g., human TIGIT) antibodies disclosed herein are particularly useful for inhibiting immune system tolerance to tumors, and accordingly can be used as an immunotherapy for subjects with cancer. For example, in certain embodiments, the instant disclosure provides a method of increasing T cell (e.g., $CD8^+$ cytotoxic T cells, $CD4^+$ helper T cells, NKT cells, effector T cells, or memory T cells) activation in response to an antigen in a subject, the method comprising administering to the subject an effective amount of an anti-TIGIT (e.g., human TIGIT or cynomolgus TIGIT) antibody or pharmaceutical composition thereof, as disclosed herein. In certain embodiments, the instant disclosure provides a method of decreasing or inhibiting regulatory T cell (Treg) activity in a subject, the method comprising administering to the subject an effective amount of an anti-TIGIT (e.g., human TIGIT or cynomolgus TIGIT) antibody or pharmaceutical composition thereof, as disclosed herein. In certain embodiments, the instant disclosure provides a method of increasing NK cell activation in response to an antigen in a subject, the method comprising administering to the subject an effective amount of an anti-TIGIT (e.g., human TIGIT or cynomolgus TIGIT) antibody or pharmaceutical composition thereof, as disclosed herein. In certain embodiments, the instant disclosure provides a method of treating cancer in a subject, the method comprising administering to the subject an effective amount of the antibody or pharmaceutical composition, as disclosed herein.

Cancers that can be treated with the anti-TIGIT (e.g., human TIGIT or cynomolgus TIGIT) antibodies or pharmaceutical compositions disclosed herein include, without limitation, a solid tumor, a hematological cancer (e.g., leukemia, lymphoma, myeloma, e.g., multiple myeloma), and a metastatic lesion. In one embodiment, the cancer is a solid tumor. Examples of solid tumors include malignancies, e.g., sarcomas and carcinomas, e.g., adenocarcinomas of the various organ systems, such as those affecting the lung, breast, ovarian, lymphoid, gastrointestinal (e.g., colon), anal, genitals and genitourinary tract (e.g., renal, urothelial, bladder cells, prostate), pharynx, CNS (e.g., brain, neural or glial cells), head and neck, skin (e.g., melanoma), and pancreas, as well as adenocarcinomas which include malignancies such as colon cancers, rectal cancer, renal-cell carcinoma, liver cancer, lung cancer (e.g., non-small cell lung cancer or small cell lung cancer), cancer of the small intestine and cancer of the esophagus. The cancer may be at an early, intermediate, late stage or metastatic cancer. In certain embodiments, the cancer is resistant to a checkpoint targeting agent (e.g., an antagonist anti-CTLA-4 antibody, an antagonist anti-PD-L1 antibody, an antagonist anti-PD-L2 antibody, or an antagonist anti-PD-1 antibody). In certain embodiments, the cancer is recurrent after treatment with a checkpoint targeting agent (e.g., an antagonist anti-CTLA-4 antibody, an antagonist anti-PD-L1 antibody, an antagonist anti-PD-L2 antibody, or an antagonist anti-PD-1 antibody).

In one embodiment, the cancer is chosen from lung cancer (e.g., lung adenocarcinoma or non-small cell lung cancer (NSCLC) (e.g., NSCLC with squamous and/or non-squamous histology, or NSCLC adenocarcinoma)), melanoma (e.g., an advanced melanoma), renal cancer (e.g., a renal cell carcinoma), liver cancer (e.g., hepatocellular carcinoma), myeloma (e.g., a multiple myeloma), a prostate cancer, a breast cancer (e.g., a breast cancer that does not express one, two or all of estrogen receptor, progesterone receptor, or Her2/neu, e.g., a triple negative breast cancer), an ovarian cancer, a colorectal cancer, a pancreatic cancer, a head and neck cancer (e.g., head and neck squamous cell carcinoma (HNSCC), anal cancer, gastro-esophageal cancer (e.g., esophageal squamous cell carcinoma), mesothelioma, nasopharyngeal cancer, thyroid cancer, cervical cancer, epithelial cancer, peritoneal cancer, or a lymphoproliferative disease (e.g., a post-transplant lymphoproliferative disease). In a specific embodiment, the cancer is a cervical cancer.

In one embodiment, the cancer is a hematological cancer, for example, a leukemia, a lymphoma, or a myeloma. In one embodiment, the cancer is a leukemia, for example, acute lymphoblastic leukemia (ALL), acute myelogenous leukemia (AML), acute myeloblastic leukemia (AML), chronic lymphocytic leukemia (CLL), chronic myelogenous leukemia (CML), chronic myeloid leukemia (CML), chronic myelomonocytic leukemia (CMML), chronic lymphocytic leukemia (CLL), or hairy cell leukemia. In one embodiment, the cancer is a lymphoma, for example, B cell lymphoma, diffuse large B-cell lymphoma (DLBCL), activated B-cell like (ABC) diffuse large B cell lymphoma, germinal center B cell (GCB) diffuse large B cell lymphoma, mantle cell lymphoma, Hodgkin lymphoma, non-Hodgkin lymphoma, relapsed non-Hodgkin lymphoma, refractory non-Hodgkin lymphoma, recurrent follicular non-Hodgkin lymphoma, Burkitt lymphoma, small lymphocytic lymphoma, follicular lymphoma, lymphoplasmacytic lymphoma, or extranodal marginal zone lymphoma. In one embodiment the cancer is a myeloma, for example, multiple myeloma.

In another embodiment, the cancer is chosen from a carcinoma (e.g., advanced or metastatic carcinoma), melanoma or a lung carcinoma, e.g., a non-small cell lung carcinoma.

In one embodiment, the cancer is a lung cancer, e.g., lung adenocarcinoma, non-small cell lung cancer, or small cell lung cancer.

In one embodiment, the cancer is a melanoma, e.g., an advanced melanoma. In one embodiment, the cancer is an advanced or unresectable melanoma that does not respond to other therapies. In other embodiments, the cancer is a melanoma with a BRAF mutation (e.g., a BRAF V600 mutation). In yet other embodiments, the anti-TIGIT (e.g., human TIGIT or cynomolgus TIGIT) antibody or pharmaceutical composition disclosed herein is administered after treatment with an anti-CTLA-4 antibody (e.g., ipilimumab) with or without a BRAF inhibitor (e.g., vemurafenib or dabrafenib).

In another embodiment, the cancer is a hepatocarcinoma, e.g., an advanced hepatocarcinoma, with or without a viral infection, e.g., a chronic viral hepatitis.

In another embodiment, the cancer is a prostate cancer, e.g., an advanced prostate cancer.

In yet another embodiment, the cancer is a myeloma, e.g., multiple myeloma.

In yet another embodiment, the cancer is a renal cancer, e.g., a renal cell carcinoma (RCC) (e.g., a metastatic RCC, clear cell renal cell carcinoma (CCRCC) or kidney papillary cell carcinoma).

In yet another embodiment, the cancer is chosen from a lung cancer, a melanoma, a renal cancer, a breast cancer, a colorectal cancer, a leukemia, or a metastatic lesion of the cancer.

In certain embodiments, the instant disclosure provides a method of preventing or treating an infectious disease in a subject, the method comprising administering to the subject an effective amount of an anti-TIGIT (e.g., human TIGIT or cynomolgus TIGIT) antibody or pharmaceutical composition thereof, as disclosed herein. In one embodiment, provided herein are methods for preventing and/or treating an infection (e.g., a viral infection, a bacterial infection, a fungal infection, a protozoal infection, or a parasitic infection). The infection prevented and/or treated in accordance with the methods can be caused by an infectious agent identified herein. In a specific embodiment, an anti-TIGIT (e.g., human TIGIT or cynomolgus TIGIT) antibody described herein or a composition thereof is the only active agent administered to a subject. In certain embodiments, an anti-TIGIT (e.g., human TIGIT or cynomolgus TIGIT) antibody described herein or a composition thereof is used in combination with anti-infective interventions (e.g., antivirals, antibacterials, antifungals, or anti-helminthics) for the treatment of infectious diseases. Therefore, in a one embodiment, the present invention relates to an antibody and/or pharmaceutical composition of the present invention for use in a method of preventing and/or treating an infectious disease, optionally wherein the antibody or pharmaceutical composition is the only active agent administered to a subject, or wherein the antibody or pharmaceutical composition is used in combination with anti-infective interventions.

Infectious diseases that can be treated and/or prevented by anti-TIGIT (e.g., human TIGIT or cynomolgus TIGIT) antibodies or pharmaceutical compositions disclosed herein are caused by infectious agents including but not limited to bacteria, parasites, fungi, protozae, and viruses. In a specific embodiment, the infectious disease treated and/or prevented by anti-TIGIT (e.g., human TIGIT or cynomolgus TIGIT) antibodies or pharmaceutical compositions disclosed herein is caused by a virus. Viral diseases or viral infections that can be prevented and/or treated in accordance with the methods described herein include, but are not limited to, those caused by hepatitis type A, hepatitis type B, hepatitis type C, influenza (e.g., influenza A or influenza B), varicella, adenovirus, herpes simplex type I (HSV-I), herpes simplex type II (HSV-II), rinderpest, rhinovirus, echovirus, rotavirus, respiratory syncytial virus, papilloma virus, papova virus, cytomegalovirus, echinovirus, arbovirus, huntavirus, coxsackie virus, mumps virus, measles virus, rubella virus, polio virus, small pox, Epstein Barr virus, human immunodeficiency virus type I (HIV-I), human immunodeficiency virus type II (HIV-II), and agents of viral diseases such as viral meningitis, encephalitis, dengue or small pox.

Bacterial infections that can be prevented and/or treated include infections caused by *Escherichia coli, Klebsiella pneumoniae, Staphylococcus aureus, Enterococcus faecalis, Proteus vulgaris, Staphylococcus viridans*, and *Pseudomonas aeruginosa*. Bacterial diseases caused by bacteria (e.g., *Escherichia coli, Klebsiella pneumoniae, Staphylococcus aureus, Enterococcus faecalis, Proteus vulgaris, Staphylococcus viridans*, and *Pseudomonas aeruginosa*) that can be prevented and/or treated in accordance with the methods described herein include, but are not limited to, *Mycobacteria rickettsia, Mycoplasma, Neisseria, S. pneumonia, Borrelia burgdorferi* (Lyme disease), *Bacillus antracis* (anthrax), tetanus, *Streptococcus, Staphylococcus, mycobacterium*, pertissus, cholera, plague, diptheria, *chlamydia, S. aureus* and *legionella*.

Protozoal diseases or protozoal infections caused by protozoa that can be prevented and/or treated in accordance with the methods described herein include, but are not limited to, *leishmania*, coccidiosis, *trypanosoma schistosoma* or malaria. Parasitic diseases or parasitic infections caused by parasites that can be prevented and/or treated in accordance with the methods described herein include, but are not limited to, *chlamydia* and *rickettsia*.

Fungal diseases or fungal infections that can be prevented and/or treated in accordance with the methods described herein include, but are not limited to, those caused by *Candida* infections, zygomycosis, *Candida* mastitis, progressive disseminated trichosporonosis with latent trichosporonemia, disseminated candidiasis, pulmonary paracoccidioidomycosis, pulmonary aspergillosis, *Pneumocystis carinii* pneumonia, cryptococcal meningitis, coccidioidal meningoencephalitis and cerebrospinal vasculitis, *Aspergillus niger* infection, *Fusarium keratitis*, paranasal sinus mycoses, *Aspergillus fumigatus* endocarditis, tibial dyschondroplasia, *Candida glabrata* vaginitis, oropharyngeal candidiasis, X-linked chronic granulomatous disease, tinea pedis, cutaneous candidiasis, mycotic placentitis, disseminated trichosporonosis, allergic bronchopulmonary aspergillosis, mycotic keratitis, *Cryptococcus neoformans* infection, fungal peritonitis, *Curvularia geniculata* infection, staphylococcal endophthalmitis, sporotrichosis, and dermatophytosis.

In certain embodiments, these methods further comprise administering an additional therapeutic agent to the subject. In certain embodiments, the additional therapeutic agent is a chemotherapeutic, a radiotherapeutic, or a checkpoint targeting agent. In certain embodiments, the chemotherapeutic agent is a hypomethylating agent (e.g., azacitidine). In certain embodiments, the chemotherapeutic agent is a DNA damage-inducing agent (e.g., gemcitabine). In certain embodiments, the checkpoint targeting agent is selected from the group consisting of an antagonist anti-CTLA-4 antibody, an antagonist anti-PD-L1 antibody, an antagonist anti-PD-L2 antibody, an antagonist anti-PD-1 antibody, an antagonist anti-TIM-3 antibody, an antagonist anti-LAG-3 antibody, an antagonist anti-VISTA antibody, an antagonist anti-CD96 antibody, an antagonist anti-CEACAM1 antibody, an agonist anti-CD137 antibody, an agonist anti-GITR antibody, and an agonist anti-OX40 antibody. In certain embodiments, the checkpoint targeting agent is selected from the group consisting of an antagonist anti-CTLA-4 antibody, an antagonist anti-PD-L1 antibody, an antagonist anti-PD-L2 antibody, and an antagonist anti-PD-1 antibody, wherein the anti-TIGIT (e.g., human TIGIT or cynomolgus TIGIT) antibodies or pharmaceutical compositions disclosed herein synergize with the checkpoint targeting agent.

In one embodiment, the present invention relates to an antibody and/or pharmaceutical composition of the present invention for use in a method of the present invention, wherein the method further comprises administering an additional therapeutic agent to the subject. In one embodiment, the present invention relates to (a) an antibody and/or pharmaceutical composition of the present invention and (b) an additional therapeutic agent for use as a medicament. In one embodiment, the present invention relates to (a) an antibody and/or pharmaceutical composition of the present invention, and (b) an additional therapeutic agent for use in a method for the treatment of cancer. In a further embodiment, the present invention relates to a pharmaceutical composition, kit or kit-of-parts comprising (a) an antibody and/or pharmaceutical composition of the present invention and (b) an additional therapeutic agent. In one embodiment, the additional therapeutic agent is a chemotherapeutic, a radiotherapeutic, or a checkpoint targeting agent.

In certain embodiments, an anti-PD-1 antibody is used in methods disclosed herein. In certain embodiments, the anti-PD-1 antibody is nivolumab, also known as BMS-936558 or MDX1106, developed by Bristol-Myers Squibb. In certain embodiments, the anti-PD-1 antibody is pembrolizumab, also known as lambrolizumab or MK-3475, developed by Merck & Co. In certain embodiments, the anti-PD-1 antibody is pidilizumab, also known as CT-011, developed by CureTech. In certain embodiments, the anti-PD-1 antibody is MEDI0680, also known as AMP-514, developed by Medimmune. In certain embodiments, the anti-PD-1 antibody is PDR001 developed by Novartis Pharmaceuticals. In certain embodiments, the anti-PD-1 antibody is REGN2810 developed by Regeneron Pharmaceuticals. In certain embodiments, the anti-PD-1 antibody is PF-06801591 developed by Pfizer. In certain embodiments, the anti-PD-1 antibody is BGB-A317 developed by BeiGene. In certain embodiments, the anti-PD-1 antibody is TSR-042 developed by AnaptysBio and Tesaro. In certain embodiments, the anti-PD-1 antibody is SHR-1210 developed by Hengrui.

Further non-limiting examples of anti-PD-1 antibodies that may be used in treatment methods disclosed herein are disclosed in the following patents and patent applications, all of which are herein incorporated by reference in their entireties for all purposes: U.S. Pat. Nos. 6,808,710; 7,332,582; 7,488,802; 8,008,449; 8,114,845; 8,168,757; 8,354,509; 8,686,119; 8,735,553; 8,747,847; 8,779,105; 8,927,697; 8,993,731; 9,102,727; 9,205,148; U.S. Publication No. US 2013/0202623 A1; U.S. Publication No. US 2013/0291136 A1; U.S. Publication No. US 2014/0044738 A1; U.S. Publication No. US 2014/0356363 A1; U.S. Publication No. US 2016/0075783 A1; and PCT Publication No. WO 2013/033091 A1; PCT Publication No. WO 2015/036394 A1; PCT Publication No. WO 2014/179664 A2; PCT Publication No. WO 2014/209804 A1; PCT Publication No. WO 2014/206107 A1; PCT Publication No. WO 2015/058573 A1; PCT Publication No. WO 2015/085847 A1; PCT Publication No. WO 2015/200119 A1; PCT Publication No. WO 2016/015685 A1; and PCT Publication No. WO 2016/020856 A1.

In certain embodiments, an anti-PD-L1 antibody is used in methods disclosed herein. In certain embodiments, the anti-PD-L1 antibody is atezolizumab developed by Genentech. In certain embodiments, the anti-PD-L1 antibody is durvalumab developed by AstraZeneca, Celgene and Medimmune. In certain embodiments, the anti-PD-L1 antibody is avelumab, also known as MSB0010718C, developed by Merck Serono and Pfizer. In certain embodiments, the anti-PD-L1 antibody is MDX-1105 developed by Bristol-Myers Squibb. In certain embodiments, the anti-PD-L1 antibody is AMP-224 developed by Amplimmune and GSK.

Non-limiting examples of anti-PD-L1 antibodies that may be used in treatment methods disclosed herein are disclosed in the following patents and patent applications, all of which are herein incorporated by reference in their entireties for all purposes: U.S. Pat. Nos. 7,943,743; 8,168,179; 8,217,149; 8,552,154; 8,779,108; 8,981,063; 9,175,082; U.S. Publication No. US 2010/0203056 A1; U.S. Publication No. US 2003/0232323 A1; U.S. Publication No. US 2013/0323249 A1; U.S. Publication No. US 2014/0341917 A1; U.S. Publication No. US 2014/0044738 A1; U.S. Publication No. US 2015/0203580 A1; U.S. Publication No. US 2015/0225483 A1; U.S. Publication No. US 2015/0346208 A1; U.S. Publication No. US 2015/0355184 A1; and PCT Publication No. WO 2014/100079 A1; PCT Publication No. WO 2014/022758 A1; PCT Publication No. WO 2014/055897 A2; PCT Publication No. WO 2015/061668 A1; PCT Publication No. WO 2015/109124 A1; PCT Publication No. WO 2015/195163 A1; PCT Publication No. WO 2016/000619 A1; and PCT Publication No. WO 2016/030350 A1.

In certain embodiments, an anti-CTLA-4 antibody is used in methods disclosed herein. In certain embodiments, the anti-CTLA-4 antibody is ipilimumab developed by Bristol-Myers Squibb.

In certain embodiments, an anti-TIGIT (e.g., human TIGIT or cynomolgus TIGIT) antibody disclosed herein is administered to a subject in combination with a compound that targets an immunomodulatory enzyme(s) such as IDO (indoleamine-(2,3)-dioxygenase) and/or TDO (tryptophan 2,3-dioxygenase). Therefore, in one embodiment, the additional therapeutic agent is a compound that targets an immunomodulatory enzyme(s), such as an inhibitor of indoleamine-(2,3)-dioxygenase (IDO). In certain embodiments, such compound is selected from the group consisting of epacadostat (Incyte Corp; see, e.g., WO 2010/005958 which is herein incorporated by reference in its entirety), F001287 (Flexus Biosciences/Bristol-Myers Squibb), indoximod (NewLink Genetics), and NLG919 (NewLink Genetics). In one embodiment, the compound is epacadostat. In another embodiment, the compound is F001287. In another embodiment, the compound is indoximod. In another embodiment, the compound is NLG919. In a specific embodiment, an anti-TIGIT (e.g., human TIGIT) antibody disclosed herein is administered to a subject in combination with an IDO inhibitor for treating cancer. The IDO inhibitor as described herein for use in treating cancer is present in a solid dosage form of a pharmaceutical composition such as a tablet, a pill or a capsule, wherein the pharmaceutical composition includes an IDO inhibitor and a pharmaceutically acceptable excipient. As such, the antibody as described herein and the IDO inhibitor as described herein can be administered separately, sequentially or concurrently as separate dosage forms. In one embodiment, the antibody is administered parenterally, and the IDO inhibitor is administered orally. In particular embodiments, the inhibitor is selected from the group consisting of epacadostat (Incyte Corporation), F001287 (Flexus Biosciences/Bristol-Myers Squibb), indoximod (NewLink Genetics), and NLG919 (NewLink Genetics). Epacadostat has been described in PCT Publication No. WO 2010/005958, which is herein incorporated by reference in its entirety for all purposes. In one embodiment, the inhibitor is epacadostat. In another embodiment, the inhibitor is F001287. In another embodiment, the inhibitor is indoximod. In another embodiment, the inhibitor is NLG919.

In certain embodiments, an anti-TIGIT (e.g., human TIGIT or cynomolgus TIGIT) antibody disclosed herein is administered to a subject in combination with a vaccine. The vaccine can be, e.g., a peptide vaccine, a DNA vaccine, or an RNA vaccine. In certain embodiments, the vaccine is a heat shock protein based tumor vaccine or a heat shock protein based pathogen vaccine. In a specific embodiment, an anti-TIGIT (e.g., human TIGIT or cynomolgus TIGIT) antibody disclosed herein is administered to a subject in combination with a heat shock protein based tumor-vaccine. Heat shock proteins (HSPs) are a family of highly conserved proteins found ubiquitously across all species. Their expression can be powerfully induced to much higher levels as a result of heat shock or other forms of stress, including exposure to toxins, oxidative stress or glucose deprivation. Five families have been classified according to molecular weight: HSP-110, -90, -70, -60 and -28. HSPs deliver immunogenic peptides through the cross-presentation pathway in antigen presenting cells (APCs) such as macrophages and dendritic cells (DCs), leading to T cell activation. HSPs function as chaperone carriers of tumor-associated antigenic peptides forming complexes able to induce tumor-specific immunity. Upon release from dying tumor cells, the HSP-antigen complexes are taken up by antigen-presenting cells (APCs) wherein the antigens are processed into peptides that bind MHC class I and class II molecules leading to the activation of anti-tumor CD8+ and CD4+ T cells. The immunity elicited by HSP complexes derived from tumor preparations is specifically directed against the unique antigenic peptide repertoire expressed by the cancer of each subject. Therefore, in one embodiment, the present invention relates to (a) an antibody and/or pharmaceutical composition of the present invention and (b) a vaccine for use as a medicament, for example for use in a method for the treatment of cancer. In one embodiment, the present invention relates to a pharmaceutical composition, kit or kit-ofparts comprising (a) an antibody and/or pharmaceutical composition of the present invention and (b) a vaccine. In one embodiment, the vaccine is a heat shock protein based tumor vaccine. In one embodiment, the vaccine is a heat shock protein based pathogen vaccine. In certain embodiments, the vaccine is as described in WO 2016/183486, incorporated herein by reference in its entirety.

A heat shock protein peptide complex (HSPPC) is a protein peptide complex consisting of a heat shock protein non-covalently complexed with antigenic peptides. HSPPCs elicit both innate and adaptive immune responses. In a specific embodiment, the antigenic peptide(s) displays antigenicity for the cancer being treated. HSPPCs are efficiently seized by APCs via membrane receptors (mainly CD91) or by binding to Toll-like receptors. HSPPC internalization results in functional maturation of the APCs with chemokine and cytokine production leading to activation of natural killer cells (NK), monocytes and Th1 and Th-2-mediated immune responses. In certain embodiments, HSPPCs used in methods disclosed herein comprise one or more heat shock proteins from the hsp60, hsp70, or hsp90 family of stress proteins complexed with antigenic peptides. In certain embodiments, HSPPCs comprise hsc70, hsp70, hsp90, hsp110, grp170, gp96, calreticulin, or combinations of two or more thereof.

In a specific embodiment, the heat shock protein peptide complex (HSPPC) comprises recombinant heat shock proteins (e.g., hsp70 or hsc70) or a peptide-binding domain thereof complexed with recombinant antigenic peptides. Recombinant heat shock proteins can be produced by recombinant DNA technology, for example, using human hsc70 sequence as described in Dworniczak and Mirault, Nucleic Acids Res. 15:5181-5197 (1987) and GenBank accession no. P11142 and/or Y00371, each of which is incorporated herein by reference in its entirety. In certain embodiments, Hsp70 sequences are as described in Hunt and Morimoto Proc. Natl. Acad. Sci. U.S.A. 82 (19), 6455-6459 (1985) and GenBank accession no. PODMV8 and/or M11717, each of which is incorporated herein by reference in its entirety. Antigenic peptides can also be prepared by recombinant DNA methods known in the art.

In certain embodiments, the antigenic peptides comprise a modified amino acid. In certain embodiments, the modified amino acid comprises a post-translational modification. In certain embodiments, the modified amino acid comprises a mimetic of a post-translational modification. In certain embodiments, the modified amino acid is a Tyr, Ser, Thr, Arg, Lys, or His that has been phosphorylated on a side chain hydroxyl or amine. In certain embodiments, the modified amino acid is a mimetic of a Tyr, Ser, Thr, Arg, Lys, or His amino acid that has been phosphorylated on a side chain hydroxyl or amine.

In a specific embodiment, an anti-TIGIT (e.g., human TIGIT or cynomolgus TIGIT) antibody disclosed herein is administered to a subject in combination with a heat shock protein peptide complex (HSPPC), e.g., heat shock protein peptide complex-96 (HSPPC-96), to treat cancer. HSPPC-96 comprises a 96 kDa heat shock protein (Hsp), gp96, complexed to antigenic peptides. HSPPC-96 is a cancer immunotherapy manufactured from a subject's tumor and contains the cancer's antigenic "fingerprint." In certain embodiments, this fingerprint contains unique antigens that are present only in that particular subject's specific cancer cells and injection of the vaccine is intended to stimulate the subject's immune system to recognize and attack any cells with the specific cancer fingerprint. Therefore, in one embodiment, the present invention relates to an antibody and/or pharmaceutical composition of the present invention in combination with a heat shock protein peptide complex (HSPPC) for use as a medicament and/or for use in a method for the treatment of cancer.

In certain embodiments, the HSPPC, e.g., HSPPC-96, is produced from the tumor tissue of a subject. In a specific embodiment, the HSPPC (e.g., HSPPC-96) is produced from a tumor of the type of cancer or metastasis thereof being treated. In another specific embodiment, the HSPPC (e.g., HSPPC-96) is autologous to the subject being treated. In certain embodiments, the tumor tissue is non-necrotic tumor tissue. In certain embodiments, at least 1 gram (e.g., at least 1, at least 2, at least 3, at least 4, at least 5, at least 6, at least 7, at least 8, at least 9, or at least 10 grams) of non-necrotic tumor tissue is used to produce a vaccine regimen. In certain embodiments, after surgical resection, non-necrotic tumor tissue is frozen prior to use in vaccine preparation. In certain embodiments, the HSPPC, e.g., HSPPC-96, is isolated from the tumor tissue by purification techniques, filtered and prepared for an injectable vaccine. In certain embodiments, a subject is administered 6-12 doses of the HSPPC, e.g., HSPCC-96. In such embodiments, the HSPPC, e.g., HSPPC-96, doses may be administered weekly for the first 4 doses and then biweekly for the 2-8 additional doses.

Further examples of HSPPCs that may be used in accordance with the methods described herein are disclosed in the following patents and patent applications, all of which are herein incorporated by reference in their entireties: U.S. Pat. Nos. 6,391,306, 6,383,492, 6,403,095, 6,410,026, 6,436,404, 6,447,780, 6,447,781 and 6,610,659.

In certain embodiments, an anti-TIGIT (e.g., human TIGIT or cynomolgus TIGIT) antibody disclosed herein is administered to a subject in combination with an adjuvant. Various adjuvants can be used depending on the treatment context. Non-limiting examples of appropriate adjuvants include, but not limited to, Complete Freund's Adjuvant (CFA), Incomplete Freund's Adjuvant (IFA), montanide ISA (incomplete Seppic adjuvant), the Ribi adjuvant system (RAS), Titer Max, muramyl peptides, Syntex Adjuvant Formulation (SAF), alum (aluminum hydroxide and/or aluminum phosphate), aluminum salt adjuvants, Gerbu® adjuvants, nitrocellulose absorbed antigen, encapsulated or entrapped antigen, 3 De-O-acylated monophosphoryl lipid A (3 D-MPL), immunostimulatory oligonucleotides, toll-like receptor (TLR) ligands, mannan-binding lectin (MBL) ligands, STING agonists, immuno-stimulating complexes such as saponins, Quil A, QS-21, QS-7, ISCOMATRIX, and others. Other adjuvants include CpG oligonucleotides and double stranded RNA molecules, such as poly(A) and poly (U). Combinations of the above adjuvants may also be used. See, e.g., U.S. Pat. Nos. 6,645,495; 7,029,678; and 7,858, 589, all of which are incorporated herein by reference in their entireties. In one embodiment, the adjuvant used herein is QS-21 STIMULON.

In certain embodiments, an anti-TIGIT (e.g., human TIGIT or cynomolgus TIGIT) antibody disclosed herein is administered to a subject in combination with an additional therapeutic agent comprising a TCR. In certain embodiments, the additional therapeutic agent is a soluble TCR. In certain embodiments, the additional therapeutic agent is a cell expressing a TCR. Therefore, in one embodiment, the present invention relates to an antibody and/or pharmaceutical composition of the present invention in combination with an additional therapeutic agent comprising a TCR for use as a medicament and/or for use in a method for the treatment of cancer.

In certain embodiments, an anti-TIGIT (e.g., human TIGIT or cynomolgus TIGIT) antibody disclosed herein is administered to a subject in combination with a cell expressing a chimeric antigen receptor (CAR). In certain embodiments, the cell is a T cell.

In certain embodiments, an anti-TIGIT (e.g., human TIGIT or cynomolgus TIGIT) antibody disclosed herein is administered to a subject in combination with a TCR mimic antibody. In certain embodiments, the TCR mimic antibody is an antibody that specifically binds to a peptide-MHC complex. For non-limiting examples of TCR mimic antibodies, see, e.g., U.S. Pat. No. 9,074,000 and U.S. Publication Nos. US 2009/0304679 A1 and US 2014/0134191 A1, all of which are incorporated herein by reference in their entireties.

In certain embodiments, an anti-TIGIT (e.g., human TIGIT or cynomolgus TIGIT) antibody disclosed herein is administered to a subject in combination with a bispecific T-cell engager (BiTE) (e.g., as described in WO2005061547A2, which is incorporated by reference herein in its entirety) and/or a dual-affinity re-targeting antibody (DART) (e.g., as described in WO2012162067A2, which is incorporated by reference herein in its entirety). In certain embodiments, the BiTE and/or DART specifically binds to a tumor-associated antigen (e.g., a polypeptide overexpressed in a tumor, a polypeptide derived from an oncovirus, a polypeptide comprising a post-translational modification specific to a tumor, a polypeptide specifically mutated in a tumor) and a molecule on an effector cell (e.g., CD3 or CD16). In certain embodiments, the tumor-associated antigen is EGFR (e.g., human EGFR), optionally wherein the BiTE and/or DART comprises the VH and VL sequences of cetuximab. In certain embodiments, the tumor-associated antigen is Her2 (e.g., human Her2), optionally wherein the BiTE and/or DART comprises the VH and VL sequences of trastuzumab. In certain embodiments, the tumor-associated antigen is CD20 (e.g., human CD20).

The anti-TIGIT (e.g., human TIGIT or cynomolgus TIGIT) antibody and the additional therapeutic agent (e.g., chemotherapeutic, radiotherapeutic, checkpoint targeting agent, IDO inhibitor, vaccine, adjuvant, a soluble TCR, a cell expressing a TCR, a cell expressing a chimeric antigen receptor, and/or a TCR mimic antibody) can be administered separately, sequentially or concurrently as separate dosage forms. In one embodiment, an anti-TIGIT (e.g., human TIGIT or cynomolgus TIGIT) antibody is administered parenterally, and an IDO inhibitor is administered orally.

An antibody or pharmaceutical composition described herein may be delivered to a subject by a variety of routes. These include, but are not limited to, parenteral, intranasal, intratracheal, oral, intradermal, topical, intramuscular, intraperitoneal, transdermal, intravenous, intratumoral, conjunctival, intra-arterial, and subcutaneous routes. Pulmonary administration can also be employed, e.g., by use of an inhaler or nebulizer, and formulation with an aerosolizing agent for use as a spray. In certain embodiments, the antibody or pharmaceutical composition described herein is delivered subcutaneously or intravenously. In certain embodiments, the antibody or pharmaceutical composition described herein is delivered intra-arterially. In certain embodiments, the antibody or pharmaceutical composition described herein is delivered intratumorally. In certain embodiments, the antibody or pharmaceutical composition described herein is delivered into a tumor draining lymph node.

The amount of an antibody or composition which will be effective in the treatment and/or prevention of a condition will depend on the nature of the disease, and can be determined by standard clinical techniques.

The precise dose to be employed in a composition will also depend on the route of administration, and the seriousness of the infection or disease caused by it, and should be decided according to the judgment of the practitioner and each subject's circumstances. For example, effective doses may also vary depending upon means of administration, target site, physiological state of the patient (including age, body weight and health), whether the patient is human or an animal, other medications administered, or whether treatment is prophylactic or therapeutic. Usually, the patient is a human, but non-human mammals, including transgenic mammals, can also be treated. Treatment dosages are optimally titrated to optimize safety and efficacy.

An anti-TIGIT (e.g., human TIGIT or cynomolgus TIGIT) antibody described herein can also be used to assay TIGIT (e.g., human TIGIT or cynomolgus TIGIT) protein levels in a biological sample using classical immunohistological methods known to those of skill in the art, including immunoassays, such as the enzyme linked immunosorbent assay (ELISA), immunoprecipitation, or Western blotting. Suitable antibody assay labels are known in the art and include enzyme labels, such as, glucose oxidase; radioisotopes, such as iodine ($^{125}$I, $^{121}$I), carbon ($^{14}$C), sulfur ($^{35}$S), tritium ($^{3}$H), indium ($^{121}$In), and technetium ($^{99}$Tc); luminescent labels, such as luminol; and fluorescent labels, such as fluorescein and rhodamine, and biotin. Such labels can be used to label an antibody described herein. Alternatively, a second antibody that recognizes an anti-TIGIT (e.g., human TIGIT or cynomolgus TIGIT) antibody described herein can be labeled and used in combination with an anti-TIGIT (e.g., human TIGIT or cynomolgus TIGIT) antibody to detect TIGIT (e.g., human TIGIT or cynomolgus TIGIT) protein levels. Therefore, in one embodiment, the present invention relates to the use of an antibody of the present invention for in vitro detection of TIGIT (e.g., human TIGIT or cynomolgus TIGIT) protein in a biological sample. In a further embodiment, the present invention relates to the use of an anti-TIGIT antibody of the invention, for assaying and/or detecting TIGIT (e.g., human TIGIT or cynomolgus TIGIT) protein levels in a biological sample in vitro, optionally wherein the anti-TIGIT antibody is conjugated to a radionuclide or detectable label, and/or carries a label described herein, and/or wherein an immunohistological method is used.

Assaying for the expression level of TIGIT (e.g., human TIGIT or cynomolgus TIGIT) protein is intended to include qualitatively or quantitatively measuring or estimating the level of TIGIT (e.g., human TIGIT or cynomolgus TIGIT) protein in a first biological sample either directly (e.g., by determining or estimating absolute protein level) or relatively (e.g., by comparing to the disease associated protein level in a second biological sample). TIGIT (e.g., human TIGIT or cynomolgus TIGIT) polypeptide expression level in the first biological sample can be measured or estimated and compared to a standard TIGIT (e.g., human TIGIT or cynomolgus TIGIT) protein level, the standard being taken, for example, from a second biological sample obtained from an individual not having the disorder or being determined by averaging levels from a population of individuals not having the disorder. As will be appreciated in the art, once the "standard" TIGIT (e.g., human TIGIT or cynomolgus TIGIT) polypeptide level is known, it can be used repeatedly as a standard for comparison. Therefore, in a further embodiment, the present invention relates to an in vitro method for assaying and/or detecting TIGIT protein levels, for example human TIGIT protein levels, in a biological sample, comprising qualitatively or quantitatively measuring or estimating the level of TIGIT protein, for example of human TIGIT protein, in a biological sample, by an immunohistological method.

As used herein, the term "biological sample" refers to any biological sample obtained from a subject, cell line, tissue, or other source of cells potentially expressing TIGIT (e.g., human TIGIT or cynomolgus TIGIT). Methods for obtaining tissue biopsies and body fluids from animals (e.g., humans or cynomolgus monkeys) are well known in the art. Biological samples include peripheral blood mononuclear cells (PBMCs).

An anti-TIGIT (e.g., human TIGIT or cynomolgus TIGIT) antibody described herein can be used for prognostic, diagnostic, monitoring and screening applications, including in vitro and in vivo applications well known and standard to the skilled artisan and based on the present description. Prognostic, diagnostic, monitoring and screening assays and kits for in vitro assessment and evaluation of immune system status and/or immune response may be utilized to predict, diagnose and monitor to evaluate patient samples including those known to have or suspected of having an immune system-dysfunction or with regard to an anticipated or desired immune system response, antigen response or vaccine response. The assessment and evaluation of immune system status and/or immune response is also useful in determining the suitability of a patient for a clinical trial of a drug or for the administration of a particular chemotherapeutic agent, a radiotherapeutic agent, or an antibody, including combinations thereof, versus a different agent or antibody. This type of prognostic and diagnostic monitoring and assessment is already in practice utilizing antibodies against the HER2 protein in breast cancer (HercepTest™, Dako) where the assay is also used to evaluate patients for antibody therapy using Herceptin®. In vivo applications include directed cell therapy and immune system modulation and radio imaging of immune responses. Therefore, in one embodiment, the present invention relates to an anti-TIGIT antibody and/or pharmaceutical composition of the present invention for use as a diagnostic. In one embodiment, the present invention relates to an anti-TIGIT antibody and/or pharmaceutical composition of the present invention for use in a method for the prediction, diagnosis and/or monitoring of a subject having or suspected to have an immune system-dysfunction and/or with regard to an anticipated or desired immune system response, antigen response or vaccine response. In another embodiment, the present invention relates to the use of anti-TIGIT antibody of the invention, for predicting, diagnosing and/or monitoring of a subject having or suspected to have an immune system-dysfunction and/or with regard to an anticipated or desired immune system response, antigen response or vaccine response by assaying and/or detecting human TIGIT protein levels in a biological sample of the subject in vitro.

In one embodiment, an anti-TIGIT (e.g., human TIGIT or cynomolgus TIGIT) antibody can be used in immunohistochemistry of biopsy samples. In one embodiment, the method is an in vitro method. In another embodiment, an anti-TIGIT (e.g., human TIGIT or cynomolgus TIGIT) antibody can be used to detect levels of TIGIT (e.g., human TIGIT or cynomolgus TIGIT), or levels of cells which contain TIGIT (e.g., human TIGIT or cynomolgus TIGIT) on their membrane surface, the levels of which can then be linked to certain disease symptoms. Anti-TIGIT (e.g., human TIGIT or cynomolgus TIGIT) antibodies described herein may carry a detectable or functional label and/or may be conjugated to a radionuclide or detectable label. When fluorescence labels are used, currently available microscopy and fluorescence-activated cell sorter analysis (FACS) or combination of both methods procedures known in the art may be utilized to identify and to quantitate the specific binding members. Anti-TIGIT (e.g., human TIGIT or cynomolgus TIGIT) antibodies described herein may carry or may be conjugated to a fluorescence label. Exemplary fluorescence labels include, for example, reactive and conjugated probes, e.g., Aminocoumarin, Fluorescein and Texas red, Alexa Fluor dyes, Cy dyes and DyLight dyes. An anti-TIGIT (e.g., human TIGIT or cynomolgus TIGIT) antibody may carry or may be conjugated to a radioactive label or radionuclide, such as the isotopes $^{3}$H, $^{14}$C, $^{32}$P, $^{35}$S, $^{36}$Cl, $^{51}$Cr, $^{57}$Co, $^{58}$Co, $^{59}$Fe, $^{67}$Cu, $^{90}$Y, $^{99}$Tc, $^{111}$In, $^{117}$Lu, $^{121}$I, $^{124}$I, $^{125}$I, $^{131}$I, $^{198}$Au, $^{211}$At, $^{213}$Bi, $^{225}$Ac and $^{186}$Re. When radioactive labels are used, currently available counting procedures known in the art may be utilized to identify and quantitate the specific binding of anti-TIGIT (e.g., human TIGIT or cynomolgus TIGIT) antibody to TIGIT (e.g., human TIGIT or cynomolgus TIGIT). In the instance where the label is an enzyme, detection may be accomplished by any of the presently utilized colorimetric, spectrophotometric, fluorospectrophotometric, amperometric or gasometric techniques as known in the art. This can be achieved by contacting a sample or a control sample with an anti-TIGIT (e.g., human TIGIT or cynomolgus TIGIT) antibody under conditions that allow for the formation of a complex between the antibody and TIGIT (e.g., human TIGIT or cynomolgus TIGIT). Any complexes formed between the antibody and TIGIT (e.g., human TIGIT or cynomolgus TIGIT) are detected and compared in the sample and the control. In light of the specific binding of the antibodies described herein for TIGIT (e.g., human TIGIT or cynomolgus TIGIT), the antibodies can be used to specifically detect TIGIT (e.g., human TIGIT or cynomolgus TIGIT) expression on the surface of cells. The antibodies described herein can also be used to purify TIGIT (e.g., human TIGIT or cynomolgus TIGIT) via immunoaffinity purification. Also included herein is an assay system which may be prepared in the form of a test kit, kit, or kit-of-parts for the quantitative analysis of the extent of the presence of, for instance, TIGIT (e.g., human TIGIT or cynomolgus TIGIT) or TIGIT (e.g., human TIGIT or cynomolgus TIGIT)/TIGIT (e.g., human TIGIT or cynomolgus TIGIT) ligand complexes. The system, test kit, kit or kit-of-parts may comprise a labeled component, e.g., a labeled antibody, and one or more additional immunochemical reagents.

5.5 Polynucleotides, Vectors and Methods of Producing Anti-TIGIT Antibodies

In another aspect, provided herein are polynucleotides comprising a nucleotide sequence encoding an antibody described herein or a fragment thereof (e.g., a light chain variable region and/or heavy chain variable region) that specifically binds to a TIGIT (e.g., human TIGIT or cynomolgus TIGIT) antigen, and vectors, e.g., vectors comprising such polynucleotides for recombinant expression in host cells (e.g., E. coli and mammalian cells). Provided herein are polynucleotides comprising nucleotide sequences encoding a heavy and/or light chain of any of the antibodies provided herein, as well as vectors comprising such polynucleotide sequences, e.g., expression vectors for their efficient expression in host cells, e.g., mammalian cells.

As used herein, an "isolated" polynucleotide or nucleic acid molecule is one which is separated from other nucleic acid molecules which are present in the natural source (e.g., in a mouse or a human) of the nucleic acid molecule. Moreover, an "isolated" nucleic acid molecule, such as a cDNA molecule, can be substantially free of other cellular material, or culture medium when produced by recombinant techniques, or substantially free of chemical precursors or other chemicals when chemically synthesized. For example, the language "substantially free" includes preparations of polynucleotide or nucleic acid molecule having less than about 15%, 10%, 5%, 2%, 1%, 0.5%, or 0.1% (in particular less than about 10%) of other material, e.g., cellular material, culture medium, other nucleic acid molecules, chemical precursors and/or other chemicals. In a specific embodiment, a nucleic acid molecule(s) encoding an antibody described herein is isolated or purified.

In particular aspects, provided herein are polynucleotides comprising nucleotide sequences encoding antibodies, which specifically bind to a TIGIT (e.g., human TIGIT or cynomolgus TIGIT) polypeptide and comprises an amino acid sequence as described herein, as well as antibodies which compete with such antibodies for binding to a TIGIT (e.g., human TIGIT or cynomolgus TIGIT) polypeptide (e.g., in a dose-dependent manner), or which binds to the same epitope as that of such antibodies.

In certain aspects, provided herein are polynucleotides comprising a nucleotide sequence encoding the light chain or heavy chain of an antibody described herein. The polynucleotides can comprise nucleotide sequences encoding a light chain comprising the VL FRs and CDRs of antibodies described herein (see, e.g., Table 1) or nucleotide sequences encoding a heavy chain comprising the VH FRs and CDRs of antibodies described herein (see, e.g., Table 1).

Also provided herein are polynucleotides encoding an anti-TIGIT (e.g., human TIGIT or cynomolgus TIGIT) antibody that are optimized, e.g., by codon/RNA optimization, replacement with heterologous signal sequences, and elimination of mRNA instability elements. Methods to generate optimized nucleic acids encoding an anti-TIGIT (e.g., human TIGIT or cynomolgus TIGIT) antibody or a fragment thereof (e.g., light chain, heavy chain, VH domain, or VL domain) for recombinant expression by introducing codon changes and/or eliminating inhibitory regions in the mRNA can be carried out by adapting the optimization methods described in, e.g., U.S. Pat. Nos. 5,965,726; 6,174,666; 6,291,664; 6,414,132; and 6,794,498, accordingly, all of which are herein incorporated by reference in their entireties. For example, potential splice sites and instability elements (e.g., A/T or A/U rich elements) within the RNA can be mutated without altering the amino acids encoded by the nucleic acid sequences to increase stability of the RNA for recombinant expression. The alterations utilize the degeneracy of the genetic code, e.g., using an alternative codon for an identical amino acid. In certain embodiments, it can be desirable to alter one or more codons to encode a conservative mutation, e.g., a similar amino acid with similar chemical structure and properties and/or function as the original amino acid. Such methods can increase expression of an anti-TIGIT (e.g., human TIGIT or cynomolgus TIGIT) antibody or fragment thereof by at least 1 fold, 2 fold, 3 fold, 4 fold, 5 fold, 10 fold, 20 fold, 30 fold, 40 fold, 50 fold, 60 fold, 70 fold, 80 fold, 90 fold, or 100 fold or more relative to the expression of an anti-TIGIT (e.g., human TIGIT or cynomolgus TIGIT) antibody encoded by polynucleotides that have not been optimized.

In certain embodiments, an optimized polynucleotide sequence encoding an anti-TIGIT (e.g., human TIGIT or cynomolgus TIGIT) antibody described herein or a fragment thereof (e.g., VL domain and/or VH domain) can hybridize to an antisense (e.g., complementary) polynucleotide of an unoptimized polynucleotide sequence encoding an anti-TIGIT (e.g., human TIGIT or cynomolgus TIGIT) antibody described herein or a fragment thereof (e.g., VL domain and/or VH domain). In specific embodiments, an optimized nucleotide sequence encoding an anti-TIGIT (e.g., human TIGIT or cynomolgus TIGIT) antibody described herein or a fragment hybridizes under high stringency conditions to antisense polynucleotide of an unoptimized polynucleotide sequence encoding an anti-TIGIT (e.g., human TIGIT or cynomolgus TIGIT) antibody described herein or a fragment thereof. In a specific embodiment, an optimized nucleotide sequence encoding an anti-TIGIT (e.g., human TIGIT or cynomolgus TIGIT) antibody described herein or a fragment thereof hybridizes under high stringency, intermediate or lower stringency hybridization conditions to an antisense polynucleotide of an unoptimized nucleotide sequence encoding an anti-TIGIT (e.g., human TIGIT or cynomolgus TIGIT) antibody described herein or a fragment thereof. Information regarding hybridization conditions has been described, see, e.g., U.S. Patent Application Publication No. US 2005/0048549 (e.g., paragraphs 72-73), which is herein incorporated by reference in its entirety.

The polynucleotides can be obtained, and the nucleotide sequence of the polynucleotides determined, by any method known in the art. Nucleotide sequences encoding antibodies described herein, e.g., antibodies described in Table 1, and modified versions of these antibodies can be determined using methods well known in the art, i.e., nucleotide codons known to encode particular amino acids are assembled in such a way to generate a nucleic acid that encodes the antibody. Such a polynucleotide encoding the antibody can be assembled from chemically synthesized oligonucleotides (e.g., as described in Kutmeier G et al., (1994), BioTechniques 17: 242-6, herein incorporated by reference in its entirety), which, briefly, involves the synthesis of overlapping oligonucleotides containing portions of the sequence encoding the antibody, annealing and ligating of those oligonucleotides, and then amplification of the ligated oligonucleotides by PCR.

Alternatively, a polynucleotide encoding an antibody described herein can be generated from nucleic acid from a suitable source (e.g., a hybridoma) using methods well known in the art (e.g., PCR and other molecular cloning methods). For example, PCR amplification using synthetic primers hybridizable to the 3' and 5' ends of a known sequence can be performed using genomic DNA obtained from hybridoma cells producing the antibody of interest. Such PCR amplification methods can be used to obtain nucleic acids comprising the sequence encoding the light chain and/or heavy chain of an antibody. Such PCR amplification methods can be used to obtain nucleic acids comprising the sequence encoding the variable light chain region and/or the variable heavy chain region of an antibody. The amplified nucleic acids can be cloned into vectors for expression in host cells and for further cloning, for example, to generate chimeric and humanized antibodies.

If a clone containing a nucleic acid encoding a particular antibody is not available, but the sequence of the antibody molecule is known, a nucleic acid encoding the immunoglobulin can be chemically synthesized or obtained from a suitable source (e.g., an antibody cDNA library or a cDNA library generated from, or nucleic acid, preferably poly A+ RNA, isolated from, any tissue or cells expressing the antibody, such as hybridoma cells selected to express an antibody described herein) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody. Amplified nucleic acids generated by PCR can then be cloned into replicable cloning vectors using any method well known in the art.

DNA encoding anti-TIGIT (e.g., human TIGIT or cynomolgus TIGIT) antibodies described herein can be readily isolated and sequenced using conventional procedures (e.g., by using oligonucleotide probes that are capable of binding specifically to genes encoding the heavy and light chains of the anti-TIGIT (e.g., human TIGIT or cynomolgus TIGIT) antibodies). Hybridoma cells can serve as a source of such DNA. Once isolated, the DNA can be placed into expression vectors, which are then transfected into host cells such as E. coli cells, simian COS cells, Chinese hamster ovary (CHO) cells (e.g., CHO cells from the CHO GS System™ (Lonza)), or myeloma cells that do not otherwise produce immunoglobulin protein, to obtain the synthesis of anti-TIGIT (e.g., human TIGIT or cynomolgus TIGIT) antibodies in the recombinant host cells.

To generate whole antibodies, PCR primers including VH or VL nucleotide sequences, a restriction site, and a flanking sequence to protect the restriction site can be used to amplify the VH or VL sequences in scFv clones. Utilizing cloning techniques known to those of skill in the art, the PCR amplified VH domains can be cloned into vectors expressing a heavy chain constant region, e.g., the human gamma 1 or human gamma 4 constant region, and the PCR amplified VL domains can be cloned into vectors expressing a light chain constant region, e.g., human kappa or lambda constant regions. In certain embodiments, the vectors for expressing the VH or VL domains comprise an EF-1α promoter, a secretion signal, a cloning site for the variable region, constant domains, and a selection marker such as neomycin. The VH and VL domains can also be cloned into one vector expressing the necessary constant regions. The heavy chain conversion vectors and light chain conversion vectors are then co-transfected into cell lines to generate stable or transient cell lines that express full-length antibodies, e.g., IgG, using techniques known to those of skill in the art.

The DNA also can be modified, for example, by substituting the coding sequence for human heavy and light chain constant domains in place of the murine sequences, or by covalently joining to the immunoglobulin coding sequence all or part of the coding sequence for a non-immunoglobulin polypeptide.

Also provided are polynucleotides that hybridize under high stringency, intermediate or lower stringency hybridization conditions to polynucleotides that encode an antibody described herein. In specific embodiments, polynucleotides described herein hybridize under high stringency, intermediate or lower stringency hybridization conditions to polynucleotides encoding a VH domain and/or VL domain provided herein.

Hybridization conditions have been described in the art and are known to one of skill in the art. For example, hybridization under stringent conditions can involve hybridization to filter-bound DNA in 6× sodium chloride/sodium citrate (SSC) at about 45° C. followed by one or more washes in 0.2×SSC/0.1% SDS at about 50-65° C.; hybridization under highly stringent conditions can involve hybridization to filter-bound nucleic acid in 6×SSC at about 45° C. followed by one or more washes in 0.1×SSC/0.2% SDS at about 68° C. Hybridization under other stringent hybridization conditions are known to those of skill in the art and have been described, see, for example, Ausubel F M et al., eds., (1989) Current Protocols in Molecular Biology, Vol. I, Green Publishing Associates, Inc. and John Wiley & Sons, Inc., New York at pages 6.3.1-6.3.6 and 2.10.3, which is herein incorporated by reference in its entirety.

In certain aspects, provided herein are cells (e.g., host cells) expressing (e.g., recombinantly) antibodies described herein which specifically bind to TIGIT (e.g., human TIGIT or cynomolgus TIGIT) and related polynucleotides and expression vectors. Provided herein are vectors (e.g., expression vectors) comprising polynucleotides comprising nucleotide sequences encoding anti-TIGIT (e.g., human TIGIT or cynomolgus TIGIT) antibodies or a fragment for recombinant expression in host cells, preferably in mammalian cells (e.g., CHO cells). Also provided herein are host cells comprising such vectors for recombinantly expressing anti-TIGIT (e.g., human TIGIT or cynomolgus TIGIT) antibodies described herein (e.g., human or humanized antibody). In a particular aspect, provided herein are methods for producing an antibody described herein, comprising expressing such antibody from a host cell.

Recombinant expression of an antibody described herein (e.g., a full-length antibody, heavy and/or light chain of an antibody, or a single chain antibody described herein) that specifically binds to TIGIT (e.g., human TIGIT or cynomolgus TIGIT) generally involves construction of an expression vector containing a polynucleotide that encodes the antibody. Once a polynucleotide encoding an antibody molecule, heavy and/or light chain of an antibody, or a fragment thereof (e.g., heavy and/or light chain variable regions) described herein has been obtained, the vector for the production of the antibody molecule can be produced by recombinant DNA technology using techniques well known in the art. Thus, methods for preparing a protein by expressing a polynucleotide containing an antibody or antibody fragment (e.g., light chain or heavy chain) encoding nucleotide sequence are described herein. Methods which are well known to those skilled in the art can be used to construct expression vectors containing antibody or antibody fragment (e.g., light chain or heavy chain) coding sequences and appropriate transcriptional and translational control signals. These methods include, for example, in vitro recombinant DNA techniques, synthetic techniques, and in vivo genetic recombination. Also provided are replicable vectors comprising a nucleotide sequence encoding an antibody molecule described herein, a heavy or light chain of an antibody, a heavy or light chain variable region of an antibody or a fragment thereof, or a heavy or light chain CDR, operably linked to a promoter. Such vectors can, for example, include the nucleotide sequence encoding the constant region of the antibody molecule (see, e.g., International Publication Nos. WO 86/05807 and WO 89/01036; and U.S. Pat. No. 5,122,464, which are herein incorporated by reference in their entireties) and variable regions of the antibody can be cloned into such a vector for expression of the entire heavy, the entire light chain, or both the entire heavy and light chains.

An expression vector can be transferred to a cell (e.g., host cell) by conventional techniques and the resulting cells can then be cultured by conventional techniques to produce an antibody described herein or a fragment thereof. Thus, provided herein are host cells containing a polynucleotide encoding an antibody described herein or fragments thereof, or a heavy or light chain thereof, or fragment thereof, or a single chain antibody described herein, operably linked to a promoter for expression of such sequences in the host cell. In certain embodiments, for the expression of double-chained antibodies, vectors encoding both the heavy and light chains, individually, can be co-expressed in the host cell for expression of the entire immunoglobulin molecule, as detailed below. In certain embodiments, a host cell contains a vector comprising a polynucleotide encoding both the heavy chain and light chain of an antibody described herein, or a fragment thereof. In specific embodiments, a host cell contains two different vectors, a first vector comprising a polynucleotide encoding a heavy chain or a heavy chain variable region of an antibody described herein, or a fragment thereof, and a second vector comprising a polynucleotide encoding a light chain or a light chain variable region of an antibody described herein, or a fragment thereof. In other embodiments, a first host cell comprises a first vector comprising a polynucleotide encoding a heavy chain or a heavy chain variable region of an antibody described herein, or a fragment thereof, and a second host cell comprises a second vector comprising a polynucleotide encoding a light chain or a light chain variable region of an antibody described herein. In specific embodiments, a heavy chain/heavy chain variable region expressed by a first cell associated with a light chain/light chain variable region of a second cell to form an anti-TIGIT (e.g., human TIGIT or cynomolgus TIGIT) antibody described herein. In certain embodiments, provided herein is a population of host cells comprising such first host cell and such second host cell.

In a particular embodiment, provided herein is a population of vectors comprising a first vector comprising a polynucleotide encoding a light chain/light chain variable region of an anti-TIGIT (e.g., human TIGIT or cynomolgus TIGIT) antibody described herein, and a second vector comprising a polynucleotide encoding a heavy chain/heavy chain variable region of an anti-TIGIT (e.g., human TIGIT or cynomolgus TIGIT) antibody described herein.

A variety of host-expression vector systems can be utilized to express antibody molecules described herein (see, e.g., U.S. Pat. No. 5,807,715, which is herein incorporated by reference in its entirety). Such host-expression systems represent vehicles by which the coding sequences of interest can be produced and subsequently purified, but also represent cells which can, when transformed or transfected with the appropriate nucleotide coding sequences, express an antibody molecule described herein in situ. These include but are not limited to microorganisms such as bacteria (e.g., *E. coli* and *B. subtilis*) transformed with, e.g., recombinant bacteriophage DNA, plasmid DNA or cosmid DNA expression vectors containing antibody coding sequences; yeast (e.g., *Saccharomyces Pichia*) transformed with, e.g., recombinant yeast expression vectors containing antibody coding sequences; insect cell systems infected with, e.g., recombinant virus expression vectors (e.g., baculovirus) containing antibody coding sequences; plant cell systems (e.g., green algae such as *Chlamydomonas reinhardtii*) infected with, e.g., recombinant virus expression vectors (e.g., cauliflower mosaic virus, CaMV; tobacco mosaic virus, TMV) or transformed with, e.g., recombinant plasmid expression vectors (e.g., Ti plasmid) containing antibody coding sequences; or mammalian cell systems (e.g., COS (e.g., COS1 or COS), CHO, BHK, MDCK, HEK 293, NS0, PER.C6, VERO, CRL7O3O, HsS78Bst, HeLa, and NIH 3T3, HEK-293T, HepG2, SP210, R1.1, B-W, L-M, BSC1, BSC40, YB/20 and BMT10 cells) harboring, e.g., recombinant expression constructs containing promoters derived from the genome of mammalian cells (e.g., metallothionein promoter) or from mammalian viruses (e.g., the adenovirus late promoter; the vaccinia virus 7.5K promoter). In a specific embodiment, cells for expressing antibodies described herein are Chinese hamster ovary (CHO) cells, for example CHO cells from the CHO GS System™ (Lonza). In certain embodiments, the heavy chain and/or light chain of an antibody produced by a CHO cell may have an N-terminal glutamine or glutamate residue replaced by pyroglutamate. In a particular embodiment, cells for expressing antibodies described herein are human cells, e.g., human cell lines. In a specific embodiment, a mammalian expression vector is pOptiVEC™ or pcDNA3.3. In a particular embodiment, bacterial cells such as *Escherichia coli*, or eukaryotic cells (e.g., mammalian cells), especially for the expression of whole recombinant antibody molecule, are used for the expression of a recombinant antibody molecule. For example, mammalian cells such as CHO cells, in conjunction with a vector such as the major intermediate early gene promoter element from human cytomegalovirus is an effective expression system for antibodies (Foecking M K & Hofstetter H (1986) Gene 45: 101-5; and Cockett M I et al., (1990) Biotechnology 8(7): 662-7, each of which is herein incorporated by reference in its entirety). In certain embodiments, antibodies described herein are produced by CHO cells or NS0 cells. In a specific embodiment, the expression of nucleotide sequences encoding antibodies described herein which specifically bind to TIGIT (e.g., human TIGIT or cynomolgus TIGIT) is regulated by a constitutive promoter, inducible promoter or tissue specific promoter.

In bacterial systems, a number of expression vectors can be advantageously selected depending upon the use intended for the antibody molecule being expressed. For example, when a large quantity of such an antibody is to be produced, for the generation of pharmaceutical compositions of an antibody molecule, vectors which direct the expression of high levels of fusion protein products that are readily purified can be desirable. Such vectors include, but are not limited to, the *E. coli* expression vector pUR278 (Ruether U & Mueller-Hill B (1983) EMBO J 2: 1791-1794), in which the antibody coding sequence can be ligated individually into the vector in frame with the lac Z coding region so that a fusion protein is produced; pIN vectors (Inouye S & Inouye M (1985) Nuc Acids Res 13: 3101-3109; Van Heeke G & Schuster S M (1989) J Biol Chem 24: 5503-5509); and the like, all of which are herein incorporated by reference in their entireties. For example, pGEX vectors can also be used to express foreign polypeptides as fusion proteins with glutathione 5-transferase (GST). In general, such fusion proteins are soluble and can easily be purified from lysed cells by adsorption and binding to matrix glutathione agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhedrosis virus (AcNPV), for example, can be used as a vector to express foreign genes. The virus grows in *Spodoptera frugiperda* cells. The antibody coding sequence can be cloned individually into non-essential regions (for example the polyhedrin gene) of the virus and placed under control of an AcNPV promoter (for example the polyhedrin promoter).

In mammalian host cells, a number of viral-based expression systems can be utilized. In cases where an adenovirus is used as an expression vector, the antibody coding sequence of interest can be ligated to an adenovirus transcription/translation control complex, e.g., the late promoter and tripartite leader sequence. This chimeric gene can then be inserted in the adenovirus genome by in vitro or in vivo recombination. Insertion in a non-essential region of the viral genome (e.g., region E1 or E3) will result in a recombinant virus that is viable and capable of expressing the antibody molecule in infected hosts (e.g., see Logan J & Shenk T (1984) PNAS 81(12): 3655-9, which is herein incorporated by reference in its entirety). Specific initiation signals can also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression can be enhanced by the inclusion of appropriate transcription enhancer elements, transcription terminators, etc. (see, e.g., Bitter G et al., (1987) Methods Enzymol. 153: 516-544, which is herein incorporated by reference in its entirety).

In addition, a host cell strain can be chosen which modulates the expression of the inserted sequences, or modifies and processes the gene product in the specific fashion desired. Such modifications (e.g., glycosylation) and processing (e.g., cleavage) of protein products can be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product can be used. Such mammalian host cells include but are not limited to CHO, VERO, BHK, Hela, MDCK, HEK 293, NIH 3T3, W138, BT483, Hs578T, HTB2, BT2O and T47D, NS0 (a murine myeloma cell line that does not endogenously produce any immunoglobulin chains), CRL7O3O, COS (e.g., COS1 or COS), PER.C6, VERO, HsS78Bst, HEK-293T, HepG2, SP210, R1.1, B-W, L-M, BSC1, BSC40, YB/20, BMT10 and HsS78Bst cells. In certain embodiments, anti-TIGIT (e.g., human TIGIT or cynomolgus TIGIT) antibodies described herein are produced in mammalian cells, such as CHO cells.

In a specific embodiment, the antibodies described herein have reduced fucose content or no fucose content. Such antibodies can be produced using techniques known to skilled in the art. For example, the antibodies can be expressed in cells deficient or lacking the ability of to fucosylate. In a specific example, cell lines with a knockout of both alleles of α1,6-fucosyltransferase can be used to produce antibodies with reduced fucose content. The Potelligent® system (Lonza) is an example of such a system that can be used to produce antibodies with reduced fucose content.

For long-term, high-yield production of recombinant proteins, stable expression cells can be generated. For example, cell lines which stably express an anti-TIGIT (e.g., human TIGIT or cynomolgus TIGIT) antibody described herein can be engineered. In specific embodiments, a cell provided herein stably expresses a light chain/light chain variable region and a heavy chain/heavy chain variable region which associate to form an antibody described herein.

In certain aspects, rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA/polynucleotide, engineered cells can be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method can advantageously be used to engineer cell lines which express an anti-TIGIT (e.g., human TIGIT or cynomolgus TIGIT) antibody described herein or a fragment thereof. Such engineered cell lines can be particularly useful in screening and evaluation of compositions that interact directly or indirectly with the antibody molecule.

A number of selection systems can be used, including but not limited to the herpes simplex virus thymidine kinase (Wigler M et al., (1977) Cell 11(1): 223-32), hypoxanthine-guanine phosphoribosyltransferase (Szybalska E H & Szybalski W (1962) PNAS 48(12): 2026-2034) and adenine phosphoribosyltransferase (Lowy I et al., (1980) Cell 22(3): 817-23) genes in tk-, hgprt- or aprt-cells, respectively, all of which are herein incorporated by reference in their entireties. Also, antimetabolite resistance can be used as the basis of selection for the following genes: dhfr, which confers resistance to methotrexate (Wigler M et al., (1980) PNAS 77(6): 3567-70; O'Hare K et al., (1981) PNAS 78: 1527-31); gpt, which confers resistance to mycophenolic acid (Mulligan R C & Berg P (1981) PNAS 78(4): 2072-6); neo, which confers resistance to the aminoglycoside G-418 (Wu G Y & Wu C H (1991) Biotherapy 3: 87-95; Tolstoshev P (1993) Ann Rev Pharmacol Toxicol 32: 573-596; Mulligan R C (1993) Science 260: 926-932; and Morgan R A & Anderson W F (1993) Ann Rev Biochem 62: 191-217; Nabel G J & Felgner P L (1993) Trends Biotechnol 11(5): 211-5); and hygro, which confers resistance to hygromycin (Santerre R F et al., (1984) Gene 30(1-3): 147-56), all of which are herein incorporated by reference in their entireties. Methods commonly known in the art of recombinant DNA technology can be routinely applied to select the desired recombinant clone and such methods are described, for example, in Ausubel F M et al., (eds.), Current Protocols in Molecular Biology, John Wiley & Sons, N Y (1993); Kriegler M, Gene Transfer and Expression, A Laboratory Manual, Stockton Press, N Y (1990); and in Chapters 12 and 13, Dracopoli N C et al., (eds.), Current Protocols in Human Genetics, John Wiley & Sons, N Y (1994); Colbère-Garapin F et al., (1981) J Mol Biol 150: 1-14, all of which are herein incorporated by reference in their entireties.

The expression levels of an antibody molecule can be increased by vector amplification (for a review, see Bebbington C R & Hentschel C C G, The use of vectors based on gene amplification for the expression of cloned genes in mammalian cells in DNA cloning, Vol. 3 (Academic Press, New York, 1987), which is herein incorporated by reference in its entirety). When a marker in the vector system expressing antibody is amplifiable, increase in the level of inhibitor present in culture of host cell will increase the number of copies of the marker gene. Since the amplified region is associated with the antibody gene, production of the antibody will also increase (Crouse G F et al., (1983) Mol Cell Biol 3: 257-66, which is herein incorporated by reference in its entirety).

The host cell can be co-transfected with two or more expression vectors described herein, the first vector encoding a heavy chain derived polypeptide and the second vector encoding a light chain derived polypeptide. The two vectors can contain identical selectable markers which enable equal expression of heavy and light chain polypeptides. The host cells can be co-transfected with different amounts of the two or more expression vectors. For example, host cells can be transfected with any one of the following ratios of a first expression vector and a second expression vector: about 1:1, 1:2, 1:3, 1:4, 1:5, 1:6, 1:7, 1:8, 1:9, 1:10, 1:12, 1:15, 1:20, 1:25, 1:30, 1:35, 1:40, 1:45, or 1:50.

Alternatively, a single vector can be used which encodes, and is capable of expressing, both heavy and light chain polypeptides. In such situations, the light chain should be placed before the heavy chain to avoid an excess of toxic free heavy chain (Proudfoot N J (1986) Nature 322: 562-565; and Köhler G (1980) PNAS 77: 2197-2199, each of which is herein incorporated by reference in its entirety). The coding sequences for the heavy and light chains can comprise cDNA or genomic DNA. The expression vector can be monocistronic or multicistronic. A multicistronic nucleic acid construct can encode 2, 3, 4, 5, 6, 7, 8, 9, 10 or more genes/nucleotide sequences, or in the range of 2-5, 5-10, or 10-20 genes/nucleotide sequences. For example, a bicistronic nucleic acid construct can comprise, in the following order, a promoter, a first gene (e.g., heavy chain of an antibody described herein), and a second gene and (e.g., light chain of an antibody described herein). In such an expression vector, the transcription of both genes can be driven by the promoter, whereas the translation of the mRNA from the first gene can be by a cap-dependent scanning mechanism and the translation of the mRNA from the second gene can be by a cap-independent mechanism, e.g., by an IRES.

Once an antibody molecule described herein has been produced by recombinant expression, it can be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. Further, the antibodies described herein can be fused to heterologous polypeptide sequences described herein or otherwise known in the art to facilitate purification.

In specific embodiments, an antibody described herein is isolated or purified. Generally, an isolated antibody is one that is substantially free of other antibodies with different antigenic specificities than the isolated antibody. For example, in a particular embodiment, a preparation of an antibody described herein is substantially free of cellular material and/or chemical precursors. The language "substantially free of cellular material" includes preparations of an antibody in which the antibody is separated from cellular components of the cells from which it is isolated or recombinantly produced. Thus, an antibody that is substantially free of cellular material includes preparations of antibody having less than about 30%, 20%, 10%, 5%, 2%, 1%, 0.5%, or 0.1% (by dry weight) of heterologous protein (also referred to herein as a "contaminating protein") and/or variants of an antibody, for example, different post-translational modified forms of an antibody or other different versions of an antibody (e.g., antibody fragments). When the antibody is recombinantly produced, it is also generally substantially free of culture medium, i.e., culture medium represents less than about 20%, 10%, 2%, 1%, 0.5%, or 0.1% of the volume of the protein preparation. When the antibody is produced by chemical synthesis, it is generally substantially free of chemical precursors or other chemicals, i.e., it is separated from chemical precursors or other chemicals which are involved in the synthesis of the protein. Accordingly, such preparations of the antibody have less than about 30%, 20%, 10%, or 5% (by dry weight) of chemical precursors or compounds other than the antibody of interest. In a specific embodiment, antibodies described herein are isolated or purified.

Antibodies or fragments thereof that specifically bind to TIGIT (e.g., human TIGIT or cynomolgus TIGIT) can be produced by any method known in the art for the synthesis of antibodies, for example, by chemical synthesis or by recombinant expression techniques. The methods described herein employ, unless otherwise indicated, conventional techniques in molecular biology, microbiology, genetic analysis, recombinant DNA, organic chemistry, biochemistry, PCR, oligonucleotide synthesis and modification, nucleic acid hybridization, and related fields within the skill of the art. These techniques are described, for example, in the references cited herein and are fully explained in the literature. See, e.g., Maniatis T et al., (1982) Molecular Cloning: A Laboratory Manual, Cold Spring Harbor Laboratory Press; Sambrook J et al., (1989), Molecular Cloning: A Laboratory Manual, Second Edition, Cold Spring Harbor Laboratory Press; Sambrook J et al., (2001) Molecular Cloning: A Laboratory Manual, Cold Spring Harbor Laboratory Press, Cold Spring Harbor, N.Y.; Ausubel F M et al., Current Protocols in Molecular Biology, John Wiley & Sons (1987 and annual updates); Current Protocols in Immunology, John Wiley & Sons (1987 and annual updates) Gait (ed.) (1984) Oligonucleotide Synthesis: A Practical Approach, IRL Press; Eckstein (ed.) (1991) Oligonucleotides and Analogues: A Practical Approach, IRL Press; Birren B et al., (eds.) (1999) Genome Analysis: A Laboratory Manual, Cold Spring Harbor Laboratory Press, all of which are herein incorporated by reference in their entireties.

In a specific embodiment, an antibody described herein is an antibody (e.g., recombinant antibody) prepared, expressed, created or isolated by any means that involves creation, e.g., via synthesis, genetic engineering of DNA sequences. In certain embodiments, such an antibody comprises sequences (e.g., DNA sequences or amino acid sequences) that do not naturally exist within the antibody germline repertoire of an animal or mammal (e.g., human) in vivo.

In one aspect, provided herein is a method of making an antibody which specifically binds to TIGIT (e.g., human TIGIT or cynomolgus TIGIT) comprising culturing a cell or host cell described herein. In one embodiment, the method is performed in vitro. In a certain aspect, provided herein is a method of making an antibody which specifically binds to TIGIT (e.g., human TIGIT or cynomolgus TIGIT) comprising expressing (e.g., recombinantly expressing) the antibody using a cell or host cell described herein (e.g., a cell or a host cell comprising polynucleotides encoding an antibody described herein). In a particular embodiment, the cell is an isolated cell. In a particular embodiment, the exogenous polynucleotides have been introduced into the cell. In a particular embodiment, the method further comprises the step of purifying the antibody obtained from the cell or host cell.

Methods for producing polyclonal antibodies are known in the art (see, for example, Chapter 11 in: Short Protocols in Molecular Biology, (2002) 5th Ed., Ausubel F M et al., eds., John Wiley and Sons, New York, which is herein incorporated by reference in its entirety).

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow E & Lane D, Antibodies: A Laboratory Manual, (Cold Spring Harbor Laboratory Press, 2nd ed. 1988); Hammerling G J et al., in: Monoclonal Antibodies and T-Cell Hybridomas 563 681 (Elsevier, N.Y., 1981), each of which is herein incorporated by reference in its entirety. The term "monoclonal antibody" as used herein is not limited to antibodies produced through hybridoma technology. For example, monoclonal antibodies can be produced recombinantly from host cells exogenously expressing an antibody described herein or a fragment thereof, for example, light chain and/or heavy chain of such antibody.

In specific embodiments, a "monoclonal antibody," as used herein, is an antibody produced by a single cell (e.g., hybridoma or host cell producing a recombinant antibody), wherein the antibody specifically binds to TIGIT (e.g., human TIGIT or cynomolgus TIGIT) as determined, e.g., by ELISA or other antigen-binding or competitive binding assay known in the art or in the examples provided herein. In particular embodiments, a monoclonal antibody can be a chimeric antibody or a humanized antibody. In certain embodiments, a monoclonal antibody is a monovalent antibody or multivalent (e.g., bivalent) antibody. In particular embodiments, a monoclonal antibody is a monospecific or multispecific antibody (e.g., bispecific antibody). Monoclonal antibodies described herein can, for example, be made by the hybridoma method as described in Kohler G & Milstein C (1975) Nature 256: 495, which is herein incorporated by reference in its entirety, or can, e.g., be isolated from phage libraries using the techniques as described herein, for example. Other methods for the preparation of clonal cell lines and of monoclonal antibodies expressed thereby are well known in the art (see, for example, Chapter 11 in: Short Protocols in Molecular Biology, (2002) 5th Ed., Ausubel F M et al., supra).

As used herein, an antibody binds to an antigen multivalently (e.g., bivalently) when the antibody comprises at least two (e.g., two or more) monovalent binding domains, each monovalent binding domain capable of binding to an epitope on the antigen. Each monovalent binding domain can bind to the same or different epitopes on the antigen.

Methods for producing and screening for specific antibodies using hybridoma technology are routine and well known in the art. For example, in the hybridoma method, a mouse or other appropriate host animal, such as a sheep, goat, rabbit, rat, hamster or macaque monkey, is immunized to elicit lymphocytes that produce or are capable of producing antibodies that will specifically bind to the protein (e.g., TIGIT (e.g., human TIGIT or cynomolgus TIGIT)) used for immunization. Alternatively, lymphocytes may be immunized in vitro. Lymphocytes then are fused with myeloma cells using a suitable fusing agent, such as polyethylene glycol, to form a hybridoma cell (Goding J W (Ed), Monoclonal Antibodies: Principles and Practice, pp. 59-103 (Academic Press, 1986), herein incorporated by reference in its entirety). Additionally, a RIMMS (repetitive immunization multiple sites) technique can be used to immunize an animal (Kilpatrick K E et al., (1997) Hybridoma 16:381-9, herein incorporated by reference in its entirety).

In certain embodiments, mice (or other animals, such as rats, monkeys, donkeys, pigs, sheep, hamster, or dogs) can be immunized with an antigen (e.g., TIGIT (e.g., human TIGIT or cynomolgus TIGIT)) and once an immune response is detected, e.g., antibodies specific for the antigen are detected in the mouse serum, the mouse spleen is harvested and splenocytes isolated. The splenocytes are then fused by well-known techniques to any suitable myeloma cells, for example, cells from cell line SP20 available from the American Type Culture Collection (ATCC®) (Manassas, Va.), to form hybridomas. Hybridomas are selected and cloned by limited dilution. In certain embodiments, lymph nodes of the immunized mice are harvested and fused with NS0 myeloma cells.

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Specific embodiments employ myeloma cells that fuse efficiently, support stable high-level production of antibody by the selected antibody-producing cells, and are sensitive to a medium such as HAT medium. Among these myeloma cell lines are murine myeloma lines, such as the NS0 cell line or those derived from MOPC-21 and MPC-11 mouse tumors available from the Salk Institute Cell Distribution Center, San Diego, Calif., USA, and SP-2 or X63-Ag8.653 cells available from the American Type Culture Collection, Rockville, Md., USA. Human myeloma and mouse-human heteromyeloma cell lines also have been described for the production of human monoclonal antibodies (Kozbor D (1984) J Immunol 133: 3001-5; Brodeur et al., Monoclonal Antibody Production Techniques and Applications, pp. 51-63 (Marcel Dekker, Inc., New York, 1987), each of which is herein incorporated by reference in its entirety).

Culture medium in which hybridoma cells are growing is assayed for production of monoclonal antibodies directed against TIGIT (e.g., human TIGIT or cynomolgus TIGIT). The binding specificity of monoclonal antibodies produced by hybridoma cells is determined by methods known in the art, for example, immunoprecipitation or by an in vitro binding assay, such as radioimmunoassay (RIA) or enzyme-linked immunoabsorbent assay (ELISA).

After hybridoma cells are identified that produce antibodies of the desired specificity, affinity, and/or activity, the clones may be subcloned by limiting dilution procedures and grown by standard methods (Goding J W (Ed), Monoclonal Antibodies: Principles and Practice, supra). Suitable culture media for this purpose include, for example, D-MEM or RPMI 1640 medium. In addition, the hybridoma cells may be grown in vivo as ascites tumors in an animal.

The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

Antibodies described herein include, e.g., antibody fragments which recognize a specific TIGIT (e.g., human TIGIT or cynomolgus TIGIT), and which can be generated by any technique known to those of skill in the art. For example, Fab and F(ab')$_2$ fragments described herein can be produced by proteolytic cleavage of immunoglobulin molecules, using enzymes such as papain (to produce Fab fragments) or pepsin (to produce F(ab')$_2$ fragments). A Fab fragment corresponds to one of the two identical arms of an antibody molecule and contains the complete light chain paired with the VH and CH1 domains of the heavy chain. A F(ab')$_2$ fragment contains the two antigen-binding arms of an antibody molecule linked by disulfide bonds in the hinge region.

Further, the antibodies described herein can also be generated using various phage display methods known in the art. In phage display methods, functional antibody domains are displayed on the surface of phage particles which carry the polynucleotide sequences encoding them. In particular, DNA sequences encoding VH and VL domains are amplified from animal cDNA libraries (e.g., human or murine cDNA libraries of affected tissues). The DNA encoding the VH and VL domains are recombined together with a scFv linker by PCR and cloned into a phagemid vector. The vector is electroporated in E. coli and the E. coli is infected with helper phage. Phage used in these methods are typically filamentous phage including fd and M13, and the VH and VL domains are usually recombinantly fused to either the phage gene III or gene VIII. Phage expressing an antigen binding domain that binds to a particular antigen can be selected or identified with antigen, e.g., using labeled antigen or antigen bound or captured to a solid surface or bead. Examples of phage display methods that can be used to make the antibodies described herein include those disclosed in Brinkman U et al., (1995) J Immunol Methods 182: 41-50; Ames R S et al., (1995) J Immunol Methods 184: 177-186; Kettleborough C A et al., (1994) Eur J Immunol 24: 952-958; Persic L et al., (1997) Gene 187: 9-18; Burton D R & Barbas C F (1994) Advan Immunol 57: 191-280; PCT Application No. PCT/GB91/001134; International Publication Nos. WO 90/02809, WO 91/10737, WO 92/01047, WO 92/18619, WO 93/1 1236, WO 95/15982, WO 95/20401, and WO 97/13844; and U.S. Pat. Nos. 5,698,426, 5,223,409, 5,403,484, 5,580,717, 5,427,908, 5,750,753, 5,821,047, 5,571,698, 5,427,908, 5,516,637, 5,780,225, 5,658,727, 5,733,743 and 5,969,108, all of which are herein incorporated by reference in their entireties.

As described in the above references, after phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria, e.g., as described below. Techniques to recombinantly produce antibody fragments such as Fab, Fab' and F(ab')$_2$ fragments can also be employed using methods known in the art such as those disclosed in PCT publication No. WO 92/22324; Mullinax R L et al., (1992) BioTechniques 12(6): 864-9; Sawai H et al., (1995) Am J Reprod Immunol 34: 26-34; and Better M et al., (1988) Science 240: 1041-1043, all of which are herein incorporated by reference in their entireties.

In certain embodiments, to generate whole antibodies, PCR primers including VH or VL nucleotide sequences, a restriction site, and a flanking sequence to protect the restriction site can be used to amplify the VH or VL sequences from a template, e.g., scFv clones. Utilizing cloning techniques known to those of skill in the art, the PCR amplified VH domains can be cloned into vectors expressing a VH constant region, and the PCR amplified VL domains can be cloned into vectors expressing a VL constant region, e.g., human kappa or lambda constant regions. The VH and VL domains can also be cloned into one vector expressing the necessary constant regions. The heavy chain conversion vectors and light chain conversion vectors are then co-transfected into cell lines to generate stable or transient cell lines that express full-length antibodies, e.g., IgG, using techniques known to those of skill in the art.

A chimeric antibody is a molecule in which different portions of the antibody are derived from different immunoglobulin molecules. For example, a chimeric antibody can contain a variable region of a mouse or rat monoclonal antibody fused to a constant region of a human antibody. Methods for producing chimeric antibodies are known in the art. See, e.g., Morrison S L (1985) Science 229: 1202-7; Oi V T & Morrison S L (1986) BioTechniques 4: 214-221; Gillies S D et al., (1989) J Immunol Methods 125: 191-202; and U.S. Pat. Nos. 5,807,715, 4,816,567, 4,816,397, and 6,331,415, all of which are herein incorporated by reference in their entireties.

A humanized antibody is capable of binding to a predetermined antigen and which comprises a framework region having substantially the amino acid sequence of a human immunoglobulin and CDRs having substantially the amino acid sequence of a non-human immunoglobulin (e.g., a murine immunoglobulin). In particular embodiments, a humanized antibody also comprises at least a portion of an immunoglobulin constant region (Fc), typically that of a human immunoglobulin. The antibody also can include the CH1, hinge, CH2, CH3, and CH4 regions of the heavy chain. A humanized antibody can be selected from any class of immunoglobulins, including IgM, IgG, IgD, IgA and IgE, and any isotype, including $IgG_1$, $IgG_2$, $IgG_3$ and $IgG_4$. Humanized antibodies can be produced using a variety of techniques known in the art, including but not limited to, CDR-grafting (European Patent No. EP 239400; International Publication No. WO 91/09967; and U.S. Pat. Nos. 5,225,539, 5,530,101, and 5,585,089), veneering or resurfacing (European Patent Nos. EP 592106 and EP 519596; Padlan E A (1991) Mol Immunol 28(4/5): 489-498; Studnicka G M et al., (1994) Prot Engineering 7(6): 805-814; and Roguska M A et al., (1994) PNAS 91: 969-973), chain shuffling (U.S. Pat. No. 5,565,332), and techniques disclosed in, e.g., U.S. Pat. Nos. 6,407,213, 5,766,886, International Publication No. WO 93/17105; Tan P et al., (2002) J Immunol 169: 1119-25; Caldas C et al., (2000) Protein Eng. 13(5): 353-60; Morea V et al., (2000) Methods 20(3): 267-79; Baca M et al., (1997) J Biol Chem 272(16): 10678-84; Roguska M A et al., (1996) Protein Eng 9(10): 895 904; Couto J R et al., (1995) Cancer Res. 55 (23 Supp): 5973s-5977s; Couto J R et al., (1995) Cancer Res 55(8): 1717-22; Sandhu J S (1994) Gene 150(2): 409-10 and Pedersen J T et al., (1994) J Mol Biol 235(3): 959-73, all of which are herein incorporated by reference in their entireties. See also U.S. Application Publication No. US 2005/0042664 A1 (Feb. 24, 2005), which is herein incorporated by reference in its entirety.

Methods for making multispecific (e.g., bispecific antibodies) have been described, see, for example, U.S. Pat. Nos. 7,951,917; 7,183,076; 8,227,577; 5,837,242; 5,989,830; 5,869,620; 6,132,992 and 8,586,713, all of which are herein incorporated by reference in their entireties.

Single domain antibodies, for example, antibodies lacking the light chains, can be produced by methods well known in the art. See Riechmann L & Muyldermans S (1999) J Immunol 231: 25-38; Nuttall S D et al., (2000) Curr Pharm Biotechnol 1(3): 253-263; Muyldermans S, (2001) J Biotechnol 74(4): 277-302; U.S. Pat. No. 6,005,079; and International Publication Nos. WO 94/04678, WO 94/25591 and WO 01/44301, all of which are herein incorporated by reference in their entireties.

Further, antibodies that specifically bind to a TIGIT (e.g., human TIGIT or cynomolgus TIGIT) antigen can, in turn, be utilized to generate anti-idiotype antibodies that "mimic" an antigen using techniques well known to those skilled in the art. See, e.g., Greenspan N S & Bona C A (1989) FASEB J 7(5): 437-444; and Nissinoff A (1991) J Immunol 147(8): 2429-2438, each of which is herein incorporated by reference in its entirety.

In particular embodiments, an antibody described herein, which binds to the same epitope of TIGIT (e.g., human TIGIT or cynomolgus TIGIT) as an anti-TIGIT (e.g., human TIGIT or cynomolgus TIGIT) antibody described herein, is a human antibody. In particular embodiments, an antibody described herein, which competitively blocks (e.g., in a dose-dependent manner) any one of the antibodies described herein, from binding to TIGIT (e.g., human TIGIT or cynomolgus TIGIT), is a human antibody. Human antibodies can be produced using any method known in the art. For example, transgenic mice which are incapable of expressing functional endogenous immunoglobulins, but which can express human immunoglobulin genes, can be used. In particular, the human heavy and light chain immunoglobulin gene complexes can be introduced randomly or by homologous recombination into mouse embryonic stem cells. Alternatively, the human variable region, constant region, and diversity region can be introduced into mouse embryonic stem cells in addition to the human heavy and light chain genes. The mouse heavy and light chain immunoglobulin genes can be rendered non-functional separately or simultaneously with the introduction of human immunoglobulin loci by homologous recombination. In particular, homozygous deletion of the $J_H$ region prevents endogenous antibody production. The modified embryonic stem cells are expanded and microinjected into blastocysts to produce chimeric mice. The chimeric mice are then bred to produce homozygous offspring which express human antibodies. The transgenic mice are immunized in the normal fashion with a selected antigen, e.g., all or a portion of an antigen (e.g., TIGIT (e.g., human TIGIT or cynomolgus TIGIT)). Monoclonal antibodies directed against the antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg N & Huszar D (1995) Int Rev Immunol 13:65-93, herein incorporated by reference in its entirety. For a detailed discussion of this technology for producing human antibodies and human monoclonal antibodies and protocols for producing such antibodies, see, e.g., International Publication Nos. WO 98/24893, WO 96/34096 and WO 96/33735; and U.S. Pat. Nos. 5,413,923, 5,625,126, 5,633,425, 5,569, 825, 5,661,016, 5,545,806, 5,814,318 and 5,939,598, all of which are herein incorporated by reference in their entireties. Examples of mice capable of producing human antibodies include the Xenomouse™ (Abgenix, Inc.; U.S. Pat. Nos. 6,075,181 and 6,150,184), the HuAb-Mouse™ (Mederex, Inc./Gen Pharm; U.S. Pat. Nos. 5,545,806 and 5,569,825), the Trans Chromo Mouse™ (Kirin) and the KM Mouse™ (Medarex/Kirin), all of which are herein incorporated by reference in their entireties.

Human antibodies that specifically bind to TIGIT (e.g., human TIGIT or cynomolgus TIGIT) can be made by a variety of methods known in the art including the phage display methods described above using antibody libraries derived from human immunoglobulin sequences. See also U.S. Pat. Nos. 4,444,887, 4,716,111, and 5,885,793; and International Publication Nos. WO 98/46645, WO 98/50433, WO 98/24893, WO 98/16654, WO 96/34096, WO 96/33735, and WO 91/10741, all of which are herein incorporated by reference in their entireties.

In certain embodiments, human antibodies can be produced using mouse-human hybridomas. For example, human peripheral blood lymphocytes transformed with Epstein-Barr virus (EBV) can be fused with mouse myeloma cells to produce mouse-human hybridomas secreting human monoclonal antibodies, and these mouse-human hybridomas can be screened to determine ones which secrete human monoclonal antibodies that specifically bind to a target antigen (e.g., TIGIT (e.g., human TIGIT or cynomolgus TIGIT)). Such methods are known and are described in the art, see, e.g., Shinmoto H et al., (2004) Cytotechnology 46: 19-23; Naganawa Y et al., (2005) Human Antibodies 14: 27-31, each of which is herein incorporated by reference in its entirety.

5.6 Kits

Also provided are kits comprising one or more antibodies described herein, or pharmaceutical compositions or conjugates thereof. In a specific embodiment, provided herein is a pharmaceutical pack or kit comprising one or more containers filled with one or more of the ingredients of the pharmaceutical compositions described herein, such as one or more antibodies provided herein. In certain embodiments, the kits contain a pharmaceutical composition described herein and any prophylactic or therapeutic agent, such as those described herein. In certain embodiments, the kits may contain a T cell mitogen, such as, e.g., phytohaemagglutinin (PHA) and/or phorbol myristate acetate (PMA), or a TCR complex stimulating antibody, such as an anti-CD3 antibody and anti-CD28 antibody. Optionally associated with such container(s) can be a notice in the form prescribed by a governmental agency regulating the manufacture, use or sale of pharmaceuticals or biological products, which notice reflects approval by the agency of manufacture, use or sale for human administration.

Also provided, are kits that can be used in the above methods. In one embodiment, a kit comprises an antibody described herein, preferably a purified antibody, in one or more containers. In a specific embodiment, kits described herein contain a substantially isolated TIGIT (e.g., human TIGIT or cynomolgus TIGIT) antigen as a control. In another specific embodiment, the kits described herein further comprise a control antibody which does not react with a TIGIT (e.g., human TIGIT or cynomolgus TIGIT) antigen. In another specific embodiment, kits described herein contain one or more elements for detecting the binding of an antibody to a TIGIT (e.g., human TIGIT or cynomolgus TIGIT) antigen (e.g., the antibody can be conjugated to a detectable substrate such as a fluorescent compound, an enzymatic substrate, a radioactive compound or a luminescent compound, or a second antibody which recognizes the first antibody can be conjugated to a detectable substrate). In specific embodiments, a kit provided herein can include a recombinantly produced or chemically synthesized TIGIT (e.g., human TIGIT or cynomolgus TIGIT) antigen. The TIGIT (e.g., human TIGIT or cynomolgus TIGIT) antigen provided in the kit can also be attached to a solid support. In a more specific embodiment, the detecting means of the above described kit includes a solid support to which a TIGIT (e.g., human TIGIT or cynomolgus TIGIT) antigen is attached. Such a kit can also include a non-attached reporter-labeled anti-human antibody or anti-mouse/rat antibody. In this embodiment, binding of the antibody to the TIGIT (e.g., human TIGIT or cynomolgus TIGIT) antigen can be detected by binding of the said reporter-labeled antibody. In one embodiment, the present invention relates to the use of a kit of the present invention for in vitro assaying and/or detecting TIGIT antigen (e.g., human TIGIT or cynomolgus TIGIT) in a biological sample.

6. EXAMPLES

The examples in this Section (i.e., Section 6) are offered by way of illustration and not by way of limitation.

6.1 Example 1: Characterization of Anti-TIGIT Antibody BA002

This example describes the characterization of BA002, an antibody that specifically binds to human TIGIT. The amino acid sequences of the heavy and light chains of BA002 are provided in Table 1.

6.1.1 Anti-Human TIGIT Antibody BA002 Binds to Purified Human and Cynomolgus TIGIT Proteins The ability of the BA002 antibody to bind to purified TIGIT protein was assessed by surface plasmon resonance (SPR).

Briefly, surface plasmon resonance experiments were performed using a Biacore T200 instrument, and the association rate ($K_a$), dissociation rate ($K_d$), and dissociation constant ($K_D$) were calculated from each experiment using a 1:1 binding model with Biacore T200 Evaluation Software.

Figure 1A:
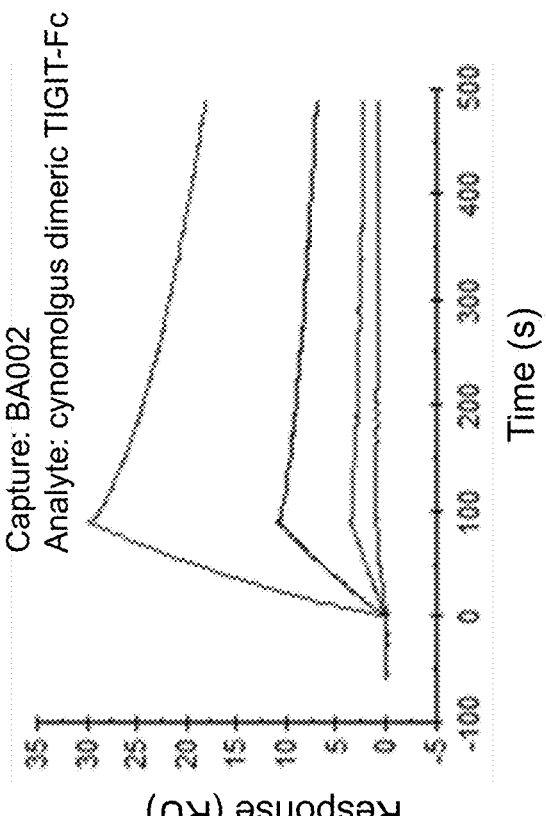
Figure 1B:
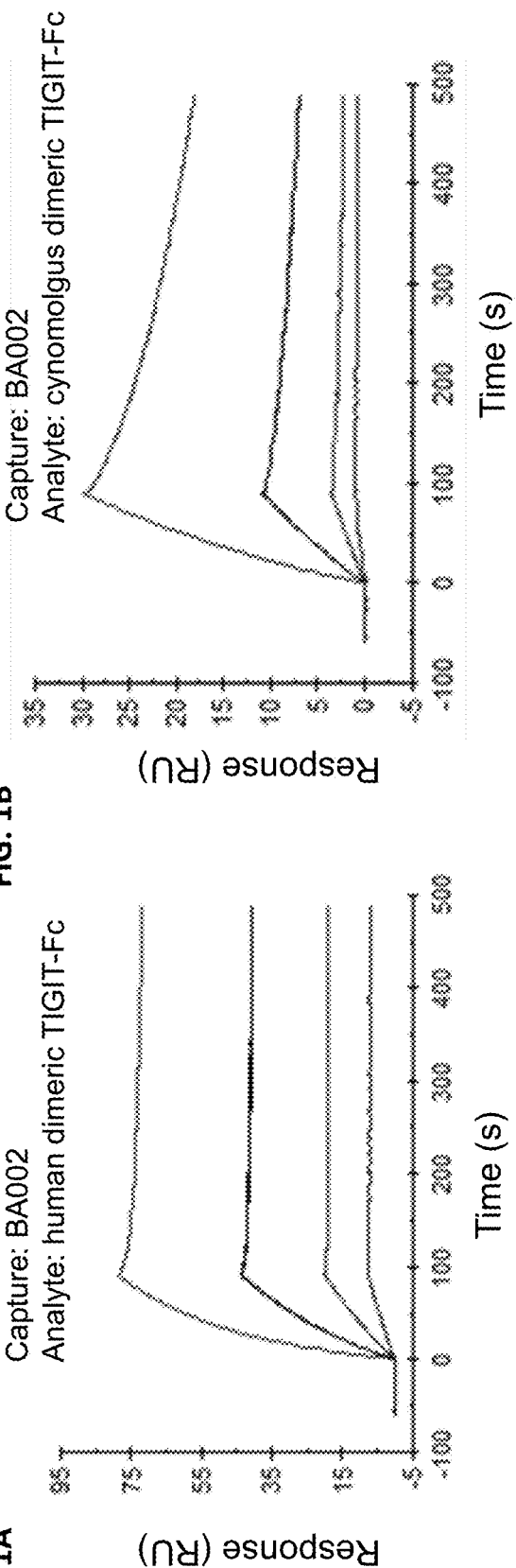

To measure the binding affinity of human and cynomolgus TIGIT to captured BA002, BA002 was captured at a flow rate of 10 μL/min on flow-cell 2, keeping flow-cell 1 as reference, on a CM5 chip on which an anti-human Fab antibody had been immobilized by amine coupling. Human and cynomolgus TIGIT fused to Fc ("TIGIT-Fc"), a dimeric form of TIGIT, were independently run over all the flow-cells at the concentrations of 20, 6.66, 2.22 and 0.74 nM at 50 μl/min for 90 seconds, followed by a dissociation phase of 400 seconds. Traces of response units vs. time after protein injection for each concentration tested are shown in FIGS. 1A (human TIGIT-Fc) and 1B (cynomolgus TIGIT-Fc), respectively. Based on these data, captured BA002 bound to human TIGIT-Fc with a calculated $K_a$ of $1.29 \times 10^6$ $M^{-1}s^{-1}$, a calculated $K_d$ of $1.60 \times 10^{-4}$ $s^{-1}$, and a calculated $K_D$ of 0.12 nM. Captured BA002 bound to cynomolgus TIGIT-Fc with a calculated $K_a$ of $4.28 \times 10^6$ $M^{-1}s^{-1}$, a calculated $K_d$ of $3.02 \times 10^{-3}$ $s^{-1}$, and a calculated $K_D$ of 0.70 nM.

Figure 1C:
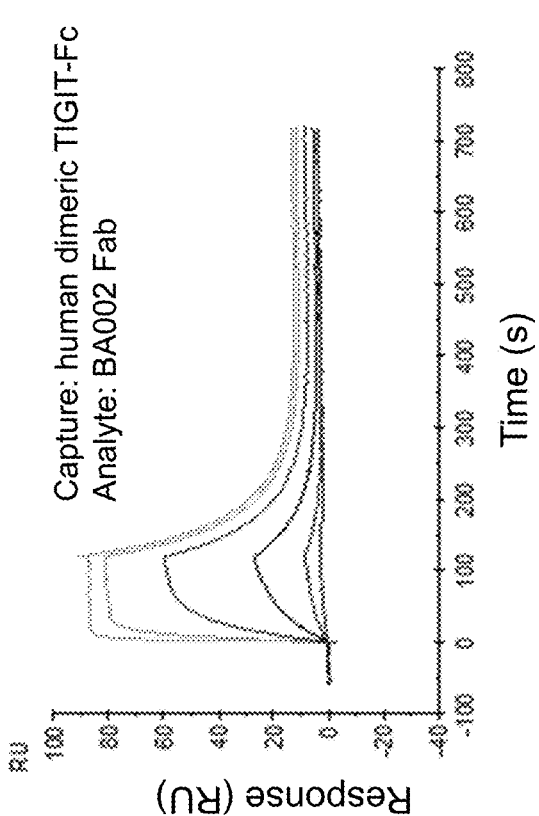

In a similar experiment assessing binding of a monomeric form of human TIGIT fused to a polyhistidine tag ("TIGIT-His") to BA002, BA002 was captured on flow-cell 2 of a Protein A chip, keeping flow-cell 1 as reference, at a flow rate of 10 μL/min. TIGIT-His was run over both flow-cells at the concentrations of 125, 25, 5, and 1 nM at 30 μL/min for 240 seconds, followed by a dissociation phase of 900 seconds. Traces of response units vs. time for each concentration tested are shown in FIG. 1C. Based on these data, captured BA002 bound to human TIGIT-His with a calculated $K_a$ of $4.1 \times 10^6$ $M^{-1}s^{-1}$, a calculated $K_d$ of $3.6 \times 10^{-2}$ $s^{-1}$, and a calculated $K_D$ of 8.6 nM. The higher calculated dissociation rate between monomeric human TIGIT (TIGIT-His) and BA002, relative to the calculated dissociation rate between dimeric human TIGIT (TIGIT-Fc) and BA002 described above, is consistent with the presence of an avidity effect with the dimeric form of TIGIT.

Figure 1D:
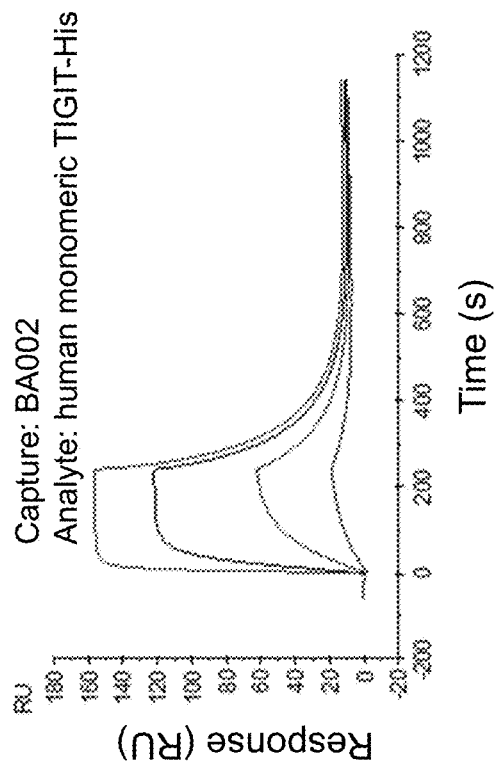

In a similar experiment measuring binding of a monovalent form of BA002 to human TIGIT-Fc, human TIGIT-Fc was captured on flow-cell 2 of a CM5 chip, keeping flow-cell 1 as reference, at a flow rate of 5 μL/min. BA002 in Fab format was run over both flow cells at the concentrations of 200, 50, 12.5, 3.125, 0.78 and 0.195 nM at 20 μL/min for 120 seconds, followed by a dissociation phase of 600 seconds. Traces of response units vs. time for each concentration tested are shown in FIG. 1D. Based on these data, immobilized human TIGIT-Fc bound to BA002 Fab with a calculated $K_a$ of $2.8 \times 10^6$ $M^{-1}s^{-1}$, a calculated $K_d$ of $1.9 \times 10^{-2}$ $s^{-1}$, and a calculated $K_D$ of 6.8 nM. The higher calculated dissociation rate between human TIGIT-Fc and BA002 Fab, relative to the calculated dissociation rate between human TIGIT-Fc and full-length BA002 described above, is consistent with the presence of an avidity effect with the bivalent form of BA002.

6.1.2 Anti-Human TIGIT Antibody BA002 Binds to Cells Expressing Human and Cynomolgus Monkey TIGIT The capacity of the human anti-TIGIT IgG1 antibody BA002 to bind to cells expressing human TIGIT or cynomolgus monkey TIGIT was tested in a variety of cell types.

Human TIGIT-Expressing Jurkat Cells

The ability of BA002 to bind to human TIGIT expressed on the surface of Jurkat cells was assessed. Briefly, Jurkat cells were transfected with a vector encoding human TIGIT, and a clone stably expressing a high level of TIGIT was selected. This stable cell line was cultured in RPMI 1640 medium supplemented with 10% heat-inactivated FBS and 2% Normocin (Invivogen, Cat #ANT-NR-1). For the antibody binding assay, the cells were seeded in a 96-well U-bottom tissue culture plate at a density of $1 \times 10^5$ cells per well and were incubated with Human TruStain FcX™ (Fc Receptor Blocking Solution, Biolegend, Cat #422302) diluted 1:50 in PBS supplemented with 2% heat-inactivated FBS (FACS Buffer) for 10 minutes at 4° C. The cells were then incubated for 30 minutes at 4° C. with a series dilution of BA002 or isotype control antibody at concentrations from 50 μg/mL to 0.64 ng/mL diluted in FACS Buffer. For antibody staining, the cells were washed twice with cold FACS Buffer and re-suspended in FACS Buffer containing R-Phycoerythrin AffiniPure F(ab')$_2$ Fragment Donkey Anti-Human IgG (H+L) (Jackson, Cat #09-116-149) at 1:200 dilution and LIVE/DEAD® Fixable Near-IR Dead Cell Stain (Life Technologies, Cat #L10119). After a 10-minute incubation on ice, the cells were washed twice with cold FACS Buffer, and the cells were analyzed by flow cytometry (BD LSR Fortessa Flow Cytometer). The data were analyzed by the FlowJo software by sequentially gating on the FSC-A vs. SSC-A, FSC-H vs FSC-A, SSC-A vs. Dead Cell Stain, and SSC-A vs PE. Mean fluorescence intensity (MFI) values were calculated, and the data were plotted by GraphPad Prism software.

As shown in FIG. 2A, BA002 bound to human TIGIT-expressing Jurkat cells in a dose-dependent manner.

Activated Primary Human T Cells

In similar experiments, the capacity of BA002 to bind to activated human CD4+ or CD8+ T cells was tested. Briefly, a frozen aliquot of human peripheral blood mononuclear cells (PBMCs) was retrieved from liquid nitrogen and immediately thawed in 37° C. water until floating ice was observed. Cells were then transferred to 9 mL of pre-warmed R10 media. 10 μL was removed and added to 390 μL viability dye to count cells and check viability using a Muse apparatus. Samples were centrifuged at 2000 rpm for two minutes and then suspended to a final concentration of $0.1 \times 10^6$ cells/mL with R10 media. A 1 μg/mL stock solution SEA was added to the PBMC cells prepared as described above to a final concentration of 100 ng/mL. 100 μL of stimulated cells were pipetted to each well of a 96 well U-bottom tissue culture plate and incubated in a tissue culture incubator at 37° C. in 5% $CO_2$ for five days.

A dose range of antibody was prepared in a 96 well round bottom plate. First, 600 μL of 50m/mL of each antibody was prepared in buffer. Antibodies were then serially diluted 1-to-3 by pipetting 200 μL of the previous dilution into 400 μL of sample buffer. A total of 12 dilutions ranging from 50 μg/mL to 0.0002 m/mL were prepared. After 5 days, the sample plate was centrifuged for two minutes at 2000 rpm, and supernatants were discarded. Samples were blocked with FcγR Block prepared in FACs buffer at 5 μL per 100 μL test (550 μL of Fc Receptor Blocking reagent diluted in 10.45 mL of FACs buffer) for 10 minutes. Sample plates were then centrifuged for two minutes at 2000 rpm, and the supernatant was discarded. The cells were then re-suspended in 100 μL of anti-TIGIT antibody or a relevant isotype control at the concentrations shown in FIGS. 2B-2C. Sample plates were incubated for 20 minutes at 4° C. Cells were washed by addition of cold sample buffer and centrifuged for two minutes at 2000 rpm, and the supernatant was discarded. This wash was repeated once.

Cells were then resuspended in a cocktail of fluorescently labeled antibodies. A cocktail of fluorescently labeled antibodies sufficient for all samples was prepared in FACs buffer. 100 μL of antibody per well was then added to a round-bottom 96-well plate. The sample plate was incubated for 20 minutes on ice. Cells were washed by addition of cold sample buffer, centrifuged for two minutes at 2000 rpm, and supernatants discarded. This wash was repeated once. A final cocktail of PE-labeled secondary anti-human IgG antibody was prepared in 11 mL of FACs buffer. 100 μL of secondary antibody was added per well to a round-bottom 96-well plate. The sample plate was incubated for 5 minutes on ice. Cells were washed by addition of cold sample buffer, centrifuged for two minutes at 2000 rpm, and the supernatants were discarded. This wash was repeated once.

Antibody binding was measured by flow cytometry using a BD LSR Fortessa Flow Cytometer. Unstained control cells were used to gate on the lymphocyte population using a plot of forward scatter-area (FSC-A) versus side scatter area (SSC-A) and another plot of FSC-A versus FSC-Height (FSC-H) for selection of single cells. Tubes of cells stained with each individual antibody were used to calculate compensation of the various colors used in the experiment. 100,000 events were recorded for each sample. Samples were analyzed by sequentially gating on the following populations: FSC-A vs SSC-A, FSC-H vs FSC-A, SSC-A vs LIVE/DEAD, CD4 vs CD8, and SSC vs CD25. Mean fluorescence intensity (MFI) was calculated.

As shown in FIGS. 2B and 2C, BA002 bound to activated primary human $CD4^+$ T cells (FIG. 2B) and activated primary human CD8+ T cells (FIG. 2C) in a dose-dependent manner.

CHO Cells Expressing Cynomolgus Monkey TIGIT

In similar experiments, the capacity of BA002 to bind to Chinese hamster ovary (CHO) cells engineered to express cynomolgus monkey TIGIT on their cell surfaces (cynomolgus TIGIT-CHO cells) was tested. Briefly, a frozen aliquot of cynomolgus TIGIT-CHO cells was thawed in 37° C. water and then transferred to a tube containing 9 mL of pre-warmed R10 media. Cells were centrifuged at 2000 rpm for two minutes. The supernatant was discarded and the cells were resuspended in 20 mL of R10 media. Cells were then transferred to a T75 flask and incubated in a tissue culture incubator at 37° C. and 8% $CO_2$ for 1 day. Cells were then removed from the incubator and treated with 5 mL of TrypLE express. Liberated cells were then diluted with 10 mL of R10 media and centrifuged for two minutes at 2000 RPM. The supernatant was discarded and the cells were resuspended in 10 mL of R10 media and assessed for count and viability. Cell samples were then centrifuged at 2000 rpm for two minutes and re-suspended to a final concentration of $1 \times 10^6$ cells/mL with R10 media. 100 μL of cells were then pipetted to each well of a 96 well U-bottom tissue culture plate for a final concentration of 100,000 cells per well.

A dose-range of antibody was prepared in 1.2 mL bullet tubes. First, 600 μL of 50 μg/mL of each antibody was prepared in FACs buffer. Antibodies were then serially diluted 1-to-5 by pipetting 120 μL of the previous dilution into 600 μL of sample buffer. A total of 12 dilutions ranging from 50 μg/mL to 0.000001024 μg/mL were prepared. Sample plates were centrifuged for two minutes at 2000 rpm, and the supernatants were discarded. Samples were washed with twice with FACs buffer. The cells were then re-suspended in 100 μL of anti-TIGIT antibody BA002 or an isotype control at the concentrations shown in FIG. 2D. Sample plates were then incubated for 30 minutes at 4° C. Cells were washed by addition of cold sample buffer and centrifuged for two minutes at 2000 rpm, and the supernatant was discarded. This wash was repeated once. Cells were then resuspended in a cocktail of live/dead stain and PE-labeled secondary anti-human IgG antibody. Sample plates were incubated for 10 minutes on ice. Cells were washed and centrifuged for two minutes at 2000 rpm, and the supernatants were discarded. This wash was repeated once.

Antibody binding was measured by flow cytometry using a BD LSR Fortessa Flow Cytometer. Unstained control cells were used to gate on the lymphocyte population using a plot of forward scatter-area (FSC-A) versus side scatter area (SSC-A) and another plot of FSC-A versus FSC-Height (FSC-H) for selection of single cells. Tubes of cells stained with each individual antibody were used to calculate compensation of the various colors used in the experiment. 100,000 events were recorded for each sample. Samples were analyzed by sequentially gating on the following populations: FSC-A vs SSC-A, FSC-H vs FSC-A, SSC-A vs LIVE/DEAD, and SSC-A vs PE. Mean fluorescence intensity (MFI) was calculated.

As shown in FIG. 2D, BA002 bound to CHO cells expressing cynomolgus monkey TIGIT in a dose-dependent manner.

6.1.3 Anti-TIGIT Antibody Selectively Binds to TIGIT

In this example, the selectivity of BA002 for TIGIT compared to its related family members CD96 and CD226 was tested. Specifically, BA002 was tested for binding to two engineered Jurkat cell lines, one that expressed human TIGIT, CD96, and CD226 on its cell surface ($TIGIT^+$ $CD96^+$ $CD226^+$), and one that expressed CD96 and CD226 but not TIGIT ($TIGIT^-$ $CD96^+$ $CD226^+$).

Briefly, frozen aliquots of TIGIT-Jurkat Clone D3 cells and wild type Jurkat cells were retrieved from liquid nitrogen and thawed in 37° C. water. Each clone was transferred to a separate tube containing 9 mL of pre-warmed R10 media. Cells were centrifuged at 2000 rpm for two minutes. The supernatant was discarded and the cells were resuspended in 20 mL of R10 media. Cells were then transferred to a T75 flask and incubated in a tissue culture incubator at 37° C. and 5% CO2 for 1 day. After incubation, cells were assessed for count and viability. Cell samples were then centrifuged at 2000 rpm for two minutes and re-suspended to a final concentration of $1 \times 10^6$ cells/mL with R10 media.

Next, 100 μL of cells were pipetted to each well of a 96 well U-bottom tissue culture plate for a final concentration of 100,000 cells per well.

A dose-range of each antibody (i.e., BA002 or isotype control) was prepared in 1.2 mL bullet tubes. First, 400 μL of 50 μg/mL of each antibody was prepared in FACs buffer. Antibodies were then serially diluted 1-to-5 by pipetting 80 μL of the previous dilution into 320 μL of sample buffer. A total of 8 dilutions ranging from 50 μg/mL to 0.00064 μg/mL were prepared.

Sample plates were centrifuged for two minutes at 2000 rpm, and supernatants were discarded. Samples were blocked with FcγR Block prepared in FACs buffer (550 μL of Fc Receptor Blocking reagent diluted in 10.45 mL of FACs buffer) for ten minutes. Sample plates were then centrifuged for two minutes at 2000 rpm, and the supernatant was discarded. The cells were then resuspended in 100 μL of BA002 or isotype control at the concentrations shown in FIGS. 3A-3B. Sample plates were incubated with antibody for 30 minutes at 4° C. Cells were then washed by addition of cold sample buffer and centrifuged for two minutes at 2000 rpm and the supernatant discarded. This wash was repeated once. Cells were then resuspended in a cocktail of live/dead stain and PE-labeled secondary anti-human IgG antibody was prepared in 20 mL of FACs buffer. Sample plates were incubated for 10 minutes on ice. Cells were washed by addition of cold FACs buffer, centrifuged for two minutes at 2000 rpm, and the supernatants were discarded. This wash was repeated once.

Antibody binding was measured by flow cytometry using a BD LSR Fortessa Flow Cytometer. Unstained control cells were used to gate on the lymphocyte population using a plot of forward scatter area (FSC-A) versus side scatter area (SSC-A) and another plot of FSC-A versus FSC-Height (FSC-H) for selection of single cells. Tubes of cells stained with each individual antibody were used to calculate compensation of the various colors used in the experiment. 100,000 events for each sample were recorded. Samples were analyzed by sequentially gating on the following populations: FSC-A vs SSC-A, FSC-H vs FSC-A, SSC-A vs LIVE/DEAD, and SSC-A vs PE. Mean fluorescence intensity (MFI) was calculated.

Figure 3A:
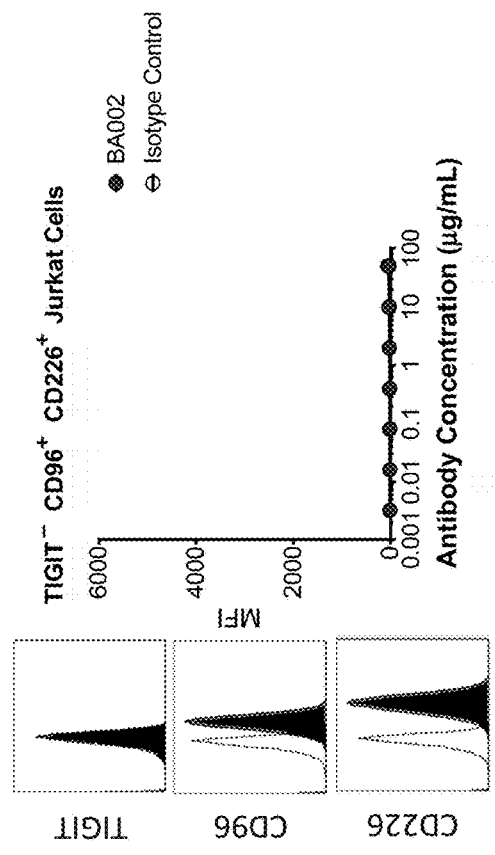
Figure 3B:
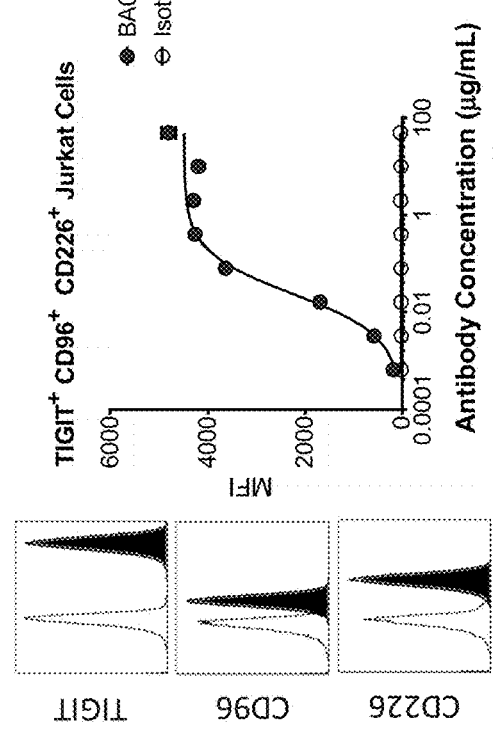

As shown in FIGS. 3A and 3B, BA002 strongly bound to Jurkat cells expressing human TIGIT but showed no cross-reactivity with the related family members CD96 and CD226.

6.1.4 Anti-TIGIT Antibody Blocks Ligand Binding to TIGIT

TIGIT Binding to CD155/PVR

In this example, the capacity of BA002 to block binding between TIGIT and its ligand CD155 (also referred to as PVR) was tested. Specifically, BA002, a series of reference anti-TIGIT antibodies, and isotype controls were tested for their ability to block binding between soluble TIGIT and CD155 in vitro.

Briefly, a 5× concentrated intermediate stock of each antibody (i.e., BA002, reference anti-TIGIT antibodies #1, 2, 3, 4, 5, and 6, and corresponding isotype controls) sufficient for two replicates was prepared in 1.2 mL bullet tubes. First, 60 μL of 250 μg/mL of each antibody was prepared in PBS. Antibodies were then serially diluted 1-to-3 by pipetting 20 μL of the previous dilution into 40 μL of sample buffer. A total of 12 working dilutions ranging from 50 μg/mL to 0.00028 μg/mL was prepared. A solution comprising 4 ng/pt of CD155-His in assay buffer was prepared. 2 μl 3×TIGIT assay buffer, 2 μL CD155-His solution, and 2 μl distilled water were combined to produce a master mixture, and then 6 μL of master mixture was added to each well of an assay plate. A solution comprising 2 ng/μL of biotinylated TIGIT (TIGIT-biotin) in assay buffer was also prepared, of which 2 μL was added per well and incubated for 60 minutes. Additionally, Ni Chelate Acceptor beads (PerkinElmer #AL108C) were diluted 250-fold with 1× assay buffer, and 10 μL of the diluted acceptor bead solution was added per well. After shaking briefly, the mixture was incubated at room temperature for 30 minutes. Streptavidin-conjugated donor beads (PE #6760002S) were then diluted 125-fold with 1× assay buffer, and 10 μL of the diluted donor bead solution was added per well. The mixture was incubated at room temperature for 30 minutes. Alpha counts were obtained and relative light unit values were calculated and normalized according to standard methods to determine percent binding between TIGIT and CD155 in the presence of each antibody tested.

As shown in FIGS. 4A-4F, BA002 showed substantial blocking of TIGIT binding to CD155. The ligand blocking activity of BA002 for CD155 was comparable to or greater than that observed for the series of reference anti-TIGIT antibodies. For ease of visualization, the same data for BA002 and isotype control are shown in each of FIGS. 4A-4F, while data for a different reference antibody is shown in each Figure.

TIGIT Binding to CD112/PVRL2

In this example, the capacity of BA002 to block binding between TIGIT and its ligand CD112 (also referred to as PVRL2) was tested. Specifically, BA002, a series of reference anti-TIGIT antibodies, and isotype controls were tested for their ability to block binding between soluble TIGIT and CD112 in vitro.

Briefly, a 5× concentrated intermediate stock of each antibody (i.e., BA002, reference anti-TIGIT antibodies #1, 2, 3, 4, 5, and 6, and corresponding isotype controls) sufficient for two replicates was prepared in 1.2 mL bullet tubes. First, 60 μL of 250 μg/mL of each antibody was prepared in PBS. Antibodies were then serially diluted 1-to-3 by pipetting 20 μL of the previous dilution into 40 μL of sample buffer. A total of 12 working dilutions ranging from 50 μg/mL to 0.00028 μg/mL was prepared. A solution comprising 4 ng/pt of CD112-Histidine in assay buffer was prepared. 2 μl 3×TIGIT assay buffer, 2 μl CD112-His solution, and 2 μl distilled water were combined to produce a master mixture, and then 6 μL of master mixture was added to each well of an assay plate. A solution comprising 2 ng/μL of biotinylated TIGIT (TIGIT-biotin) in assay buffer was also prepared, of which 2 μL was added per well and incubated for 60 minutes. Additionally, Ni Chelate Acceptor beads (PerkinElmer #AL108C) were diluted 250-fold with 1× assay buffer, and 10 μL of the diluted acceptor bead solution was added per well. After shaking briefly, the mixture was incubated at room temperature for 30 minutes. Streptavidin-conjugated donor beads (PE #6760002S) were then diluted 125-fold with 1× assay buffer, and 10 μL of the diluted donor bead solution was added per well. The mixture was incubated at room temperature for 30 minutes. Alpha counts were obtained and relative light unit values were calculated and normalized according to standard methods to determine percent binding between TIGIT and CD112 in the presence of each antibody tested.

As shown in FIGS. 5A-5F, BA002 showed substantial blocking of TIGIT binding to CD112. The ligand blocking activity of BA002 for CD112 was comparable to or greater than that observed for the series of reference anti-TIGIT antibodies. For ease of visualization, the same data for BA002 and isotype control are shown in each of FIGS. 5A-5F, while data for a different reference antibody is shown in each Figure.

6.2 Example 2: Functionality of Anti-TIGIT Antibody and Combination Therapies 6.2.1 Anti-TIGIT Antibody Enhances $T_H1$ Cytokine Secretion by Primary Cells Anti-TIGIT Antibody Enhances IFNγ Secretion by Stimulated PBMCs In this example, the capacity of BA002 and a series of reference anti-TIGIT antibodies to promote secretion of IFNγ by PBMCs stimulated with Staphylococcal Enterotoxin A (SEA) was tested. The anti-TIGIT antibodies were also tested for cooperativity with an anti-PD-1 antibody in this assay.

A 5× concentrated intermediate stock of each antibody (i.e., BA002, reference anti-TIGIT antibodies #1, 3, 5, or 6, or an isotype control) was prepared in 1.2 mL bullet tubes. One set of tubes also received 25 μg/mL of anti-PD-1 antibody, while another set of tubes also received 25 μg/mL of IgG4 isotype antibody, each representing a 5× concentrated intermediate stock of anti-PD-1 or IgG4 isotype antibody. First, 400 μL of 50 μg/mL of each anti-TIGIT antibody supplemented with 25 μg/mL of anti-PD-1 or IgG4 isotype antibody was prepared in R10 media. 20 μL of antibody was then added per well to a round-bottom 96-well plate. Frozen aliquots of human PBMCs were retrieved from liquid nitrogen and immediately thawed in 37° C. water until floating ice was observed. Cells were transferred to 9 mL of pre-warmed R10 media and immediately centrifuged at 2000 rpm for two minutes. To count cells and check viability, 10 μL of sample was removed and added to 390 μL of viability dye, mixed, and read using a Muse apparatus.

Samples were centrifuged at 2000 rpm for two minutes and resuspended to an intermediate concentration. An intermediate stock concentration of SEA was made by adding 10 μL of 1000 μg/mL SEA to 90 μL R10 to make an intermediate concentration of 100 μg/mL. To stimulate the cells, 12 μL of a 100 μg/mL intermediate stock of SEA was added to the 9.60 mL of cells prepared above. 80 μL of cells and SEA mixture was added into corresponding wells and incubated in tissue culture incubator at 37° C. and 5% $CO_2$ within a humidified chamber for four days. A total of $0.1 \times 10^6$ cells/well and final concentration of 100 ng/mL of SEA was used.

After four days of incubation, plates were removed from the incubator and gently agitated by hand. The plates were then centrifuged for two minutes at 2000 rpm. 5 μL of supernatant was transferred to a 384-well AlphaLISA plate for cytokine analysis. AlphaLISA kits (Perkin Elmer) were used for measurement of IFNγ secretion. Briefly, assay buffer was prepared by pipetting 2.5 mL of 10× AlphaLISA HiBlock Buffer to 22.5 mL water. Human IFNγ analyte was used to prepare a standard dilution according to manufacturer instructions. A mixture of 1.6× AlphaLISA anti-IFNγ acceptor beads and biotinylated anti-IFNγ antibody was prepared in assay buffer. 8 μL was added to each well and incubated in darkness at room temperature, rotating at 500 rpm for 90 minutes. A 2.3× Streptavidin Donor Bead intermediate stock was prepared in assay buffer. 10 μL were added to each well and incubated in darkness at room temperature, rotating at 500 rpm for 20 minutes. AlphaLISA plates were briefly centrifuged at 2000 rpm. Relative light units (RLU) were measured using the AlphaScreen protocol on an EnVision Plate Reader.

As shown in FIG. 6, BA002 enhanced IFNγ secretion by SEA-stimulated PBMCs to a greater degree than reference antibodies or isotype control. In addition, the combination of BA002 and the anti-PD-1 antibody resulted in a substantial increase in IFNγ secretion compared to treatment with BA002 alone. This increase was greater than that seen for the reference anti-TIGIT antibodies.

Anti-TIGIT Antibody Enhances IL-2 Secretion by Stimulated PBMCs

In this example, the capacity of BA002 and a reference anti-TIGIT antibody to promote secretion of the cytokine interleukin-2 (IL-2) by PBMCs stimulated with SEA was tested. The anti-TIGIT antibodies were also tested for cooperativity with an anti-CTLA-4 antibody in this assay.

A 5× concentrated intermediate stock of each antibody (i.e., BA002, reference anti-TIGIT antibody #4, or an isotype control) was prepared in 1.2 mL bullet tubes. One set of tubes also received 25 μg/mL of anti-CTLA-4 antibody, while another set of tubes also received 25 μg/mL of IgG1 isotype antibody, each representing a 5× concentrated intermediate stock of anti-CTLA-4 or anti-IgG1 isotype antibody. First, 400 μL of 50 μg/mL of each anti-TIGIT antibody supplemented with 25 μg/mL of anti-CTLA-4 or IgG1 isotype antibody was prepared in R10 media. 20 μL of antibody was then added per well to a round-bottom 96-well plate. Frozen aliquots of human PBMCs were retrieved from liquid nitrogen and immediately thawed in 37° C. water until floating ice was observed. Cells were transferred to 9 mL of pre-warmed R10 media and immediately centrifuged at 2000 rpm for two minutes. To count cells and check viability, 10 μL of sample was removed and added to 390 μL of viability dye, mixed, and read using a Muse apparatus.

Samples were centrifuged at 2000 rpm for two minutes and resuspended to an intermediate concentration. An intermediate stock concentration of SEA was made by adding 10 μL of 1000 μg/mL SEA to 90 μL R10 to make an intermediate concentration of 100 μg/mL. To stimulate the cells, 12 μL of a 100 μg/mL intermediate stock of SEA was added to the 9.60 mL of cells prepared above. 80 μL of cells and SEA mixture was added into corresponding wells and incubated in tissue culture incubator at 37° C. and 5% $CO_2$ within a humidified chamber for four days. A total of $0.1 \times 10^6$ cells/well and final concentration of 100 ng/mL of SEA was used.

After four days of incubation, plates were removed from the incubator and gently agitated by hand. The plates were then centrifuged for two minutes at 2000 rpm. 5 μL of supernatant was transferred to a 384-well AlphaLISA plate for cytokine analysis AlphaLISA kits (Perkin Elmer) were used for measurement of IL-2 secretion. Briefly, assay buffer was prepared by pipetting 2.5 mL of 10× AlphaLISA Immunoassay Buffer to 22.5 mL water. Human IL-2 analyte was used to prepare a standard dilution. A mixture of 1.6× AlphaLISA anti-IL-2 acceptor beads and biotinylated anti-IL-2 antibody was prepared in assay buffer. 8 μL was added to each well and incubated in darkness at room temperature, rotating at 500 rpm for 90 minutes. A 2.3× Streptavidin Donor Bead intermediate stock was prepared in assay buffer. 10 μL was added to each well and incubated in darkness at room temperature, rotating at 500 rpm for 20 minutes. AlphaLISA plates were briefly centrifuged at 2000 rpm. Relative light units (RLU) were measured using the AlphaScreen protocol on an EnVision Plate Reader.

As shown in FIGS. 7A-7B, the combination of BA002 and the anti-CTLA-4 antibody resulted in a substantial increase in IL-2 secretion compared to treatment with BA002 or the anti-CTLA-4 antibody alone. This increase was greater than that seen for the reference anti-TIGIT antibody tested in this experiment, reference antibody #4.

6.3 Example 3: Fc Variants of Anti-TIGIT Antibody

6.3.1 Characterization of Anti-TIGIT Antibody Variants with Different Fc Regions In this example, the impact of Fc region/FcγR interaction on the binding and functional activity of BA002 was analyzed. In particular, the VH region of BA002 was expressed with various Fc backbones, as summarized in Table 4.

TABLE 4

Fc variants of BA002.

| Antibody Name | Antibody Description (numbered according to the EU numbering system) | Heavy Chain SEQ ID NO: | Light Chain SEQ ID NO: |
|---|---|---|---|
| BA002 | IgG1 | 11 | 27 |
| BA003 | N297A variant of BA002 | 12 | 27 |
| BA004 | L234F/L235F/N297A variant of BA002 | 13 | 27 |
| BA005 | S239D/I332E variant of BA002 | 14 | 27 |
| BA006 | S239D/A330L/I332E variant of BA002 | 15 | 27 |
| BA007 | L235V/F243L/R292P/Y300L/P396L variant of BA002 | 16 | 27 |
| BA008 | S267E/L328F variant of BA002 | 17 | 27 |
| BA009 | IgG4 S228P variant of BA002 | 18 | 27 |

In addition, BA002_AF, an afucosylated version of BA002 with identical heavy and light chain sequences, was expressed.

These variants of BA002 were then tested in binding and functional assays, as described below.

Binding to Activated Primary Human T Cells

BA006 was tested for its ability to bind to activated primary CD4$^+$ T cells, using the same experimental design and conditions as described for BA002 in Section 6.1.2. As shown in FIG. 8A, BA006 bound to activated primary CD4$^+$ T cells in a dose-dependent manner.

Binding to CHO Cells Expressing Cynomolgus Monkey TIGIT

BA006 was tested for its ability to bind to cynomolgus monkey TIGIT expressed on the surface of engineered CHO cells, using the same experimental design and conditions as described for BA002 in Section 6.1.2. As shown in FIG. 8B, BA006 bound to CHO cells expressing cynomolgus monkey TIGIT in a dose-dependent manner.

Cell Binding and Selectivity for Human TIGIT

The Fc variant anti-TIGIT antibody BA006 was tested for its ability to bind to human TIGIT, as well as its selectivity for human TIGIT over its related family members CD96 and CD226. Specifically, BA006 or isotype control were tested for binding to (i) TIGIT CD96$^+$ CD226$^+$ Jurkat cells, or (ii) TIGIT$^-$ CD96$^+$ CD226$^+$ Jurkat cells, using the same experimental design and conditions as described for BA002 in Section 6.1.3. In these experiments, BA006 strongly bound to Jurkat cells expressing human TIGIT (FIG. 8C), but showed no cross-reactivity with the related family members CD96 and CD226 (FIG. 8D).

Fc Variants of BA002 Further Enhance IL-2 Secretion by Stimulated PBMCs Alone and in Combination with Anti-PD-1 Antibody In this example, the capability of Fc variants of BA002 to promote secretion of IL-2 by PBMCs stimulated with SEA was tested. The anti-TIGIT antibodies were also tested for cooperativity with an anti-PD-1 antibody in this assay.

A 5× concentrated intermediate stock of each antibody (i.e., BA002, BA002_AF, BA003, BA005, BA006, BA007, BA008, BA009, or isotype controls for IgG1 and IgG4) was prepared in 1.2 mL bullet tubes. One set of tubes also received 25 µg/mL of anti-PD-1 antibody, while another set of tubes also received 25 µg/mL of IgG4 isotype control antibody, each representing a 5× concentrated intermediate stock of anti-PD-1 or IgG4 isotype control antibody. First, 400 µL of 50 µg/mL of each anti-TIGIT antibody supplemented with 25 µg/mL of anti-PD-1 or IgG4 isotype antibody was prepared in R10 media. 20 µL of antibody was then added per well to a round-bottom 96-well plate. Frozen aliquots of human PBMCs were retrieved from liquid nitrogen and immediately thawed in 37° C. water until floating ice was observed. Cells were transferred to 9 mL of pre-warmed R10 media and immediately centrifuged at 2000 rpm for two minutes. Cells were counted and checked for viability.

Samples were centrifuged at 2000 rpm for two minutes and resuspended to an intermediate concentration. An intermediate stock concentration of SEA was made by adding 10 µL of 1000 µg/mL SEA to 90 µL R10 to make an intermediate concentration of 100 µg/mL. To stimulate the cells, 12 µL of a 100 µg/mL intermediate stock of SEA was added to the 9.60 mL of cells prepared above. 80 µL of cells and SEA mixture was added into corresponding wells and incubated in tissue culture incubator at 37° C. and 5% CO$_2$ within a humidified chamber for four days. A total of 0.1×10$^6$ cells/well and final concentration of 100 ng/mL of SEA was used.

After four days of incubation, plates were removed from the incubator and gently agitated by hand. The plates were then centrifuged for two minutes at 2000 rpm. 5 µL of supernatant was transferred to a 384-well AlphaLISA plate for cytokine analysis. AlphaLISA kits (Perkin Elmer) were used for measurement of IL-2 secretion. Briefly, assay buffer was prepared by pipetting 2.5 mL of 10× AlphaLISA Immunoassay Buffer to 22.5 mL water. Human IL-2 analyte was used to prepare a standard dilution. A mixture of 1.6× AlphaLISA anti-IL-2 acceptor beads and biotinylated anti-IL-2 antibody was prepared in assay buffer. 8 µL was added to each well and incubated in darkness at room temperature, rotating at 500 rpm for 90 minutes. A 2.3× Streptavidin Donor Bead intermediate stock was prepared in assay buffer. 10 µL was added to each well and incubated in darkness at room temperature, rotating at 500 rpm for 20 minutes. AlphaLISA plates were briefly centrifuged at 2000 rpm. Relative light units (RLU) were measured using the AlphaScreen protocol on an EnVision Plate Reader. This experiment was run for four replicates using PBMCs obtained from two different donors.

As shown in FIGS. 9A and 9B, Fc variants of BA002 further enhanced IL-2 secretion by SEA-stimulated PBMCs beyond the effect observed for BA002. In particular, BA002_AF, BA005, BA006, and BA007 each induced greater IL-2 secretion than BA002, which in turn induced greater IL-2 secretion than BA003, BA008, BA009, or isotype control. Combining Fc variants of BA002 with an anti-PD-1 antibody also produced a further improvement in IL-2 secretion by SEA-stimulated PBMCs.

Fc Variants of BA002 Further Enhanced Activation of CD4$^+$ and CD8$^+$ T Cells Alone and in Combination with Anti-PD-1 Antibody In this example, the capability of Fc variants of BA002 to promote T cell activation was tested. The anti-TIGIT antibodies were also tested for cooperativity with an anti-PD-1 antibody in this assay.

A 5× concentrated intermediate stock of antibody (i.e., BA002, BA002_AF, BA003, BA005, BA006, BA007, BA008, BA009, isotype IgG1 control, or isotype IgG4 control, each with a matching quantity of either an anti-PD-1 antibody or an isotype IgG4 control) sufficient for four replicates for two donors was prepared in 1.2 mL bullet tubes. First, 400 µL of 50 µg/mL of each antibody was prepared in R10 media. 20 µL of antibody solution per well was then added to a round-bottom 96-well plate. Frozen aliquots of indicated human PBMC donors were retrieved from liquid nitrogen and thawed in 37° C. water. Cells were transferred to 9 mL of pre-warmed R10 media and immediately centrifuged at 2000 rpm for two minutes. Cell were then counted and viability was assessed. Cell samples were then centrifuged at 2000 rpm for two minutes and resuspended to an intermediate concentration. An intermediate stock concentration of SEA was made by diluting 10 µL of 1000 µg/mL of SEA in 90 µL of R10 medium to make an intermediate concentration of 100 µg/mL. To stimulate the cells, 12 µL of a 100 µg/mL intermediate stock of SEA was added to 7.20 mL of the cells prepared above. 60 µL of cells and SEA mixture was added into corresponding wells and incubated in a humidified chamber at 37° C. and 5% $CO_2$ for five days. A total of $0.1 \times 10^6$ cells/well and final concentration of 100 ng/mL of SEA was used.

After 5 days, the sample plate was centrifuged for two minutes at 2000 rpm, and supernatants were discarded. Samples were washed twice and blocked with FcγR block at 5 µL per 100 µL test (i.e., 550 µL of Fc Receptor Blocking reagent diluted in 10.45 mL of FACs buffer) for 10 minutes. Sample plates were then centrifuged for two minutes at 2000 rpm and the supernatant was discarded. A cocktail of fluorescent-labeled antibodies sufficient for all samples was prepared in 11 mL of FACs buffer. 100 µL of fluorescent antibody cocktail was then added per well to a round-bottom 96-well plate using a multi-channel a pipette. The sample plate was incubated for 20 minutes on ice. Cells were washed by addition of cold sample buffer, centrifuged for two minutes at 2000 rpm, and the supernatants were discarded. This wash was repeated once before proceeding to flow cytometry analysis. Samples were analyzed by sequentially gating on the following populations: FSC-A vs SSC-A, FSC-H vs FSC-A, SSC-A vs LIVE/DEAD, CD4 vs CD8, and SSC vs CD25. Mean fluorescence intensity (MFI) of CD4+CD25+ T cells or CD8+CD25+ T cells were calculated and exported to Excel for analysis. GraphPad Prism was used to plot the data.

As shown in FIGS. 9C and 9D, the Fc variants BA005, BA006, and BA007, and an afucosylated form of BA002 (BA002_AF), enhanced CD4+ and CD8+ T cell activation to a substantially greater degree than isotype controls. This enhancement was further increased when these antibodies were combined with an anti-PD-1 antibody.

Anti-TIGIT Antibodies Show Dose-Dependent Enhancement of IL-2 Secretion by SEA-Stimulated PBMCs Alone and in Combination with an Anti-PD-1 Antibody In a further example, BA002 and several Fc variants thereof (i.e., BA005, BA006, and BA002_AF) were each tested for their ability to promote IL-2 secretion by SEA-stimulated PBMCs from different donors at various antibody concentrations. In one experiment, a dose titration was performed for antibodies BA002, BA002_AF, BA005, BA006, and isotype control, each alone (FIG. 10A). In a second experiment, a dose titration was performed for antibodies BA002, BA002_AF, BA006, and isotype control, each in combination with anti-PD-1 antibody (FIG. 10B). In a third experiment, a dose titration was performed for antibodies BA002, BA006, and isotype control in PBMCs obtained from a third donor in the presence of CD155-Fc, each antibody alone (FIG. 10C).

For each of the first two experiments described above in this section, a 5× concentrated intermediate stock of antibody sufficient for three replicates per donor was prepared in 1.2 mL bullet tubes. First, 400 µL of 250 µg/mL of each antibody was prepared in R10 media. Antibodies were then serially diluted 1-to-4 by pipetting 100 µL of the previous dilution into 300 µL of sample buffer. A total of 8 dilutions ranging from 50-0.003052 µg/mL were prepared (see concentrations shown in FIGS. 10A-10C). 20 µl of each antibody mixture was then added per well of a round-bottom 96-well plate. For the second experiment (i.e., the combination of anti-TIGIT antibody and anti-PD-1 antibody), either anti-PD-1 antibody or an isotype IgG4 control antibody were prepared as a 5× concentrated intermediate stock. 20 µl of anti-PD-1 antibody or isotype IgG4 control mixture was then added per well to a round-bottom 96-well plate.

Frozen aliquots of indicated human PBMCs were retrieved from liquid nitrogen and immediately thawed in 37° C. water. Cells were transferred to 9 mL of pre-warmed R10 media and centrifuged at 2000 rpm for two minutes. Cells were counted and assessed for viability. Samples were centrifuged at 2000 rpm for two minutes and resuspended. An intermediate stock concentration of SEA was made by diluting 10 µL of 1000 µg/mL of SEA to 90 µL of R10 to make an intermediate concentration of 100 µg/mL. To stimulate the cells, 50 µL of a 100 µg/mL intermediate stock of SEA was added to the 30 mL of cells prepared above. 60 µL of the cell and SEA mixture was added into corresponding wells and incubated in a humidified chamber at 37° C. and 5% $CO_2$ for four days. A total of $0.1 \times 10^6$ cells/well and a final concentration of 100 ng/mL of SEA was used.

After four days of incubation, the plates were removed from incubator, gently agitated by hand, and centrifuged for two minutes at 2000 rpm. 5 µL of the supernatant was transferred to a 384-well AlphaLISA plate (Perkin Elmer) for cytokine analysis. AlphaLISA kits were used for the measurements of IL-2 in accordance with manufacturer instructions. Briefly, assay buffer was prepared by pipetting 2.5 mL of 10× AlphaLISA Immunoassay Buffer to 22.5 mL water. Human IL-2 analyte was used to prepare a standard dilution. A mixture of 1.6× AlphaLISA anti-IL-2 acceptor beads and biotinylated antibody anti-IL-2 was prepared in assay buffer. 8 µL was added to each well and incubated in darkness at room temperature, rotating at 500 rpm for 90 minutes. A 2.3× Streptavidin donor bead intermediate stock was prepared in assay buffer. 10 µL were added to each well and incubated in darkness at room temperature, rotating at 500 rpm for 20 minutes. AlphaLISA plates were briefly centrifuged at 2000 rpm. Relative light units (RLU) were measured using the AlphaScreen protocol on an EnVision Plate Reader.

As shown in FIG. 10A, BA006 showed the highest enhancement of IL-2 secretion by SEA-stimulated PBMCs when administered alone. BA005, BA002_AF, and BA002 also showed enhancement of IL-2 secretion when administered alone. As shown in FIG. 10B, BA006, BA002, and BA002_AF each also showed enhancement of IL-2 secretion by SEA-stimulated PBMCs when combined with an anti-PD-1 antibody, with BA006 inducing the strongest level of IL-2 secretion.

For the third experiment described above in this section, the ability of BA006 and BA002 to enhance IL-2 secretion by PBMCs in the presence of plate-coated CD155-Fc was assessed across a range of antibody concentrations.

To prepare plates coated with CD155-Fc, 50 μg of recombinant human CD155-Fc protein was reconstituted in 100 μL PBS to make a stock concentration of 500 μg/mL. The reconstituted protein was then diluted to a working concentration of 1 μg/mL by adding 24 μL of the 500 μg/mL CD155-Fc stock solution to 11.976 mL of PBS. A 96-well high-binding plate was then coated with CD155-Fc protein by adding 100 μL of the working concentration of CD155-Fc protein solution to each well of the 96-well plate. The plate was then sealed with an adhesive and incubated overnight at 4° C. The next day, the plate was centrifuged at 2000 rpm for two minutes. The supernatant was discarded and antibodies were added as described below.

A 5× concentrated intermediate stock of antibody sufficient for three replicates per donor was prepared in 1.2 mL bullet tubes. First, 420 μL of 500 μg/mL of each antibody was prepared in R10 media. Antibodies were then serially diluted 1-to-3 by transferring 140 μL of the previous dilution into 280 μL of R10 media. A total of eight dilutions ranging from 100-0.045725 μg/mL were prepared. 20 μl of antibody mixture was then added to corresponding wells of a round-bottom 96-well plate.

Frozen aliquots of human PBMCs were retrieved from liquid nitrogen and immediately thawed in 37° C. water. Cells were transferred to 9 mL of pre-warmed R10 media and immediately centrifuged at 2000 rpm for two minutes. Cells were then counted and viability was assessed. Cells were centrifuged at 2000 rpm for two minutes and resuspended. An intermediate stock concentration of SEA was made by diluting 10 μL of 1000 μg/mL of SEA in 90 μL of R10 to make an intermediate concentration of 100 μg/mL. To stimulate the cells, 12 μL of the 100 μg/mL intermediate stock of SEA was added to 9.60 mL of cells. 80 μL of cells and SEA mixture was added into corresponding wells and incubated in a humidified chamber at 37° C. and 5% $CO_2$ for four days. A total of $0.1 \times 10^6$ cells/well and a final concentration of 100 ng/mL of SEA was used.

After four days of incubation, plates were removed from the incubator, gently agitated by hand, and then centrifuged for two minutes at 2000 rpm. 5 μL of the supernatant was transferred to a 384-well AlphaLISA plate (Perkin Elmer) for cytokine analysis. AlphaLISA kits were used for the measurements of IL-2 in accordance with manufacturer instructions. Briefly, assay buffer was prepared by adding 2.5 mL of 10× AlphaLISA Immunoassay Buffer to 22.5 mL water. Human IL-2 analyte was used to prepare a standard dilution in accordance with manufacturer instructions. A mixture of 1.6× AlphaLISA anti-IL-2 acceptor beads and biotinylated antibody anti-IL-2 mix was prepared in assay buffer. 8 μL was added to each well and incubated in darkness at room temperature, rotating at 500 rpm for 90 minutes. A 2.3× streptavidin donor bead intermediate stock was prepared in assay buffer. 10 μL was added to each well and incubated in darkness at room temperature, rotating at 500 rpm for 20 minutes. AlphaLISA plates were briefly centrifuged at 2000 rpm. Relative light units (RLU) were measured using the AlphaScreen protocol on an EnVision Plate Reader.

As shown in FIG. 10C, BA006 and BA002 enhanced IL-2 secretion in a dose-dependent manner from SEA-stimulated PBMCs co-cultured with plate-bound CD155-Fc. BA006 enhanced IL-2 secretion to a greater degree than BA002, which in turn increased IL-2 secretion relative to isotype control.

In further experiments, the activation of PBMCs by BA006 in the presence of a lower concentration of SEA was tested. The experiment was set up similarly as provided in section 6.2.1, except that a 10 μg/mL intermediate stock of SEA was used. The final cell culture contained a total of $1.2 \times 10^5$ cells/well and a final concentration of 10 ng/mL of SEA peptide. After four days of incubation, IL-2 production from the cells was measured by AlphaLISA kit (Perkin Elmer).

As shown in FIGS. 10D and 10E, BA006 enhanced IL-2 secretion in a dose-dependent manner in PBMCs from two different donors in the presence of 10 ng/mL SEA. The $EC_{50}$ values measured from these two experiments were 68 ng/mL and 56 ng/mL, respectively. Thus, BA006 effectively increased the sensitivity of PBMCs to the SEA antigen.

Fc Variants of Anti-TIGIT Antibody Stimulate IFNγ Secretion by Stimulated PBMCs

In this example, the capability of Fc variants of BA002 to promote secretion of IFNγ by PBMCs stimulated with SEA was tested.

A 5× concentrated intermediate stock of each antibody (i.e., BA002, BA002_AF, BA003, BA005, BA006, BA007, BA008, BA009, or isotype controls for IgG1 and IgG4) was prepared in 1.2 mL bullet tubes. First, 400 μL of 50 μg/mL of each antibody was prepared in R10 media. 20 μL of antibody was then added per well to a round-bottom 96-well plate. Frozen aliquots of human PBMCs were retrieved from liquid nitrogen and immediately thawed in 37° C. water until floating ice was observed. Cells were transferred to 9 mL of pre-warmed R10 media and immediately centrifuged at 2000 rpm for two minutes. To count cells and check viability, 10 μL of sample was removed and added to 390 μL of viability dye, mixed, and read using a Muse apparatus.

Samples were centrifuged at 2000 rpm for two minutes and resuspended to an intermediate concentration. An intermediate stock concentration of SEA was made by adding 10 μL of 1000 μg/mL SEA to 90 μL R10 to make an intermediate concentration of 100 μg/mL. To stimulate the cells, 12 μL of a 100 μg/mL intermediate stock of SEA was added to the 7.20 mL of cells prepared above. 60 μL of cells and SEA mixture was added into corresponding wells and incubated in tissue culture incubator at 37° C. and 5% $CO_2$ within a humidified chamber for four days. A total of $0.1 \times 10^6$ cells/well and final concentration of 100 ng/mL of SEA was used.

After four days of incubation, plates were removed from the incubator and gently agitated by hand. The plates were then centrifuged for two minutes at 2000 rpm. 5 μL of supernatant was transferred to a 384-well AlphaLISA plate for cytokine analysis. AlphaLISA kits (Perkin Elmer) were used for measurement of IFNγ secretion. Briefly, assay buffer was prepared by pipetting 2.5 mL of 10× AlphaLISA HiBlock Buffer to 22.5 mL water. Human IFNγ analyte was used to prepare a standard dilution according to manufacturer instructions. A mixture of 1.6× AlphaLISA anti-IFNγ acceptor beads and biotinylated anti-IFNγ antibody was prepared in assay buffer. 8 μL was added to each well and incubated in darkness at room temperature, rotating at 500 rpm for 90 minutes. A 2.3× Streptavidin Donor Bead intermediate stock was prepared in assay buffer. 10 μL were added to each well and incubated in darkness at room temperature, rotating at 500 rpm for 20 minutes. AlphaLISA plates were briefly centrifuged at 2000 rpm. Relative light units (RLU) were measured using the AlphaScreen protocol on an EnVision Plate Reader.

As shown in FIGS. 11A-11B, BA002 and its Fc variants enhanced IFNγ secretion by SEA-stimulated PBMCs from two different donors.

6.3.2 Anti-TIGIT Antibody Fc Variants Showed Varying Capability to Signal Through FcγRIIA and FcγRIIIA FcγRIIA Signaling In one example, the capacity of BA002 Fc variants to activate reporter cells expressing FcγRIIA$^{H131}$ was tested. Briefly, target cells (i.e., Jurkat cells engineered to express human TIGIT) were added to the wells of an ADCP assay plate (2.4×10$^6$ cells/mL). Serial dilutions of antibody (i.e., anti-TIGIT antibody BA002 or Fc variants thereof, or appropriate isotype controls (Evitria); one antibody per well) were added to the assay plate wells with ADCP assay buffer. 150,000 effector cells (i.e., Jurkat NFAT-luciferase reporter cells overexpressing the FcγRIIA CD32A with a high affinity 131 H/H polymorphism, less than six weeks in culture; Promega) were added to each well, and the mixtures were then incubated for 20 hours at 37° C. Binding of antibody/antigen complex on target cell surfaces to CD32A on effector cell surfaces would result in signaling to the reporter construct and expression of luciferase.

The next day, plates were equilibrated to room temperature for 15 minutes and then 75 μL of Bio-Glo Luciferase Assay Reagent (Promega Catalog #G7940) was added per well. The mixtures were then incubated at room temperature for 5-10 minutes, and luminescence was measured using a plate reader (Envision). Relative Light Units (RLU) were calculated as the induced RLU–background RLU.

As shown in FIG. 12A, for FcγRIIA binding and signaling, BA005 exhibited the highest level of signaling followed in order by BA008, BA006, BA007, BA002, and BA002_AF. BA003 and isotype controls showed substantially no signaling.

FcγRIIIA Signaling

In another example, the capacity of BA002 Fc variants to activate reporter cells expressing FcγRIIIA$^{V158}$ was tested. Briefly, target cells (i.e., Jurkat cells engineered to express human TIGIT) were added to the wells of an ADCC assay plate (2.4×10$^6$ cells/mL). Serial dilutions of antibody (i.e., anti-TIGIT antibody BA002 or Fc variants thereof, or appropriate isotype controls (Evitria); one antibody per well) were added to the assay plate wells with ADCC assay buffer. 150,000 effector cells (i.e., Jurkat NFAT-luciferase reporter cells overexpressing the FcγRIIIA CD16A with a high affinity 158 V/V polymorphism, less than six weeks in culture; Promega) were added to each well, and the mixtures were then incubated for 20 hours at 37° C. Binding of antibody/antigen complex on target cell surfaces to CD16A on effector cell surfaces would result in signaling to the reporter construct and expression of luciferase.

The next day, plates were equilibrated to room temperature for 15 minutes and then 75 μL of Bio-Glo Luciferase Assay Reagent (Promega Catalog #G7940) was added per well. The mixtures were then incubated at room temperature for 5-10 minutes, and luminescence was measured using a plate reader (Envision). RLU was calculated as the induced RLU–background RLU.

As shown in FIG. 12B, for FcγRIIIA binding and signaling, BA006 exhibited the highest level of signaling, followed in order by BA002_AF, BA005, BA007, and BA002. BA003 and isotype controls showed substantially no signaling.

6.3.3 Fc Variants of BA002 Enhanced Killing of TIGIT$^+$ Jurkat Cells in Co-Culture with CD16+NK Cells Fc variants of BA002 were examined for their capacity to induce antibody-dependent cell-mediated cytotoxicity (ADCC) activity in a co-culture of TIGIT-expressing Jurkat cells and CD16-expressing natural killer (NK) cells. Briefly, Jurkat cells were cultured in RPMI 1640 (Corning Catalog #10-040-CM, Lot 35316005) supplemented with 10% fetal bovine serum (Benchmark Catalog #100-106, Lot A69E00F) and 1% Pen Strep Glutamine (Gibco Catalog #10378-016, Lot 1835954). NK cells were cultured in NK MACS Basal Medium (MACS Catalog #130-107-209) supplemented with 2% NK MACS Medium Supplement (MACS Catalog #130-107-210, Lot 5160804070), 5% human serum (Sigma Catalog #H4522, Lot SLBQ9160V), 1% Pen Strep Glutamine (Gibco Catalog #10378-016, Lot 1835954), 100 Units/mL IL-2 (R&D Systems Catalog #202-16, Lot AE6016102), and 100 Units/mL IL-15 (R&D Systems Catalog #247-ILB, Lot TLM1016102). Two million Jurkat cells were pelleted by centrifugation for 5 minutes at 1200 rpm. The cells were stained by resuspending the pellet in 1 mL of 0.5 μM CellTrace Far Red (Invitrogen Catalog #C34565, Lot 1764050) in PBS (Corning Catalog #21-040-CV, Lot 00217005) and incubating for 30 minutes at 37° C. and 5% $CO_2$. After incubation, 9 mL of PBS was added and the cells were pelleted by centrifugation for 5 minutes at 1200 rpm. The cell pellet was then resuspended in Jurkat culture media. Antibodies were diluted in Jurkat culture media containing 1 μM CellEvent Caspase-3/7 Green Detection Reagent (Invitrogen Catalog #C10423, Lot 1849709) at six times their final concentration. Stained Jurkat cells were diluted to 0.5 million cells per mL and NK cells to 0.75 million cells per mL. The assay was performed in 384-well microscopy plates (Greiner, Cat. No. 781936, Lot E161233K) by pipetting 10 μL of the antibodies (final concentrations: 0.1, 1, and 10 μg/mL), 30 μL stained Jurkat cells (15000 cells), and 20 μL NK cells (15000 cells) per well.

Live imaging was performed immediately afterward, using an ImageXpress Micro Confocal High-Content microscope (Molecular Devices) under environmental control (37° C., 5% $CO_2$) and images were acquired every hour from the Cy5 (CellTrace Far Red) and FITC (Caspase 3/7) channels for Jurkat cells and Caspase 3/7-positive Jurkat cells, respectively, over the course of three hours. Image analysis was performed using the MetaXpress analysis software (Molecular Devices). Jurkat cells were identified from the Cy5 channel and the amount of Caspase 3/7 signal was quantified per cell from the FITC channel. Cells with Caspase 3/7 intensity above the background were designated as apoptotic. The number of apoptotic cells was normalized against the total cell count per condition to determine a percent killing measurement.

As shown in FIG. 13A, Fc variants that exhibited improved binding to FcγRIIIA (BA006, BA007, BA005, and BA002_AF) promoted killing of TIGIT-expressing Jurkat cells to a greater degree than BA002, which in turn promoted killing of TIGIT-expressing Jurkat cells to a greater degree than BA003, which contains the "Fc-silent" N297A mutation, and isotype control.

6.3.4 BA002 and BA006 Preferentially Kill Regulatory T Cells as Compared to Effector T Cells In one example, BA002 and BA006 were examined for their capacity to induce ADCC in primary regulatory T cells (Treg) and effector T cells (Teff). Briefly, antibody BA002, antibody BA006, and an IgG1 isotype control antibody were examined for ADCC activity in a co-culture of CD16-expressing NK cells and either (i) primary effector T cells or (ii) primary regulatory T cells. Primary T cells were isolated from PBMCs and expanded over 10 days according to methods known in the art. The identity of the T effector cells and T regulatory cells was confirmed by flow cytometric analysis of appropriate markers. Before the ADCC assay, T effector cells and T regulatory cells were either rested in X-VIVO 15 media (Lonza Catalog #04-418Q, Lot 0000542070) supplemented with 50 Units/mL IL-2 (R&D Systems Catalog #202-16, Lot AE6016102), or stimulated in X-VIVO 15 media supplemented with 50 Units/mL IL-2 and 25 µL per mL CD3/CD28 T cell activator (Stemcell Catalog #10971, Lot 16L75402), for 16 hours. NK cells were cultured in NK MACS Basal Medium (MACS Catalog #130-107-209) supplemented with 2% NK MACS Medium Supplement (MACS Catalog #130-107-210, Lot 5160804070), 5% human serum (Sigma Catalog #H4522, Lot SLBQ9160V), 1% Pen Strep Glutamine (Gibco Catalog #10378-016, Lot 1835954), 100 Units/mL IL-2 (R&D Systems Catalog #202-16, Lot AE6016102), and 100 Units/mL IL-15 (R&D Systems Catalog #247-ILB, Lot TLM1016102). T cells were pelleted by centrifugation for 5 minutes at 1200 rpm. The cells were stained by resuspending the pellet in 1 mL of 0.5 µM CellTrace Far Red (Invitrogen Catalog #C34565, Lot 1764050) in PBS (Corning Catalog #21-040-CV, Lot 00217005) and incubated for 30 minutes at 37° C. and 5% $CO_2$. After incubation, 9 mL of PBS was added and the cells were pelleted by centrifugation for 5 minutes at 1200 rpm. The cell pellet was resuspended in X-VIVO 15 media. Antibodies were diluted in X-VIVO 15 media containing 1 µM CellEvent Caspase-3/7 Green Detection Reagent (Invitrogen Catalog #C10423, Lot 1849709) at six times their final concentration. Stained T cells were diluted to 0.5 million cells per mL, and NK cells to 0.75 million cells per ml. The assay was performed in 384-well microscopy plates (Greiner Catalog #781936, Lot E161233K) by pipetting 10 µl of the antibodies (final concentrations: 1, and 10 µg/mL), 30 µL stained Jurkat cells (15,000 cells), and 20 µL NK cells (15,000 cells) per well.

Live imaging was performed immediately afterward using an ImageXpress Micro Confocal High-Content microscope (Molecular Devices) under environmental control (37° C., 5% $CO_2$) and images were acquired every hour from the Cy5 (CellTrace Far Red) and FITC (Caspase 3/7) channels for T cells and Caspase 3/7-positive T cells, respectively, over the course of three hours. Image analysis was performed using the MetaXpress analysis software (Molecular Devices). T cells were identified from the Cy5 channel and the amount of Caspase 3/7 signal was quantified per cell from the FITC channel. Cells with Caspase 3/7 intensity above the background were designated as apoptotic. The number of apoptotic cells was normalized against the total cell count per condition to determine a percent killing measurement.

As shown in FIG. 13B, both the anti-TIGIT antibody BA002 and its Fc variant, BA006, preferentially killed regulatory T cells as compared to effector T cells at antibody concentrations of 1 µg/mL and 10 µg/mL. BA006 generally exhibited higher levels of T cell killing, and preferential regulatory T cell killing, than did BA002.

Without wishing to be bound by any particular mechanism or theory, it is contemplated that BA002 blocks the interaction between TIGIT and PVR, thereby inhibiting TIGIT-mediated T cell and NK cell inhibitory mechanisms and promoting CD226-mediated co-stimulatory signaling. This may result in enhancement of T cell effector function and TH1 cytokine secretion. It is also contemplated that BA006 further enhances binding and signaling through FcγRIIIA and thereby promotes stronger interactions between the T cell and APC. This in turn may enhance T cell signaling while at the same time maintaining potent antagonism of TIGIT. Thus, it is contemplated that by strengthening the immune synapse between the T cell and APC, BA006 may be able to further enhance T cell effector function and cytokine secretion.

6.4 Example 4: Characterization of an Fc Variant Anti-Human TIGIT Antibody

This example describes further characterization of BA006.

6.4.1 BA006 Promotes Secretion of IL-2 by SEA-Stimulated PBMCs from a Human Donor BA006 was tested for its ability to promote secretion of IL-2 by SEA-stimulated PBMCs from a human donor.

A 5× concentrated intermediate stock of antibody BA006, antibody BA002, or isotype control antibodies for BA002 was prepared in 1.2 mL bullet tubes. Intermediate stocks of a panel of reference anti-TIGIT antibodies and an isotype control antibody for BA006 were also prepared. First, 400 µL of 50 µg/mL of each antibody was prepared in R10 media. 20 µL of antibody was then added per well to a round-bottom 96-well plate. Frozen aliquots of human PBMCs were retrieved from liquid nitrogen and immediately thawed in 37° C. water until floating ice was observed. Cells were transferred to 9 mL of pre-warmed R10 media and immediately centrifuged at 2000 rpm for two minutes. Cells were counted and checked for viability.

Samples were centrifuged at 2000 rpm for two minutes and resuspended to an intermediate concentration. An intermediate stock concentration of SEA was made by adding 10 µL of 1000 µg/mL SEA to 90 µL R10 to make an intermediate concentration of 100 µg/mL. To stimulate the cells, 12 µL of a 100 µg/mL intermediate stock of SEA was added to the 7.20 mL of cells prepared above. 60 µL of cells and SEA mixture was added into corresponding wells and incubated in tissue culture incubator at 37° C. and 5% $CO_2$ within a humidified chamber for four days. A total of $0.1 \times 10^6$ cells/well and final concentration of 100 ng/mL of SEA was used.

After four days of incubation, plates were removed from the incubator and gently agitated by hand. The plates were then centrifuged for two minutes at 2000 rpm. 5 µL of supernatant was transferred to a 384-well AlphaLISA plate for cytokine analysis. AlphaLISA kits (Perkin Elmer) were used for measurement of IL-2 secretion. Briefly, assay buffer was prepared by pipetting 2.5 mL of 10× AlphaLISA Immunoassay Buffer to 22.5 mL water. Human IL-2 analyte was used to prepare a standard dilution. A mixture of 1.6× AlphaLISA anti-IL-2 acceptor beads and biotinylated anti-IL-2 antibody was prepared in assay buffer. 8 µL was added to each well and incubated in darkness at room temperature, rotating at 500 rpm for 90 minutes. A 2.3× Streptavidin Donor Bead intermediate stock was prepared in assay buffer. 10 µL was added to each well and incubated in darkness at room temperature, rotating at 500 rpm for 20 minutes. AlphaLISA plates were briefly centrifuged at 2000 rpm. Relative light units (RLU) were measured using the AlphaScreen protocol on an EnVision Plate Reader. This experiment was run for four replicates using PBMCs obtained from two different donors.

As shown in FIG. 14, the anti-TIGIT antibodies BA002 and BA006 each enhanced IL-2 secretion by SEA-stimulated PBMCs, compared to isotype controls and reference antibodies, with BA006 inducing substantially greater IL-2 secretion compared to the other anti-TIGIT antibodies tested.

6.4.2 Combination of Anti-TIGIT Antibodies with Antibodies that Modulate Other Immune Checkpoint Molecules In this example, BA002 and its Fc variant, BA006, were tested for their capacity to promote IL-2 secretion by SEA-stimulated PBMCs when administered alone or in combination with antibodies targeting various immune checkpoint molecules (anti-PD-1, anti-PD-L1, anti-CTLA-4, and anti-LAG-3 antagonist antibodies and anti-CD137 and anti-OX40 agonist antibodies).

A 5× concentrated intermediate stock of each antibody sufficient for eight replicates for two donors was prepared in 1.2 mL bullet tubes. First, 600 µL of 50 µg/mL of each antibody was prepared in R10 media. For samples that would receive a combination of two antibodies (i.e., pairwise combinations between (i) either BA002 or BA006, and (ii) either an anti-PD-1 antagonist antibody, anti-PD-L1 antagonist antibody, anti-CD137 agonist antibody, or anti-OX40 agonist antibody), both antibodies were prepared in the same 1.2 mL bullet tube. 20 µl of antibody mixture was then added per well to a round-bottom 96-well plate to reach final concentrations of 10 µg/mL BA002 or BA006 in combination with 5 µg/mL anti-PD-1 antibody, anti-PD-L1 antibody, or anti-OX40 antibody, or 5 µg/mL BA002 or BA006 in combination with 10 µg/mL anti-CTLA-4 antibody, anti-LAG-3 antibody, or anti-CD137 antibody.

Frozen aliquots of human PBMCs were retrieved from liquid nitrogen and immediately thawed in 37° C. water. Cells were transferred to 9 mL of pre-warmed R10 media and immediately centrifuged at 2000 rpm for two minutes. Cells were counted and assessed for viability. Samples were centrifuged at 2000 rpm for two minutes and resuspended to an intermediate concentration. An intermediate stock concentration of SEA was made by diluting 10 µL of 1000 µg/mL of SEA in 90 µL of R10 to make an intermediate concentration of 100 µg/mL. To stimulate the cells, 40 µL of the 100 µg/mL intermediate stock of SEA was added to the 32 mL of cells prepared as described above. 80 µL of cells and SEA mixture was added into corresponding wells and incubated in a humidified chamber at 37° C. and 5% $CO_2$ for four days. A total of $0.1 \times 10^6$ cells/well and a final concentration of 100 ng/mL of SEA was used.

After four days of incubation, the plates were removed from the incubator and gently agitated by hand. The plates were then centrifuged for two minutes at 2000 rpm. 5 µL of the supernatant was added to a 384-well AlphaLISA plate (Perkin Elmer) for cytokine analysis. AlphaLISA kits were used for the measurements of IL-2 in accordance with manufacturer instructions. Briefly, assay buffer was prepared by pipetting 2.5 mL of 10× AlphaLISA Immunoassay Buffer to 22.5 mL water. Human IL-2 analyte was used to prepare a standard dilution. A 1.6× AlphaLISA anti-IL-2 Acceptor beads+biotinylated antibody anti-IL-2 mix was prepared in assay buffer. 8 µL were added to each well and incubated in darkness at room temperature, rotating at 500 rpm for 90 minutes. A 2.3× Streptavidin Donor Bead intermediate stock was prepared in assay buffer. 10 µL was added to each well and incubated in darkness at room temperature, rotating at 500 rpm for 20 minutes. AlphaLISA plates were briefly centrifuged at 2000 rpm. Relative light units (RLU) were then measured using the AlphaScreen protocol on an EnVision Plate Reader.

Figure 15A:
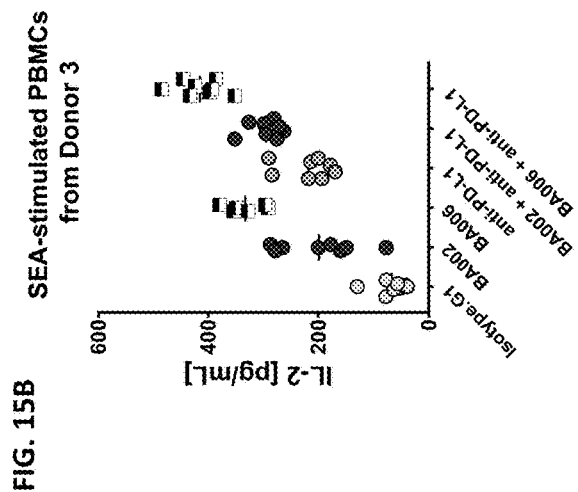
Figure 15B:
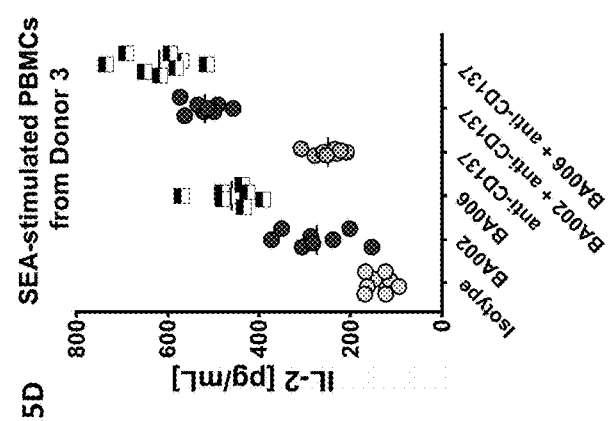
Figure 15C:
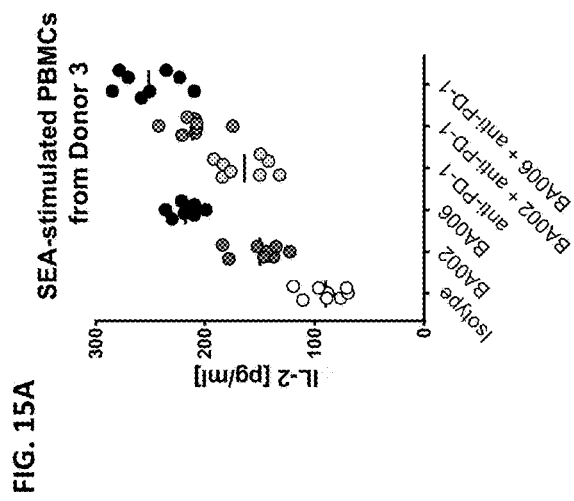
Figure 15D:
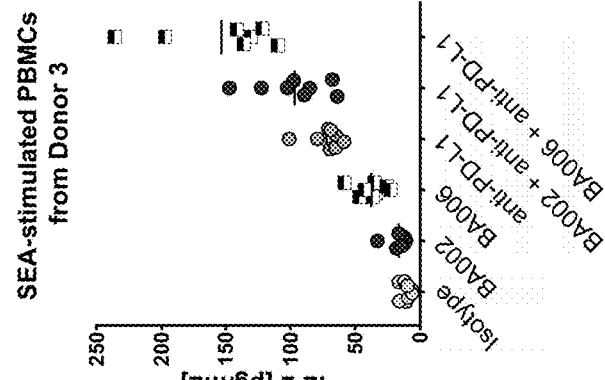

As shown in FIGS. 15A-15I, the anti-TIGIT antibodies BA002 and BA006 enhanced IL-2 secretion by SEA-stimulated PBMCs when provided alone. IL-2 secretion was further enhanced when antibody BA002 or BA006 was administered in combination with an anti-PD-1 antagonist antibody (FIG. 15A), either one of two anti-PD-L1 antagonist antibodies (FIGS. 15B-15C), an anti-CD137 agonist antibody (FIG. 15D), an anti-CTLA-4 antagonistic antibody (FIG. 15E), an anti-LAG3 antagonistic antibody tested with cells from two different donors (FIGS. 15F and 15G), or an anti-OX40 agonistic antibody tested with cells from two different donors (FIGS. 15H and 15I).

The abilities of BA002 and BA006 to activate cynomolgus PBMCs were examined by a similar method. Briefly, primary cynomolgus monkey PBMCs from donors 12 and 13 were stimulated with 100 ng/mL of staphylococcal enterotoxin A (SEA) superantigen in the presence of 10 µg/mL of BA002 or BA006, and 10 µg/mL of an anti-PD-1 antibody or an isotype control antibody for 4 days. The amounts of IL-2 and IFNγ in the culture supernatants were measured using AlphaLISA kits.

As shown in FIG. 16A, BA002 and BA006 enhanced IL-2 secretion from the cynomolgus PBMCs either alone or in combination with the anti-PD-1 antibody. Similarly, as shown in FIG. 16B, BA002 and BA006 enhanced IFNγ secretion from the cynomolgus PBMCs either alone or in combination with the anti-PD-1 antibody.

6.4.3 Anti-TIGIT Antibodies Enhance T Cell Memory Recall

In this example, the functions of BA002 and BA006 were tested in type I and type II T cell memory recall assays.

Type I T Cell Memory Recall

In the type I T cell memory recall assay, frozen aliquots of primary cytomegalovirus (CMV)-reactive HLA-A*02:01 PBMCs from a human donor were retrieved from liquid nitrogen and immediately thawed in 37° C. water until floating ice was observed. Cells were transferred to 9 mL of pre-warmed X-Vivo 15 media and immediately centrifuged at 1500 rpm, 5 min. Cells were then re-suspended in 10 mL of pre-warmed R10 media. To count cells and check the viability, 20 µL of sample was removed and added to 380 µL of viability dye, mixed and read using a Muse apparatus. Cells were then re-suspended to a 2× intermediate concentration and total volume of 10 mL.

The primary PBMCs were stimulated with a final concentration of 1.75 µg/mL of CMV pp65 peptide (NLVPMVATV; SEQ ID NO: 61), and treated with 10 µg/mL of BA002, BA006, anti-TIGIT reference antibody #7, or an isotype control antibody. Specifically, 35 µL of a 1000 µg/mL stock of CMVpp65 peptide was added to the 10 mL of cells prepared above. The cells were gently mixed by inverting, and 100 µL of the mixture were pipetted into corresponding wells. The anti-TIGIT antibodies were similarly prepared into 2× intermediate stocks, and 100 µL of each antibody was added to the wells. The cells at a final density of $2.5 \times 10^5$ cells/well were incubated in tissue culture incubator at 37° C. and 5% $CO_2$ within a humidified chamber.

Fresh CMVpp65 peptide and anti-TIGIT antibodies were added daily for 5 days. Specifically, the cells were centrifuged at 1500 rpm, 2 min, 20 µL of supernatant was removed, and 10 µL of CMV pp65 peptide and 10 µL of an anti-TIGIT antibody were added to the cells. The final concentrations of the CMV pp65 peptide and anti-TIGIT antibody were 1.75 µg/mL and 10 µg/mL, respectively. IFNγ secretion was assessed daily for six days by AlphaLISA kit (Perkin Elmer) according to the manufacturer's protocol.

As shown in FIG. 17A, BA002 and BA006 both induced increasing IFNγ secretion over time in the type I memory recall assay relative to reference antibody #7 or isotype control, and BA006 induced greater levels of IFNγ than BA002.

To characterize the expression of TIGIT on memory T cells, CMV-reactive HLA-A*02:01 PBMCs were stimulated with 1.75 μg/mL CMV pp65 peptide for 5 days as described above. CD8 effector memory T cells were enriched by sequentially gating on the FSC-A vs. SSC-A, FSC-H vs FSC-A, SSC-A vs SSC-H, CD3 vs SSC-A, CD4 vs. CD8, and CD45R0 vs. CD197. CD8 effector memory T cells were identified as $CD8^+$ $CD4^-$ $CD45RO^+$ $CD197^-$. The expression levels of TIGIT, CD226, and CD96 on CD8 effector memory T cells were determined by flow cytometry.

As shown in FIG. 17B, TIGIT, CD226, and CD96 were all expressed on the CD8 effector memory T cells. This result suggested that an anti-TIGIT antibody could have a direct effect on CD8 effector memory T cells.

To further characterize the function of the anti-TIGIT antibodies in T cell memory recall, CMV-reactive HLA-A*02:01 PBMCs were stimulated with 1.75 μg/mL CMV pp65 peptide in the presence of 10 μg/mL BA002, BA006, anti-TIGIT reference antibody #7, and/or an anti-PD-1 antibody for 5 days as described above. The secretion of IFNγ and TNFα was assessed by AlphaLISA kits (Perkin Elmer) according to the manufacturer's protocol. In a similar experiment, CMV-reactive HLA-A*02:01 PBMCs were stimulated with 1.75 μg/mL CMV pp65 peptide in the presence of 10 μg/mL BA002, BA006, anti-TIGIT reference antibody #7, and/or an anti-PD-1 antibody for 6 days as described above. CD8 effector memory T cells were identified as $CD8^+$ $CD45RO^+$ $CD197^-$, and CD4 effector memory T cells were identified as $CD4^+$ $CD45RO^+$ $CD197^-$, and T cell proliferation was assessed by Ki67 expression by flow cytometry.

As shown in FIGS. 17C and 17D, BA002 and BA006 both enhanced IFNγ and TNFα secretion in the type I memory recall assay, and BA006 was more potent than BA002. Addition of the anti-PD-1 antibody further increased IFNγ and TNFα secretion. BA002 and BA006 also enhanced CD8 effector memory T cell proliferation in the type I memory recall assay, and BA006 was more potent than BA002 (FIG. 17E). Addition of the anti-PD-1 antibody did not substantially increase the CD8 effector memory T cell proliferation in the BA006 treatment group. The proliferation of CD4 effector memory T cells was not as substantially affected by BA002, BA006, or the anti-PD-1 antibody (FIG. 17F).

Type II T Cell Memory Recall

In the type II T cell memory recall assay, 1 μg/mL of CMV whole antigen (Astarte Biologics, Cat #1004), known to be primarily processed and presented on MHC class II molecules (though these antigens may also be cross-presented on MHC class I molecules), were used for stimulating CMV-reactive PBMCs. Specifically, 200 μL of a 100 μg/mL stock of CMV whole antigen was added to 10 mL of donor PBMCs in R10 medium. The cells were gently mixed by inverting, and 100 μL of the mixture was pipetted into corresponding wells. 10 μg/mL of an anti-PD-1 antibody was added to some of the wells. The cells were incubated in tissue culture incubator at 37° C. and 5% CO2 within a humidified chamber for 4 days at a density of 220,000 cells/well (Donor 11) or 250,000 cells/well (Donor 10). The cell samples were analyzed by sequentially gating on FSC-A vs. SSC-A, FSC-H vs FSC-A, SSC-A vs SSC-H, CD3 vs SSC-A, and CD4 vs CD8. The $CD4^+$ T cell subset was identified as $CD4^+$ $CD8^-$, and the $CD8^+$ T cell subset was identified as $CD8^+$ $CD4^-$. Within each subset, naïve T cells, effector T cells ($T_{Eff}$), effector memory T cells ($T_{EM}$), and central memory T cells ($T_{CM}$) were identified as $CD45RO^-$ $CD197^+$, $CD45RO^-CD197^-$, $CD45RO^+$ $CD197^-$, and $CD45RO^+$ $CD197^+$, respectively. Each subset was analyzed for its expression of TIGIT as detected by an APC-conjugated anti-TIGIT antibody.

As shown in FIG. 18A, the CMV whole antigen increased the expression level of TIGIT on $CD4^+$ $T_{Eff}$, $T_{EM}$, and $T_{CM}$ cells, and the anti-PD-1 antibody further enhanced TIGIT expression on $T_{EM}$ and $T_{CM}$ cells. Increased TIGIT expression was also observed on $CD8^+$ $T_{Eff}$, $T_{EM}$, and $T_{CM}$ cells (FIG. 18B), likely due to the cross-presentation of the antigens on MHC class I molecules.

To further characterize the function of anti-TIGIT antibodies in type II T cell memory recall, CMV-reactive PBMCs were incubated with 1 μg/mL of CMV whole antigen in the presence or absence of 10 μg/mL of BA002, BA006, anti-TIGIT reference antibody #7, and/or an anti-PD-1 antibody for 4 days. IFNγ secretion in the culture medium was analyzed by AlphaLISA kits (Perkin Elmer) according to the manufacturer's protocol.

As shown in FIGS. 18C and 18D, BA002 and BA006, when combined with the anti-PD-1 antibody, both enhanced IFNγ secretion from the PBMCs, and BA006 was more potent than B A002.

6.4.4 Anti-TIGIT Antibodies Enhance Antigen-Specific T Cell Cytotoxicity

In this example, the effects of BA002 and BA006 on T cell cytotoxicity were tested. Specifically, primary human T cells ectopically expressing an NY-ESO-1 TCR were co-cultured with NY-ESO-1 expressing U251MG tumor cells for 13 days to model T cell exhaustion. For live imaging, KARPAS 299 cells ectopically expressing NY-ESO-1 were first incubated with 1 μM CellTrace Far Red Cell Proliferation Dye (Life Technologies) in PBS for 30 minutes at 37° C. and 5% $CO_2$ to label the cell bodies. The labeled cells were resuspended in fresh culture media and seeded at a density of 15,000 cells per well in a 384-well microscopy plate. The exhausted T cells were then added at a density of 30,000 cells per well. BA002, BA006, or a corresponding isotype control antibody was added to the co-culture at the concentration of 10 μg/mL in combination with 10 μg/mL of an anti-PD-1 antibody or an isotype control antibody.

Live images were collected using an ImageXpress Micro Confocal High-Content microscope (Molecular Devices) at 37° C. and 5% $CO_2$ in the Cy5 channel (CellTrace Far Red Cell Proliferation Dye) every two hours over a course of 24 hours. In total, for each condition at each time point, eight images (20× magnification) were acquired with an average of 1,211 cells (±88 cells, standard deviation). Image analysis to quantify the amount of killed KARPAS 299 cells was performed using MetaXpress analysis software (Molecular Devices).

As shown in FIG. 19, BA002 and BA006, either alone or in combination with the anti-PD-1 antibody, enhanced the cytotoxicity of the T cells against the antigen-expressing tumor cells.

6.4.5 Anti-TIGIT Antibodies Enhance NK Cell Activity

In this example, the effects of BA002 and BA006 on NK cell activation were studied.

Briefly, freshly thawed PBMCs were cultured in RPMI medium supplemented with 10% fetal bovine serum and 100UI of IL-2 and IL-15. The cells were treated with 20 μg/mL of BA002, BA006, reference antibody #1 (human IgG1), reference antibody #1 Fc-enhanced variant (human IgG1 with S239D/A330L/I332E substitutions in the Fc region), or a corresponding isotype control antibody for 5 hours. K562 cells were optionally added as target cells for co-culture at the amount of 10% of the PBMCs.

To stain the NK cell activation marker CD107a, an anti-CD107a antibody conjugated with APC (Biolegend) was added to the cell culture at a 1:400 dilution. Monensin (eBiosciences) was also added to prevent acidification of endocytic vesicles, thereby avoiding degradation of CD107a that was re-internalized from the cell surface. Additionally, Brefeldin A (eBiosciences) was added to the cell culture to prevent exocytosis of cytokine-containing vesicles, thereby allowing visualization of cytokine production following stimulation.

Following the treatment, the PBMCs were stained for cell surface markers for 30 min using an anti-CD56 antibody conjugated with BUV737 (BD Biosciences) and an anti-CD3 antibody conjugated with BV421 (Biolegend). After washing, the cells were incubated in BD Cytofix/Cytoperm solution for 20 min at 4° C. for fixation and permeabilization. The cells were then washed twice and incubated for 30 min at 4° C. with an anti-IFNγ antibody conjugated with AlexaFluor700 and an anti-TNFα antibody conjugated with PECy7 (BD Biosciences) in BD Perm/Wash solution. The stained cells were analyzed by flow cytometry.

As shown in FIG. 20A, the lymphocyte population was identified by a first plot gating on forward scatter-Area (FSC-A) versus side scatter Area (SSC-A), and a second plot gating on FSC-A versus FSC-Height (FSC-H) for selection of single cells. The NK cells were further identified from the lymphocyte population as $CD3^-$ $CD56^+$. The activated NK cells were identified as $CD107a^+$.

As shown in FIG. 20B, the anti-TIGIT antibodies enhanced the activation marker of CD107a on the NK cells from PBMCs. The anti-TIGIT antibodies also increased the production of IFNγ (FIG. 20C) and TNFα (FIG. 20D) in the NK cells. Similar effects were observed with the NK cells in PBMCs co-cultured with K562 target cells (FIGS. 20E-20G). BA006 showed more potent effects on NK cell activation than BA002. Similarly, the reference antibody #1 variant comprising S239D/A330L/I332E substitutions in the Fc region was more potent in NK cell activation than reference antibody #1 comprising a wild type IgG1 Fc region.

6.5 Example 5: Epitope Mapping

The epitopes of BA002 and BA006 were studied by hydrogen-deuterium exchange (HDX) mass spectrometry and antigen mutagenesis.

6.5.1 Epitope Mapping of Anti-TIGIT Antibody by HDX

The interaction of TIGIT with the $F(ab')_2$ fragment of BA002 (BA002-$F(ab')_2$) was evaluated using the methods described below.

TIGIT Interaction with Anti-Human TIGIT F(Ab')$_2$

10 μL human TIGIT (6.16 μg) or 20 μL human TIGIT and F(ab')$_2$ mixture (6.16 μg: 30.8 μg) was incubated with 110 μL deuterium oxide labeling buffer (50 mM sodium phosphate, 100 mM sodium chloride at pD 7.4) for 0 sec, 60 sec, 300 sec, 1800 sec, 7200 sec and 14400 sec at 24° C. Hydrogen/deuterium exchange was quenched by adding 125 μL of 4 M guanidine hydrochloride, 0.85 M TCEP buffer (final pH 2.5). Subsequently, the quenched samples were subjected to on column pepsin/protease XIII digestion and LC-MS analysis as described below. The mass spectra were recorded in MS only mode.

HDX Data Analysis

Raw MS data was processed using HDX WorkBench software for the analysis of H/D exchange MS data. The deuterium levels were calculated using the average mass difference between the deuterated peptide and its native form ($t_0$). For the calculation of deuterium incorporation, the mass spectra for a given peptide were combined across the extracted ion chromatogram peak and the weighted average m/z was calculated. The mass increase from the mass of the native peptide (0 minute) to the weighted averaged mass corresponds to the level of deuterium incorporation.

Pepsin/Protease XIII Digestion and LC-MS

5 μg of native or human TIGIT in 120 μL control buffer (50 mM phosphate, 100 mM sodium chloride at pH 7.4) was denatured by adding 120 μL of 4 M guanidine hydrochloride, 0.85 M TCEP buffer (final pH is 2.5) and incubating the mixture for three minutes at 24° C. The mixture was then subjected to on-column pepsin/protease XIII digestion using a packed pepsin/protease XIII (w/w, 1:1) column, and the resultant peptides was analyzed using an UPLC-MS system comprised of a Waters Acquity UPLC coupled to a Q Exactive™ Hybrid Quadrupole-Orbitrap Mass Spectrometer (Thermo). The peptides were separated on a 50 mm×1 mm C8 column with a 20.5 min gradient from 2-28% solvent B (0.2% formic acid in acetonitrile). Peptide identification was performed by searching MS/MS data against the human TIGIT sequence with Mascot. The mass tolerance for the precursor and product ions was 10 ppm and 0.05 Da, respectively.

Epitope Binding of Anti-Human TIGIT F(Ab')2

Most of the TIGIT peptides displayed identical or similar deuterium levels with and without BA002-F(ab')$_2$ present. Several peptide segments, however, were found to have significantly decreased deuterium incorporation upon BA002-F(ab')$_2$ binding. All the residues in this paragraph are numbered according to the full length TIGIT sequence set forth in SEQ ID NO: 29. Two regions, consisting of residues 110-125 (YHTYPDGTYTGRIFLE, SEQ ID NO: 31) and residues 54-57 (VTQV, SEQ ID NO: 32), exhibited substantial deuterium protection when human TIGIT was bound to BA002-F(ab')$_2$. An additional region consisting of residues 68-81 (ICNADLGWHISPSF, SEQ ID NO: 33) also showed deuterium protection when human TIGIT was bound to BA002-F(ab')$_2$. Thus, these regions correspond to one or more epitopes, or portions thereof, of BA002 on human TIGIT, as shown in FIG. 21.

6.5.2 Epitope Mapping of Anti-TIGIT Antibody by Antigen Mutagenesis

In this example, the binding of BA006, as well as six reference antibodies, to human TIGIT and mutant proteins was characterized by surface plasmon resonance (SPR). Briefly, the structure of the extracellular domain of human TIGIT was obtained from the PDB database (reference No. 3UDW) and was isolated from the structure of a TIGIT-PVR complex. Among the amino acid residues located within the epitope regions identified from Section 6.5.1, T34, Q35, I47, N49, L52, H55, P58, H90, T96, T98, R100, and F102 were found to have a side chain facing the PVR-binding surface (FIG. 22A). These residues were selected for antigen mutagenesis analysis. The amino acid sequences of the mutated human TIGIT proteins are provided in Table 3.

In the SPR experiment, the anti-TIGIT antibodies were individually captured at a flow rate of 10 μl/min on flow-cells 2, 3 and 4, keeping the flow-cell 1 as reference, on a CM5 chip on which an anti-human Fab antibody had been immobilized by amine coupling. The wild-type and mutant TIGIT proteins were independently run over all the flow-cells at a concentration of 100 nM at 50 μl/min for 90 seconds, followed by a dissociation phase of 400 seconds. The maximum binding response was measured based on the sensorgrams, and the percentages of binding of each antibody relative to the affinity to the wild-type TIGIT protein are shown in Table 5.

TABLE 5

Binding of anti-TIGIT antibodies to wild-type and mutant TIGIT.

| TIGIT | SEQ ID NO | BA006 | Ref. 1 | Ref. 2 | Ref. 3 | Ref. 4 | Ref. 5 | Ref. 6 |
|---|---|---|---|---|---|---|---|---|
| WT | 42 | + | + | + | + | + | + | + |
| T34A | 43 | + | + | + | + | + | + | + |
| Q35A | 44 | − | +/− | +/− | +* | + | + | +/− |
| I47E | 45 | − | + | + | − | + | +* | − |
| N49A | 46 | +/− | + | + | + | + | + | +/− |
| L52A | 47 | + | − | + | +* | + | +/−* | − |
| L52E | 48 | +/− | − | + | +/−* | +* | − | − |
| H55A | 49 | + | − | + | +* | +* | + | +* |
| P58A | 50 | + | + | + | + | + | + | + |
| H90A | 51 | +/− | +/− | +/− | + | + | + | +/− |
| T96A | 52 | − | + | + | + | + | + | + |
| T96I | 53 | − | + | + | + | + | + | + |
| T98A | 54 | + | + | + | + | + | + | + |
| R100A | 55 | + | + | + | + | + | + | + |
| F102A | 56 | + | + | +/− | + | + | + | + |
| C48Y, N49S, A50V | 57 | +/− | + | + | + | + | + | +* |
| I56V, S57A, P58S, S59V | 58 | + | + | +/− | + | + | +* | +/−* |
| T96I, T98K | 59 | − | + | + | + | + | + | + |

+: at least 70% relative to the binding affinity to wild-type TIGIT protein
+/−: less than 70% and at least 20% relative to the binding affinity to wild-type TIGIT protein
−: less than 20% relative to the binding affinity to wild-type TIGIT protein
*faster dissociation rate observed As shown in Table 5, the single mutations of Q35A, I47E, N49A, H90A, T96A, and T96I reduced the binding of BA006 to human TIGIT, suggesting that BA006 likely binds to TIGIT via one or more conformational epitopes comprising Q35, I47, N49, H90, and/or T96 (FIG. 22B). BA006 was not sensitive to the mutations of L52A, H55A, F102A, and I56V/S57A/P58S/S59V in these experiments, indicating that BA006 likely did not bind directly to L52, H55, I56, S57, P58, S59, or F102 of human TIGIT. This set of epitopes is unique and is not identical to the epitope mapping results of the reference antibodies.

6.6 Example 6: In Vivo Pharmacology of an Anti-TIGIT Antibody in a Mouse Model As described above, BA002 and BA006 robustly enhanced T cell activities in vitro. However, these antibodies did not bind to murine TIGIT protein. In order to study the in vivo functions of BA002 and BA006 in mouse models, surrogate antibodies that bound to murine TIGIT were generated. Briefly, the VH and VL regions of a TIGIT reference antibody were linked to murine heavy chain and light chain constant regions, respectively. Surrogate antibody mIgG2a, surrogate antibody mIgG2a-N297Q, surrogate antibody mIgG1, and surrogate antibody mIgG2 (Fc enhanced) have different Fc regions, but share the same light chain sequence. It is generally recognized in the art that mIgG2a is functionally similar to human IgG1. The amino acid sequences of these antibodies are shown in Table 6.

TABLE 6

Amino acid sequences of mouse surrogate anti-TIGIT antibodies.

| Description | Amino Acid Sequence | SEQ ID NO: |
|---|---|---|
| Surrogate antibody VH | XVQLVESGGGLTQPGKSLKLSCEASGFTFSSFTMHW VRQSPGKGLEWVAFIRSGSGIVFYADAVRGRFTISR DNAKNLLFLQMNDLKSEDTAMYYCARRPLGHNTF DSWGQGTLVTVSS, wherein X is glutamate (E) or pyroglutamate (pE) | 62 |
| Surrogate antibody VL | DIVMTQSPSSLAVSPGEKVTMTCKSSQSLYYSGVKE NLLAWYQQKPGQSPKLLIYYASIRFTGVPDRFTGSG SGTDYTLTITSVQAEDMGQYFCQQGINNPLTFGDGT KLEIK | 63 |
| Surrogate antibody mIgG2a full length heavy chain without C-terminal lysine (used in the experiments in Sections 6.6.2, 6.6.3, and 6.6.4) | XVQLVESGGGLTQPGKSLKLSCEASGFTFSSFTMHW VRQSPGKGLEWVAFIRSGSGIVFYADAVRGRFTISR DNAKNLLFLQMNDLKSEDTAMYYCARRPLGHNTF DSWGQGTLVTVSSAKTTAPSVYPLAPVCGDTTGSSV TLGCLVKGYFPEPVTLTWNSGSLSSGVHTFPAVLQS DLYTLSSSVTVTSSTWPSQSITCNVAHPASSTKVDKK IEPRGPTIKPCPPCKCPAPNLLGGPSVFIFPPKIKDV LMISLSPIVTCVVVDVSEDDPDVQISWFVNNVEVHTA QTQTHREDYNSTLRVVSALPIQHQDWMSGKEFKCK VNNKDLPAPIERTISKPKGSVRAPQVYVLPPPEEEMT KKQVTLTCMVTDFMPEDIYVEWTNNGKTELNYKN TEPVLDSDGSYFMYSKLRVEKKNWVERNSYSCSVV HEGLHNHHTTKSFSRTPG, wherein X is glutamate (E) or pyroglutamate (pE) | 64 |
| Surrogate antibody mIgG2a full length heavy chain with C-terminal lysine (used in the experiments in Section 6.6.1) | XVQLVESGGGLTQPGKSLKLSCEASGFTFSSFTMHW VRQSPGKGLEWVAFIRSGSGIVFYADAVRGRFTISR DNAKNLLFLQMNDLKSEDTAMYYCARRPLGHNTF DSWGQGTLVTVSSAKTTAPSVYPLAPVCGDTTGSSV TLGCLVKGYFPEPVTLTWNSGSLSSGVHTFPAVLQS DLYTLSSSVTVTSSTWPSQSITCNVAHPASSTKVDKK IEPRGPTIKPCPPCKCPAPNLLGGPSVFIFPPKIKDV LMISLSPIVTCVVVDVSEDDPDVQISWFVNNVEVHTA QTQTHREDYNSTLRVVSALPIQHQDWMSGKEFKCK VNNKDLPAPIERTISKPKGSVRAPQVYVLPPPEEEMT KKQVTLTCMVTDFMPEDIYVEWTNNGKTELNYKN TEPVLDSDGSYFMYSKLRVEKKNWVERNSYSCSVV HEGLHNHHTTKSFSRTPGK, wherein X is glutamate (E) or pyroglutamate (pE) | 65 |
| Surrogate antibody mIgG2a-N297Q full length heavy chain with C-terminal lysine (used | XVQLVESGGGLTQPGKSLKLSCEASGFTFSSFTMHW VRQSPGKGLEWVAFIRSGSGIVFYADAVRGRFTISR DNAKNLLFLQMNDLKSEDTAMYYCARRPLGHNTF DSWGQGTLVTVSSAKTTAPSVYPLAPVCGDTTGSSV TLGCLVKGYFPEPVTLTWNSGSLSSGVHTFPAVLQS DLYTLSSSVTVTSSTWPSQSITCNVAHPASSTKVDKK IEPRGPTIKPCPPCKCPAPNLLGGPSVFIFPPKIKDV LMISLSPIVTCVVVDVSEDDPDVQISWFVNNVEVHTA QTQTHREDYQSTLRVVSALPIQHQDWMSGKEFKCK VNNKDLPAPIERTISKPKGSVRAPQVYVLPPPEEEMT KKQVTLTCMVTDFMPEDIYVEWTNNGKTELNYKN TEPVLDSDGSYFMYSKLRVEKKNWVERNSYSCSVV HEGLHNHHTTKSFSRTPGK, wherein X is glutamate (E) or pyroglutamate (pE) | 66 |

TABLE 6-continued

Amino acid sequences of mouse surrogate anti-TIGIT antibodies.

| Description | Amino Acid Sequence | SEQ ID NO: |
|---|---|---|
| Surrogate antibody-mIgG1 full length heavy chain with C-terminal lysine (used in the experiments in Section 6.6.1) | XVQLVESGGGLTQPGKSLKLSCEASGFTFSSFTMHW VRQSPGKGLEWVAFIRSGSGIVFYADAVRGRFTISR DNAKNLLFLQMNDLKSEDTAMYYCARRPLGHNTF DSWGQGTLVTVSSAKTTPPSVYPLAPGSAAQTNSM VTLGCLVKGYFPEPVTVTWNSGSLSSGVHTFPAVLQ SDLYTLSSSVTVPSSTWPSETVTCNVAHPASSTKVD KKIVPRDCGCKPCICTVPEVSSVFIFPPKPKDVLTIT LTPKVTCVVVDISKDDPEVQFSWFVDDVEVHTAQTQ PREEQFNSTFRSVSELPIMHQDWLNGKEFKCRVNSA AFPAPIEKTISKTKGRPKAPQVYTIPPPKEQMAKDKV SLTCMITDFFPEDITVEWQWNGQPAENYKNTQPIMD TDGSYFVYSKLNVQKSNWEAGNTFTCSVLHEGLHN HHTEKSLSHSPGK, wherein X is glutamate (E) or pyroglutamate (pE) | 67 |
| Surrogate antibody mIgG2 (Fc enhanced) full length heavy chain without C-terminal lysine (used in the experiments in Sections 6.6.2, 6.6.3, and 6.6.4) | XVQLVESGGGLTQPGKSLKLSCEASGFTFSSFTMHW VRQSPGKGLEWVAFIRSGSGIVFYADAVRGRFTISR DNAKNLLFLQMNDLKSEDTAMYYCARRPLGHNTF DSWGQGTLVTVSSAKTTAPSVYPLAPVCGDTTGSSV TLGCLVKGYFPEPVTLTWNSGSLSSGVHTFPAVLQS DLYTLSSSVTVTSSTWPSQSITCNVAHPASSTKVDKK IEPRGPTIKPCPPCKCPAPNLLGGPDVFIFPPKIKDV LMISLSPIVTCVVVDVSEDDPDVQISWFVNNVEVHTA QTQTHREDYNSTLRVVSALPIQHQDWMSGKEFKCK VNNKDLPLPEERTISKPKGSVRAPQVYVLPPPEEEMT KKQVTLTCMVTDFMPEDIYVEWTNNGKTELNYKN TEPVLDSDGSYFMYSKLRVEKKNWVERNSYSCSVV HEGLHNHHTTKSFSRTPG, wherein X is glutamate (E) or pyroglutamate (pE) | 68 |
| Surrogate antibody IgK full length light chain | DIVMTQSPSSLAVSPGEKVTMTCKSSQSLYYSGVKE NLLAWYQQKPGQSPKLLIYYASIRFTGVPDRFTGSG SGTDYTLTITSVQAEDMGQYFCQQGINNPLTFGDGT KLEIKRADAAPTVSIFPPSSEQLTSGGASVVCFLNNF YPKDINVKWKIDGSERQNGVLNSWTDQDSKDSTYS MSSTLTLTKDEYERHNSYTCEATHKTSTSPIVKSFNR NEC | 69 |

6.6.1 Anti-TIGIT Antibodies Inhibited Tumor Growth in an Early Intervention Model The mouse surrogate antibodies were tested in an early intervention mouse model. Specifically, Balb/c mice (Jackson Labs #000651) 6-8 weeks of age were first acclimated for two weeks and were shaved and tagged. CT26 mouse colorectal carcinoma cells (ATCC® CRL-2638™) were expanded in tissue culture in RPMI medium supplemented with 10% heat-inactivated FBS and normocin for 1 week. The mice were injected subcutaneously with $1 \times 10^5$ CT26 cells suspended in 100 μL of PBS. The implanted tumor cells were allowed to establish for 7 days to reach the size of approximately 35-40 mm³. The mice were then randomized and treated with 200 μg of surrogate antibody mIgG2a, surrogate antibody mIgG2a-N297Q, surrogate antibody mIgG1, or an isotype control antibody (mIgG2a) twice a week via intraperitoneal administration. For comparison, 200 μg of an anti-PD-1 antibody was administered to the mice intraperitoneally twice a week. The tumor volumes were measured biweekly by caliper, and were calculated as length×width×0.5.

As shown in FIGS. 23A-23F, surrogate antibody mIgG2a led to a complete response in one out of five mice and substantially suppressed tumor growth in three out of five mice. The anti-PD-1 antibody also reduced the rate of tumor growth. By contrast, surrogate antibody mIgG2a-N297Q and surrogate antibody mIgG1 had little effect on tumor growth. This result corroborated the in vitro observation that the effector function of Fc enhanced the ability of an anti-TIGIT antibody to activate T cell immunity.

Next tested were combination treatments of an anti-TIGIT antibody and an anti-PD-1 antibody in the early intervention model. Mice harboring CT26 tumors were generated as described above, and were treated with 200 μg of surrogate antibody mIgG2a, surrogate antibody mIgG2a-N297Q, surrogate antibody mIgG1, or an isotype control antibody (mIgG2a) in combination with 200 μg of the anti-PD-1 antibody twice a week via intraperitoneal administration.

As shown in FIGS. 24A-24G, the combination treatment of surrogate antibody mIgG2a and the anti-PD-1 antibody led to a complete response in three out of five mice. By contrast, the combination of surrogate antibody mIgG2a-N297Q and the anti-PD-1 antibody had little effect on tumor growth relative to the anti-PD-1 antibody alone.

6.6.2 Anti-TIGIT Antibodies Inhibit Tumor Growth in a Late Intervention Model The anti-TIGIT antibodies and combinations were also examined in a late intervention mouse model. Specifically, Balb/c mice (Jackson Labs #000651) 6-8 weeks of age were first acclimated for two weeks and were shaved and tagged. CT26 mouse colorectal carcinoma cells (ATCC® CRL-2638TM) were expanded in tissue culture in RPMI medium supplemented with 10% heat-inactivated FBS and normocin for 1 week. The mice were injected with $5 \times 10^4$ CT26 cells in 100 μL of PBS subcutaneously. The implanted tumor cells were allowed to establish for 12 days, when the mean tumor size was 85 mm³. The mice without detectable tumors or with tumor volumes greater than 300 mm³ were excluded from the study. On days 12, 16, and 20 post-tumor implantation, the mice were injected intraperitoneally with 100 μg of surrogate antibody mIgG2a or surrogate antibody mIgG2a (Fc enhanced), or the respective isotype control antibody. The tumor volumes were measured biweekly by caliper, and were calculated as length×width²×0.5.

As shown in FIGS. 25A-25E, surrogate antibody mIgG2a and surrogate antibody mIgG2a (Fc enhanced) both reduced tumor growth, and surrogate antibody mIgG2a (Fc enhanced) was more potent than surrogate antibody mIgG2a.

The effect of combining an anti-TIGIT antibody with another checkpoint targeting molecule on tumor suppression was also tested in the late intervention model. Specifically, the mice were inoculated as described above, and the mean tumor size 12 days after inoculation was 70-120 mm³. The mice were treated with 100 µg of surrogate antibody mIgG2a (Fc enhanced), 100 µg of an anti-PD-1 antibody or an anti-CTLA-4 antibody, or a combination thereof on days 12, 16, and 20 post-tumor implantation. Tumor growth was monitored bi-weekly using a digital caliper.

As shown in FIGS. 26A and 26B, combinations of surrogate antibody mIgG2a (Fc enhanced) with the anti-PD-1 antibody or the anti-CTLA-4 antibody substantially reduced tumor growth in this animal model.

6.6.3 Anti-TIGIT Antibodies Promote Infiltration of $CD8^+$ T Cells into Tumors

The inhibition of tumor growth by the anti-TIGIT antibodies could be due to activation of effector T cells or suppression of regulatory T cells (Tregs). To understand the mechanism of this regulation, BALB/c mice were inoculated with $5 \times 10^4$ CT26 cells subcutaneously. When the tumors reached approximately 50-80 $mm^3$ after 12-14 days, the mice were randomized and treated with a single dose of 100 µg of surrogate antibody mIgG2a, surrogate antibody mIgG2a (Fc enhanced), or the respective isotype control antibody via intraperitoneal administration. An anti-GITR antibody in the mIgG2a format ("DTA-1 (mIgG2a)") that was known to deplete Tregs was used as a positive control. The mice were sacrificed at 0, 24, 72, or 120 hours post-treatment for collection of tumor and tumor-draining lymph node (TDLN) samples (FIG. 27A).

As shown in FIGS. 27B-27F, administration of surrogate antibody mIgG2a or surrogate antibody mIgG2a (Fc enhanced) did not substantially affect the amount of intratumoral $FoxP3^+$ Tregs, intratumoral $CD4^+$ non-Tregs, or TDLN $FoxP3^+$ Tregs, but significantly increased the amount of intratumoral $CD8^+$ T cells. Thus, while not wishing to be bound by theory, it was hypothesized that surrogate antibody mIgG2a or surrogate antibody mIgG2a (Fc enhanced) inhibited tumor growth by promoting infiltration of $CD8^+$ T cells in the tumors.

6.6.4 Anti-TIGIT Antibodies Activate Effector T Cells in an FcγRIV-Dependent Manner As described above, surrogate antibody mIgG2a (Fc enhanced) was more potent than surrogate antibody mIgG2a in tumor suppression, suggesting that the ability of the Fc to bind to Fcγ receptors might play a role in the function of anti-TIGIT antibodies. Murine FcγRIV was known as a primary receptor of mIgG2a, and the Fc region of surrogate antibody mIgG2a (Fc enhanced) was known to bind to murine FcγRIV with a higher affinity than the Fc region of surrogate antibody mIgG2a. Thus, the ability of surrogate antibody mIgG2a (Fc enhanced) to enhance FcγRIV signaling was examined. Briefly, CHO cells engineered to express murine TIGIT were cultured in RPMI 1640 medium supplemented with 10% FBS, 10 mM HEPES, 1× Pen/Strep-Glutamine, and 1 µg/mL puromycin. The cells were resuspended in fresh culture medium at $2.4 \times 10^6$ cells/mL, and 25 µL of the cells were added to each well of a white 96-well assay plate. A dilution series of surrogate antibody mIgG2a, or its isotype control antibody, or surrogate antibody mIgG2a (Fc enhanced) or its isotype control antibody were prepared in culture medium, and 25 µl of the antibody was added to the cells. Effector T cells (Jurkat cells) stably expressing murine FcγRIV and having a firefly luciferase reporter under the control of a nuclear factor of activated T-cells (NFAT)-responsive promoter (ADCC V variant, Promega) were thawed and resuspended at $6 \times 10^6$ cells/mL in RPMI 1640 supplemented with 4% FBS, and 25 µl of the effector cells were added to each well. The co-culture was incubated at 37 C, 5% CO2 for 20 hours. 75 µl of Bio-Glo Luciferase assay reagent was added to each well, and luminescence values were measured with a plate reader (Envision) after 5-10 minutes of incubation at room temperature.

As shown in FIG. 28A, surrogate antibody mIgG2a (Fc enhanced) induced a stronger NFAT activity in the effector T cells than surrogate antibody mIgG2a, indicating that surrogate antibody mIgG2a (Fc enhanced) had greater effector function.

To further elucidate the function of FcγRIV in T cell activation mediated by anti-TIGIT antibodies, C57BL/6 mice were pretreated with 100 µg of an anti-FcγRIV antibody (Biolegend, Catalog #149502) or vehicle control by intraperitoneal injection. After 30 minutes, the mice were injected intraperitoneally with 100 µg of the SEB superantigen together with 100 µg of surrogate antibody mIgG2a, an anti-CTLA-4 antibody (mIgG2a), or an isotype control antibody. T cells were isolated from the peripheral blood after 3 days, and SEB-specific ($V\beta8^+$) $CD4^+$ or $CD8^+$ effector T cells ($CD44^+$ $CD62L^-$) were quantified by flow cytometry for proliferation (% Ki67 positive).

As shown in FIGS. 28B and 28C, the anti-FcγRIV antibody significantly reduced the proliferation of antigen-specific $CD4^+$ and $CD8^+$ effector T cells mediated by surrogate antibody mIgG2a or the anti-CTLA-4 antibody. Thus, FcγR co-engagement enhanced T cell co-stimulation mediated by the anti-TIGIT and anti-CTLA-4 antibodies in this murine model of T cell priming.

The invention is not to be limited in scope by the specific embodiments described herein. Indeed, various modifications of the invention in addition to those described will become apparent to those skilled in the art from the foregoing description and accompanying figures. Such modifications are intended to fall within the scope of the appended claims.

All references (e.g., publications or patents or patent applications) cited herein are incorporated herein by reference in their entireties and for all purposes to the same extent as if each individual reference (e.g., publication or patent or patent application) was specifically and individually indicated to be incorporated by reference in its entirety for all purposes.

Other embodiments are within the following claims.

What is claimed:

1. An isolated antibody that specifically binds to human TIGIT, the antibody comprising a heavy chain variable region (VH) comprising the CDRH1, CDRH2, and CDRH3 amino acid sequences of the VH amino acid sequence set forth in SEQ ID NO: 9, and a light chain variable region (VL) comprising the CDRL1, CDRL2, and CDRL3 amino acid sequences of the VL amino acid sequence set forth in SEQ ID NO: 10.

2. The isolated antibody of claim 1, wherein the antibody comprises the CDRH1, CDRH2, CDRH3, CDRL1, CDRL2, and CDRL3 amino acid sequences of SEQ ID NOs 1, 3, 5, 6, 7, and 8; or 2, 4, 5, 6, 7, and 8, respectively.

3. The isolated antibody of claim 1, wherein the VH comprises an amino acid sequence that is at least 75% identical to the amino acid sequence of SEQ ID NO: 9.

4. The isolated antibody of claim 3, wherein the VH comprises the amino acid sequence of SEQ ID NO: 9.

5. The isolated antibody of claim 1, wherein the VL comprises an amino acid sequence that is at least 75% identical to the amino acid sequence of SEQ ID NO: 10.

6. The isolated antibody of claim 5, wherein the VL comprises the amino acid of SEQ ID NO: 10.

7. The isolated antibody of claim 1 wherein the VH and VL comprise the amino acid sequences of SEQ ID NOs: 9 and 10, respectively.

8. The isolated antibody of claim 1, wherein:
   (a) the VH comprises an amino acid sequence derived from a human IGHV1 69*01 germline sequence;
   (b) the VH comprises an amino acid sequence derived from a human IGHV1 69*06 germline sequence;
   (c) the VH comprises an amino acid sequence derived from a human IGHV1 69*12 germline sequence;
   (d) the VL comprises an amino acid sequence derived from a human IGLV2 14*01 germline sequence;
   (e) the VL comprises an amino acid sequence derived from a human IGLV2 23*02 germline sequence; and/or
   (f) the VL comprises an amino acid sequence derived from a human IGLV2 11*01 germline sequence.

9. The isolated antibody of claim 1, wherein the VH comprises an amino acid region that is at least 75% identical to the amino acid sequence of SEQ ID NO: 34 or 35.

10. The isolated antibody of claim 1, wherein the VL comprises an amino acid region that is at least 75% identical to the amino acid sequence of any one of SEQ ID NOs: 37-39 and 60.

11. The isolated antibody of claim 1, wherein the antibody further comprises a heavy chain constant region selected from the group consisting of human $IgG_1$, $IgG_2$, $IgG_3$, $IgG_4$, $IgA_1$, and $IgA_2$.

12. The isolated antibody of claim 11, wherein the antibody comprises an $IgG_1$ heavy chain constant region, wherein:
   (a) the $IgG_1$ heavy chain constant region comprises the amino acid sequence of SEQ ID NO: 19;
   (b) the amino acid sequence of the $IgG_1$ heavy chain constant region comprises an N297A mutation, numbered according to the EU numbering system;
   (c) the $IgG_1$ heavy chain constant region comprises the amino acid sequence of SEQ ID NO: 20;

(d) the amino acid sequence of the IgG₁ heavy chain constant region comprises L234F, L235F, and N297A mutations, numbered according to the EU numbering system;
(e) the IgG₁ heavy chain constant region comprises the amino acid sequence of SEQ ID NO: 21;
(f) the amino acid sequence of the IgG₁ heavy chain constant region comprises S239D and I332E mutations, numbered according to the EU numbering system;
(g) the IgG₁ heavy chain constant region comprises the amino acid sequence of SEQ ID NO: 22;
(h) the amino acid sequence of the IgG₁ heavy chain constant region comprises S239D, A330L, and I332E mutations, numbered according to the EU numbering system;
(i) the IgG₁ heavy chain constant region comprises the amino acid sequence of SEQ ID NO: 23;
(j) the amino acid sequence of the IgG₁ heavy chain constant region comprises L235V, F243L, R292P, Y300L, and P396L mutations, numbered according to the EU numbering system;
(k) the IgG₁ heavy chain constant region comprises the amino acid sequence of SEQ ID NO: 24;
(l) the amino acid sequence of the IgG₁ heavy chain constant region comprises S267E and L328F mutations, numbered according to the EU numbering system;
(m) the IgG₁ heavy chain constant region comprises the amino acid sequence of SEQ ID NO: 25; or
(n) the IgG₁ heavy chain constant region is afucosylated.

13. The isolated antibody of claim 11, wherein the antibody comprises an IgG₄ heavy chain constant region, wherein:
(a) the amino acid sequence of the IgG₄ heavy chain constant region comprises an S228P mutation, numbered according to the EU numbering system; and/or
(b) the IgG₄ heavy chain constant region comprises the amino acid sequence of SEQ ID NO: 26.

14. The isolated antibody of claim 1, wherein the antibody comprises a light chain constant region comprising the amino acid sequence of SEQ ID NO: 28.

15. The isolated antibody of claim 1, wherein the antibody comprises a heavy chain comprising an amino acid sequence selected from the group consisting of SEQ ID NOs: 11-18.

16. The isolated antibody of claim 1, wherein the antibody comprises a light chain comprising the amino acid sequence of SEQ ID NO: 27.

17. An isolated antibody that specifically binds to human TIGIT, wherein:
(a) a heavy chain comprising an amino acid sequence selected from the group consisting of SEQ ID NOs: 11-18; and/or
(b) a light chain comprising the amino acid sequence of SEQ ID NO: 27.

18. The isolated antibody of claim 17, wherein the heavy chain and light chain comprise the amino acid sequences of SEQ ID NOs: 11 and 27, respectively.

19. The isolated antibody of claim 1, wherein:
(a) the antibody is a human antibody;
(b) the antibody is a bispecific antibody;
(c) the antibody is an antagonistic antibody;
(d) the antibody preferentially kills regulatory T cells over effector T cells in a population of peripheral blood mononuclear cells (PBMCs) in vitro;
(e) the antibody decreases or inhibits binding of human TIGIT to PVR or PVRL2 relative to the level of binding in the absence of the antibody;
(f) the antibody induces IL-2 and/or IFNγ production by PBMCs stimulated with staphylococcal enterotoxin A (SEA);
(g) the antibody is conjugated to a cytotoxic agent, cytostatic agent, toxin, radionuclide, or detectable label; and/or
(h) the antibody is cross-linked to a second antibody or a fragment thereof.

20. A pharmaceutical composition comprising the antibody of claim 1 and a pharmaceutically acceptable carrier or excipient.

21. An isolated polynucleotide encoding the VH and/or VL, or a heavy chain and/or light chain, of the antibody of claim 1.

22. A vector comprising the polynucleotide of claim 21.

23. A recombinant host cell comprising the polynucleotide of claim 21.

24. A recombinant host cell comprising a first polynucleotide encoding the VH, or a heavy chain, of the antibody of claim 1, and a second polynucleotide encoding the VL, or the light chain, of the antibody of claim 1.

25. A method of producing an antibody that specifically binds to human TIGIT, or an antigen-binding fragment thereof, the method comprising culturing the host cell of claim 23 such that the polynucleotide is expressed and the antibody, or antigen-binding fragment, is produced.

26. A method of producing an antibody that specifically binds to human TIGIT, or an antigen-binding fragment thereof, the method comprising culturing the host cell of claim 24 such that the first polynucleotide and the second polynucleotide are expressed and the antibody, or antigen-binding fragment, is produced.

27. A method of increasing T cell activation in response to an antigen in a subject, the method comprising administering to the subject an effective amount of the antibody of claim 1.

28. A method of decreasing or inhibiting Treg activity in response to an antigen in a subject, the method comprising administering to the subject an effective amount of the antibody of claim 1.

29. A method of increasing NK cell activation in response to an antigen in a subject, the method comprising administering to the subject an effective amount of the antibody of claim 1.

30. A method of treating cancer in a subject, the method comprising administering to the subject an effective amount of the antibody of claim 1, optionally wherein the antibody is administered intravenously, subcutaneously, intratumorally, or is delivered to a tumor draining lymph node.

31. A method of treating an infectious disease in a subject, the method comprising administering to the subject an effective amount of the antibody of claim 1.

32. The pharmaceutical composition of claim 20, wherein the antibody comprises:
(a) an IgG₁ heavy chain constant region, wherein
(i) the IgG₁ heavy chain constant region comprises the amino acid sequence of SEQ ID NO: 19,
(ii) the amino acid sequence of the IgG₁ heavy chain constant region comprises an N297A mutation, numbered according to the EU numbering system,
(iii) the IgG₁ heavy chain constant region comprises the amino acid sequence of SEQ ID NO: 20,
(iv) the amino acid sequence of the IgG₁ heavy chain constant region comprises L234F, L235F, and N297A mutations, numbered according to the EU numbering system, (v) the IgG$_1$ heavy chain constant region comprises the amino acid sequence of SEQ ID NO: 21,
(vi) the amino acid sequence of the IgG$_1$ heavy chain constant region comprises S239D and I332E mutations, numbered according to the EU numbering system,
(vii) the IgG$_1$ heavy chain constant region comprises the amino acid sequence of SEQ ID NO: 22,
(viii) the amino acid sequence of the IgG$_1$ heavy chain constant region comprises S239D, A330L, and I332E mutations, numbered according to the EU numbering system,
(ix) the IgG$_1$ heavy chain constant region comprises the amino acid sequence of SEQ ID NO: 23,
(x) the amino acid sequence of the IgG$_1$ heavy chain constant region comprises L235V, F243L, R292P, Y300L, and P396L mutations, numbered according to the EU numbering system,
(xi) the IgG$_1$ heavy chain constant region comprises the amino acid sequence of SEQ ID NO: 24,
(xii) the amino acid sequence of the IgG$_1$ heavy chain constant region comprises S267E and L328F mutations, numbered according to the EU numbering system,
(xiii) the IgG$_1$ heavy chain constant region comprises the amino acid sequence of SEQ ID NO: 25, or
(xiv) the IgG$_1$ heavy chain constant region is afucosylated;
(b) an IgG$_4$ heavy chain constant region, wherein
(i) the amino acid sequence of the IgG$_4$ heavy chain constant region comprises an S228P mutation, numbered according to the EU numbering system, and/or
(ii) the IgG$_4$ heavy chain constant region comprises the amino acid sequence of SEQ ID NO: 26; or
(c) a heavy chain comprising an amino acid sequence selected from the group consisting of SEQ ID NOs: 11-18.

33. The polynucleotide of claim 21, wherein the antibody comprises:
(a) an IgG$_1$ heavy chain constant region, wherein
(i) the IgG$_1$ heavy chain constant region comprises the amino acid sequence of SEQ ID NO: 19,
(ii) the amino acid sequence of the IgG$_1$ heavy chain constant region comprises an N297A mutation, numbered according to the EU numbering system,
(iii) the IgG$_1$ heavy chain constant region comprises the amino acid sequence of SEQ ID NO: 20,
(iv) the amino acid sequence of the IgG$_1$ heavy chain constant region comprises L234F, L235F, and N297A mutations, numbered according to the EU numbering system,
(v) the IgG$_1$ heavy chain constant region comprises the amino acid sequence of SEQ ID NO: 21,
(vi) the amino acid sequence of the IgG$_1$ heavy chain constant region comprises S239D and I332E mutations, numbered according to the EU numbering system,
(vii) the IgG$_1$ heavy chain constant region comprises the amino acid sequence of SEQ ID NO: 22,
(viii) the amino acid sequence of the IgG$_1$ heavy chain constant region comprises S239D, A330L, and I332E mutations, numbered according to the EU numbering system,
(ix) the IgG$_1$ heavy chain constant region comprises the amino acid sequence of SEQ ID NO: 23,
(x) the amino acid sequence of the IgG$_1$ heavy chain constant region comprises L235V, F243L, R292P, Y300L, and P396L mutations, numbered according to the EU numbering system,
(xi) the IgG$_1$ heavy chain constant region comprises the amino acid sequence of SEQ ID NO: 24,
(xii) the amino acid sequence of the IgG$_1$ heavy chain constant region comprises S267E and L328F mutations, numbered according to the EU numbering system,
(xiii) the IgG$_1$ heavy chain constant region comprises the amino acid sequence of SEQ ID NO: 25, or
(xiv) the IgG$_1$ heavy chain constant region is afucosylated;
(b) an IgG$_4$ heavy chain constant region, wherein
(i) the amino acid sequence of the IgG$_4$ heavy chain constant region comprises an S228P mutation, numbered according to the EU numbering system, and/or
(ii) the IgG$_4$ heavy chain constant region comprises the amino acid sequence of SEQ ID NO: 26; or
(c) a heavy chain comprising an amino acid sequence selected from the group consisting of SEQ ID NOs: 11-18.

34. A vector comprising the polynucleotide of claim 33.
35. A recombinant host cell comprising the polynucleotide of claim 33.
36. The host cell of claim 24, wherein the antibody comprises:
(a) an IgG$_1$ heavy chain constant region, wherein
(i) the IgG$_1$ heavy chain constant region comprises the amino acid sequence of SEQ ID NO: 19,
(ii) the amino acid sequence of the IgG$_1$ heavy chain constant region comprises an N297A mutation, numbered according to the EU numbering system,
(iii) the IgG$_1$ heavy chain constant region comprises the amino acid sequence of SEQ ID NO: 20,
(iv) the amino acid sequence of the IgG$_1$ heavy chain constant region comprises L234F, L235F, and N297A mutations, numbered according to the EU numbering system,
(v) the IgG$_1$ heavy chain constant region comprises the amino acid sequence of SEQ ID NO: 21,
(vi) the amino acid sequence of the IgG$_1$ heavy chain constant region comprises S239D and I332E mutations, numbered according to the EU numbering system,
(vii) the IgG$_1$ heavy chain constant region comprises the amino acid sequence of SEQ ID NO: 22,
(viii) the amino acid sequence of the IgG$_1$ heavy chain constant region comprises S239D, A330L, and I332E mutations, numbered according to the EU numbering system,
(ix) the IgG$_1$ heavy chain constant region comprises the amino acid sequence of SEQ ID NO: 23,
(x) the amino acid sequence of the IgG$_1$ heavy chain constant region comprises L235V, F243L, R292P, Y300L, and P396L mutations, numbered according to the EU numbering system,
(xi) the IgG$_1$ heavy chain constant region comprises the amino acid sequence of SEQ ID NO: 24,
(xii) the amino acid sequence of the IgG$_1$ heavy chain constant region comprises S267E and L328F mutations, numbered according to the EU numbering system,
(xiii) the IgG$_1$ heavy chain constant region comprises the amino acid sequence of SEQ ID NO: 25, or
(xiv) the IgG$_1$ heavy chain constant region is afucosylated;

(b) an IgG$_4$ heavy chain constant region, wherein
  (i) the amino acid sequence of the IgG$_4$ heavy chain constant region comprises an S228P mutation, numbered according to the EU numbering system, and/or
  (ii) the IgG$_4$ heavy chain constant region comprises the amino acid sequence of SEQ ID NO: 26; or
(c) a heavy chain comprising an amino acid sequence selected from the group consisting of SEQ ID NOs: 11-18.

37. A method of producing an antibody that specifically binds to human TIGIT, or an antigen-binding fragment thereof, the method comprising culturing the host cell of claim 34 such that the polynucleotide is expressed and the antibody, or antigen-binding fragment, is produced.

38. A method of producing an antibody that specifically binds to human TIGIT, or an antigen-binding fragment thereof, the method comprising culturing the host cell of claim 35 such that the first polynucleotide and the second polynucleotide are expressed and the antibody, or antigen-binding fragment, is produced.

39. The method of claim 27, wherein the antibody comprises:
(a) an IgG$_1$ heavy chain constant region, wherein
  (i) the IgG$_1$ heavy chain constant region comprises the amino acid sequence of SEQ ID NO: 19,
  (ii) the amino acid sequence of the IgG$_1$ heavy chain constant region comprises an N297A mutation, numbered according to the EU numbering system,
  (iii) the IgG$_1$ heavy chain constant region comprises the amino acid sequence of SEQ ID NO: 20,
  (iv) the amino acid sequence of the IgG$_1$ heavy chain constant region comprises L234F, L235F, and N297A mutations, numbered according to the EU numbering system,
  (v) the IgG$_1$ heavy chain constant region comprises the amino acid sequence of SEQ ID NO: 21,
  (vi) the amino acid sequence of the IgG$_1$ heavy chain constant region comprises S239D and I332E mutations, numbered according to the EU numbering system,
  (vii) the IgG$_1$ heavy chain constant region comprises the amino acid sequence of SEQ ID NO: 22,
  (viii) the amino acid sequence of the IgG$_1$ heavy chain constant region comprises S239D, A330L, and I332E mutations, numbered according to the EU numbering system,
  (ix) the IgG$_1$ heavy chain constant region comprises the amino acid sequence of SEQ ID NO: 23,
  (x) the amino acid sequence of the IgG$_1$ heavy chain constant region comprises L235V, F243L, R292P, Y300L, and P396L mutations, numbered according to the EU numbering system,
  (xi) the IgG$_1$ heavy chain constant region comprises the amino acid sequence of SEQ ID NO: 24,
  (xii) the amino acid sequence of the IgG$_1$ heavy chain constant region comprises S267E and L328F mutations, numbered according to the EU numbering system,
  (xiii) the IgG$_1$ heavy chain constant region comprises the amino acid sequence of SEQ ID NO: 25, or
  (xiv) the IgG$_1$ heavy chain constant region is afucosylated;
(b) an IgG$_4$ heavy chain constant region, wherein
  (i) the amino acid sequence of the IgG$_4$ heavy chain constant region comprises an S228P mutation, numbered according to the EU numbering system, and/or
  (ii) the IgG$_4$ heavy chain constant region comprises the amino acid sequence of SEQ ID NO: 26; or
(c) a heavy chain comprising an amino acid sequence selected from the group consisting of SEQ ID NOs: 11-18.

40. The method of claim 28, wherein the antibody comprises:
(a) an IgG$_1$ heavy chain constant region, wherein
  (i) the IgG$_1$ heavy chain constant region comprises the amino acid sequence of SEQ ID NO: 19,
  (ii) the amino acid sequence of the IgG$_1$ heavy chain constant region comprises an N297A mutation, numbered according to the EU numbering system,
  (iii) the IgG$_1$ heavy chain constant region comprises the amino acid sequence of SEQ ID NO: 20,
  (iv) the amino acid sequence of the IgG$_1$ heavy chain constant region comprises L234F, L235F, and N297A mutations, numbered according to the EU numbering system,
  (v) the IgG$_1$ heavy chain constant region comprises the amino acid sequence of SEQ ID NO: 21,
  (vi) the amino acid sequence of the IgG$_1$ heavy chain constant region comprises S239D and I332E mutations, numbered according to the EU numbering system,
  (vii) the IgG$_1$ heavy chain constant region comprises the amino acid sequence of SEQ ID NO: 22,
  (viii) the amino acid sequence of the IgG$_1$ heavy chain constant region comprises S239D, A330L, and I332E mutations, numbered according to the EU numbering system,
  (ix) the IgG$_1$ heavy chain constant region comprises the amino acid sequence of SEQ ID NO: 23,
  (x) the amino acid sequence of the IgG$_1$ heavy chain constant region comprises L235V, F243L, R292P, Y300L, and P396L mutations, numbered according to the EU numbering system,
  (xi) the IgG$_1$ heavy chain constant region comprises the amino acid sequence of SEQ ID NO: 24,
  (xii) the amino acid sequence of the IgG$_1$ heavy chain constant region comprises S267E and L328F mutations, numbered according to the EU numbering system,
  (xiii) the IgG$_1$ heavy chain constant region comprises the amino acid sequence of SEQ ID NO: 25, or
  (xiv) the IgG$_1$ heavy chain constant region is afucosylated;
(b) an IgG$_4$ heavy chain constant region, wherein
  (i) the amino acid sequence of the IgG$_4$ heavy chain constant region comprises an S228P mutation, numbered according to the EU numbering system, and/or
  (ii) the IgG$_4$ heavy chain constant region comprises the amino acid sequence of SEQ ID NO: 26; or
(c) a heavy chain comprising an amino acid sequence selected from the group consisting of SEQ ID NOs: 11-18.

41. The method of claim 29, wherein the antibody comprises:
(a) an IgG$_1$ heavy chain constant region, wherein
  (i) the IgG$_1$ heavy chain constant region comprises the amino acid sequence of SEQ ID NO: 19,
  (ii) the amino acid sequence of the IgG$_1$ heavy chain constant region comprises an N297A mutation, numbered according to the EU numbering system,
  (iii) the IgG$_1$ heavy chain constant region comprises the amino acid sequence of SEQ ID NO: 20, (iv) the amino acid sequence of the IgG₁ heavy chain constant region comprises L234F, L235F, and N297A mutations, numbered according to the EU numbering system,
(v) the IgG₁ heavy chain constant region comprises the amino acid sequence of SEQ ID NO: 21,
(vi) the amino acid sequence of the IgG₁ heavy chain constant region comprises S239D and I332E mutations, numbered according to the EU numbering system,
(vii) the IgG₁ heavy chain constant region comprises the amino acid sequence of SEQ ID NO: 22,
(viii) the amino acid sequence of the IgG₁ heavy chain constant region comprises S239D, A330L, and I332E mutations, numbered according to the EU numbering system,
(ix) the IgG₁ heavy chain constant region comprises the amino acid sequence of SEQ ID NO: 23,
(x) the amino acid sequence of the IgG₁ heavy chain constant region comprises L235V, F243L, R292P, Y300L, and P396L mutations, numbered according to the EU numbering system,
(xi) the IgG₁ heavy chain constant region comprises the amino acid sequence of SEQ ID NO: 24,
(xii) the amino acid sequence of the IgG₁ heavy chain constant region comprises S267E and L328F mutations, numbered according to the EU numbering system,
(xiii) the IgG₁ heavy chain constant region comprises the amino acid sequence of SEQ ID NO: 25, or
(xiv) the IgG₁ heavy chain constant region is afucosylated;
(b) an IgG₄ heavy chain constant region, wherein
(i) the amino acid sequence of the IgG₄ heavy chain constant region comprises an S228P mutation, numbered according to the EU numbering system, and/or
(ii) the IgG₄ heavy chain constant region comprises the amino acid sequence of SEQ ID NO: 26; or
(c) a heavy chain comprising an amino acid sequence selected from the group consisting of SEQ ID NOs: 11-18.

42. The method of claim 30, wherein the antibody comprises:
(a) an IgG₁ heavy chain constant region, wherein
(i) the IgG₁ heavy chain constant region comprises the amino acid sequence of SEQ ID NO: 19,
(ii) the amino acid sequence of the IgG₁ heavy chain constant region comprises an N297A mutation, numbered according to the EU numbering system,
(iii) the IgG₁ heavy chain constant region comprises the amino acid sequence of SEQ ID NO: 20,
(iv) the amino acid sequence of the IgG₁ heavy chain constant region comprises L234F, L235F, and N297A mutations, numbered according to the EU numbering system,
(v) the IgG₁ heavy chain constant region comprises the amino acid sequence of SEQ ID NO: 21,
(vi) the amino acid sequence of the IgG₁ heavy chain constant region comprises S239D and I332E mutations, numbered according to the EU numbering system,
(vii) the IgG₁ heavy chain constant region comprises the amino acid sequence of SEQ ID NO: 22,
(viii) the amino acid sequence of the IgG₁ heavy chain constant region comprises S239D, A330L, and I332E mutations, numbered according to the EU numbering system,
(ix) the IgG₁ heavy chain constant region comprises the amino acid sequence of SEQ ID NO: 23,
(x) the amino acid sequence of the IgG₁ heavy chain constant region comprises L235V, F243L, R292P, Y300L, and P396L mutations, numbered according to the EU numbering system,
(xi) the IgG₁ heavy chain constant region comprises the amino acid sequence of SEQ ID NO: 24,
(xii) the amino acid sequence of the IgG₁ heavy chain constant region comprises S267E and L328F mutations, numbered according to the EU numbering system,
(xiii) the IgG₁ heavy chain constant region comprises the amino acid sequence of SEQ ID NO: 25, or
(xiv) the IgG₁ heavy chain constant region is afucosylated;
(b) an IgG₄ heavy chain constant region, wherein
(i) the amino acid sequence of the IgG₄ heavy chain constant region comprises an S228P mutation, numbered according to the EU numbering system, and/or
(ii) the IgG₄ heavy chain constant region comprises the amino acid sequence of SEQ ID NO: 26; or
(c) a heavy chain comprising an amino acid sequence selected from the group consisting of SEQ ID NOs: 11-18.

43. The method of claim 31, wherein the antibody comprises:
(a) an IgG₁ heavy chain constant region, wherein
(i) the IgG₁ heavy chain constant region comprises the amino acid sequence of SEQ ID NO: 19,
(ii) the amino acid sequence of the IgG₁ heavy chain constant region comprises an N297A mutation, numbered according to the EU numbering system,
(iii) the IgG₁ heavy chain constant region comprises the amino acid sequence of SEQ ID NO: 20,
(iv) the amino acid sequence of the IgG₁ heavy chain constant region comprises L234F, L235F, and N297A mutations, numbered according to the EU numbering system,
(v) the IgG₁ heavy chain constant region comprises the amino acid sequence of SEQ ID NO: 21,
(vi) the amino acid sequence of the IgG₁ heavy chain constant region comprises S239D and I332E mutations, numbered according to the EU numbering system,
(vii) the IgG₁ heavy chain constant region comprises the amino acid sequence of SEQ ID NO: 22,
(viii) the amino acid sequence of the IgG₁ heavy chain constant region comprises S239D, A330L, and I332E mutations, numbered according to the EU numbering system,
(ix) the IgG₁ heavy chain constant region comprises the amino acid sequence of SEQ ID NO: 23,
(x) the amino acid sequence of the IgG₁ heavy chain constant region comprises L235V, F243L, R292P, Y300L, and P396L mutations, numbered according to the EU numbering system,
(xi) the IgG₁ heavy chain constant region comprises the amino acid sequence of SEQ ID NO: 24,
(xii) the amino acid sequence of the IgG₁ heavy chain constant region comprises S267E and L328F mutations, numbered according to the EU numbering system,
(xiii) the IgG₁ heavy chain constant region comprises the amino acid sequence of SEQ ID NO: 25, or
(xiv) the IgG₁ heavy chain constant region is afucosylated;

(b) an IgG$_4$ heavy chain constant region, wherein
  (i) the amino acid sequence of the IgG$_4$ heavy chain constant region comprises an S228P mutation, numbered according to the EU numbering system, and/or
  (ii) the IgG$_4$ heavy chain constant region comprises the amino acid sequence of SEQ ID NO: 26; or
(c) a heavy chain comprising an amino acid sequence selected from the group consisting of SEQ ID NOs: 11-18.

44. The isolated antibody of claim 2, wherein the antibody further comprises a heavy chain constant region selected from the group consisting of human IgG$_1$, IgG$_2$, IgG$_3$, IgG$_4$, IgA$_1$, and IgA$_2$.

45. The isolated antibody of claim 44, wherein the antibody comprises an IgG$_1$ heavy chain constant region, wherein:
  (a) the IgG$_1$ heavy chain constant region comprises the amino acid sequence of SEQ ID NO: 19;
  (b) the amino acid sequence of the IgG$_1$ heavy chain constant region comprises an N297A mutation, numbered according to the EU numbering system;
  (c) the IgG$_1$ heavy chain constant region comprises the amino acid sequence of SEQ ID NO: 20;
  (d) the amino acid sequence of the IgG$_1$ heavy chain constant region comprises L234F, L235F, and N297A mutations, numbered according to the EU numbering system;
  (e) the IgG$_1$ heavy chain constant region comprises the amino acid sequence of SEQ ID NO: 21;
  (f) the amino acid sequence of the IgG$_1$ heavy chain constant region comprises S239D and I332E mutations, numbered according to the EU numbering system;
  (g) the IgG$_1$ heavy chain constant region comprises the amino acid sequence of SEQ ID NO: 22;
  (h) the amino acid sequence of the IgG$_1$ heavy chain constant region comprises S239D, A330L, and I332E mutations, numbered according to the EU numbering system;
  (i) the IgG$_1$ heavy chain constant region comprises the amino acid sequence of SEQ ID NO: 23;
  (j) the amino acid sequence of the IgG$_1$ heavy chain constant region comprises L235V, F243L, R292P, Y300L, and P396L mutations, numbered according to the EU numbering system;
  (k) the IgG$_1$ heavy chain constant region comprises the amino acid sequence of SEQ ID NO: 24;
  (l) the amino acid sequence of the IgG$_1$ heavy chain constant region comprises S267E and L328F mutations, numbered according to the EU numbering system;
  (m) the IgG$_1$ heavy chain constant region comprises the amino acid sequence of SEQ ID NO: 25; or
  (n) the IgG$_1$ heavy chain constant region is afucosylated.

46. The isolated antibody of claim 44, wherein the antibody comprises an IgG$_4$ heavy chain constant region, wherein:
  (a) the amino acid sequence of the IgG$_4$ heavy chain constant region comprises an S228P mutation, numbered according to the EU numbering system; and/or
  (b) the IgG$_4$ heavy chain constant region comprises the amino acid sequence of SEQ ID NO: 26.

47. A pharmaceutical composition comprising the antibody of claim 2 and a pharmaceutically acceptable carrier or excipient.

48. An isolated polynucleotide encoding the VH and/or VL, or a heavy chain and/or light chain, of the antibody of claim 2.

49. A vector comprising the polynucleotide of claim 48.

50. A recombinant host cell comprising the polynucleotide of claim 48.

51. A recombinant host cell comprising a first polynucleotide encoding the VH, or a heavy chain, of the antibody of claim 2, and a second polynucleotide encoding the VL, or the light chain, of the antibody of claim 2.

52. A method of producing an antibody that specifically binds to human TIGIT, or an antigen-binding fragment thereof, the method comprising culturing the host cell of claim 50 such that the polynucleotide is expressed and the antibody, or antigen-binding fragment, is produced.

53. A method of producing an antibody that specifically binds to human TIGIT, or an antigen-binding fragment thereof, the method comprising culturing the host cell of claim 51 such that the first polynucleotide and the second polynucleotide are expressed and the antibody, or antigen-binding fragment, is produced.

54. A method of increasing T cell activation in response to an antigen in a subject, the method comprising administering to the subject an effective amount of the antibody of claim 2.

55. A method of decreasing or inhibiting Treg activity in response to an antigen in a subject, the method comprising administering to the subject an effective amount of the antibody of claim 2.

56. A method of increasing NK cell activation in response to an antigen in a subject, the method comprising administering to the subject an effective amount of the antibody of claim 2.

57. A method of treating cancer in a subject, the method comprising administering to the subject an effective amount of the antibody of claim 2, optionally wherein the antibody is administered intravenously, subcutaneously, intratumorally, or is delivered to a tumor draining lymph node.

58. A method of treating an infectious disease in a subject, the method comprising administering to the subject an effective amount of the antibody of claim 2.

59. The pharmaceutical composition of claim 47, wherein the antibody comprises:
  (a) an IgG$_1$ heavy chain constant region, wherein
    (i) the IgG$_1$ heavy chain constant region comprises the amino acid sequence of SEQ ID NO: 19,
    (ii) the amino acid sequence of the IgG$_1$ heavy chain constant region comprises an N297A mutation, numbered according to the EU numbering system,
    (iii) the IgG$_1$ heavy chain constant region comprises the amino acid sequence of SEQ ID NO: 20,
    (iv) the amino acid sequence of the IgG$_1$ heavy chain constant region comprises L234F, L235F, and N297A mutations, numbered according to the EU numbering system,
    (v) the IgG$_1$ heavy chain constant region comprises the amino acid sequence of SEQ ID NO: 21,
    (vi) the amino acid sequence of the IgG$_1$ heavy chain constant region comprises S239D and I332E mutations, numbered according to the EU numbering system,
    (vii) the IgG$_1$ heavy chain constant region comprises the amino acid sequence of SEQ ID NO: 22,
    (viii) the amino acid sequence of the IgG$_1$ heavy chain constant region comprises S239D, A330L, and I332E mutations, numbered according to the EU numbering system,
    (ix) the IgG$_1$ heavy chain constant region comprises the amino acid sequence of SEQ ID NO: 23, (x) the amino acid sequence of the IgG₁ heavy chain constant region comprises L235V, F243L, R292P, Y300L, and P396L mutations, numbered according to the EU numbering system, (xi) the IgG₁ heavy chain constant region comprises the amino acid sequence of SEQ ID NO: 24, (xii) the amino acid sequence of the IgG₁ heavy chain constant region comprises S267E and L328F mutations, numbered according to the EU numbering system, (xiii) the IgG₁ heavy chain constant region comprises the amino acid sequence of SEQ ID NO: 25, or (xiv) the IgG₁ heavy chain constant region is afucosylated;

(b) an IgG₄ heavy chain constant region, wherein
(i) the amino acid sequence of the IgG₄ heavy chain constant region comprises an S228P mutation, numbered according to the EU numbering system, and/or
(ii) the IgG₄ heavy chain constant region comprises the amino acid sequence of SEQ ID NO: 26; or (c) a heavy chain comprising an amino acid sequence selected from the group consisting of SEQ ID NOs: 11-18.

60. The polynucleotide of claim 48, wherein the antibody comprises:

(a) an IgG₁ heavy chain constant region, wherein
(i) the IgG₁ heavy chain constant region comprises the amino acid sequence of SEQ ID NO: 19,
(ii) the amino acid sequence of the IgG₁ heavy chain constant region comprises an N297A mutation, numbered according to the EU numbering system,
(iii) the IgG₁ heavy chain constant region comprises the amino acid sequence of SEQ ID NO: 20,
(iv) the amino acid sequence of the IgG₁ heavy chain constant region comprises L234F, L235F, and N297A mutations, numbered according to the EU numbering system,
(v) the IgG₁ heavy chain constant region comprises the amino acid sequence of SEQ ID NO: 21,
(vi) the amino acid sequence of the IgG₁ heavy chain constant region comprises S239D and I332E mutations, numbered according to the EU numbering system,
(vii) the IgG₁ heavy chain constant region comprises the amino acid sequence of SEQ ID NO: 22,
(viii) the amino acid sequence of the IgG₁ heavy chain constant region comprises S239D, A330L, and I332E mutations, numbered according to the EU numbering system,
(ix) the IgG₁ heavy chain constant region comprises the amino acid sequence of SEQ ID NO: 23,
(x) the amino acid sequence of the IgG₁ heavy chain constant region comprises L235V, F243L, R292P, Y300L, and P396L mutations, numbered according to the EU numbering system,
(xi) the IgG₁ heavy chain constant region comprises the amino acid sequence of SEQ ID NO: 24,
(xii) the amino acid sequence of the IgG₁ heavy chain constant region comprises S267E and L328F mutations, numbered according to the EU numbering system,
(xiii) the IgG₁ heavy chain constant region comprises the amino acid sequence of SEQ ID NO: 25, or
(xiv) the IgG₁ heavy chain constant region is afucosylated;

(b) an IgG₄ heavy chain constant region, wherein
(i) the amino acid sequence of the IgG₄ heavy chain constant region comprises an S228P mutation, numbered according to the EU numbering system, and/or
(ii) the IgG₄ heavy chain constant region comprises the amino acid sequence of SEQ ID NO: 26; or (c) a heavy chain comprising an amino acid sequence selected from the group consisting of SEQ ID NOs: 11-18.

61. A vector comprising the polynucleotide of claim 60.

62. A recombinant host cell comprising the polynucleotide of claim 60.

63. The host cell of claim 51, wherein the antibody comprises:

(a) an IgG₁ heavy chain constant region, wherein
(i) the IgG₁ heavy chain constant region comprises the amino acid sequence of SEQ ID NO: 19,
(ii) the amino acid sequence of the IgG₁ heavy chain constant region comprises an N297A mutation, numbered according to the EU numbering system,
(iii) the IgG₁ heavy chain constant region comprises the amino acid sequence of SEQ ID NO: 20,
(iv) the amino acid sequence of the IgG₁ heavy chain constant region comprises L234F, L235F, and N297A mutations, numbered according to the EU numbering system,
(v) the IgG₁ heavy chain constant region comprises the amino acid sequence of SEQ ID NO: 21,
(vi) the amino acid sequence of the IgG₁ heavy chain constant region comprises S239D and I332E mutations, numbered according to the EU numbering system,
(vii) the IgG₁ heavy chain constant region comprises the amino acid sequence of SEQ ID NO: 22,
(viii) the amino acid sequence of the IgG₁ heavy chain constant region comprises S239D, A330L, and I332E mutations, numbered according to the EU numbering system,
(ix) the IgG₁ heavy chain constant region comprises the amino acid sequence of SEQ ID NO: 23,
(x) the amino acid sequence of the IgG₁ heavy chain constant region comprises L235V, F243L, R292P, Y300L, and P396L mutations, numbered according to the EU numbering system,
(xi) the IgG₁ heavy chain constant region comprises the amino acid sequence of SEQ ID NO: 24,
(xii) the amino acid sequence of the IgG₁ heavy chain constant region comprises S267E and L328F mutations, numbered according to the EU numbering system,
(xiii) the IgG₁ heavy chain constant region comprises the amino acid sequence of SEQ ID NO: 25, or
(xiv) the IgG₁ heavy chain constant region is afucosylated;

(b) an IgG₄ heavy chain constant region, wherein
(i) the amino acid sequence of the IgG₄ heavy chain constant region comprises an S228P mutation, numbered according to the EU numbering system, and/or
(ii) the IgG₄ heavy chain constant region comprises the amino acid sequence of SEQ ID NO: 26; or (c) a heavy chain comprising an amino acid sequence selected from the group consisting of SEQ ID NOs: 11-18.

64. A method of producing an antibody that specifically binds to human TIGIT, or an antigen-binding fragment thereof, the method comprising culturing the host cell of claim 62 such that the polynucleotide is expressed and the antibody, or antigen-binding fragment, is produced.

65. A method of producing an antibody that specifically binds to human TIGIT, or an antigen-binding fragment thereof, the method comprising culturing the host cell of claim 63 such that the first polynucleotide and the second polynucleotide are expressed and the antibody, or antigen-binding fragment, is produced.

66. The method of claim 54, wherein the antibody comprises:
(a) an IgG$_1$ heavy chain constant region, wherein
   (i) the IgG$_1$ heavy chain constant region comprises the amino acid sequence of SEQ ID NO: 19,
   (ii) the amino acid sequence of the IgG$_1$ heavy chain constant region comprises an N297A mutation, numbered according to the EU numbering system,
   (iii) the IgG$_1$ heavy chain constant region comprises the amino acid sequence of SEQ ID NO: 20,
   (iv) the amino acid sequence of the IgG$_1$ heavy chain constant region comprises L234F, L235F, and N297A mutations, numbered according to the EU numbering system,
   (v) the IgG$_1$ heavy chain constant region comprises the amino acid sequence of SEQ ID NO: 21,
   (vi) the amino acid sequence of the IgG$_1$ heavy chain constant region comprises S239D and I332E mutations, numbered according to the EU numbering system,
   (vii) the IgG$_1$ heavy chain constant region comprises the amino acid sequence of SEQ ID NO: 22,
   (viii) the amino acid sequence of the IgG$_1$ heavy chain constant region comprises S239D, A330L, and I332E mutations, numbered according to the EU numbering system,
   (ix) the IgG$_1$ heavy chain constant region comprises the amino acid sequence of SEQ ID NO: 23,
   (x) the amino acid sequence of the IgG$_1$ heavy chain constant region comprises L235V, F243L, R292P, Y300L, and P396L mutations, numbered according to the EU numbering system,
   (xi) the IgG$_1$ heavy chain constant region comprises the amino acid sequence of SEQ ID NO: 24,
   (xii) the amino acid sequence of the IgG$_1$ heavy chain constant region comprises S267E and L328F mutations, numbered according to the EU numbering system,
   (xiii) the IgG$_1$ heavy chain constant region comprises the amino acid sequence of SEQ ID NO: 25, or
   (xiv) the IgG$_1$ heavy chain constant region is afucosylated;
(b) an IgG$_4$ heavy chain constant region, wherein
   (i) the amino acid sequence of the IgG$_4$ heavy chain constant region comprises an S228P mutation, numbered according to the EU numbering system, and/or
   (ii) the IgG$_4$ heavy chain constant region comprises the amino acid sequence of SEQ ID NO: 26; or
(c) a heavy chain comprising an amino acid sequence selected from the group consisting of SEQ ID NOs: 11-18.

67. The method of claim 55, wherein the antibody comprises:
(a) an IgG$_1$ heavy chain constant region, wherein
   (i) the IgG$_1$ heavy chain constant region comprises the amino acid sequence of SEQ ID NO: 19,
   (ii) the amino acid sequence of the IgG$_1$ heavy chain constant region comprises an N297A mutation, numbered according to the EU numbering system,
   (iii) the IgG$_1$ heavy chain constant region comprises the amino acid sequence of SEQ ID NO: 20,
   (iv) the amino acid sequence of the IgG$_1$ heavy chain constant region comprises L234F, L235F, and N297A mutations, numbered according to the EU numbering system,
   (v) the IgG$_1$ heavy chain constant region comprises the amino acid sequence of SEQ ID NO: 21,
   (vi) the amino acid sequence of the IgG$_1$ heavy chain constant region comprises S239D and I332E mutations, numbered according to the EU numbering system,
   (vii) the IgG$_1$ heavy chain constant region comprises the amino acid sequence of SEQ ID NO: 22,
   (viii) the amino acid sequence of the IgG$_1$ heavy chain constant region comprises S239D, A330L, and I332E mutations, numbered according to the EU numbering system,
   (ix) the IgG$_1$ heavy chain constant region comprises the amino acid sequence of SEQ ID NO: 23,
   (x) the amino acid sequence of the IgG$_1$ heavy chain constant region comprises L235V, F243L, R292P, Y300L, and P396L mutations, numbered according to the EU numbering system,
   (xi) the IgG$_1$ heavy chain constant region comprises the amino acid sequence of SEQ ID NO: 24,
   (xii) the amino acid sequence of the IgG$_1$ heavy chain constant region comprises S267E and L328F mutations, numbered according to the EU numbering system,
   (xiii) the IgG$_1$ heavy chain constant region comprises the amino acid sequence of SEQ ID NO: 25, or
   (xiv) the IgG$_1$ heavy chain constant region is afucosylated;
(b) an IgG$_4$ heavy chain constant region, wherein
   (i) the amino acid sequence of the IgG$_4$ heavy chain constant region comprises an S228P mutation, numbered according to the EU numbering system, and/or
   (ii) the IgG$_4$ heavy chain constant region comprises the amino acid sequence of SEQ ID NO: 26; or
(c) a heavy chain comprising an amino acid sequence selected from the group consisting of SEQ ID NOs: 11-18.

68. The method of claim 56, wherein the antibody comprises:
(a) an IgG$_1$ heavy chain constant region, wherein
   (i) the IgG$_1$ heavy chain constant region comprises the amino acid sequence of SEQ ID NO: 19,
   (ii) the amino acid sequence of the IgG$_1$ heavy chain constant region comprises an N297A mutation, numbered according to the EU numbering system,
   (iii) the IgG$_1$ heavy chain constant region comprises the amino acid sequence of SEQ ID NO: 20,
   (iv) the amino acid sequence of the IgG$_1$ heavy chain constant region comprises L234F, L235F, and N297A mutations, numbered according to the EU numbering system,
   (v) the IgG$_1$ heavy chain constant region comprises the amino acid sequence of SEQ ID NO: 21,
   (vi) the amino acid sequence of the IgG$_1$ heavy chain constant region comprises S239D and I332E mutations, numbered according to the EU numbering system,
   (vii) the IgG$_1$ heavy chain constant region comprises the amino acid sequence of SEQ ID NO: 22,
   (viii) the amino acid sequence of the IgG$_1$ heavy chain constant region comprises S239D, A330L, and I332E mutations, numbered according to the EU numbering system, (ix) the IgG₁ heavy chain constant region comprises the amino acid sequence of SEQ ID NO: 23,
(x) the amino acid sequence of the IgG₁ heavy chain constant region comprises L235V, F243L, R292P, Y300L, and P396L mutations, numbered according to the EU numbering system,
(xi) the IgG₁ heavy chain constant region comprises the amino acid sequence of SEQ ID NO: 24,
(xii) the amino acid sequence of the IgG₁ heavy chain constant region comprises S267E and L328F mutations, numbered according to the EU numbering system,
(xiii) the IgG₁ heavy chain constant region comprises the amino acid sequence of SEQ ID NO: 25, or
(xiv) the IgG₁ heavy chain constant region is afucosylated;
(b) an IgG₄ heavy chain constant region, wherein
(i) the amino acid sequence of the IgG₄ heavy chain constant region comprises an S228P mutation, numbered according to the EU numbering system, and/or
(ii) the IgG₄ heavy chain constant region comprises the amino acid sequence of SEQ ID NO: 26; or
(c) a heavy chain comprising an amino acid sequence selected from the group consisting of SEQ ID NOs: 11-18.

69. The method of claim 57, wherein the antibody comprises:
(a) an IgG₁ heavy chain constant region, wherein
(i) the IgG₁ heavy chain constant region comprises the amino acid sequence of SEQ ID NO: 19,
(ii) the amino acid sequence of the IgG₁ heavy chain constant region comprises an N297A mutation, numbered according to the EU numbering system,
(iii) the IgG₁ heavy chain constant region comprises the amino acid sequence of SEQ ID NO: 20,
(iv) the amino acid sequence of the IgG₁ heavy chain constant region comprises L234F, L235F, and N297A mutations, numbered according to the EU numbering system,
(v) the IgG₁ heavy chain constant region comprises the amino acid sequence of SEQ ID NO: 21,
(vi) the amino acid sequence of the IgG₁ heavy chain constant region comprises S239D and I332E mutations, numbered according to the EU numbering system,
(vii) the IgG₁ heavy chain constant region comprises the amino acid sequence of SEQ ID NO: 22,
(viii) the amino acid sequence of the IgG₁ heavy chain constant region comprises S239D, A330L, and I332E mutations, numbered according to the EU numbering system,
(ix) the IgG₁ heavy chain constant region comprises the amino acid sequence of SEQ ID NO: 23,
(x) the amino acid sequence of the IgG₁ heavy chain constant region comprises L235V, F243L, R292P, Y300L, and P396L mutations, numbered according to the EU numbering system,
(xi) the IgG₁ heavy chain constant region comprises the amino acid sequence of SEQ ID NO: 24,
(xii) the amino acid sequence of the IgG₁ heavy chain constant region comprises S267E and L328F mutations, numbered according to the EU numbering system,
(xiii) the IgG₁ heavy chain constant region comprises the amino acid sequence of SEQ ID NO: 25, or
(xiv) the IgG₁ heavy chain constant region is afucosylated;
(b) an IgG₄ heavy chain constant region, wherein
(i) the amino acid sequence of the IgG₄ heavy chain constant region comprises an S228P mutation, numbered according to the EU numbering system, and/or
(ii) the IgG₄ heavy chain constant region comprises the amino acid sequence of SEQ ID NO: 26; or
(c) a heavy chain comprising an amino acid sequence selected from the group consisting of SEQ ID NOs: 11-18.

70. The method of claim 58, wherein the antibody comprises:
(a) an IgG₁ heavy chain constant region, wherein
(i) the IgG₁ heavy chain constant region comprises the amino acid sequence of SEQ ID NO: 19,
(ii) the amino acid sequence of the IgG₁ heavy chain constant region comprises an N297A mutation, numbered according to the EU numbering system,
(iii) the IgG₁ heavy chain constant region comprises the amino acid sequence of SEQ ID NO: 20,
(iv) the amino acid sequence of the IgG₁ heavy chain constant region comprises L234F, L235F, and N297A mutations, numbered according to the EU numbering system,
(v) the IgG₁ heavy chain constant region comprises the amino acid sequence of SEQ ID NO: 21,
(vi) the amino acid sequence of the IgG₁ heavy chain constant region comprises S239D and I332E mutations, numbered according to the EU numbering system,
(vii) the IgG₁ heavy chain constant region comprises the amino acid sequence of SEQ ID NO: 22,
(viii) the amino acid sequence of the IgG₁ heavy chain constant region comprises S239D, A330L, and I332E mutations, numbered according to the EU numbering system,
(ix) the IgG₁ heavy chain constant region comprises the amino acid sequence of SEQ ID NO: 23,
(x) the amino acid sequence of the IgG₁ heavy chain constant region comprises L235V, F243L, R292P, Y300L, and P396L mutations, numbered according to the EU numbering system,
(xi) the IgG₁ heavy chain constant region comprises the amino acid sequence of SEQ ID NO: 24,
(xii) the amino acid sequence of the IgG₁ heavy chain constant region comprises S267E and L328F mutations, numbered according to the EU numbering system,
(xiii) the IgG₁ heavy chain constant region comprises the amino acid sequence of SEQ ID NO: 25, or
(xiv) the IgG₁ heavy chain constant region is afucosylated;
(b) an IgG₄ heavy chain constant region, wherein
(i) the amino acid sequence of the IgG₄ heavy chain constant region comprises an S228P mutation, numbered according to the EU numbering system, and/or
(ii) the IgG₄ heavy chain constant region comprises the amino acid sequence of SEQ ID NO: 26; or
(c) a heavy chain comprising an amino acid sequence selected from the group consisting of SEQ ID NOs: 11-18.

* * * * *